(12) United States Patent
Anilkumar et al.

(10) Patent No.: US 8,546,420 B2
(45) Date of Patent: Oct. 1, 2013

(54) 4, 5-RING ANNULATED INDOLE DERIVATIVES FOR TREATING OR PREVENTING OF HCV AND RELATED VIRAL INFECTIONS

(75) Inventors: Gopinadhan N. Anilkumar, Edison, NJ (US); Yueheng Jiang, Whitehouse Station, NJ (US); Stuart B. Rosenblum, West Orange, NJ (US); Srikanth Venkatraman, Edison, NJ (US); Francisco Velazquez, Clinton, NJ (US); Neng-Yang Shih, Lexington, MA (US); F. George Njoroge, Warren, NJ (US); Joseph A. Kozlowski, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 704 days.

(21) Appl. No.: 12/519,728

(22) PCT Filed: Dec. 17, 2007

(86) PCT No.: PCT/US2007/025765
§ 371 (c)(1),
(2), (4) Date: Mar. 1, 2010

(87) PCT Pub. No.: WO2008/082488
PCT Pub. Date: Jul. 10, 2008

(65) Prior Publication Data
US 2010/0196319 A1 Aug. 5, 2010

Related U.S. Application Data

(60) Provisional application No. 60/876,613, filed on Dec. 22, 2006.

(51) Int. Cl.
*A01N 43/42* (2006.01)
*A61K 31/44* (2006.01)
*C07D 471/00* (2006.01)
*C07D 491/00* (2006.01)

(52) U.S. Cl.
USPC ............................. 514/292; 546/85; 548/430

(58) Field of Classification Search
USPC ............................. 514/292; 546/85; 548/430
See application file for complete search history.

(56) References Cited

U.S. PATENT DOCUMENTS

| | | | |
|---|---|---|---|
| 3,632,805 A | 1/1972 | Yamamoto et al. | |
| 4,634,697 A | 1/1987 | Hamashima | |
| 4,812,561 A | 3/1989 | Hamashima et al. | |
| 4,933,443 A | 6/1990 | Hamashima et al. | |
| 5,017,380 A | 5/1991 | Hamashima et al. | |
| 6,107,310 A * | 8/2000 | Birch et al. | 514/318 |
| 6,596,753 B2 | 7/2003 | Bernard et al. | |
| 6,800,434 B2 | 10/2004 | Saksena et al. | |
| 6,838,475 B2 | 1/2005 | Arasappan et al. | |
| 6,846,802 B2 | 1/2005 | Chen et al. | |
| 6,911,428 B2 | 6/2005 | Zhu et al. | |
| 6,914,122 B2 | 7/2005 | Venkatraman et al. | |
| 7,012,066 B2 | 3/2006 | Saksena et al. | |
| 2002/0160962 A1 | 10/2002 | Saksena et al. | |
| 2004/0077704 A1 | 4/2004 | Beight et al. | |
| 2005/0075331 A1 | 4/2005 | Pratt et al. | |
| 2005/0101770 A1 | 5/2005 | Presta | |
| 2005/0176648 A1 | 8/2005 | Saksena et al. | |
| 2005/0249702 A1 | 11/2005 | Njoroge et al. | |
| 2007/0274951 A1 | 11/2007 | Tong et al. | |
| 2010/0098661 A1 | 4/2010 | Chen et al. | |
| 2010/0196319 A1 | 8/2010 | Anilkumar et al. | |
| 2010/0239527 A1 | 9/2010 | Anilkumar et al. | |
| 2010/0260711 A1 | 10/2010 | Chen et al. | |
| 2010/0322901 A1 | 12/2010 | Bennett et al. | |
| 2011/0033417 A1 | 2/2011 | Anilkumar et al. | |

(Continued)

FOREIGN PATENT DOCUMENTS

| AU | 2002313410 B2 | 7/2002 |
|---|---|---|
| DE | 648639 C | 8/1937 |

(Continued)

OTHER PUBLICATIONS

Fawcett, et al., Polynuclear Heterocyclic Aromatic Types. III. Pyrroloquinoline Derivatives, J. of the Chem. Society, 2254-61 (1928).*
Dewar, Attempts to Find New Antimalarials. XXI, J. of the Chem. Society, 615-619 (1944).*
Muratake, et al., Total Synthesis of Natural (+)-Duocarmycin SA, Chemical & Pharmaceutical Bulletin, 43(6), 1064-6 (1995).*
Yasuzawa, et al., Duocarmycins, potent antitumor antibiotics produced by *Streptomyces* sp. structures and chemistry, Chemical & Pharmaceutical Bulletin 43(3), 378-91 (1995).*
Wolff, Manfred E., Burger's Medicinal Chemistry and Drug Discovery, Fifth Ed., vol. 1: Principles and Practice, John Wiley & Sons, 1995, 975.*

(Continued)

*Primary Examiner* — Erich A Leeser
(74) *Attorney, Agent, or Firm* — Melissa B. Wenk; Sheldon O. Heber

(57) ABSTRACT

The present invention relates to 4,5-ring annulated indole derivatives of formula (I), compositions comprising at least one 4,5-ring annulated indole derivatives, and methods of using the 4,5-ring annulated indole derivatives for treating or preventing a viral infection or a virus-related disorder in a patient,

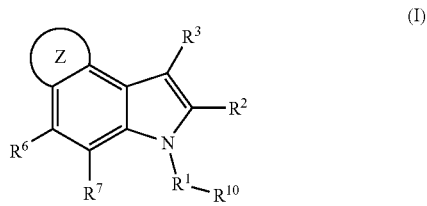

(I)

wherein ring Z of formula (I), is cyclohexyl, cyclohexenyl, 6-membered heterocycloalkyl, 6-membered heterocycloalkenyl, 6-membered aryl or 6-membered heteroaryl, wherein $R^1$, $R^2$, $R^3$, $R^6$, $R^7$ and $R^{10}$ are as described herein.

19 Claims, No Drawings

(56) References Cited

U.S. PATENT DOCUMENTS

| | | | |
|---|---|---|---|
| 2011/0104109 | A1 | 5/2011 | Bennett et al. |
| 2011/0104110 | A1 | 5/2011 | Anikumar et al. |
| 2011/0165118 | A1 | 7/2011 | Chan et al. |

FOREIGN PATENT DOCUMENTS

| | | | |
|---|---|---|---|
| EP | 0449196 | A2 | 10/1991 |
| FR | 2 768 146 | * | 9/1997 |
| FR | 2768146 | A1 | 3/1999 |
| JP | 07053558 | * | 2/1995 |
| JP | 2003/342276 | * | 3/2003 |
| JP | 4-149429 | | 5/2004 |
| WO | 96/37619 | A1 | 11/1996 |
| WO | 98/14181 | A1 | 4/1998 |
| WO | 98/17679 | A1 | 4/1998 |
| WO | 98/22496 | A2 | 5/1998 |
| WO | 99/07734 | A2 | 2/1999 |
| WO | 02/30895 | A1 | 4/2002 |
| WO | 02/068412 | A1 | 9/2002 |
| WO | WO 02/068412 | * | 9/2002 |
| WO | 2004/035571 | A1 | 4/2004 |
| WO | 2004/106328 | A1 | 12/2004 |
| WO | 2005/034941 | A1 | 4/2005 |
| WO | 2005/084315 | A2 | 9/2005 |
| WO | 2005/087731 | A1 | 9/2005 |
| WO | 2005/111018 | A1 | 11/2005 |
| WO | 2006/020082 | A1 | 2/2006 |
| WO | 2006/032541 | A1 | 3/2006 |
| WO | 2006/034337 | A2 | 3/2006 |
| WO | 2006/046030 | A2 | 5/2006 |
| WO | 2006/076529 | A1 | 7/2006 |
| WO | 2007/029029 | A2 | 3/2007 |
| WO | 2007/038209 | A2 | 4/2007 |
| WO | 2007/084413 | A2 | 7/2007 |
| WO | 2007/084435 | A2 | 7/2007 |
| WO | 2008/082484 | A1 | 7/2008 |

OTHER PUBLICATIONS

Banker, Gilbert S. et al., Modem Pharmaceutics, Marcel Dekker, New York, 1996.*
Kuyper, et al., High-Affinity Inhibitors of Dihydrofolate Reductase: Antimicrobial and Anticancer Activities of 7,8-Dialkyl-1,3-diaminopyrrolo[3,2-f]quinazolines with Small Molecular Size, Journal of Medicinal Chemistry (1996), 39(4), 892-903.*
Boger, et al., A Comparative Study of the Solvolysis Reactivity, Regioselectivity, and Stereochemistry of the Duocarmycin A and SA Alkylation Subunits, Bioorganic & Medicinal Chemistry Letters, 6(16), 1955-1960 (1996).*
Chae, et al., Palladium-catalyzed Regioselective Hydrodebromination of Dibromoindoles: Application to the Enantioselective Synthesis of Indolodioxane U86192A, J. Org. Chem., 69, 3336-3339 (2004).*
Basaric, et al., Structure Elucidation of the Photoproducts Obtained by the Photolysis of N-acetyl-2-styrylpyrroles, J. of Photochemistry and Photobiology A: Chemistry 154, 123-130 (2003).*
Yamashkin, et al., The Rules Linking Structures and Electronic Absorption Spectra of Isomeric Pyrroloquinolines, Chemistry of Heterocyclic Compounds, vol. 39, No. 10, 1343-1347 (2003).*
Yamashkin, et al., Synthesis of Substituted Pyrrolo[3,2-f]quinolines, Chemistry of Heterocyclic Compounds, vol. 33, No. 8, 942-948 (1997).*
Beaulieu et al., "Inhibitors of the HCV NS5B polymerase: New hope for the treatment of hepatitis C infections", Current Opinion in Investigational Drugs, 2004, vol. 5, pp. 838-850, No. 8.
Behrens et al., "identification and properties of the RNA-dependent RNA polymerase of hepatitis C virus", The EMBO Journal, 1996, vol. 15, pp. 12-22, No. 1.
Bioworld Today, 9 (217):4 Nov. 10, 1998, pp. 1-5.
Birnbock et al., "Sulfate Derivatives of 2-Phenylindols as Novel Steroid Sulfatase Inhibitors", Biochemical Pharmacology, 1990, vol. 39, pp. 1709-1713, No. 11.
Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.
Chemical and Pharmaceutical Bulletin, vol. 19, 1971, p. 263-270.
Denmark et al., "Palladium-Catalyzed Cross-Coupling Reactions of Silanolates: A Paradigm Shift in Silicon-Based Cross-Coupling Reactions", Chem. Eur. J., 2006, vol. 12, pp. 4954-4963.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, vol. 71, pp. 7461-7469, No. 10.
Elzouki et al., "Serine protease inhibitors in patients with chronic viral hepatitis", Journal of Hepatology, 1997, vol. 27, pp. 42-48.
Ferrari et al., "Characterization of Soluble Hepatitis C Virus RNA-Dependent RNA Polymerase Expressed in *Escherichia coli*", Journal of Virology, 1999, vol. 73, pp. 1649-1654, No. 2.
Fonseca et al., "Synthesis and antiviral evaluation of benzimidazoles, quinoxalines and indoles from dehydroabietic acid", Bioorganic & Medicinal Chemistry, 2004, vol. 12, pp. 103-112.
Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.
Goldsmith et al., "Studies in the Benzindole Series", J. Org. Chem, 1952, vol. 18, pp. 507-514.
Gopalsamy et al., "Design and synthesis of 2,3,4,9-tetrahydro-1H-carbazole and 1,2,3,4-tetrahydro-cydopenta[b] indole derivatives as non-nucleoside inhibitors of hepatitis C virus NS5B RNA-dependent RNA polymerase", Bioorganic & Medicinal Chemistry Letters, 2006, vol. 16, pp. 2532-2534.
Humphrey et al., "Practical Methodologies for the Synthesis of Indoles", Chem. Rev., 2006, vol. 106, pp. 2875-2911.
International Search Report for International Application No. PCT/US2007/025754, mailed May 13, 2008, (4 pages).
Written Opinion for PCT/US2007/025754, filed Dec. 17, 2007, (7 pages).
International Search Report for International Application No. PCT/US2007/025765, mailed May 13, 2008, (6 pages).
Written Opinion for PCT/US2007/025765, filed Dec. 17, 2007, (8 pages).
International Search Report for International Application No. PCT/US2007/025757, mailed Mar. 6, 2009, (8 pages).
Written Opinion for PCT/US2007/025757, filed Dec. 17, 2007 (12 pages).
International Search Report for International Application No. PCT/US2008/010130, mailed Jan. 22, 2009, (5 pages).
Written Opinion for PCT/US2008/010130, filed Aug. 27, 2008 (9 pages).
International Search Report for International Application No. PCT/US2008/010149, mailed Feb. 2, 2009, (5 pages).
Written Opinion for PCT/US2008/010149, filed Aug. 27, 2008 (6 pages).
International Search Report for International Application No. PCT/US2008/083351, mailed Feb. 27, 2009, (3 pages).
Written Opinion for PCT/US2008/083351, filed Nov. 13, 2008 (5 pages).
International Search Report for International Application No. PCT/US2008/010147, mailed May 4, 2009, (3 pages).
Written Opinion for PCT/US2008/010147, filed Aug. 27, 2008 (6 pages).
International Search Report for International Application No. PCT/US2008/083358, mailed Mar. 6, 2009, (2 pages).
Written Opinion for PCT/US2008/083358, filed Nov. 13, 2008 (5 pages).
International Search Report for International Application No. PCT/US2008/010148, mailed Dec. 9, 2008, (3 pages).
Written Opinion for PCT/US2008/010148, filed Aug. 27, 2008 (7 pages).
International Search Report for International Application No. PCT/US2009/046822, mailed Oct. 7, 2009, (5 pages).
Written Opinion for PCT/US2009/046822, filed Jun. 10, 2009 (8 pages).

Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.

Journal of Heterocyclic Chemistry, vol. 12, 1975, pp. 351-358.

Journal of Medicinal Chemistry, vol. 23, No. 7, 1980, pp. 764-773.

Journal of Organic Chemistry, vol. 27, 1962, pp. 3782-3786.

Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.

Lindsay et al., "Sml2-Promoted Radical Addition Reactions with N-(2-Indolylacyl)oxazolidinones: Synthesis of Bisindole Compounds", Journal of Organic Chemistry, 2007, vol. 72, pp. 4181-4188, No. 11.

Llinas-Brunet et al., "Peptide-Based Inhibitors of the Hepatitis C Virus Serine Protease", Bioorganic & Medicinal Chemistry Letters, 1998, vol. 8, pp. 1713-1718.

Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.

Martin, et al., "Affinity selection of a camelized VH domain antibody inhibitor of hepatitis C virus N53 protease", Protein Engineering, 1997, vol. 10, pp. 607-614, No. 5.

Martin et al., "Design of Selective Eglin Inhibitors of HCV NS3 Proteinase", Biochemistry, 1998, vol. 37, pp. 11459-11468.

Muratake et al., "Synthesis of Duocarmycin SA by Way of Methyl 4-(Methoxycarbonyl)oxy-3H-pyrrolo[3,2-f] quinoline-2-carboxylate as a Tricyclic Heteroaromatic Intermediate", Chem. Pharm. Bulletin, 1998, vol. 46, pp. 400-412, No. 3.

Ni et al., "Progress and development of small molecule HCV antivirals", Current Opinion in Drug Discovery & Development, 2004, vol. 7, pp. 446-459, No. 4.

Rawal et al., "Photocyclization of Pyrrole Analogues of Stilbene: an Expedient Approach to Anti-tumour Agent CC-1065", Journal Chem. Soc., Chem. Commun., 1984, pp. 1526-1527.

Sechi et al., "Design and Synthesis of Novel Indole β-Diketo Acid Derivatives as HIV-1 Integrase Inhibitors", J. Med. Chem., 2004, vol. 47, pp. 5298-5310, No. 21.

Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.

Tan et al., "Hepatitis C Therapeutics: Current Status and Emerging Strategies", Nature Reviews, 2002, vol. 1, pp. 867-881.

* cited by examiner

4,5-RING ANNULATED INDOLE DERIVATIVES FOR TREATING OR PREVENTING OF HCV AND RELATED VIRAL INFECTIONS

Related Applications

This application is the national stage application under 35 U.S.C. 371 of International Patent Application No. PCT/US2007/025765, filed Dec. 17, 2007, which claims priority to US Provisional Application No. 60/876,613, filed Dec. 22, 2006. Each of the aforementioned PCT and priority applications is incorporated by reference in its entirety.

FIELD OF THE INVENTION

The present invention relates to 4,5-ring annulated indole derivatives, compositions comprising at least one 4,5-ring annulated indole derivatives, and methods of using the 4,5-ring annulated indole derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the *hepacivirus* genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$—C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase, with and without bound ligands, has provided important structural insights useful for the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides 4,5-ring annulated indole deriviatives (herein referred to as the "Compounds of Formula (I)"):

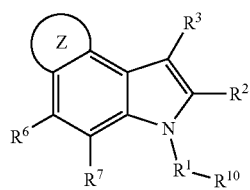

and pharmaceutically acceptable salts, solvates, prodrugs and esters thereof,
wherein
ring Z of formula (I), is cyclohexyl, cyclohexenyl, 6-membered heterocycloalkyl, 6-membered heterocycloalkenyl, 6-membered aryl or 6-membered heteroaryl, wherein ring Z may be: (i) optionally substituted on one or more ring carbon atoms with substituents, which are the same or different, and which are selected from alkyl, alkenyl, aryl, heteroaryl, cycloalkyl, heterocycloalkyl, halo, haloalkyl, hydroxyalkyl, hydroxy, —CN, —C(O)R$^8$, —C(O)OR$^9$, —C(O)N(R$^9$)$_2$, —[C(R$^{12}$)$_2$]$_q$—OR$^9$, —[C(R$^{12}$)$_2$]$_q$—N(R$^9$)$_2$, —NHC(O)R$^8$, —NHSO$_2$R$^{11}$, —S(O)$_p$R$^{11}$ or —SO$_2$N(R$^9$)$_2$; and/or (ii) optionally substituted on a ring nitrogen atom with substituents, which are the same or different, and which are selected from alkyl, aryl, haloalkyl, heteroaryl, hydroxyalkyl, —C(O)R$^8$, —C(O)OR$^9$, —C(O)N(R$^9$)$_2$, —[C(R$^{12}$)$_2$]$_r$—OR$^9$, —[C(R$^{12}$)$_2$]$_r$—N(R$^9$)$_2$, —NHC(O)R$^8$, —NHSO$_2$R$^{11}$, —S(O)$_p$R$^{11}$ or —SO$_2$N(R$^9$)$_2$;

R$^1$ is a bond, —[C(R$^{12}$)$_2$]$_r$—, —[C(R$^{12}$)$_2$]$_r$—O—[C(R$^{12}$)$_2$]$_q$—, —[C(R$^{12}$)$_2$]$_r$—N(R$^9$)—[C(R$^{12}$)$_2$]$_q$—, —[C(R$^{12}$)$_2$]$_q$—CH═CH—[C(R$^{12}$)$_2$]$_q$—, —[C(R$^{12}$)$_2$]$_q$—C≡C—[C(R$^{12}$)$_2$]$_q$—, or —[C(R$^{12}$)$_2$]$_q$—SO$_2$—[C(R$^{12}$)$_2$]$_q$—;

R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—C(O)N(R$^9$)C═N(R$^9$)$_2$, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl, —[C(R$^{12}$)$_2$]$_q$-heterocycloalkenyl, —[C(R$^{12}$)$_2$]$_q$—C(O)N(R$^9$) SOR$^{11}$, —[C(R$^{12}$)$_2$]$_q$—C(O)N(R$^9$)SO$_2$R$^{11}$, —[C(R$^{12}$)$_2$]$_q$—C(O)N(R$^9$)SO$_2$N(R$^9$)$_2$, alkyl,

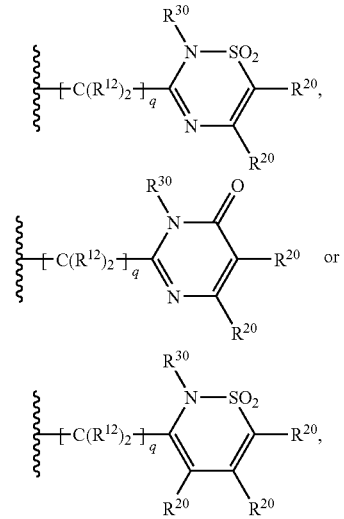

wherein an aryl, cycloalkyl, cycloalkenyl, heterocycloalkyl, heterocycloalkenyl or heteroaryl, group can be optionally substituted with up to 4 substituents, which are each independently selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

R$^3$ is —H, —[C(R$^{12}$)$_2$]$_q$-alkyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl or —[C(R$^{12}$)$_2$]$_1$-heterocycloalkenyl,

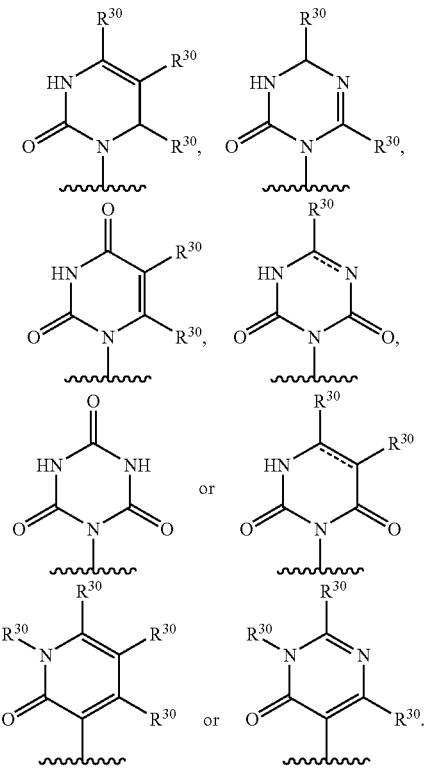

wherein an aryl, cycloalkyl, cycloalkenyl, heterocycloalkyl, heterocycloalkenyl or heteroaryl group can be optionally substituted with up to 3 substituents, which are the same or different, and are selected from alkyl, aryl, heteroaryl-, halo, haloalkyl, hydroxyalkyl, hydroxy, —CN, —C(O)R$^8$, —C(O)OR$^9$, —C(O)N(R$^9$)$_2$, —[C(R$^{12}$)$_2$]$_q$—OR$^9$, —[C(R$^{12}$)$_2$]$_q$—N(R$^9$)$_2$, —NHC(O)R$^8$, —NHSO$_2$R$^{11}$, —S(O)$_p$R$^{11}$ or —SO$_2$N(R$^9$)$_2$;

R$^6$ and R$^7$ are each, independently, H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—NR$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_1$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$;

each occurrence of R$^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, [C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

each occurrence of R$^9$ is independently H, alkyl, alkenyl, alkynyl, aryl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

R$^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$-alkyl, —[C(R$^{12}$)$_2$]$_q$—NHSO$_2$-cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, hydroxy, —OR$^9$, —CN, —[C(R$^{12}$)$_2$]$_q$-cycloalkyl, —[C(R$^{12}$)$_2$]$_1$-cycloalkenyl, —[C(R$^{12}$)$_2$]$_q$-heterocycloalkyl, —[C(R$^{12}$)$_2$]$_q$heterocycloalkenyl, —[C(R$^{12}$)$_2$]$_q$-haloalkyl, —[C(R$^{12}$)$_2$]$_q$hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_1$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

The Compounds of Formula (I) or pharmaceutically acceptable salts, solvates, prodrugs or esters thereof can be useful for treating or preventing a viral infection in a patient.

The Compounds of Formula (I) or pharmaceutically acceptable salts, solvates, prodrugs or esters thereof can be useful for treating or preventing a virus-related disorder in a patient.

Also provided by the invention are methods for treating or preventing a viral infection or a virus-related disorder in a patient, comprising administering to the patient an effective amount of at least one Compound of Formula (I).

The present invention further provides pharmaceutical compositions comprising an effective amount of at least one Compound of Formula (I) or a pharmaceutically acceptable salt, solvate thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

The present invention provides Compounds of Formula (I), pharmaceutical compositions comprising at least one Compound of Formula (I), and methods of using the Compounds of Formula (I) for treating or preventing a viral infection or a virus-related disorder in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, hydroxy, —O-alkyl, -alkylene-O-alkyl, —O-haloalkyl, -alkylthio, —$NH_2$, —NH(alkyl), —N(alkyl)$_2$, —NH-aryl, —NH-heteroaryl, —NHC(O)-alkyl, —NHC(O)NH-alkyl, —$NHSO_2$-alkyl, —$NHSO_2$-aryl, —$NHSO_2$-heteroaryl, —NH(cycloalkyl), —OC(O)-alkyl, —OC(O)-aryl, —OC(O)-cycloalkyl, —C(O)alkyl, —C(O)$NH_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

The term "alkylene" as used herein, refers to an alkyl group, as defined above, wherein one of the alkyl group's hydrogen atoms is replaced with a bond. Illustrative examples of alkylene include, but are not limited to, —$CH_2$—, —$CH_2CH_2$—, —$CH_2CH_2CH_2$—, —$CH_2CH_2CH_2CH_2$—, —$CH(CH_3)CH_2CH_2$—, —$CH_2CH(CH_3)CH_2$— and —$CH_2CH_2CH(CH_3)$—. In one embodiment, an alkylene group is a straight chain alkylene group. In another embodiment, an alkylene group is a branched alkylene group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "6-membered cycloalkenyl" as used herein, refers to a cycloalkenyl group, as defined above, which has 6 ring carbon atoms.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of illustrative haloalkyl groups include —$CH_2F$, —$CHF_2$, —$CF_3$, —$CH_2Cl$ and —$CCl_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)$CH_2CH_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

The term "6-membered heteroaryl" as used herein, refers to a heteroaryl group, as defined above, which has 6 ring atoms.

The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

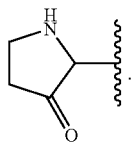

In one embodiment, a heterocycloalkyl group is a 6-membered heterocycloalkyl group. In another embodiment, a heterocycloalkyl group is a 5-membered heterocycloalkyl group.

The term "6-membered heterocycloalkyl" as used herein, refers to a heterocycloalkyl group, as defined above, which has 6 ring atoms.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

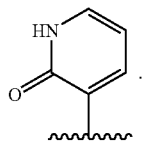

In one embodiment, a heterocycloalkenyl group is a 6-membered heterocycloalkenyl group. In another embodiment, a heterocycloalkenyl group is a 5-membered heterocycloalkenyl group.

The term "6-membered heterocycloalkenyl" as used herein, refers to a heterocycloalkenyl group, as defined above, which has 6 ring atoms.

The term "ring system substituent" as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, —O-alkyl, -alkylene-O-alkyl, —O-aryl, aralkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkylene-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

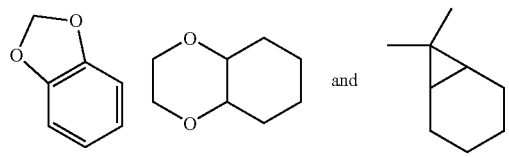

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^{11}$, etc.) occurs more than once in any constituent or in Formula (I) or (II), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g, a drug precursor) that is transformed in vivo to yield a Compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a Compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a Compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the Compounds of Formula (I) are contemplated in the present invention.

The Compounds of Formula (I) may form salts, and all such salts are contemplated within the scope of this invention. Reference to a Compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a Compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxyethyl), aryl (for example, phenyl optionally substituted with, for example, halogen, $C_{1-4}$-alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The Compounds of Formula (I) may contain asymmetric or chiral centers, and, therefore, exist in different stereoisomeric forms. It is intended that all stereoisomeric forms of the Compounds of Formula (I) as well as mixtures thereof, including racemic mixtures, form part of the present invention. In addition, the present invention embraces all geometric and positional isomers. For example, if a Compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Compounds of Formula (I) may be atropisomers (e.g., substituted biaryls) and are considered as part of this invention. Enantiomers can also be separated by use of chiral HPLC column.

The straight line — as a bond generally indicates a mixture of, or either of, the possible isomers, non-limiting example(s) include, containing (R)- and (S)-stereochemistry. For example,

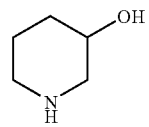

means containing both

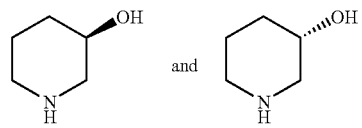 [SMILES: O[C@@H]1CCCNC1 ; O[C@H]1CCCNC1]

A dashed line ( - - - ) represents an optional bond.
Lines drawn into the ring systems, such as, for example:

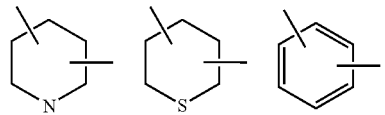

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

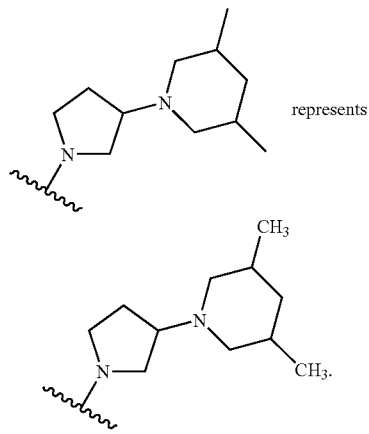

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a Compound of Formula (I) incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled Compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled Compounds of Formula (I) can generally be prepared by following procedures analogous to those disclosed in the Schemes and/or in the Examples herein below, by substituting an appropriate isotopically labelled reagent for a non-isotopically labelled reagent.

Polymorphic forms of the Compounds of Formula (I), and of the salts, solvates, hydrates, esters and prodrugs of the Compounds of Formula (I), are intended to be included in the present invention.

The following abbreviations are used below and have the following meanings: BINAP is racemic-2,2'-bis(diphenylphosphino)-1,1'-binaphthyl; CSA is camphorsulfonic acid; DBPD is 2-(Di-t-butylphosphino)biphenyl, DBU is 1,8-diazabicyclo[5.4.0]undec-7-ene, DBN is 1,5-diazabicyclo[4.3.0]non-5-ene; DCC is dicyclohexylcarbodiimide; DCM is dichloromethane; Dibal-H is diisobutylaluminum hydride; DMF is dimethylformamide; EDCI is 1-(3-dimethylaminopropyl)-3-ethylcarbodiimide; HATU is N-(diethylamino)-1H-1,2,3-triazolo[4,5-b]pyridine-1-ylmethylene]-N-methylmethanaminium Hexafluorophosphate N-oxide; HOBT is 1-hydroxybenzotriazole; LAH is lithium aluminum hydride; LDA is lithium diisopropylamide; m-CPBA is m-chloroperbenzoic acid; NaBH(OAc)$_3$ is sodium triacetoxyborohydride; NaBH$_4$ is sodium borohydride; NaBH$_3$CN is sodium cyanoborohydride; NaHMDS is sodium hexamethyl disilylazide; p-TsOH is p-toluenesulfonic acid; p-TsCl is p-toluenesulfonyl chloride; PPTS is pyridinium p-toluenesulfonate; TMAD is N,N,N',N'-tetramethylazodicarboxamide; HRMS is high resolution mass spectrometry; HPLC is high performance liquid chromatography; LRMS is low resolution mass spectrometry; Tr is triphenylmethyl; Tris is tris (hydroxymethyl)aminomethane; THF is tetrahydrofuran; TFA is trifluoroacetic acid; Ci/mmol is Curie/mmol (a measure of specific activity); and Ki represents the dissociation constant for a substrate/receptor complex.

The Compounds of Formula (I)

The present invention provides Compounds of Formula (I):

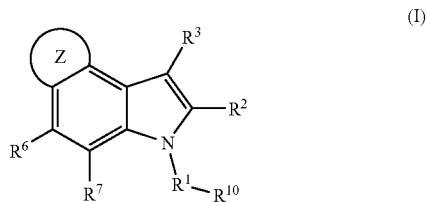

and pharmaceutically acceptable salts, solvates, prodrugs and esters thereof, wherein $R^1$, $R^2$, $R^3$, $R^6$, $R^7$, $R^{10}$ and Z are defined above for the Compounds of Formula (I).

In one embodiment, $R^1$ is a bond.
In another embodiment, $R^1$ is —CH$_2$—.
In another embodiment, $R^1$ is —[C(R$^{12}$)$_2$]$_r$—.
In another embodiment, $R^1$ is —[C(R$^{12}$)$_2$]$_r$—O—[C(R$^{12}$)$_2$]$_q$—.
In still another embodiment, $R^1$ is —[C(R$^{12}$)$_2$]$_r$—NR$^9$—[C(R$^{12}$)$_2$]$_q$—.
In yet another embodiment, $R^1$ is —[C(R$^{12}$)$_2$]$_r$—C≡C—[C(R$^{12}$)$_2$]$_q$—.
In a further embodiment, $R^1$ is —[C(R$^{12}$)$_2$]$_q$—C≡C—[C(R$^{12}$)$_2$]$_q$—.
In another embodiment, $R^1$ is —[C(R$^{12}$)$_2$]$_q$—SO$_2$—[C(R$^{12}$)$_2$]$_q$—.
In one embodiment, $R^{10}$ is —H.
In another embodiment, $R^{10}$ is aryl.
In still another embodiment, $R^{10}$ is cycloalkyl.
In yet another embodiment, $R^{10}$ is cycloalkenyl.
In a further embodiment, $R^{10}$ is heterocycloalkyl.
In another embodiment, $R^{10}$ is heterocycloalkenyl.
In another embodiment, $R^{10}$ is heteroaryl.
In another embodiment, $R^{10}$ is bicyclic heteroaryl.
In one embodiment, $R^{10}$ is aryl or heteroaryl.
In another embodiment, $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In another embodiment, $R^{10}$ is quinoline, quinolinone, pteridine or pteridinone each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In still another embodiment, $R^{10}$ is pteridine or pteridinone, either of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In one embodiment, R$^{10}$ is quinoline or quinolinone, either of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In another embodiment, R$^{10}$ is phenyl, pyridyl or pyrimidinyl, each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In another embodiment, R$^{10}$ is phenyl, which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In another embodiment, R$^{10}$ is pyridyl.

In still another embodiments, R$^{10}$ is:

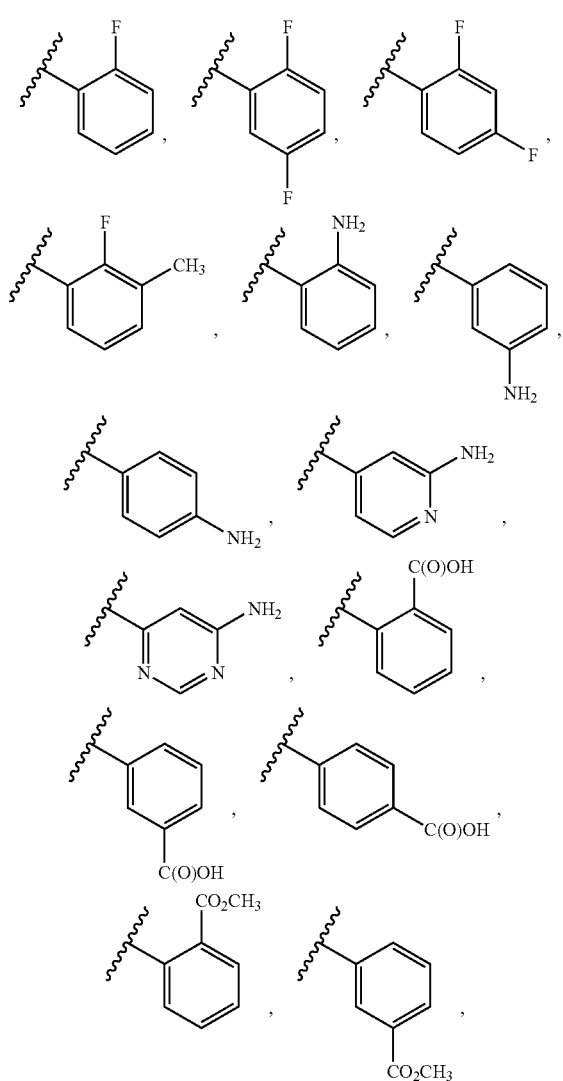

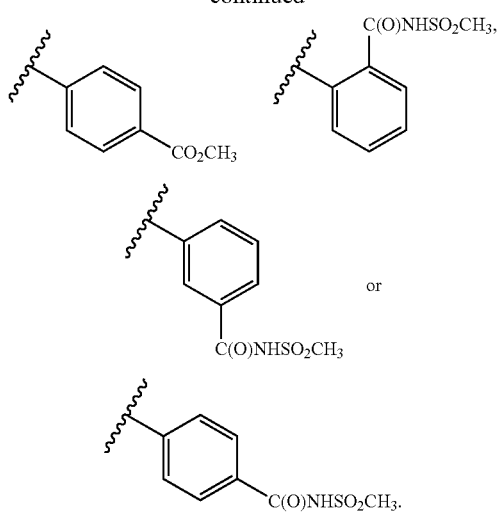

In another embodiment, R$^{10}$ is:

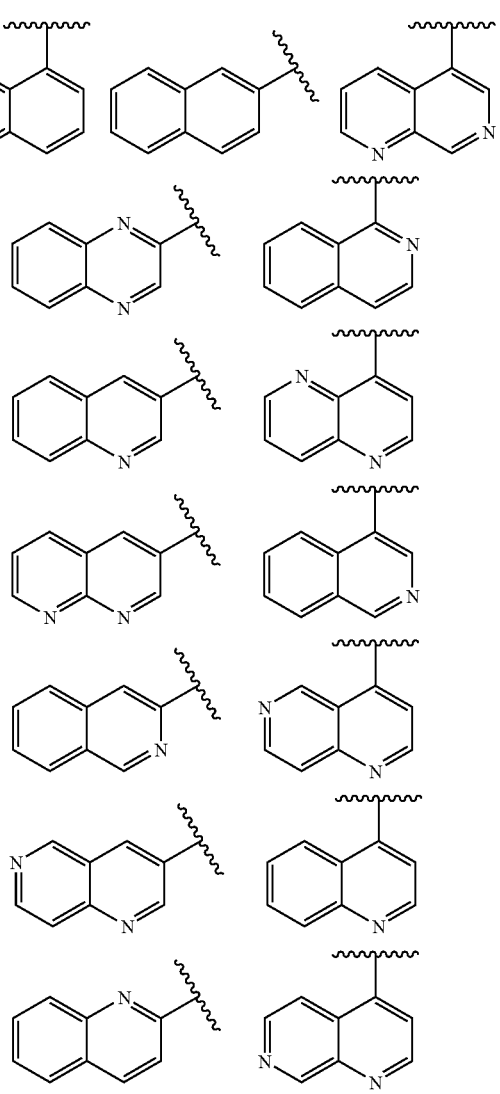

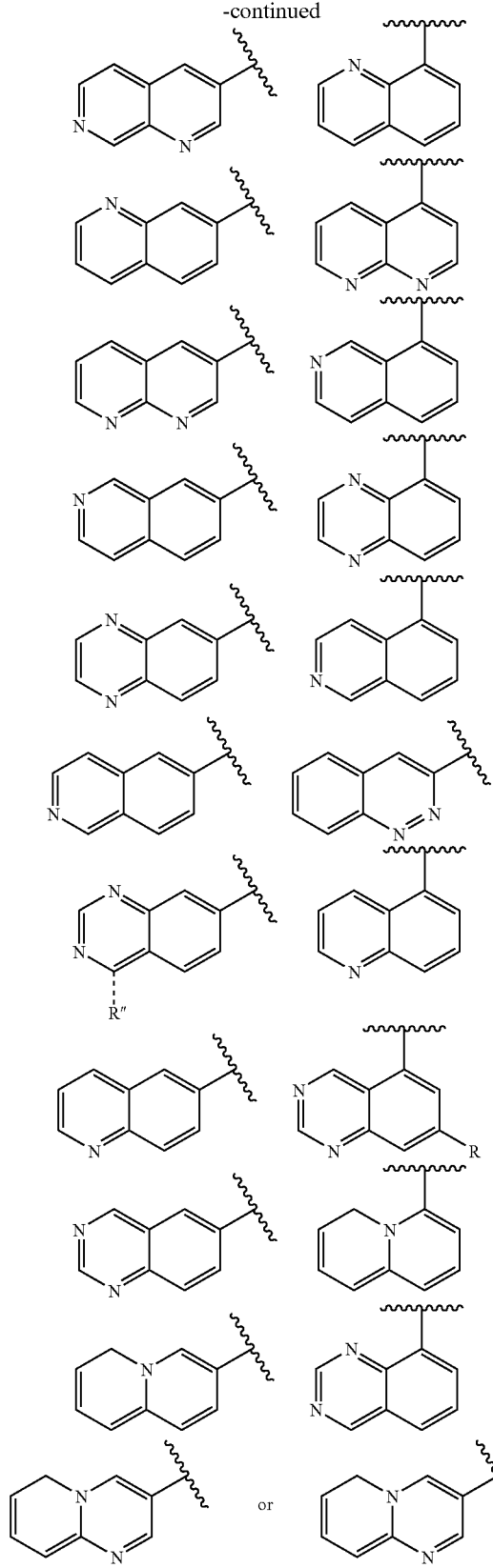
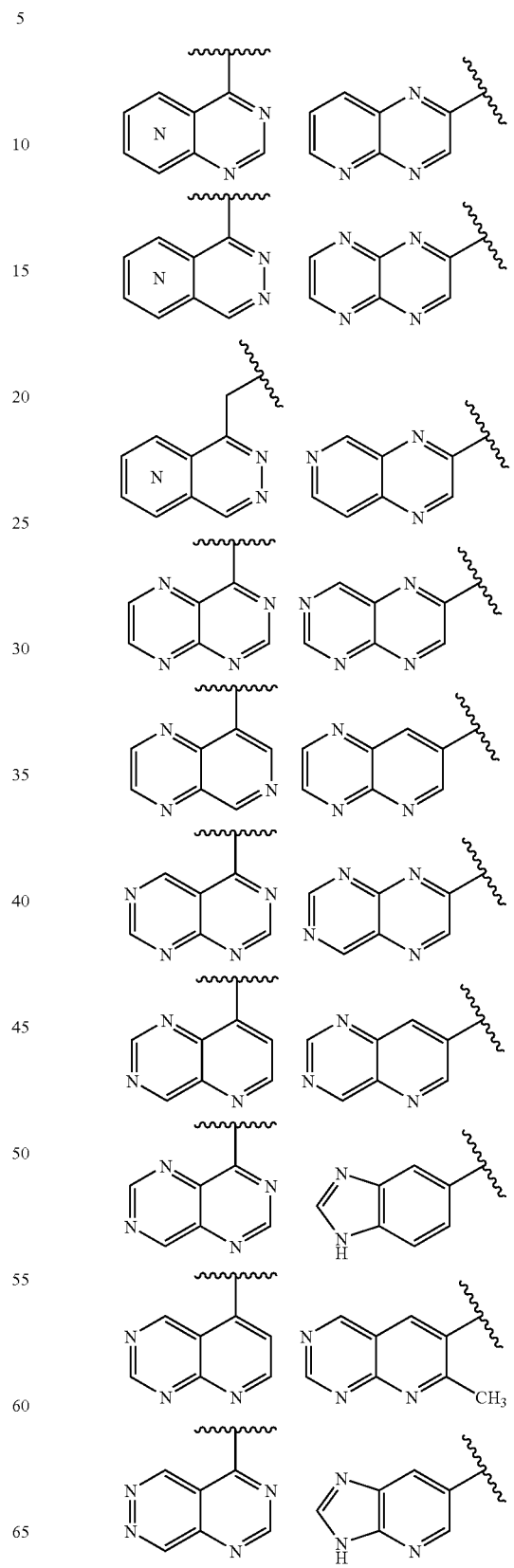
—O-haloalkyl, —OH, —CN, —NH$_2$, —NH-alkyl, —N(alkyl)$_2$ or —NHSO$_2$-alkyl.
In another embodiment, R$^{10}$ is:
each of which can be optionally substituted with up to 3 substituents, which are the same or different, and are selected from alkyl, cycloalkyl, heterocycloalkyl, halo, haloalkyl,

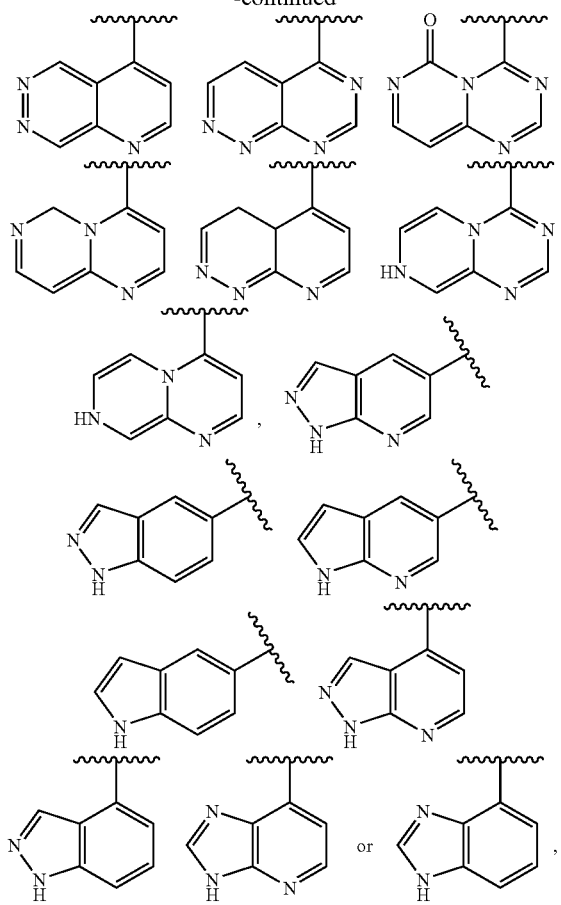

each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; wherein the letter "N" inside a ring indicates that the ring has 1 or 2 ring nitrogen atoms.

In one embodiment, R$^1$ is —[C(R$^{12}$)$_2$]$_r$—, each occurrence of R$^{12}$ is H, and R$^{10}$ is —H.

In another embodiment, R$^1$ is —[C(R$^{12}$)$_2$]$_r$—, each occurrence of R$^{12}$ is H, and R$^{10}$ is alkyl.

In another embodiment, R$^1$ is —[C(R$^{12}$)$_2$]$_r$—, each occurrence of R$^{12}$ is H, and R$^{10}$ is aryl.

In still another embodiment, R$^1$ is —[C(R$^{12}$)$_2$]$_r$—, each occurrence of R$^{12}$ is H, and R$^{10}$ is cycloalkyl.

In yet another embodiment, R$^1$ is —[C(R$^{12}$)$_2$]$_r$—, each occurrence of R$^{12}$ is H, and R$^{10}$ is cycloalkenyl.

In a further embodiment, R$^1$ is —[C(R$^{12}$)$_2$]$_r$—, each occurrence of R$^{12}$ is H, and R$^{10}$ is heterocycloalkyl.

In another embodiment, R$^1$ is —[C(R$^{12}$)$_2$]$_r$—, each occurrence of R$^{12}$ is H, and R$^{10}$ is heterocycloalkenyl.

In another embodiment, R$^1$ is —[C(R$^{12}$)$_2$]$_r$—, each occurrence of R$^{12}$ is H, and R$^{10}$ is heteroaryl.

In another embodiment, —R$^1$—R$^{10}$ is methyl.

In another embodiment, —R$^1$—R$^{10}$ is benzyl.

In still another embodiment, R$^1$ is alkylene, having from 1 to 6 carbon atoms, and R$^{10}$ is:

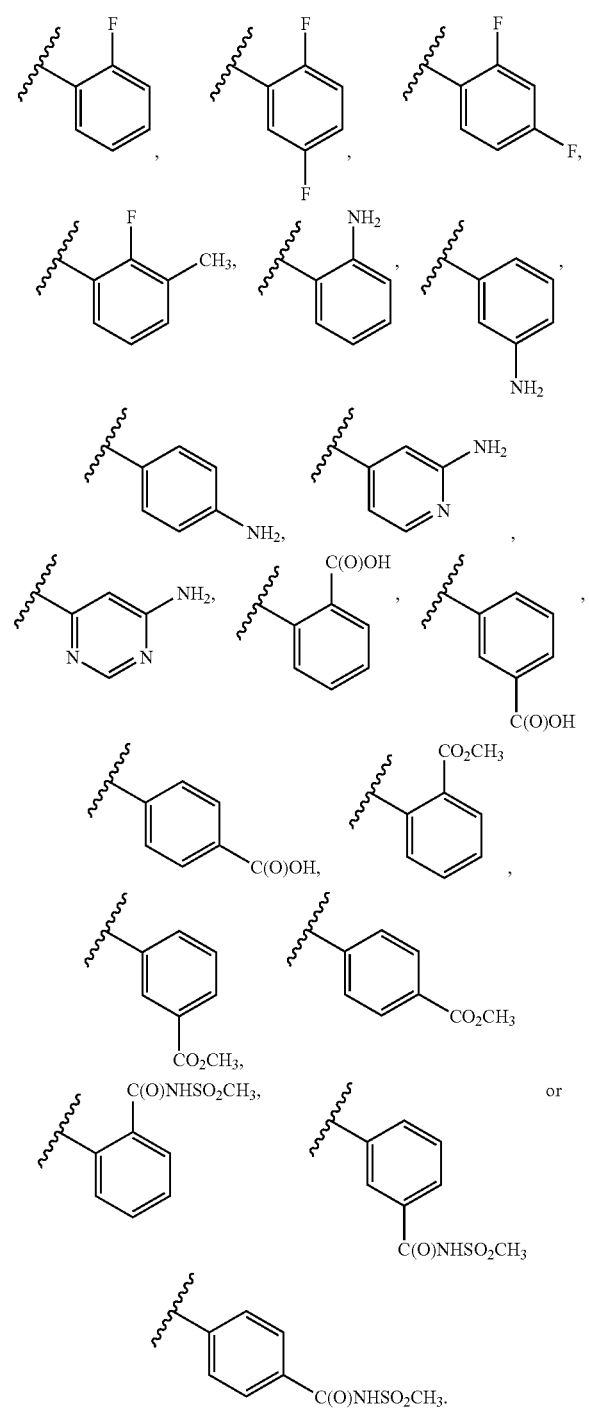

In yet another embodiment, R$^1$ is —CH$_2$— and R$^{10}$ is:

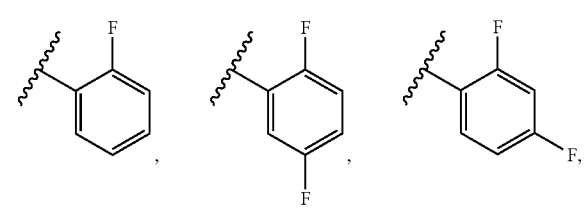

-continued
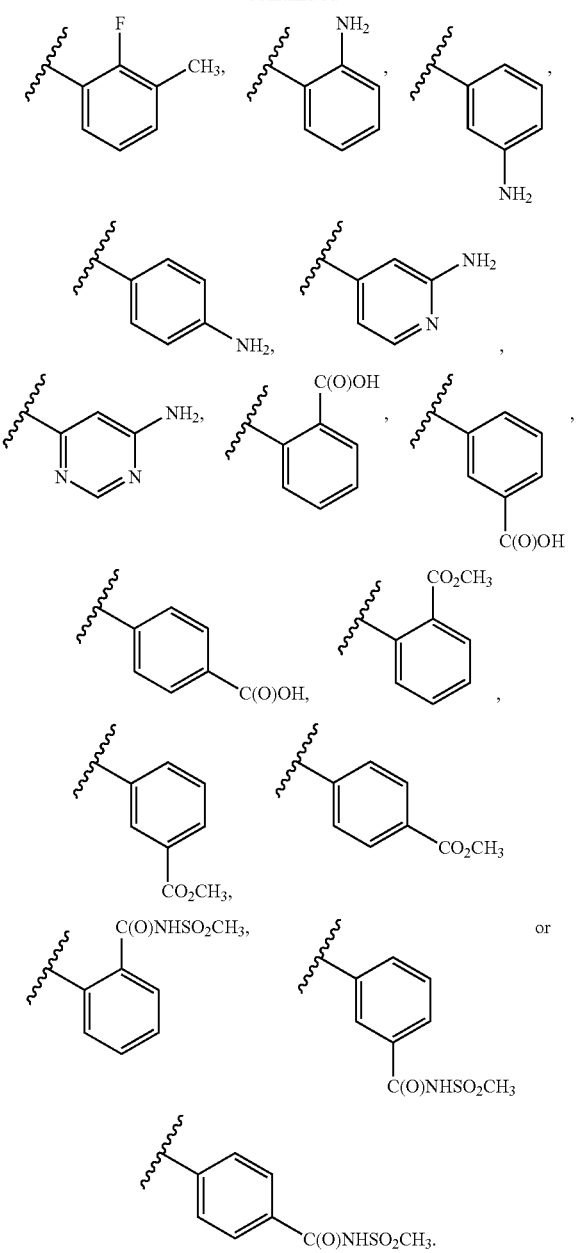
In another embodiment, $R^1$ is —$CH_2$— and $R^{10}$ is:
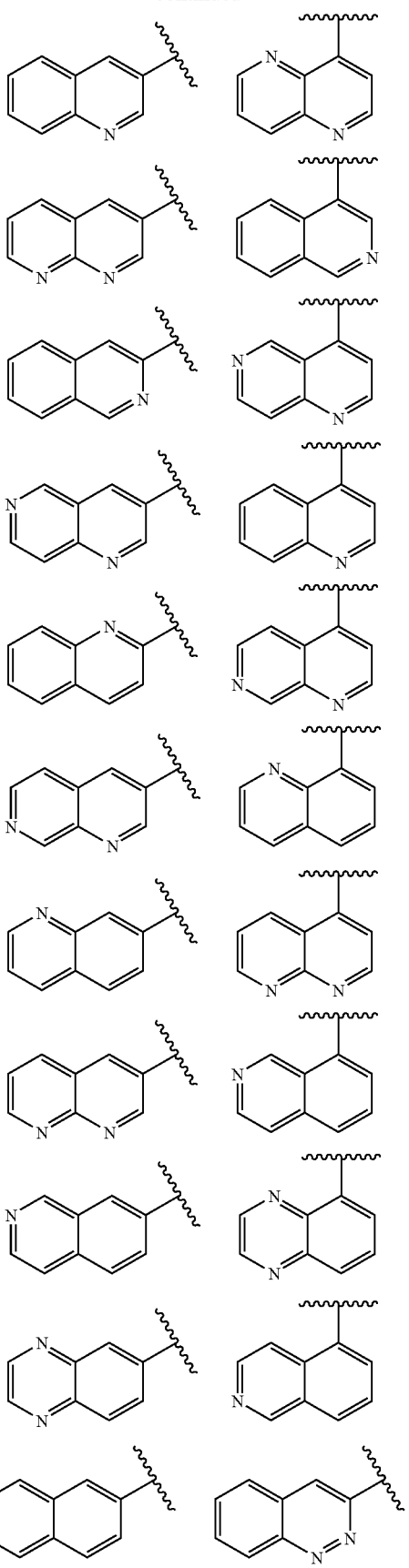

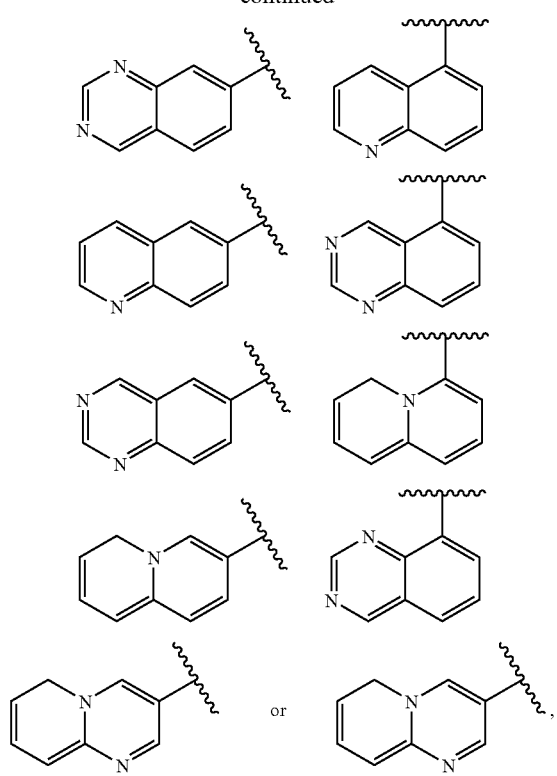
each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.
In still another embodiment, R$^1$ is —CH$_2$— and R$^{10}$ is:
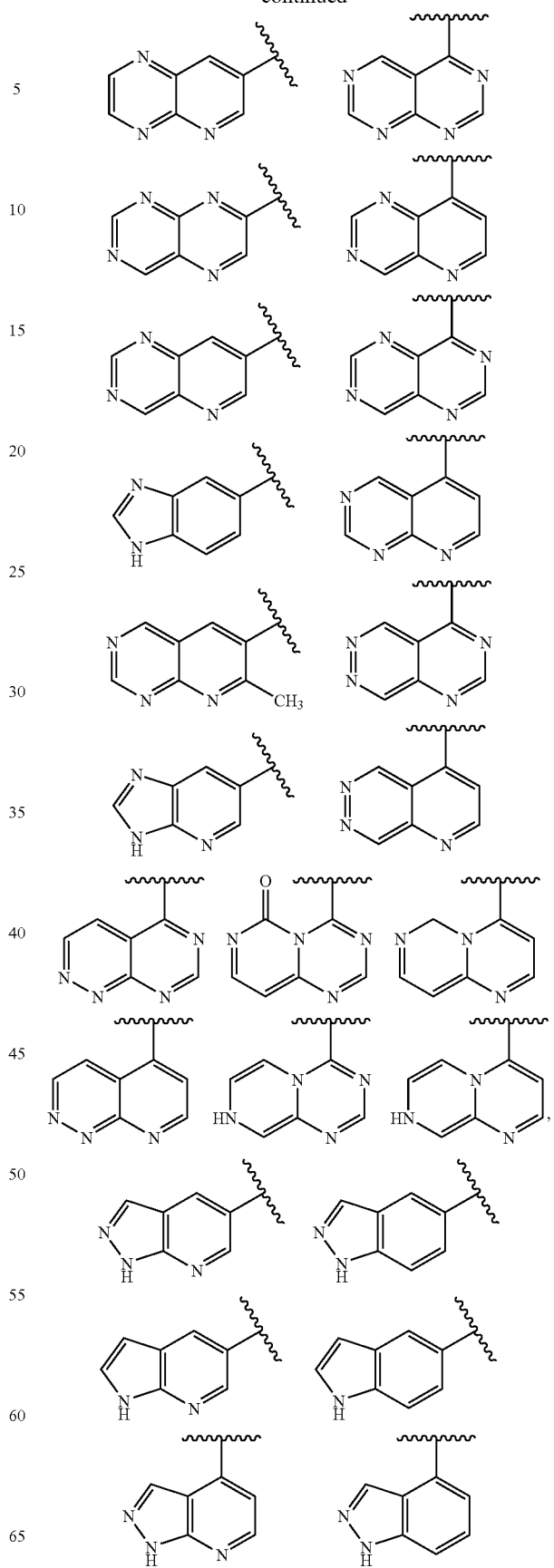

-continued

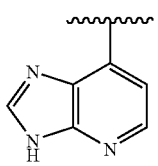 or 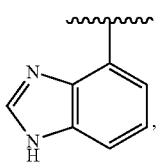, each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; wherein the letter "N" inside a ring indicates that the ring has 1 or 2 ring nitrogen atoms.

In one embodiment, $R^2$ is —C(O)OR$^9$.
In another embodiment, $R^2$ is —C(O)N(R$^9$)$_2$.
In one embodiment, $R^2$ is —C(O)NH$_2$.
In another embodiment, $R^2$ is —C(O)N(R$^9$)SO$_2$R$^{11}$.
In still another embodiment, $R^2$ is —C(O)NHSO$_2$R$^{11}$.
In another embodiment, $R^2$ is —C(O)NHSO$_2$R$^{11}$ and R$^{11}$ is alkyl or cycloalkyl.
In yet another embodiment, $R^2$ is alkyl.
In a further embodiment, $R^2$ is —[C(R$^{12}$)$_2$]$_q$-aryl.
In another embodiment, $R^2$ is —[C(R$^{12}$)$_2$]$_q$-cycloalkyl.
In another embodiment, $R^2$ is —[C(R$^{12}$)$_2$]$_q$-cycloalkenyl.
In another embodiment, $R^2$ is —[C(R$^{12}$)$_2$]$_q$-heterocloalkyl.
In still another embodiment, —[C(R$^{12}$)$_2$]$_q$-heteroaryl-.
In yet another embodiment, $R^2$ is —[C(R$^{12}$)$_2$]$_q$-heterocloalkenyl.
In a further embodiment, $R^2$ is -arylthiazin-yl.
In another embodiment, $R^2$ is arylthiadiazol-yl-.
In one embodiment, $R^2$ is —C(O)OH.
In another embodiment, $R^2$ is —C(O)OCH$_3$
In another embodiment, $R^2$ is —C(O)OCH$_2$CH$_3$.
In still another embodiment, $R^2$ is —C(O)NHSO$_2$CH$_3$.
In yet another embodiment, $R^2$ is —C(O)NHSO$_2$CH$_2$CH$_3$.
In another embodiment, $R^2$ is —C(O)NHSO$_2$-isopropyl.
In another embodiment, $R^2$ is —C(O)NHSO$_2$-(t-butyl).
In another embodiment, $R^2$ is —C(O)NHSO$_2$-cyclopropyl.
In a further embodiment, $R^2$ is:

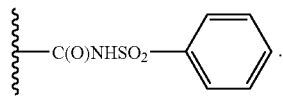.

In another embodiment, $R^2$ is:

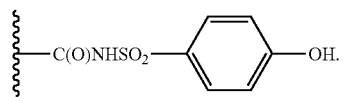.

In another embodiment, $R^2$ is:

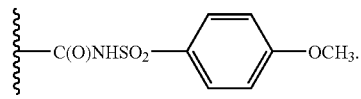

In yet another embodiment, $R^2$ is:

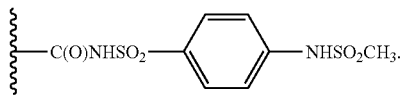.

In one embodiment, $R^2$ is:

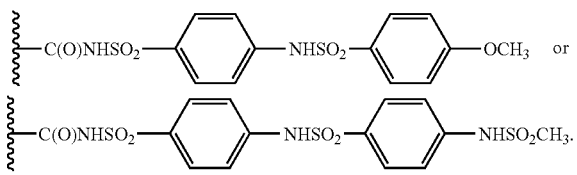

In another embodiment, $R^2$ is —C(O)OH, —CO$_2$CH$_3$, —C(O)NHSO$_2$CH$_3$, —C(O)NHSO$_2$CH$_2$CH$_3$, —C(O)NHSO$_2$-(t-butyl),

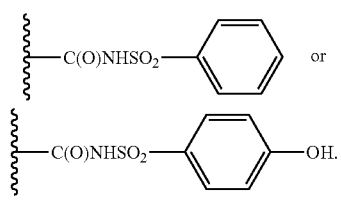

In one embodiment, $R^2$ is:

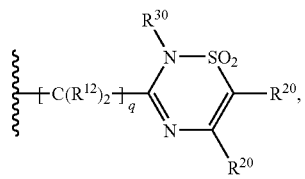

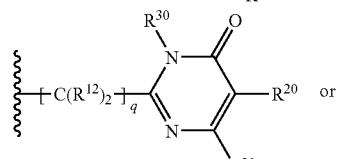 or

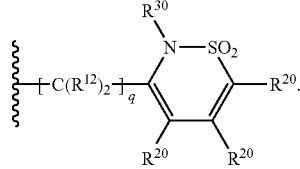

In another embodiment, $R^2$ is:

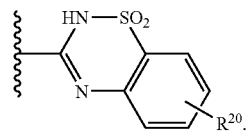

In still another embodiment, $R^2$ is —C(O)OH, —C(O)Oalkyl, —C(O)NH$_2$, —C(O)NH-alkyl, —C(O)NH-cycloalkyl, —C(O)NHSO$_2$R$^{11}$, heteroaryl,

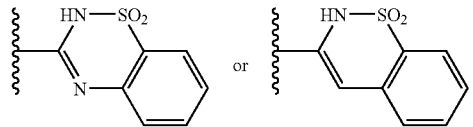 [SMILES: *C1=Nc2ccccc2S(=O)(=O)N1 ; *C1=Cc2ccccc2S(=O)(=O)N1] or wherein a heteroaryl, arylthiazin-yl- or arylthiadiazol-yl-group can be optionally substituted with up to 3 substituents, which are the same or different, and are selected from alkyl, aryl, heteroaryl, halo, haloalkyl, hydroxyalkyl, hydroxy, —CN, —C(O)R$^8$, —C(O)OR$^9$, —C(O)N(R$^9$)$_2$, —[C(R$^{12}$)$_2$]$_q$—OR$^9$, —[C(R$^{12}$)$_2$]$_q$—N(R$^9$)$_2$, —NHC(O)R$^8$, —NHSO$_2$R$^{11}$, —S(O)$_p$R$^{11}$ or —SO$_2$N(R$^9$)$_2$.

In one embodiment, $R^2$ is —C(O)OH, —C(O)NHSO$_2$-alkyl, —C(O)NHSO$_2$-aryl, —C(O)NHSO$_2$-cycloalkyl or —C(O)NHSO$_2$-alkylene-cycloalkyl.

In another embodiment, $R^2$ is —C(O)OH, —C(O)NHSO$_2$CH$_3$ or —C(O)NHSO$_2$-cyclopropyl.

In one embodiment, $R^3$ is —H.

In another embodiment, $R^3$ is —[C(R$^{12}$)$_2$]$_q$-alkyl.

In another embodiment, $R^3$ is —[C(R$^{12}$)$_2$]$_q$-aryl.

In still another embodiment, $R^3$ is —[C(R$^{12}$)$_2$]$_q$-cycloalkyl.

In yet another embodiment, $R^3$ is —[C(R$^{12}$)$_2$]$_q$-cycloalkenyl.

In a further embodiment, $R^3$ is —[C(R$^{12}$)$_2$]$_q$-heterocycloalkyl.

In another embodiment, $R^3$ is —[C(R$^{12}$)$_2$]$_q$-heterocycloalkenyl.

In another embodiment, $R^3$ is —[C(R$^{12}$)$_2$]$_q$-heteroaryl.

In one embodiment, $R^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R$^9$)$_2$, —N(R$^9$)$_2$, —O-haloalkyl, —NHC(O)NH$_2$, —NHC(O)NH-alkyl, —NHSO$_2$R$^{11}$, —S(O)$_2$R$^{11}$ or —SO$_2$NHR$^{11}$.

In another embodiment, $R^3$ is pyridyl or phenyl which is unsubstituted or optionally and independently substituted with 1 to 3 substituents, which are the same or different, and are selected from alkyl, aryl, heteroaryl-, halo, haloalkyl, hydroxyalkyl, hydroxy, —CN, —C(O)R$^8$, —C(O)N(R$^9$)$_2$, —[C(R$^{12}$)$_2$]$_q$—OR$^9$, —[C(R$^{12}$)$_2$]$_q$—N(R$^9$)$_2$, or —NHC(O)R$^8$.

In another embodiment, $R^3$ is:

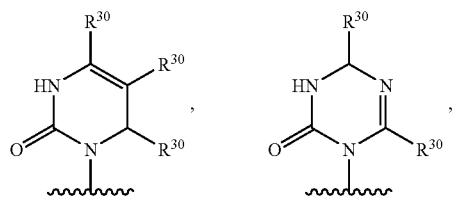

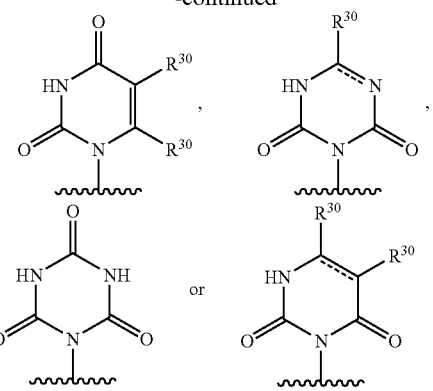

In another embodiment, $R^3$ is:

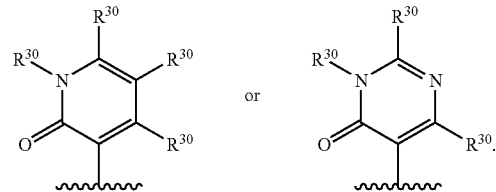

In still another embodiment, $R^3$ is:

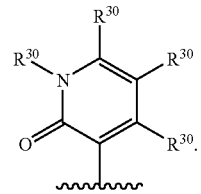

In one embodiment, $R^3$ is:

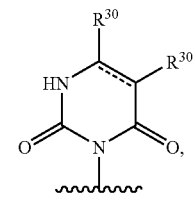

wherein both R$^{30}$ groups, together with the carbon atoms to which they are attached, join to form a –3- to 7-membered ring selected from aryl, cycloalkyl, heteroaryl and heterocycloalkyl.

In another embodiment, $R^3$ is aryl.
In another embodiment, $R^3$ is phenyl.
In still another embodiment, $R^3$ is benzyl.
In yet another embodiment, $R^3$ is:

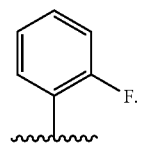

In another embodiment, $R^3$ is:

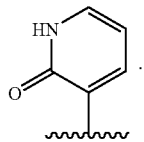

In one embodiment, $R^6$ is —H.
In another embodiment, $R^6$ is alkyl.
In another embodiment, $R^6$ is haloalkyl.
In another embodiment, $R^6$ is hydroxyalkyl.
In still another embodiment, $R^6$ is aryl.
In yet another embodiment, $R^6$ is halo.
In a further embodiment, $R^6$ is —OH.
In another embodiment, $R^6$ is —O-haloalkyl.
In one embodiment, $R^6$ is -alkoxy.
In another embodiment, $R^6$ is —CN.
In another embodiment, $R^6$ is —$[C(R^{12})_2]_q$—$OR^9$.
In another embodiment, $R^6$ is —$[C(R^{12})_2]_q$—$N(R^9)_2$.
In still another embodiment, $R^6$ is —$C(O)R^8$.
In another embodiment, $R^6$ is —$C(O)OR^9$.
In yet another embodiment, $R^6$ is —$C(O)N(R^9)_2$.
In a further embodiment, $R^6$ is —$NHC(O)R^8$.
In another embodiment, $R^6$ is —$NHSO_2R^{11}$.
In another embodiment, $R^6$ is —$S(O)_pR^{11}$
In another embodiment, $R^6$ is —$SO_2N(R^9)_2$.
In one embodiment, $R^7$ is —H.
In another embodiment, $R^7$ is alkyl.
In another embodiment, $R^7$ is haloalkyl.
In another embodiment, $R^7$ is hydroxyalkyl.
In still another embodiment, $R^7$ is aryl.
In yet another embodiment, $R^7$ is halo.
In a further embodiment, $R^7$ is —OH.
In another embodiment, $R^7$ is —O-haloalkyl.
In one embodiment, $R^7$ is -alkoxy.
In another embodiment, $R^7$ is —CN.
In another embodiment, $R^7$ is —$[C(R^{12})_2]_q$—$OR^9$.
In another embodiment, $R^7$ is —$[C(R^{12})_2]_q$—$N(R^9)_2$.
In still another embodiment, $R^7$ is —$C(O)R^8$.
In another embodiment, $R^7$ is —$C(O)OR^9$.
In yet another embodiment, $R^7$ is —$C(O)N(R^9)_2$.
In a further embodiment, $R^7$ is —$NHC(O)R^8$.
In another embodiment, $R^7$ is —$NHSO_2R^{11}$.
In another embodiment, $R^7$ is —$S(O)_pR^{11}$
In another embodiment, $R^7$ is —$SO_2N(R^9)_2$.
In one embodiment, $R^6$ and $R^7$ are each —H.
In another embodiment, one, but not both, of $R^6$ and $R^7$ is —H.
In another embodiment, each of $R^6$ and $R^7$ are other than —H.
In a further embodiment, $R^6$ and $R^7$ are each independently selected from H, alkyl, F, Cl, —$CF_3$, —OH, —O-alkyl, —$OCF_3$, —$NH_2$ or —$NHSO_2$-alkyl.
In one embodiment, ring Z is cyclohexyl.
In another embodiment, ring Z is 6-membered heterocycloalkyl, 6-membered heteroaryl, 6-membered heteroaryl or cyclohexyl.
In another embodiment, ring Z is a 6-membered heterocycloalkyl.
In still another embodiment, ring Z is a 6-membered heterocycloalkenyl.
In yet another embodiment, ring Z is a 6-membered heteroaryl.
In still another embodiment, ring Z is a cyclopentyl.

In one embodiment, ring Z is:

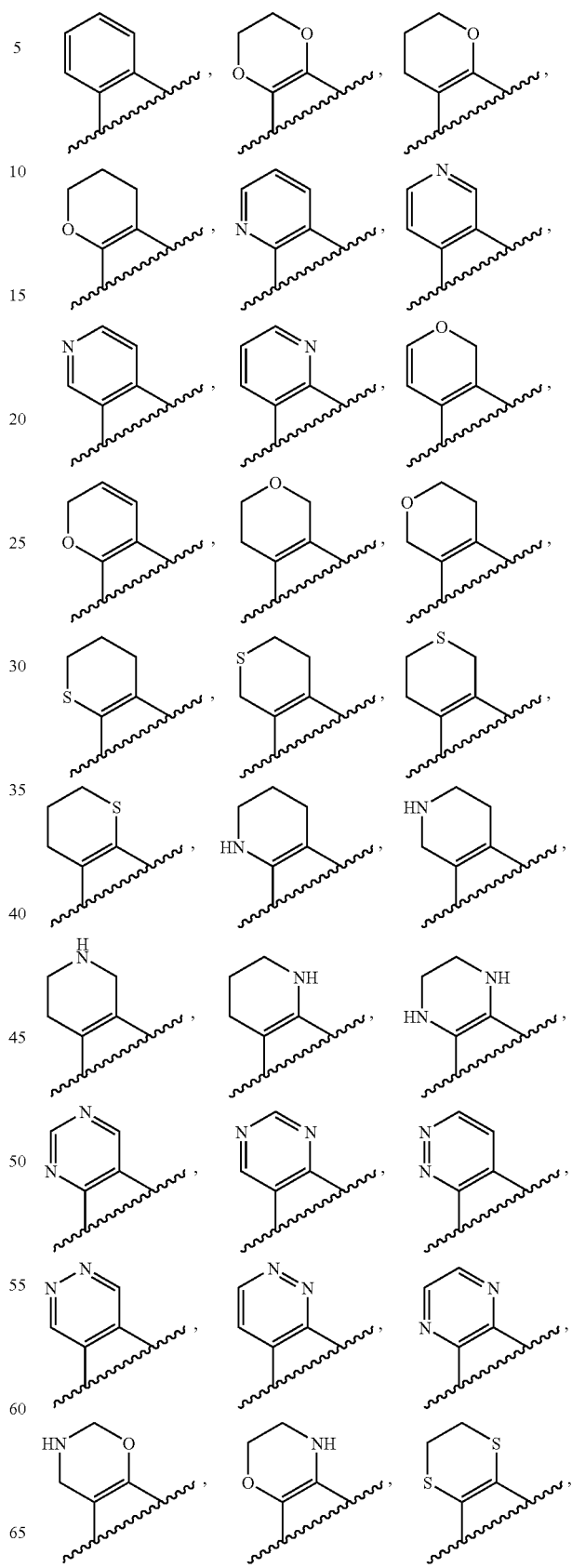

-continued

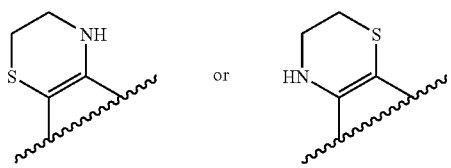 or

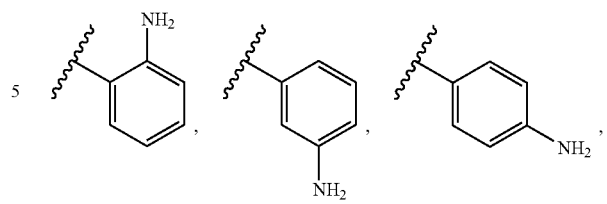

wherein the Z groups depicted above can be unsubstituted or optionally substituted with up to 3 groups, which are the same or different, and are defined as set forth above for the Compounds of Formula (I).

In another embodiment, ring Z is:

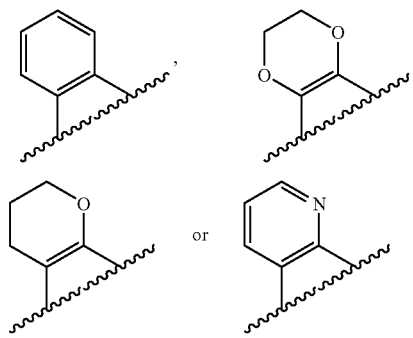

wherein the Z groups depicted above can be unsubstituted or optionally substituted with up to 3 groups, which are the same or different, and are defined as set forth above for the Compounds of Formula (I).

In one embodiment, $R^1$ is a single bond or an alkylene group having from 1 to 6 carbon atoms, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, $R^1$ is —CH$_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In one embodiment, $R^1$ is —CH$_2$—, $R^{10}$ is

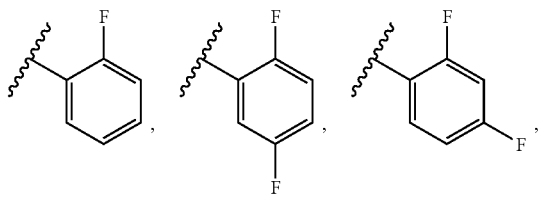

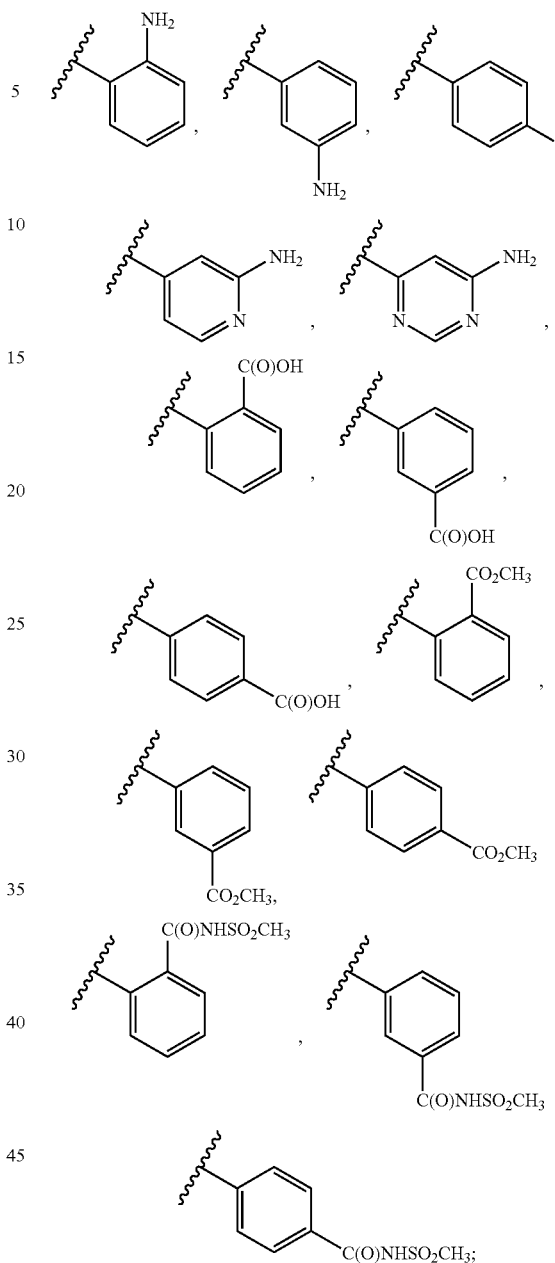

and $R^2$ is —C(O)OH or —C(O)NHSO$_2$R$^{11}$.

In another embodiment, $R^1$ is —CH$_2$—, $R^{10}$ is

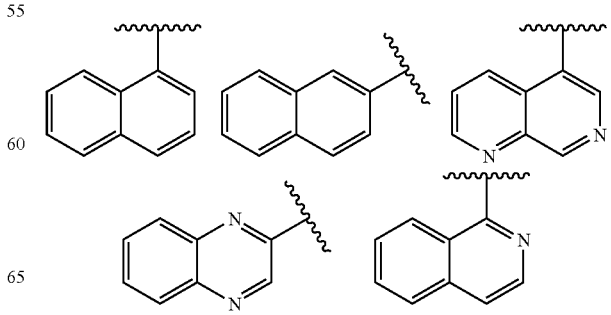

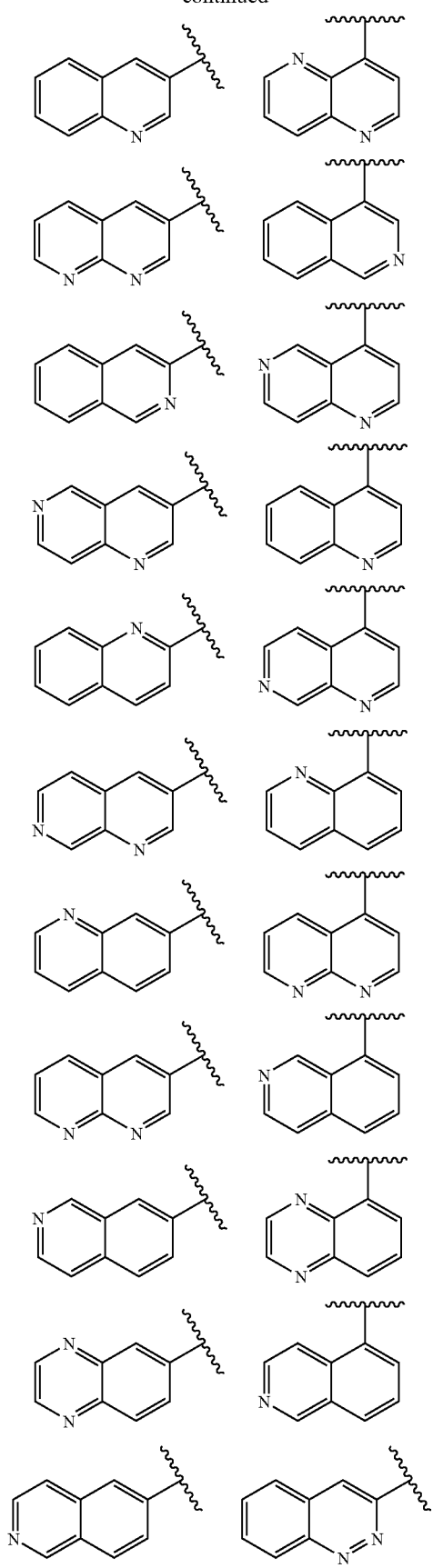
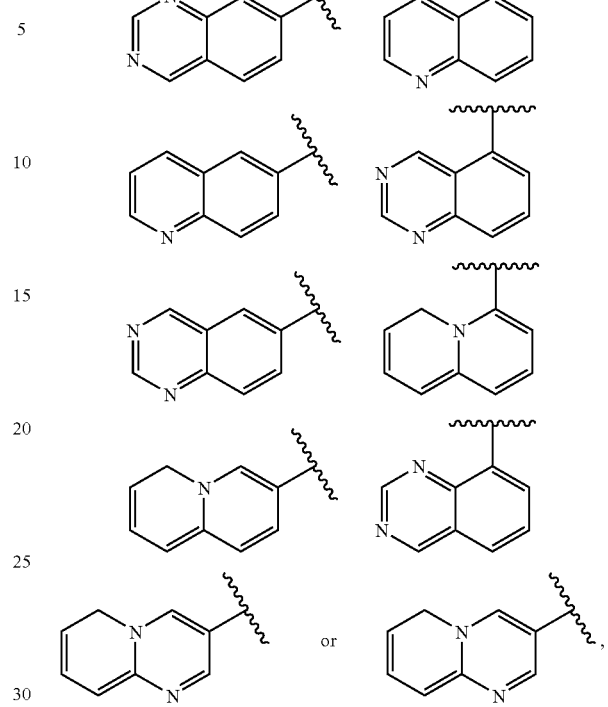
each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; and R$^2$ is —C(O)OH or —C(O)NHSO$_2$R$^{11}$.
In another embodiment, R$^1$ is —CH$_2$—, R$^{10}$ is
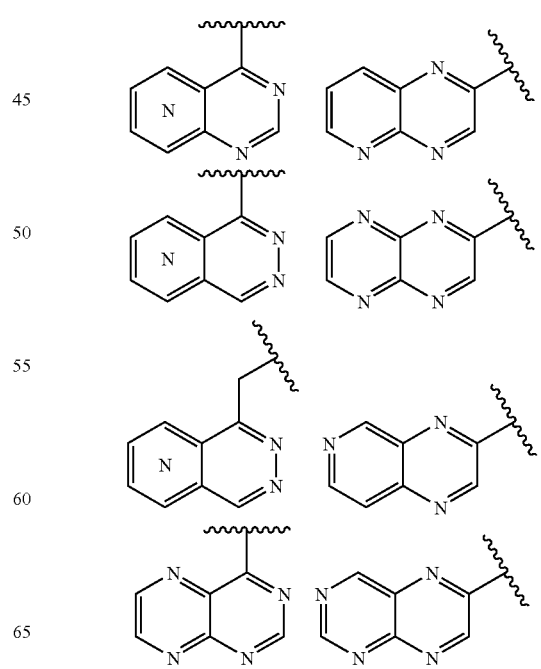

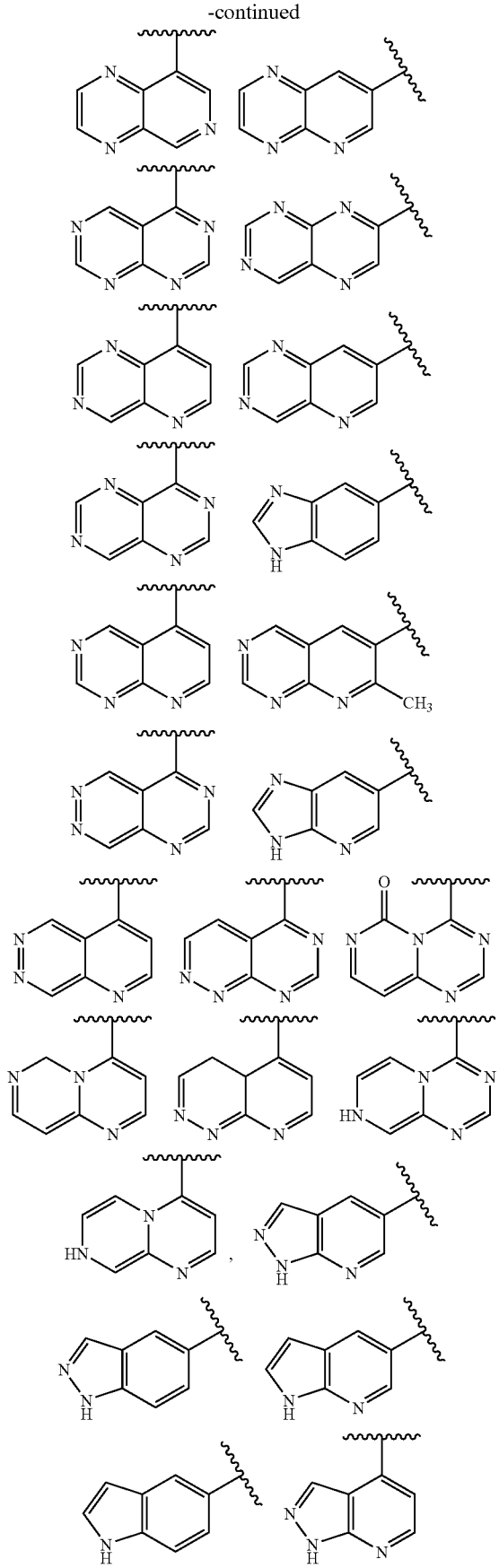

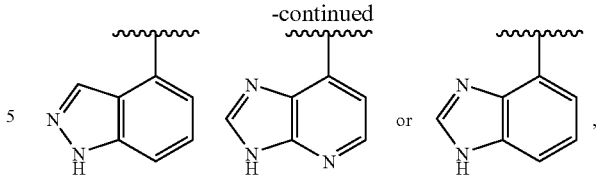

each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; and R$^2$ is —C(O)OH or —C(O)NHSO$_2$R$^{11}$.

In yet another embodiment, R$^1$ is a single bond or an alkylene group having from 1 to 6 carbon atoms; R$^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; and R$^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl.

In a further embodiment, R$^1$ is —CH$_2$—, and R$^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; and R$^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl.

In one embodiment, R$^1$ is —CH$_2$—, and R$^{10}$ is

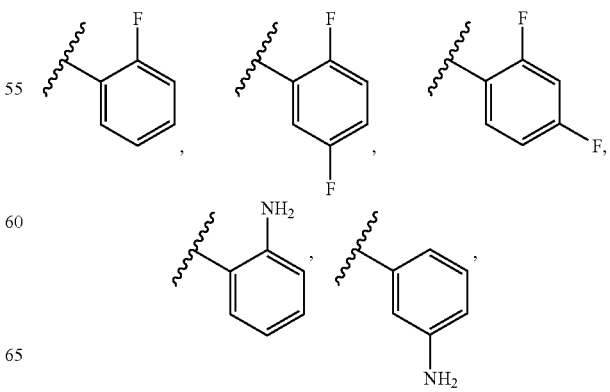

-continued

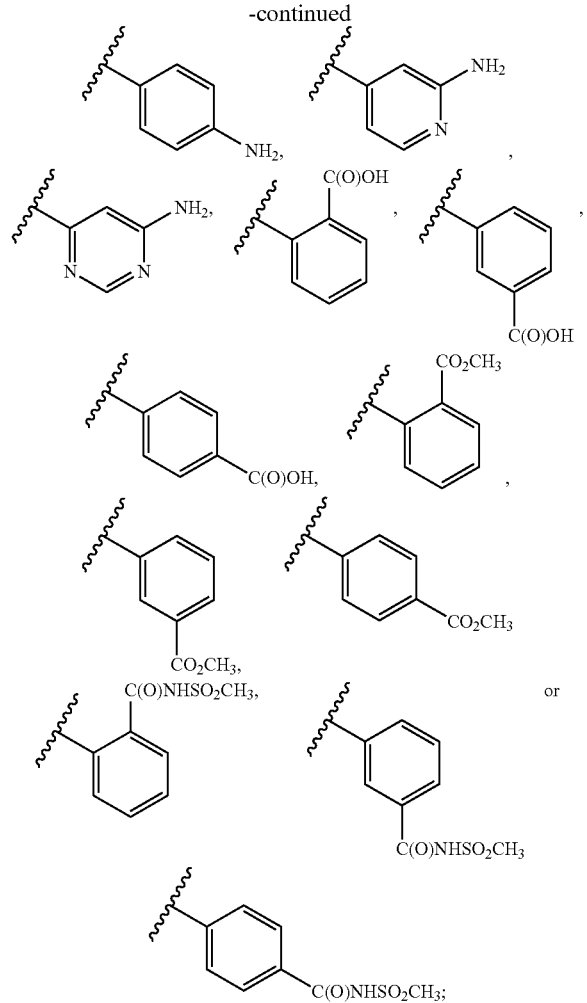

and R³ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH₂, —OH, —NH₂, —C(O)NHalkyl, —O-haloalkyl, —NHalkyl, —NHC(O)NH₂, —NHC(O)NHalkyl, —NHSO₂alkyl, —S(O)₂alkyl or —SO₂NHalkyl.

In another embodiment, R¹ is a single bond or an alkylene group having from 1 to 6 carbon atoms; R¹⁰ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)₂, —OH, —O-benzyl, -alkylene-OR⁹, —OR⁹, —N(R⁹)₂, —NHC(O)R⁸, —NHSO₂R¹¹, —S(O)ₚR¹¹ or —SO₂N(R⁹)₂; and R³ is:

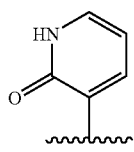 or 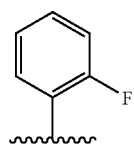

In another embodiment, R¹ is —CH₂—, and R¹⁰ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)₂, —OH, —O-benzyl, -alkylene-OR⁹, —OR⁹, —N(R⁹)₂, —NHC(O)R⁸, —NHSO₂R¹¹, —S(O)ₚR¹¹ or —SO₂N(R⁹)₂; and R³ is:

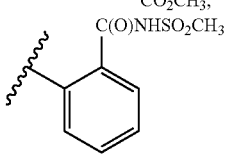 or 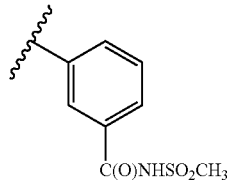

In still another embodiment, R¹ is —CH₂—, R¹⁰ is

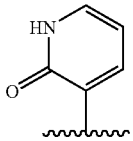 , 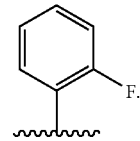 [SMILES: *c1ccccc1F] ,

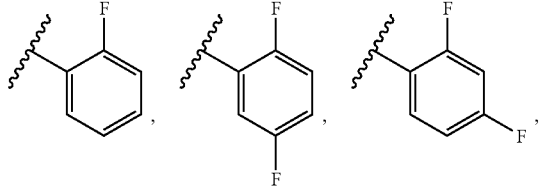

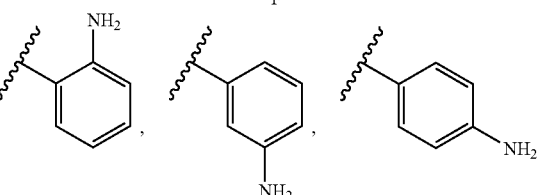

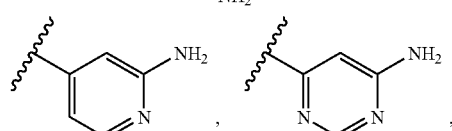

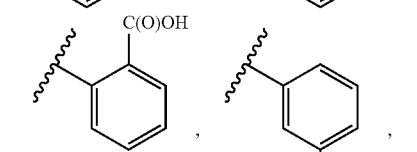

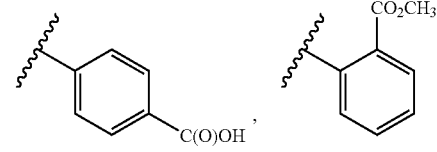

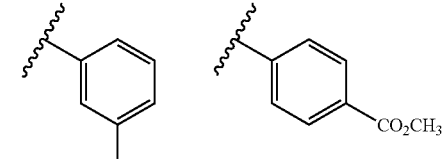

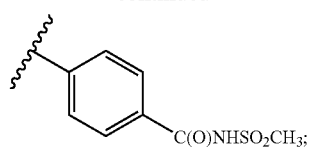
and R³ is:
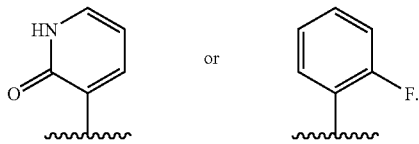 [SMILES: *c1ccc[nH]c1=O ; *c1ccccc1F]
In still another embodiment, R¹ is —CH₂—, R¹⁰ is
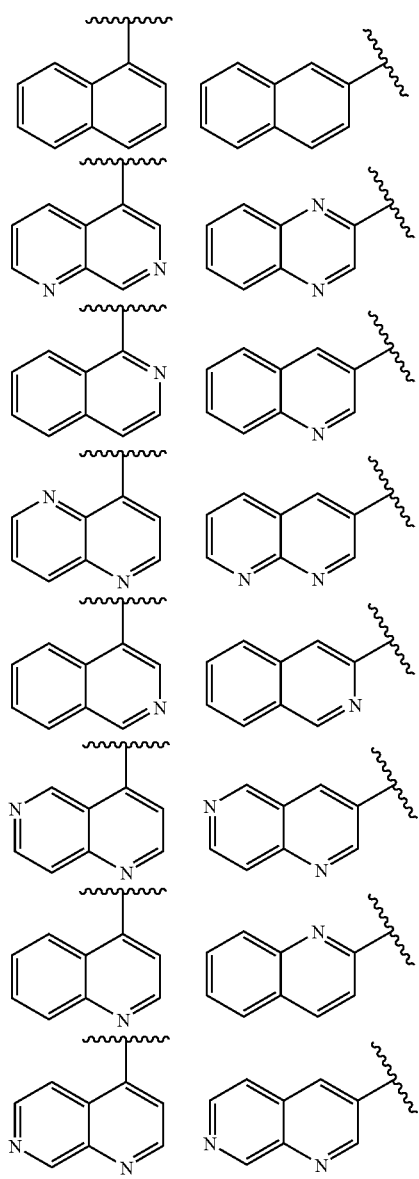
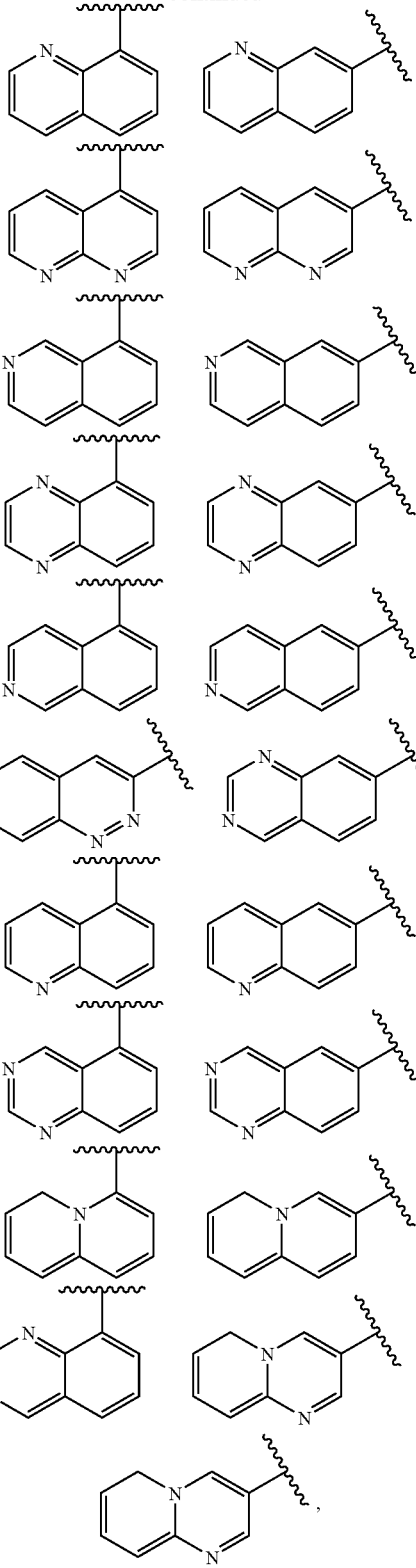
each of which can be optionally substituted with up to 3 substituents, which are the same or different, and are selected from alkyl, cycloalkyl, heterocycloalkyl, halo, haloalkyl, —O-haloalkyl, —OH, —CN, —NH₂, —NH-alkyl, —N(alkyl)₂ or —NHSO₂-alkyl; and R³ is:

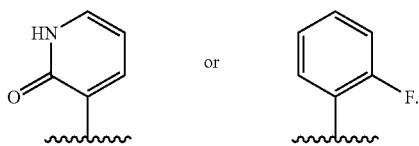 [SMILES: *c1ccc[nH]c1=O ; *c1ccccc1F]

In still another embodiment, R¹ is —CH₂—, R¹⁰ is

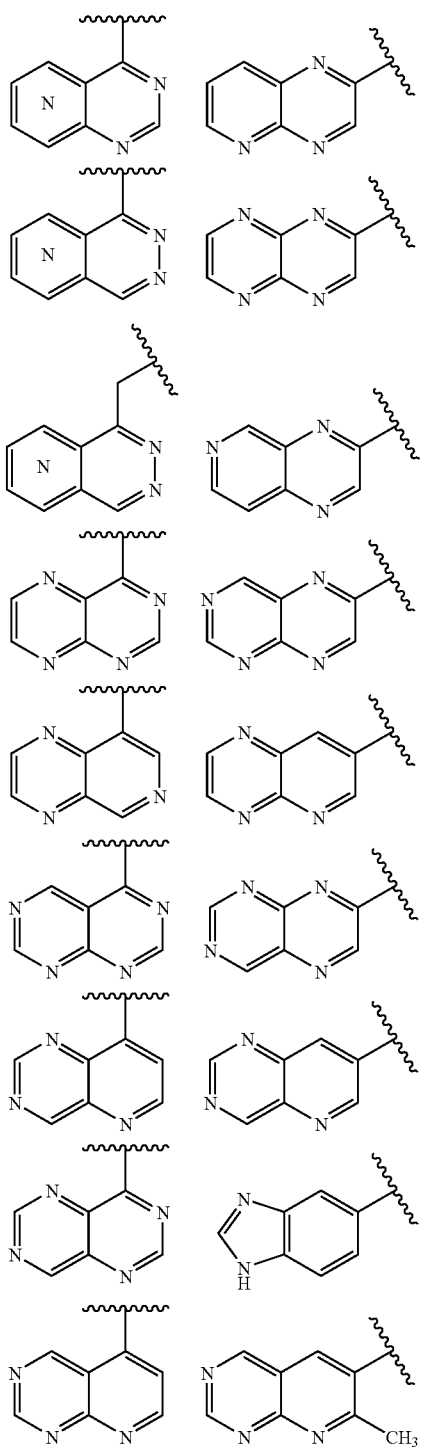

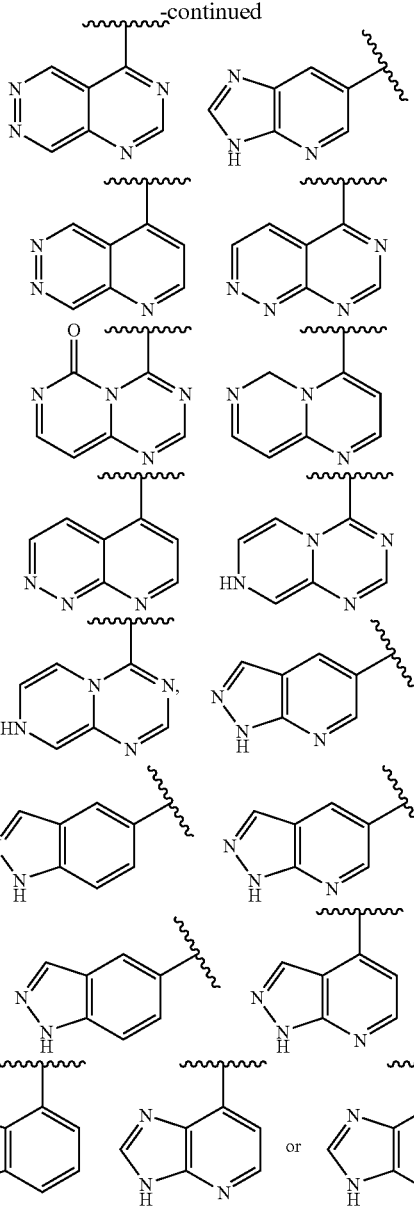

each of which
can be optionally substituted with up to 3 substituents, which are the same or different, and are selected from alkyl, cycloalkyl, heterocycloalkyl, halo, haloalkyl, —O-haloalkyl, —OH, —CN, —NH₂, —NH-alkyl, —N(alkyl)₂ or —NHSO₂-alkyl; and R³ is:

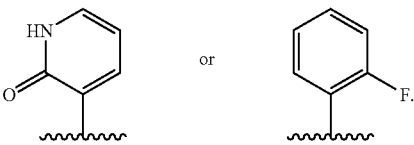

In yet another embodiment, R¹ is a single bond or an alkylene group having from 1 to 6 carbon atoms, R¹⁰ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; and ring Z is:

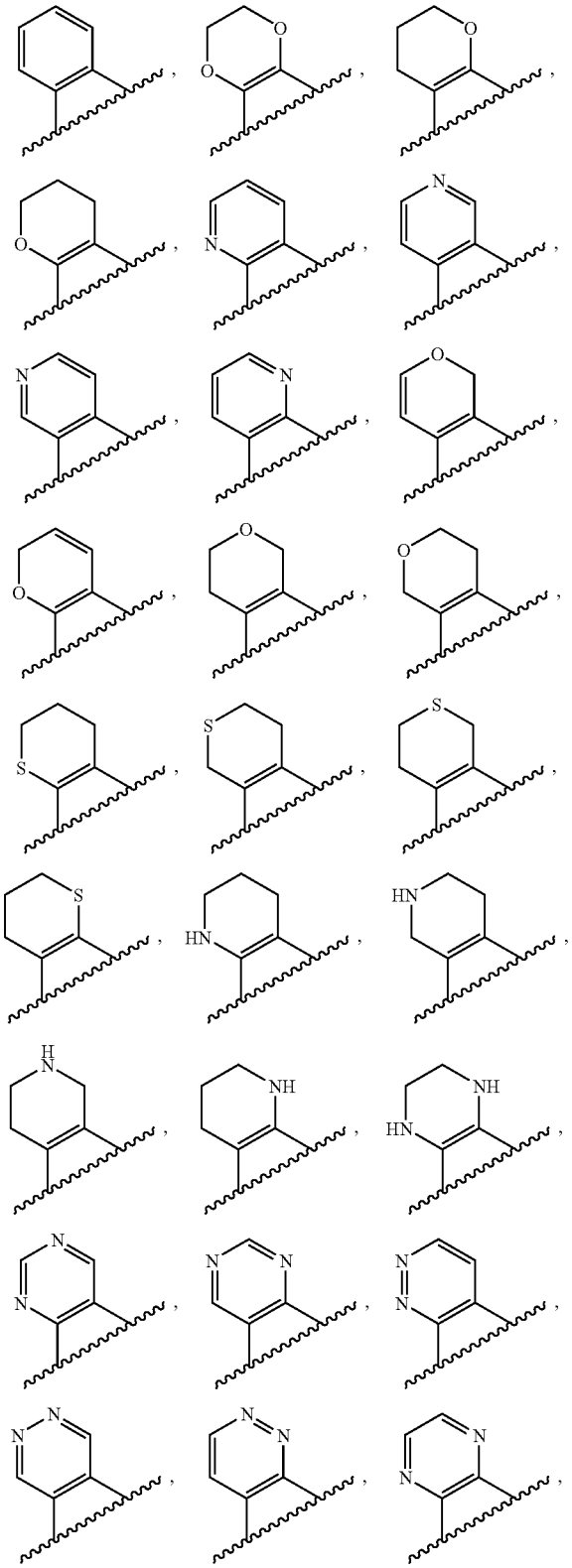

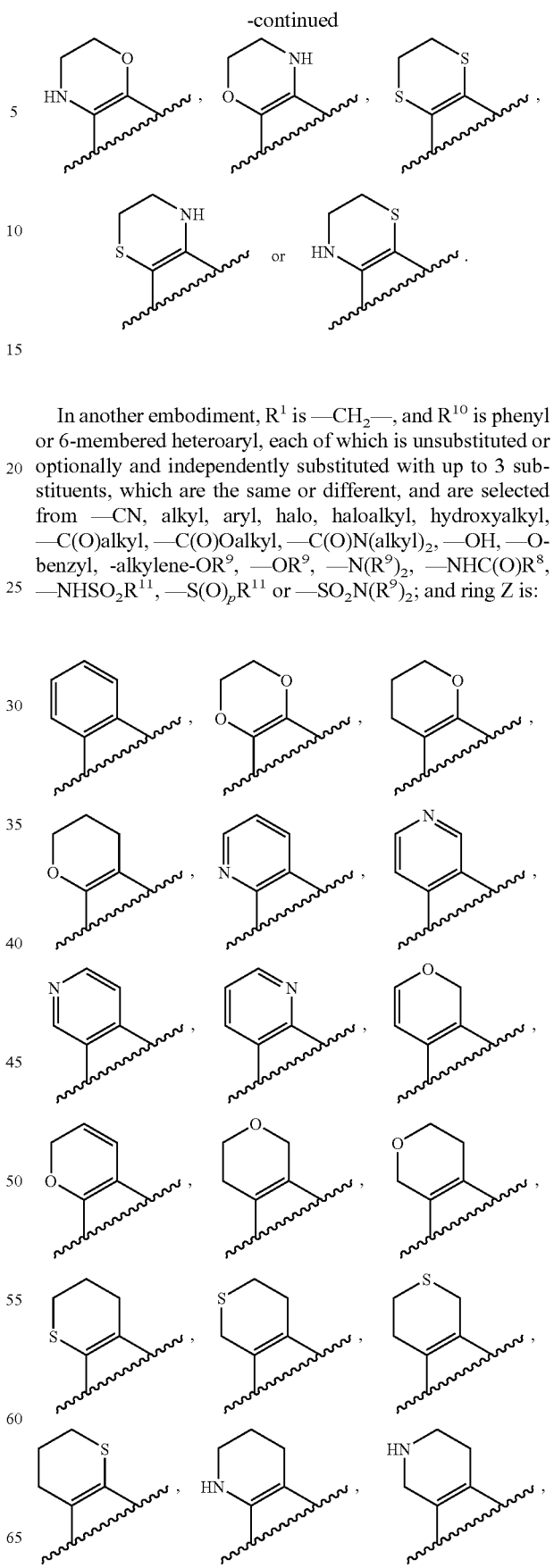

In another embodiment, R$^1$ is —CH$_2$—, and R$^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; and ring Z is:

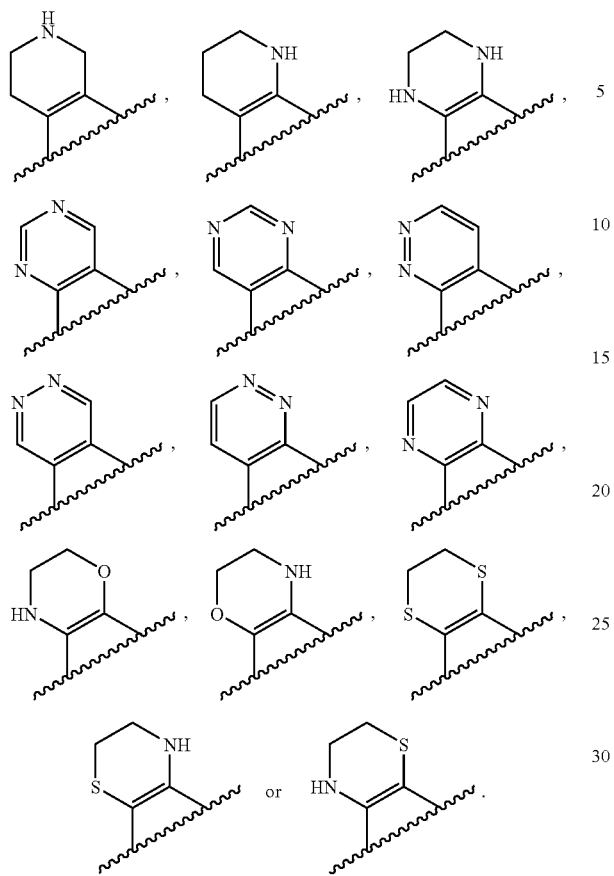
In a further embodiment, R¹ is —CH₂—, and R¹⁰ is
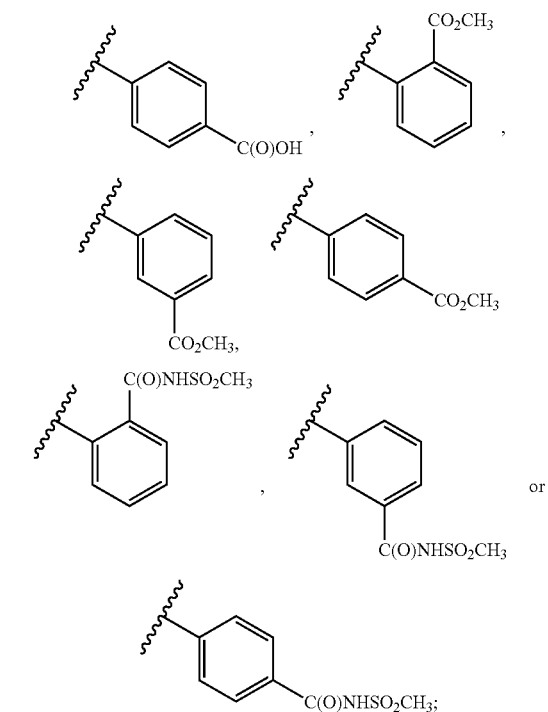
and ring Z is:
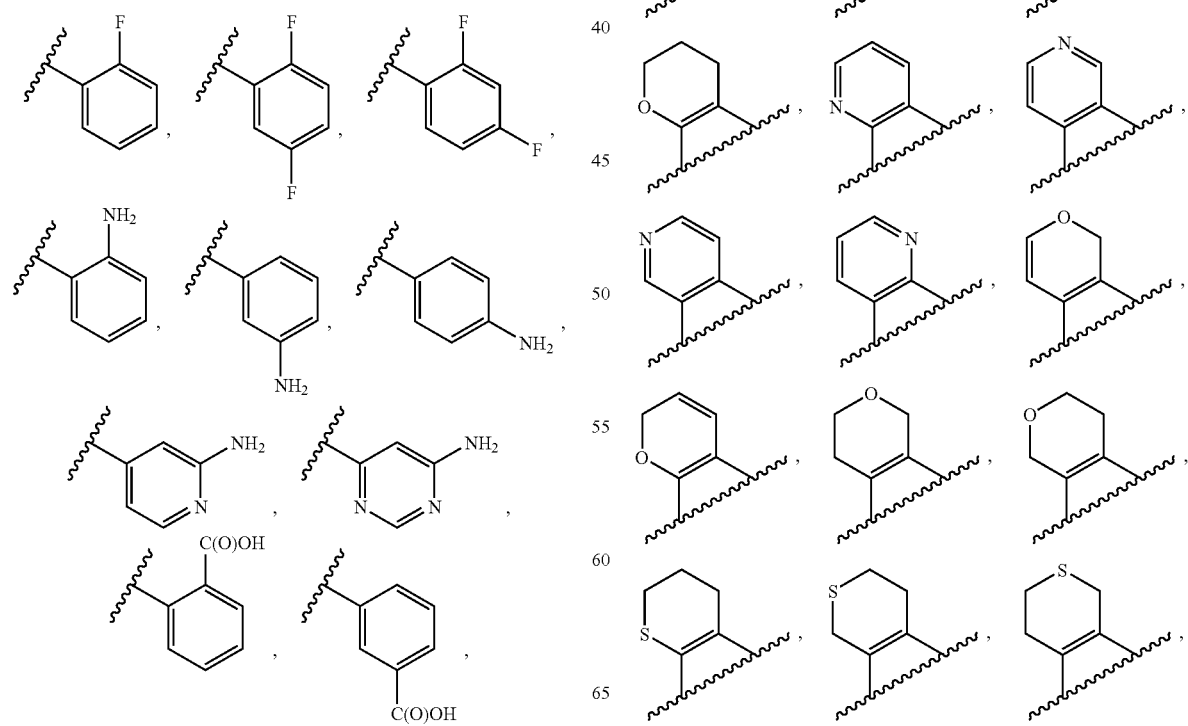

-continued
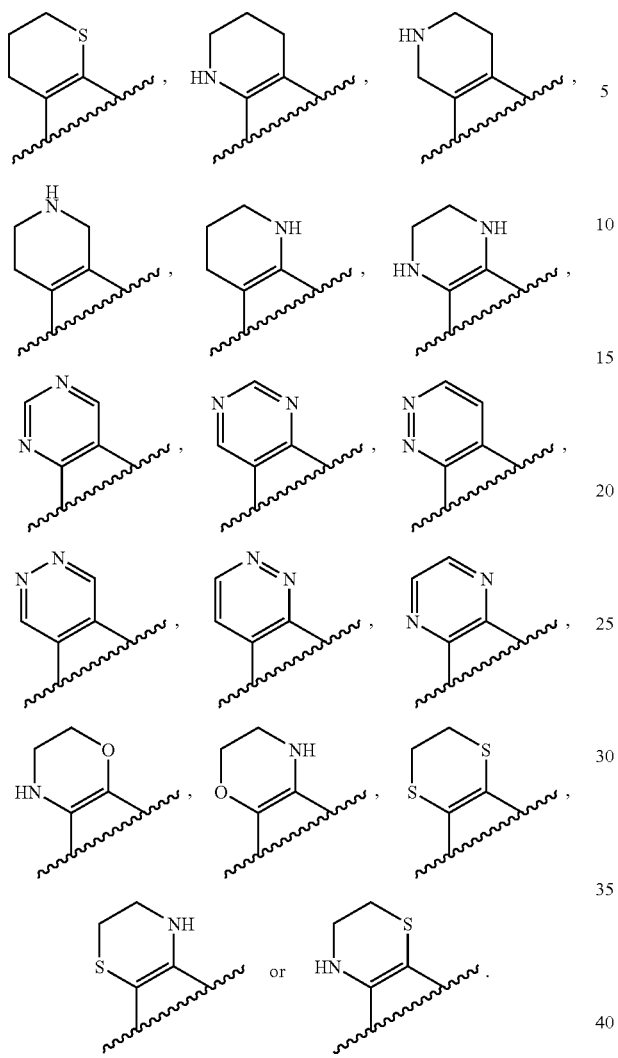
In one embodiment, $R^1$ is —CH$_2$—, and $R^{10}$ is
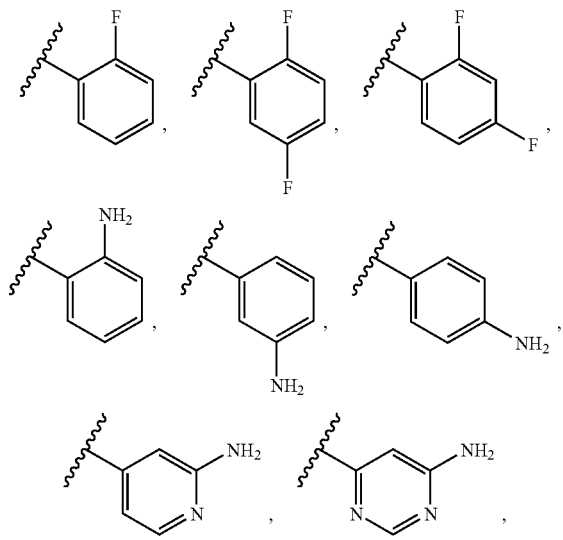
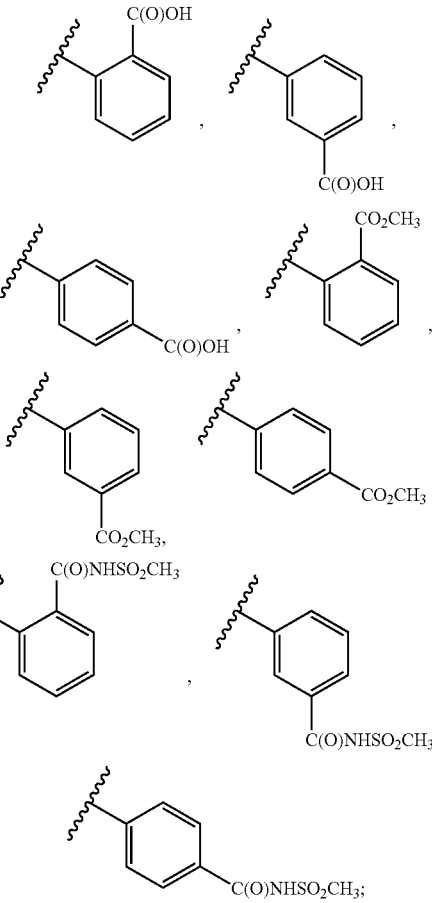
$R^2$ is —C(O)OH or —C(O)NHSO$_2$R$^{11}$; and ring Z is:
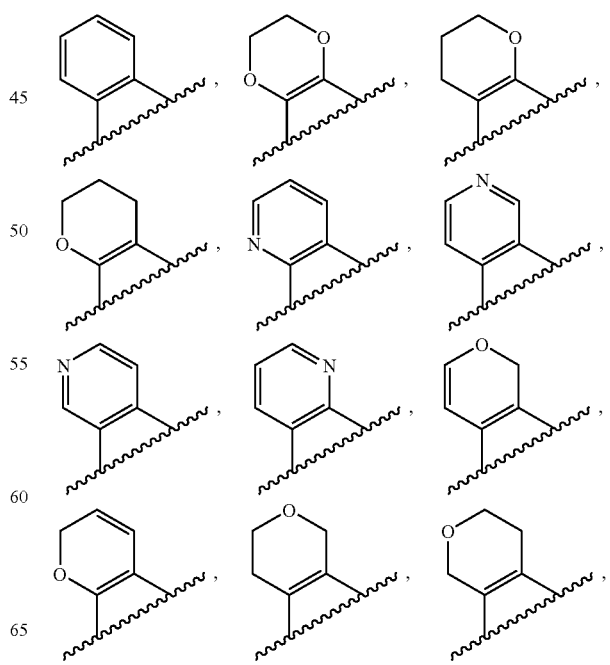

-continued

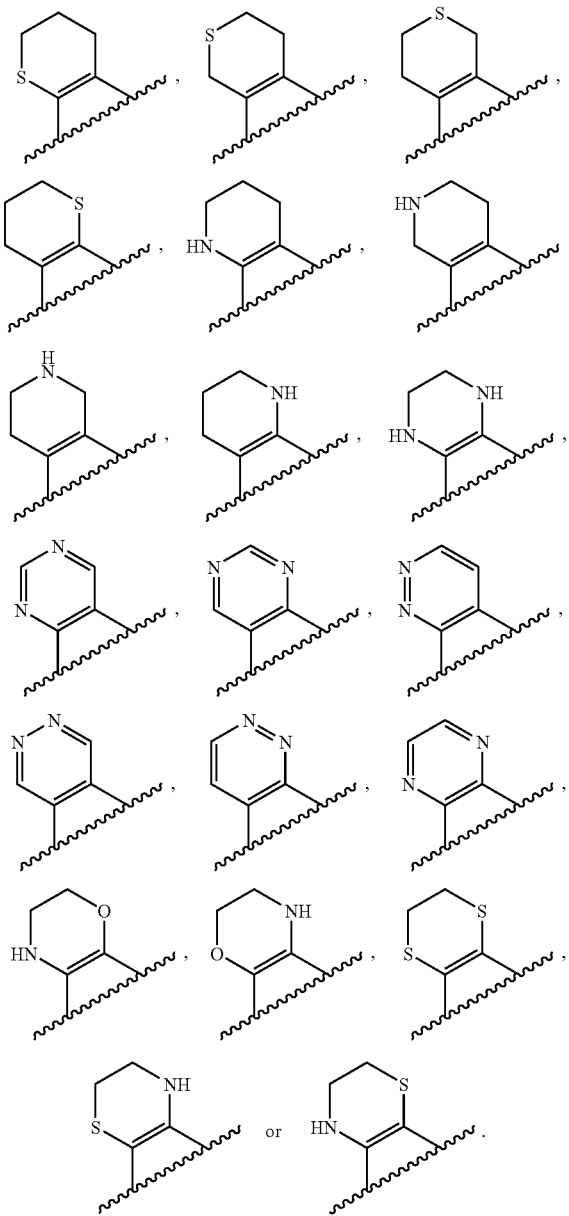

In another embodiment, $R^1$ is a single bond or an alkylene group having from 1 to 6 carbon atoms; $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; $R^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

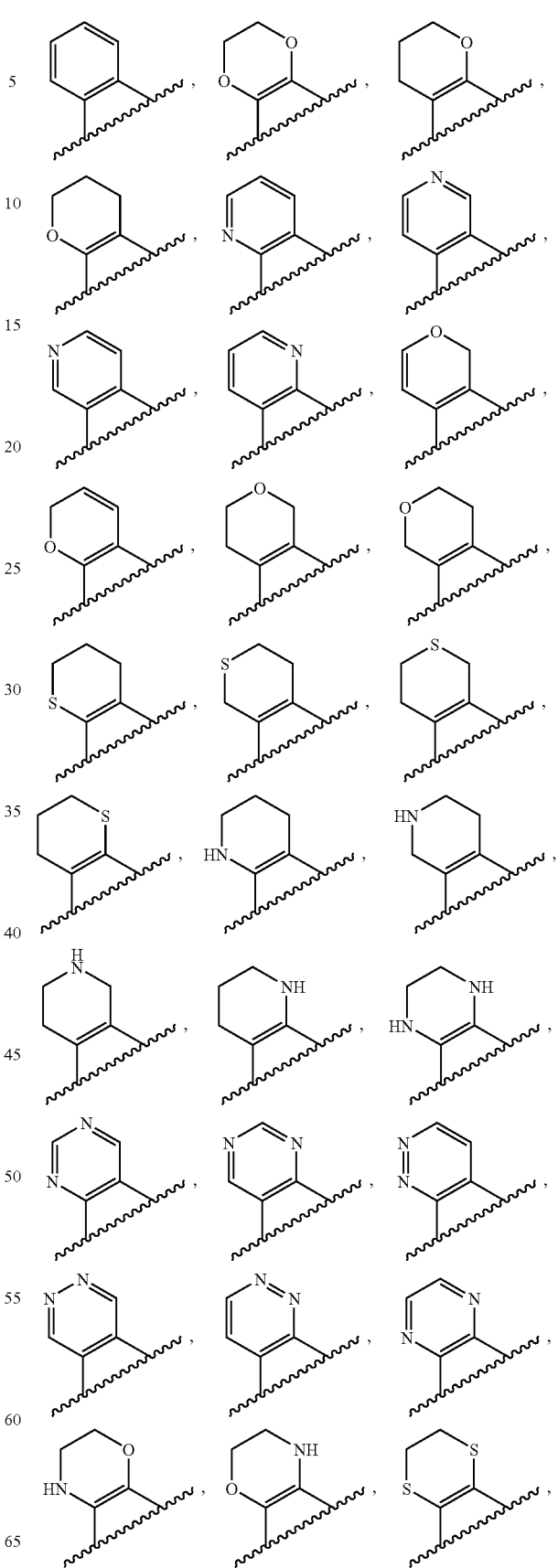

-continued

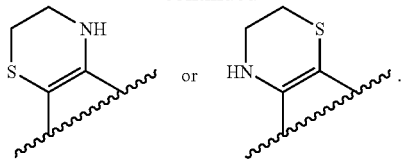

which can be substituted as set forth above for the compounds of formula (I).

In still another embodiment, $R^1$ is —CH$_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; $R^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

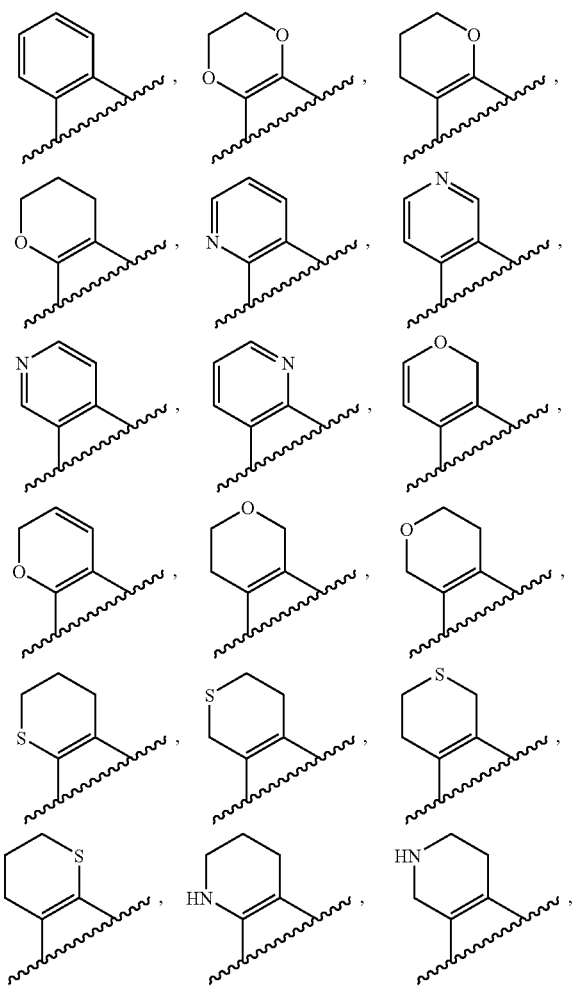

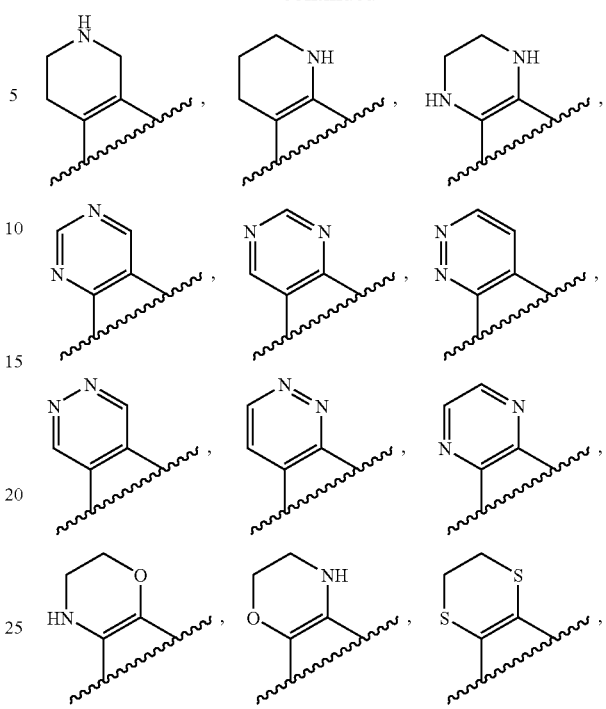

In yet another embodiment, $R^1$ is —CH$_2$—, and $R^{10}$ is

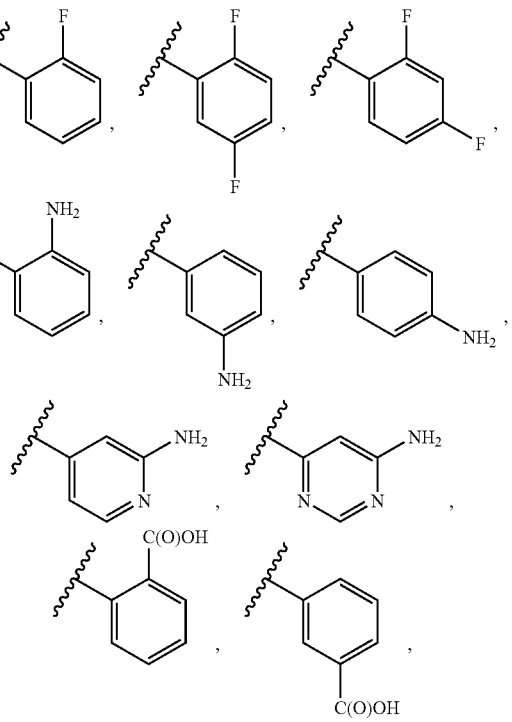

-continued

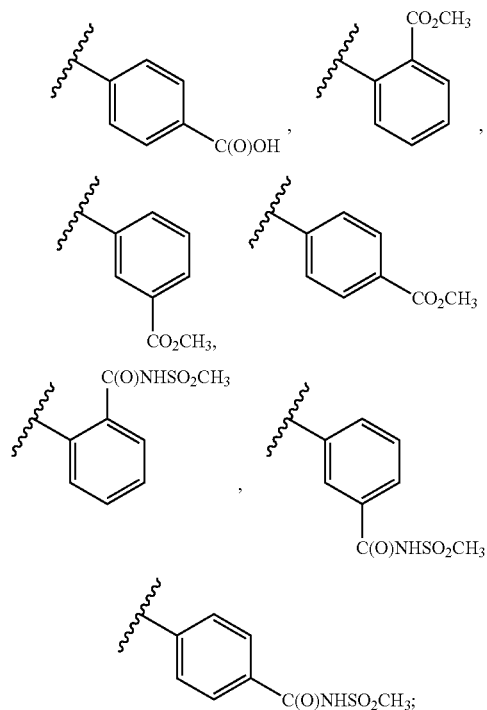

$R^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

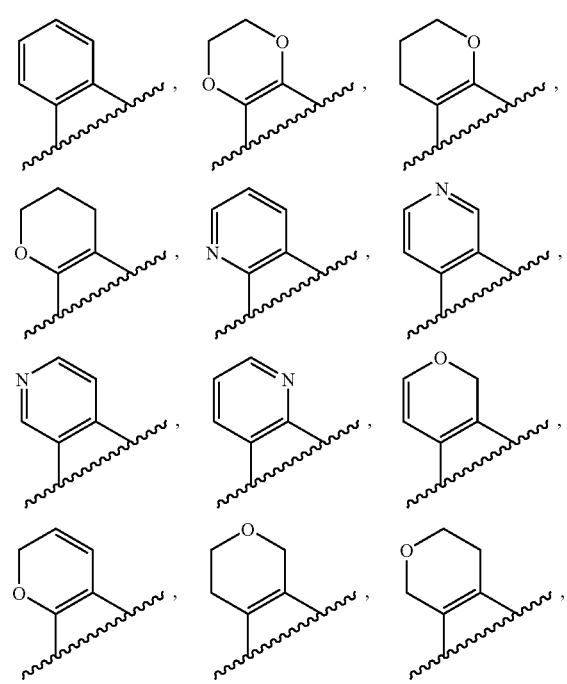

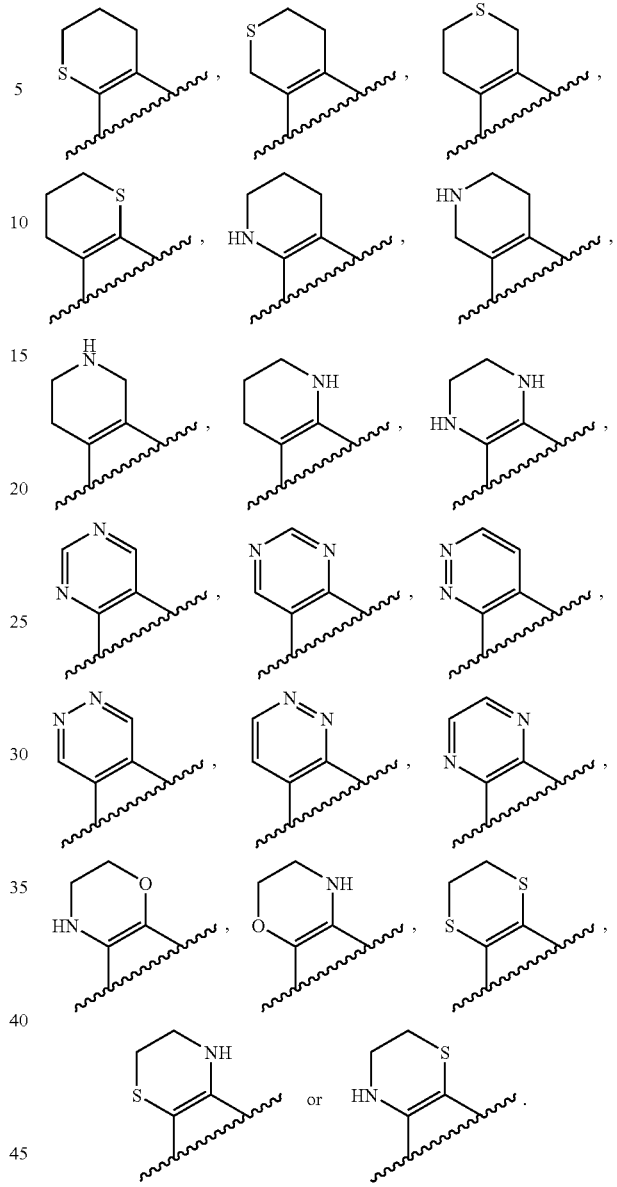

In a further embodiment, $R^1$ is a single bond or an alkylene group having from 1 to 6 carbon atoms; $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; $R^3$ is:

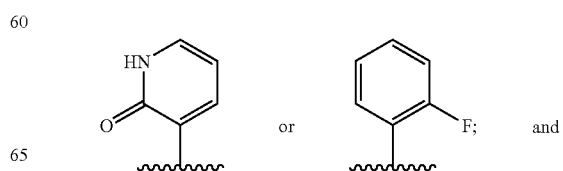

ring Z is:

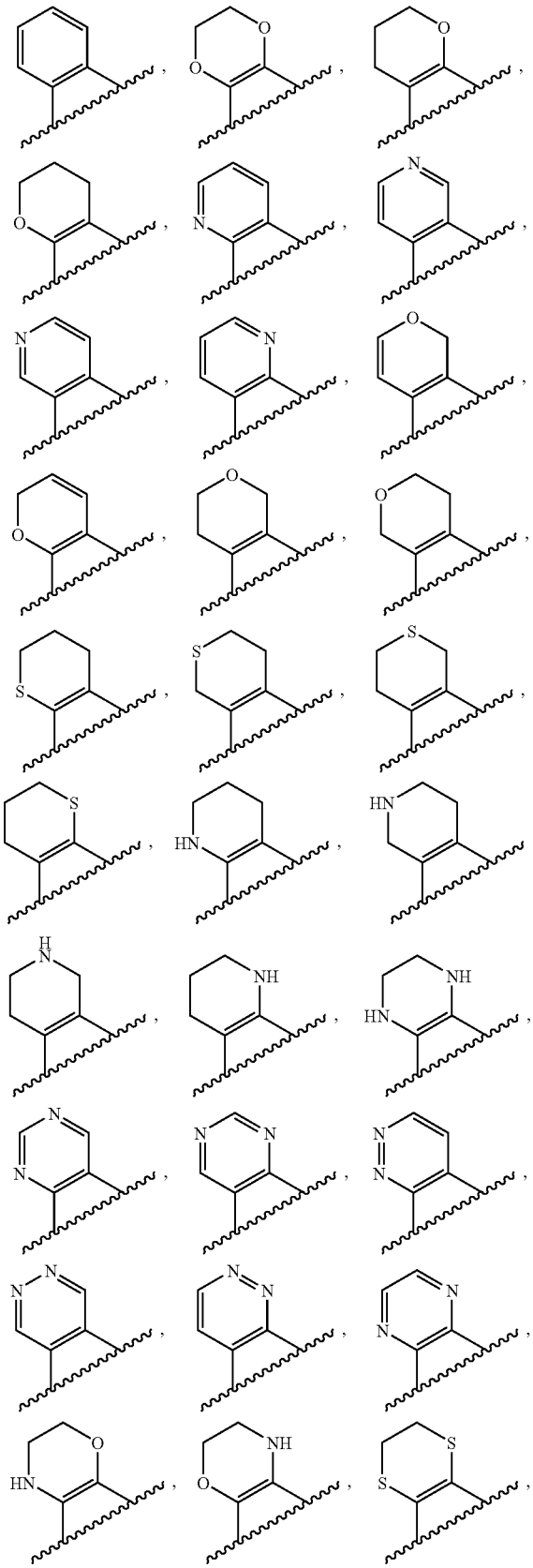

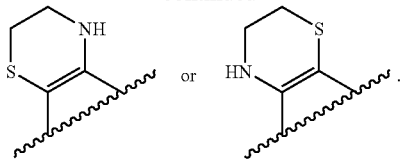

In one embodiment, $R^1$ is —$CH_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; $R^3$ is:

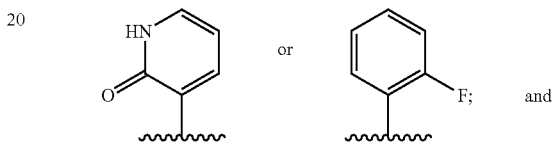

and ring Z is:

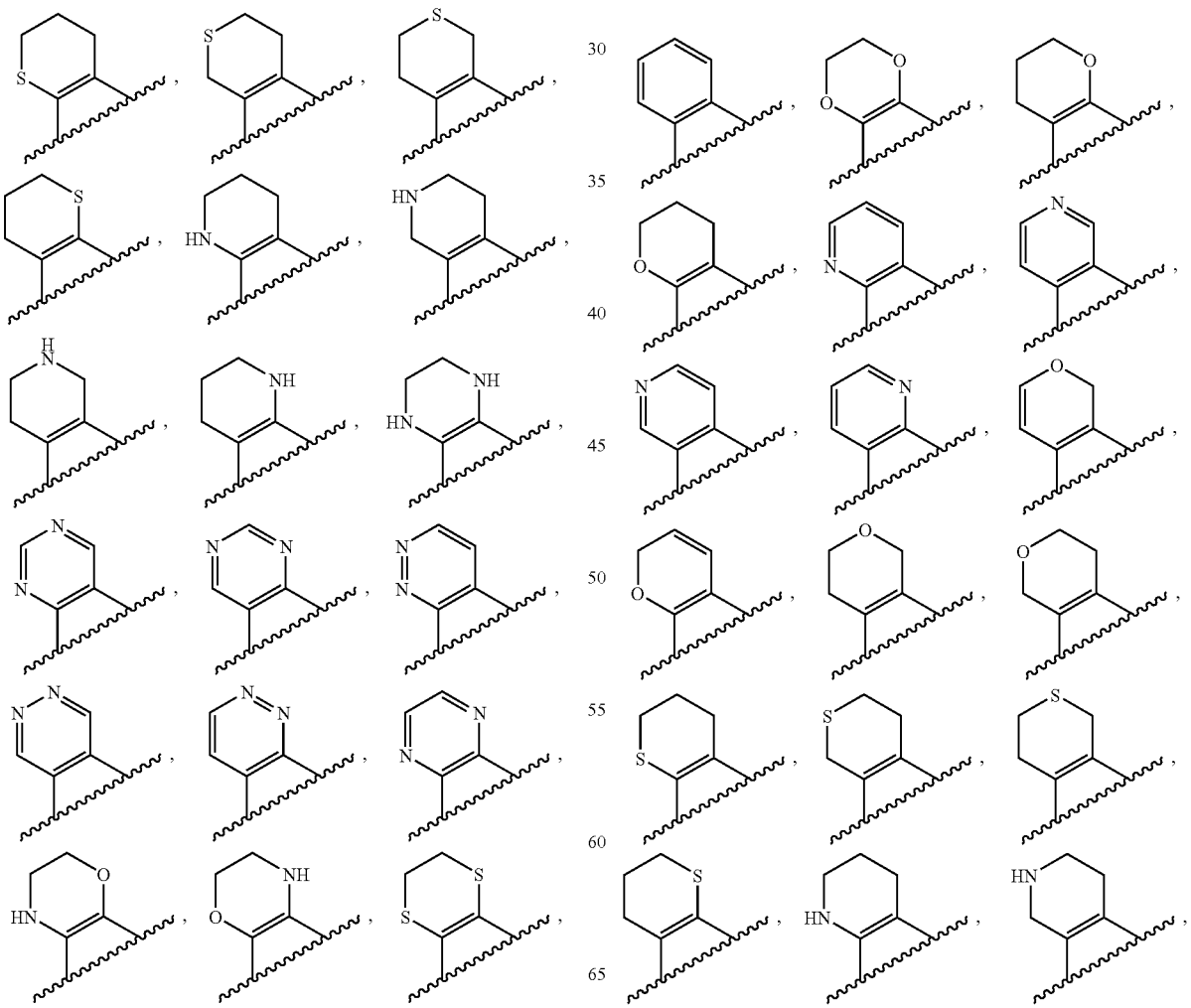

-continued
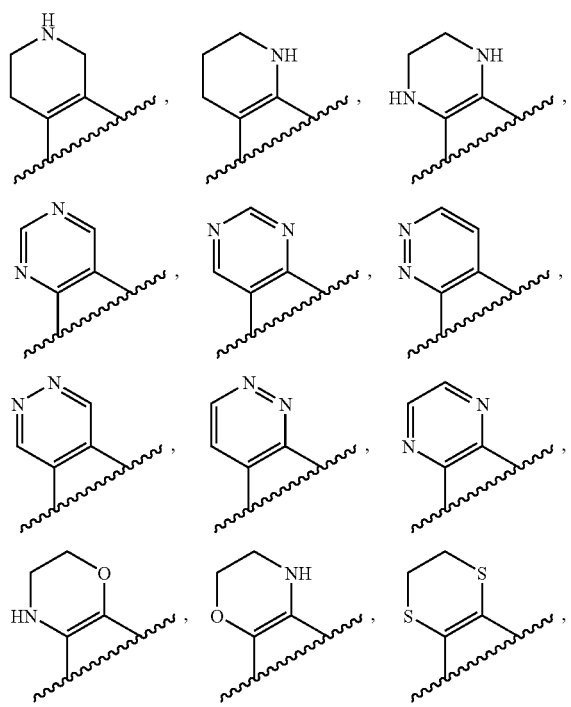
In another embodiment, $R^1$ is —$CH_2$—, and $R^{10}$ is
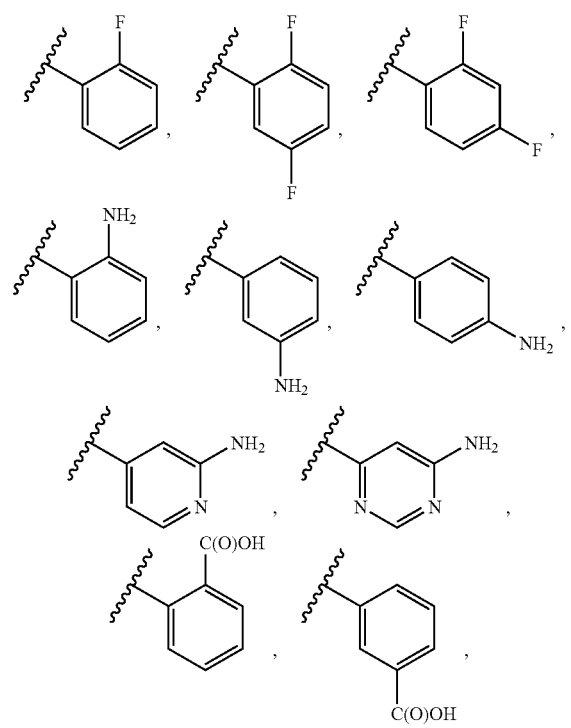
-continued
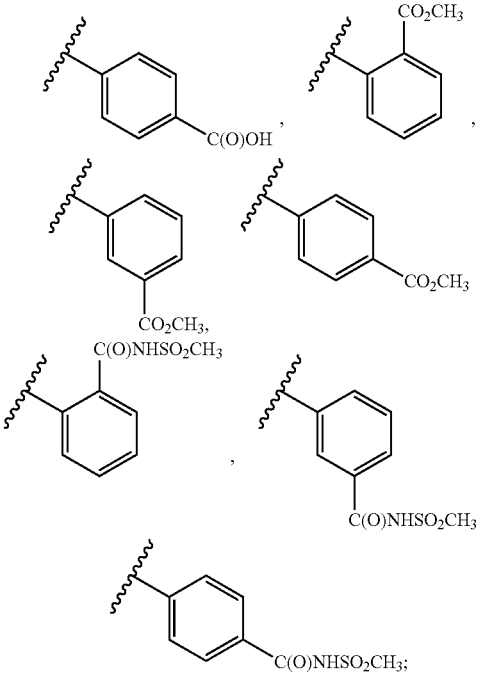
$R^3$ is:
and ring Z is:

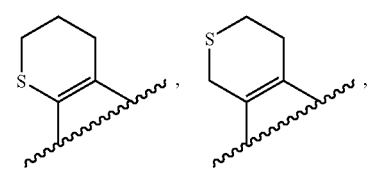
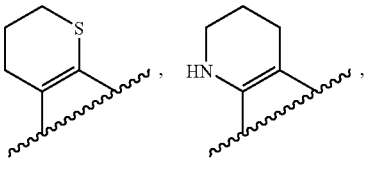
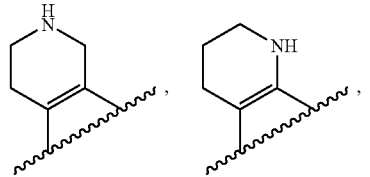
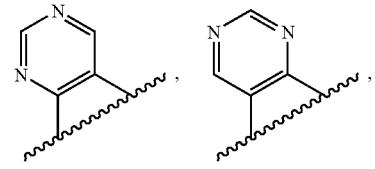
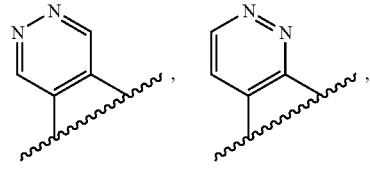
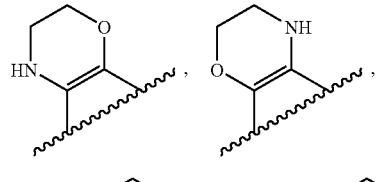
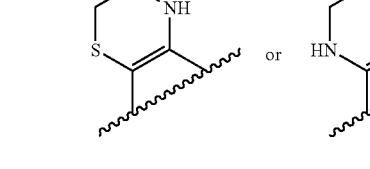
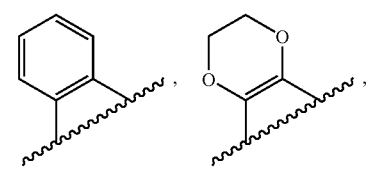

In another embodiment, R¹ is a single bond or an alkylene group having from 1 to 6 carbon atoms, R¹⁰ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)₂, —OH, —O-benzyl, -alkylene-OR⁹, —OR⁹, —N(R⁹)₂, —NHC(O)R⁸, —NHSO₂R¹¹, —S(O)ₚR¹¹ or —SO₂N(R⁹)₂; and ring Z is:

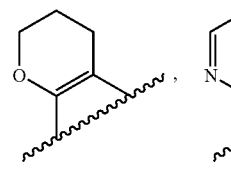

In one embodiment, R¹ is —CH₂—, and R¹⁰ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, or —SO$_2$N(R$^9$)$_2$; and ring Z is:
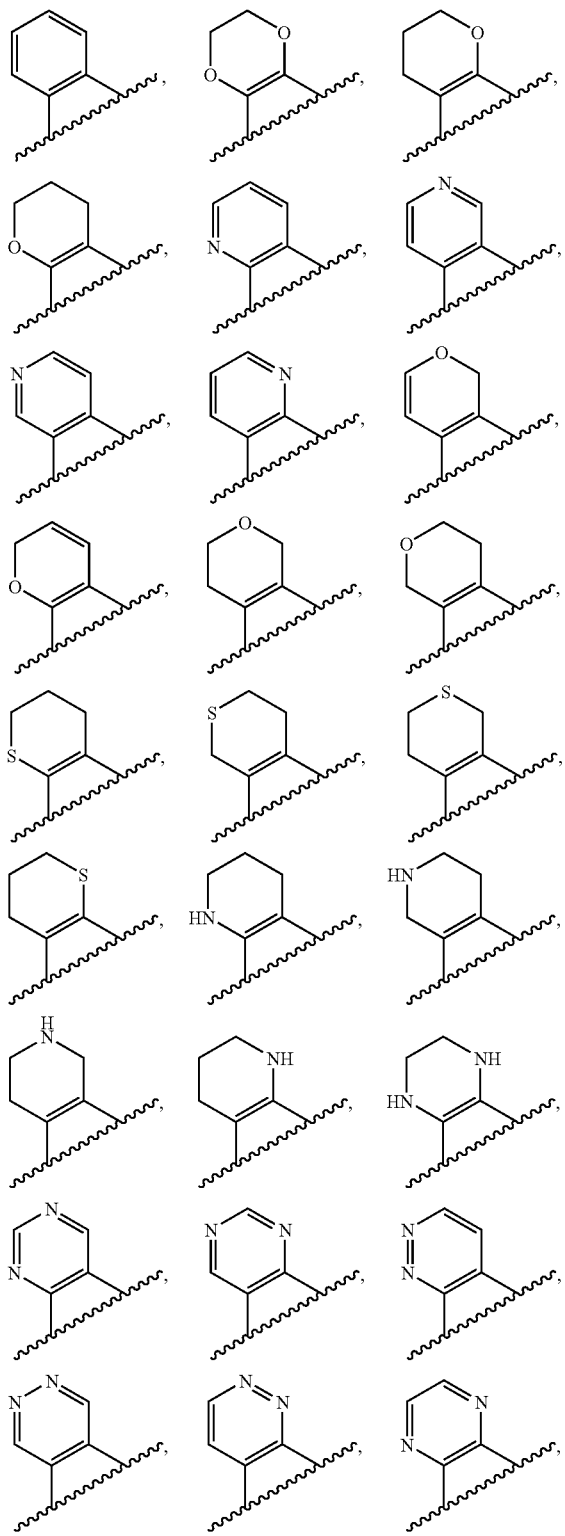
-continued
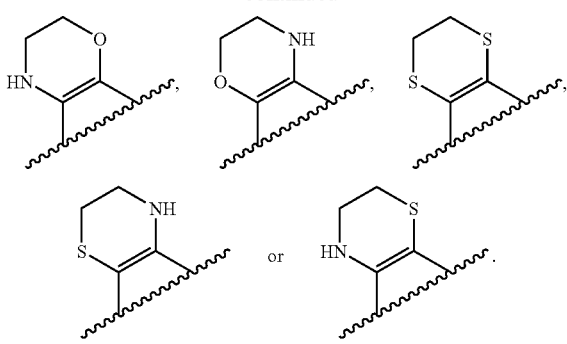
In another embodiment, R$^1$ is —CH$_2$—, and R$^{10}$ is
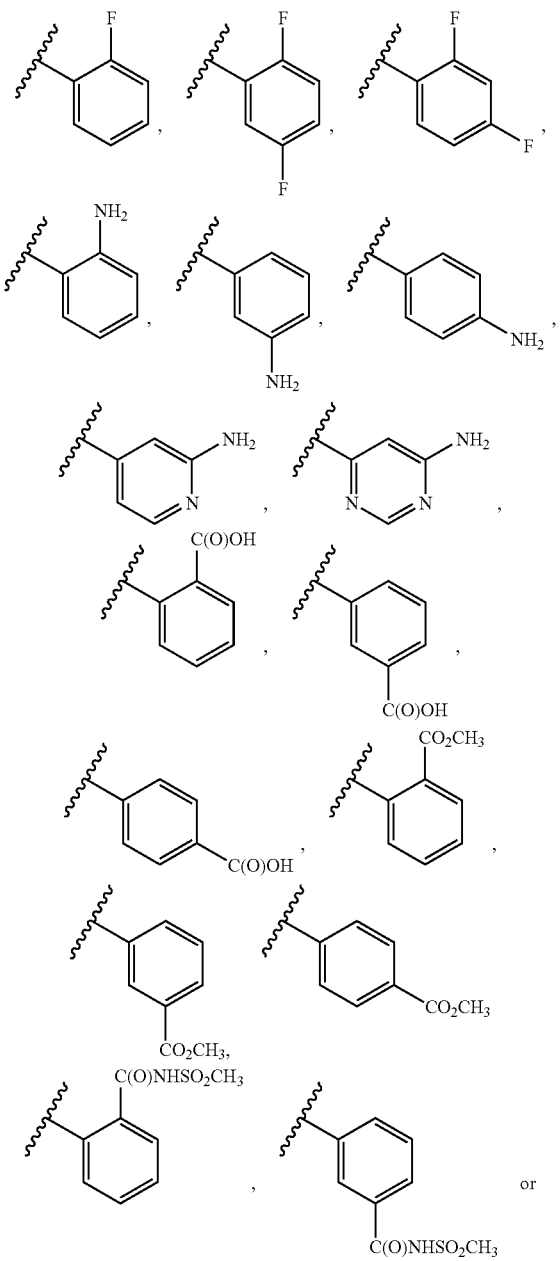

-continued
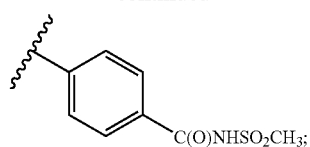
and ring Z is:
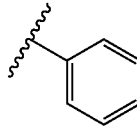
In still another embodiment, $R^1$ is —$CH_2$—, $R^{10}$ is
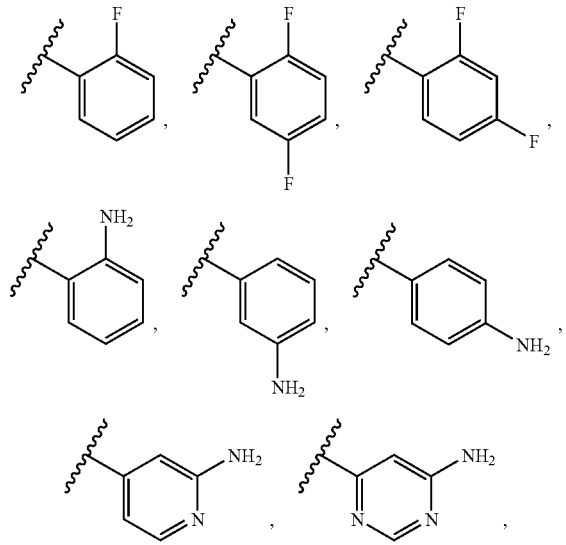
-continued
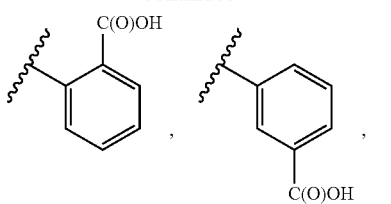
$R^2$ is —C(O)OH or —C(O)NHSO$_2$R$^{11}$; and ring Z is:
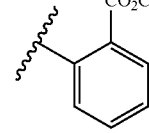

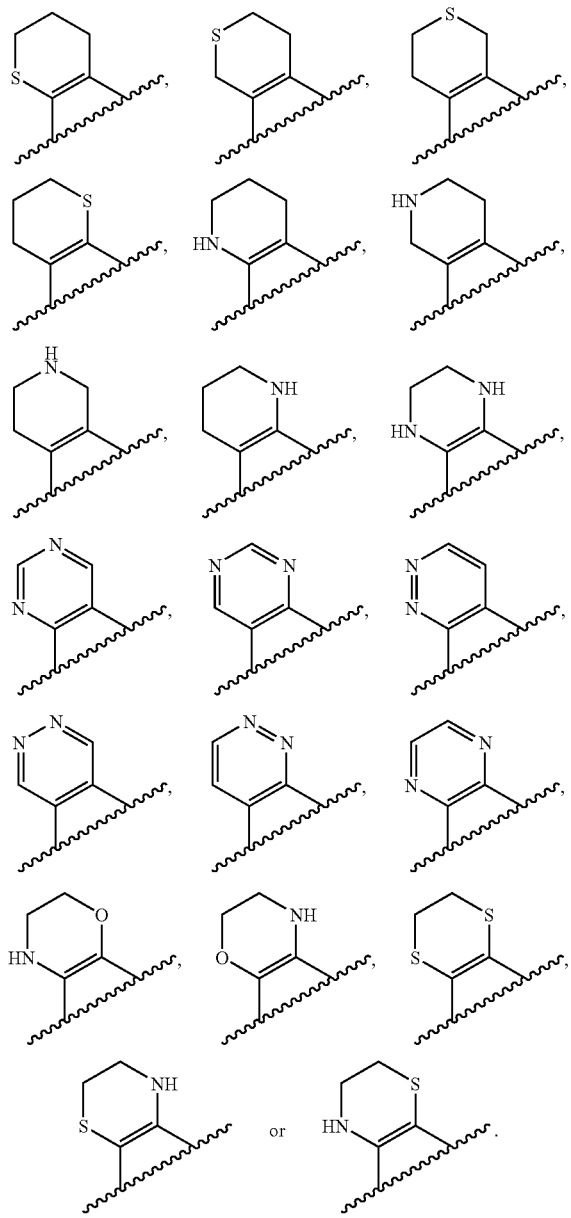

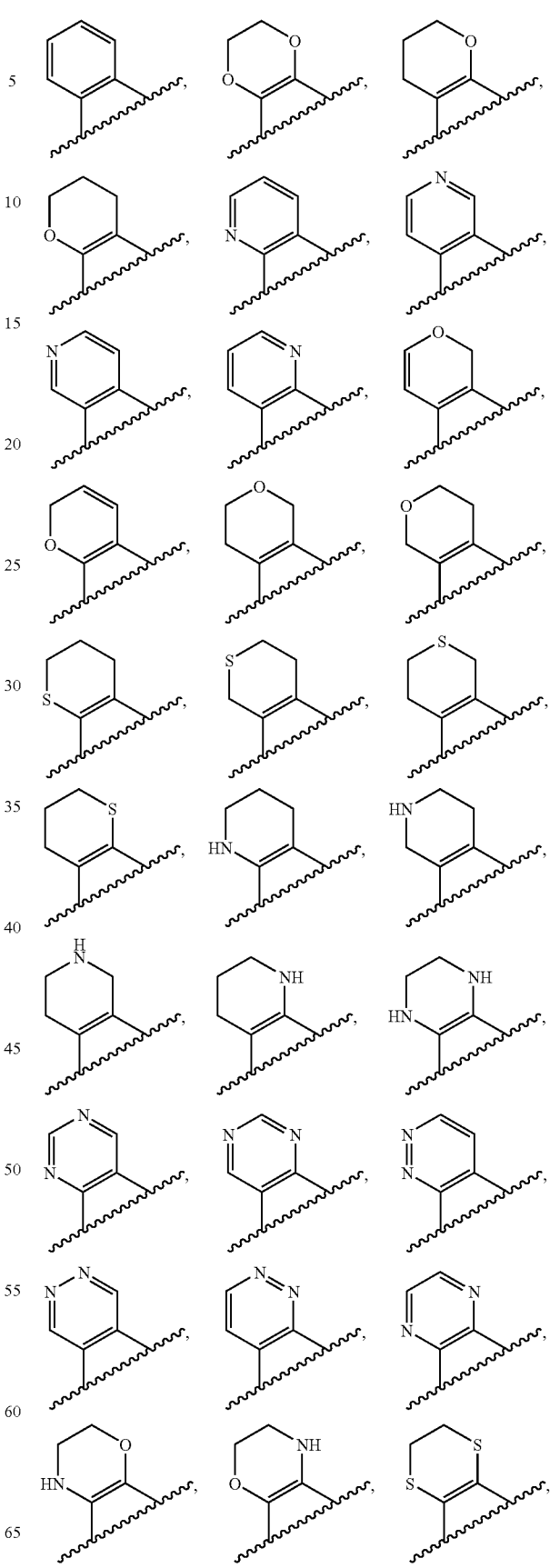

In yet another embodiment, R¹ is a single bond or an alkylene group having from 1 to 6 carbon atoms; $R^{10}$ is phenyl or 6-membered heteroaryl, which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)₂, —OH, —O-benzyl, -alkylene-$OR^9$, —$OR^9$, —$N(R^9)_2$, —$NHC(O)R^8$, —$NHSO_2R^{11}$, —$S(O)_pR^{11}$ or —$SO_2N(R^9)_2$; R³ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH₂, —OH, —NH₂, —C(O)NHalkyl, —O-haloalkyl, —NHalkyl, —NHC(O)NH₂, —NHC(O)NH-alkyl, —NHSO₂alkyl, —S(O)₂alkyl or —SO₂NHalkyl; and -continued

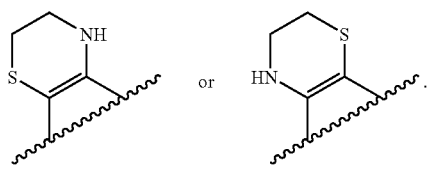

In another embodiment, $R^1$ is —$CH_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; $R^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

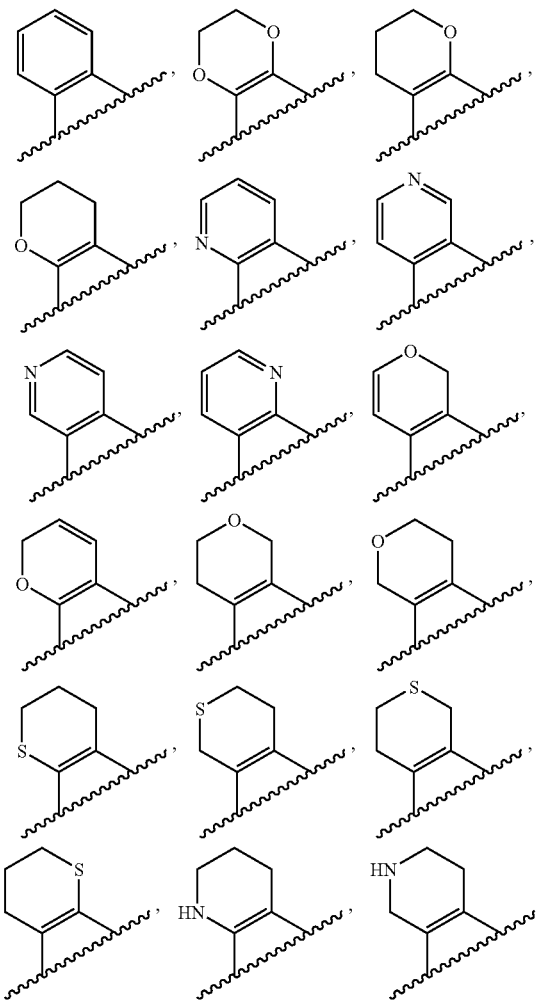

-continued

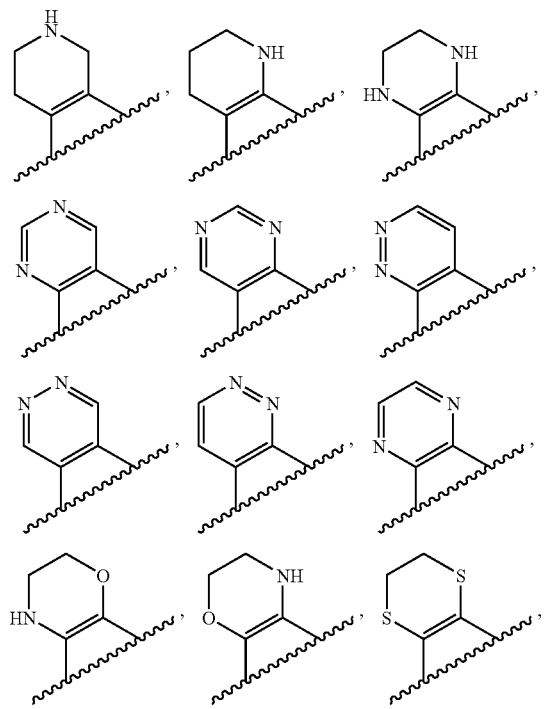

In a further embodiment, $R^1$ is —$CH_2$—, and $R^{10}$ is

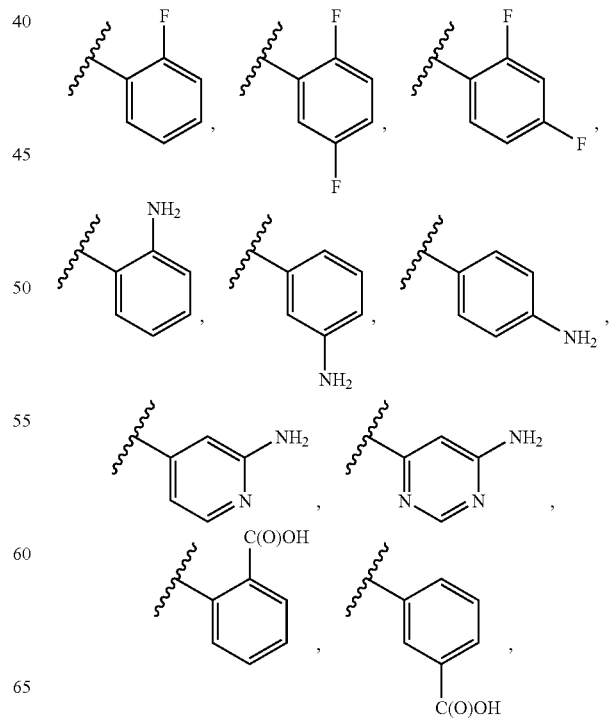

-continued

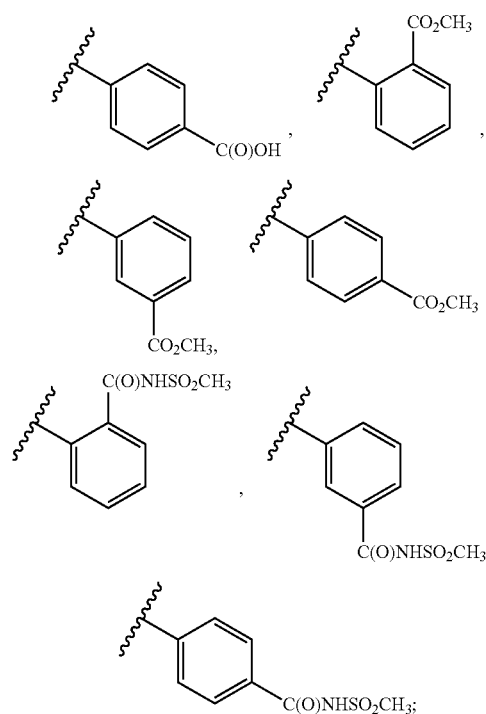

R[3] is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

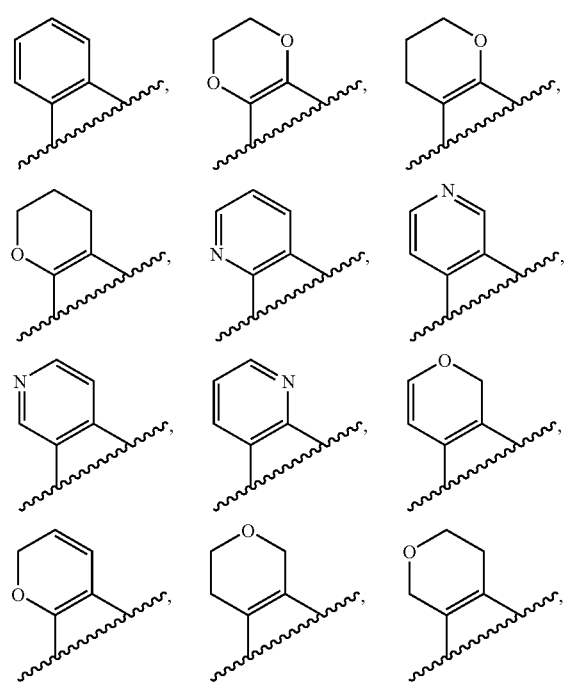

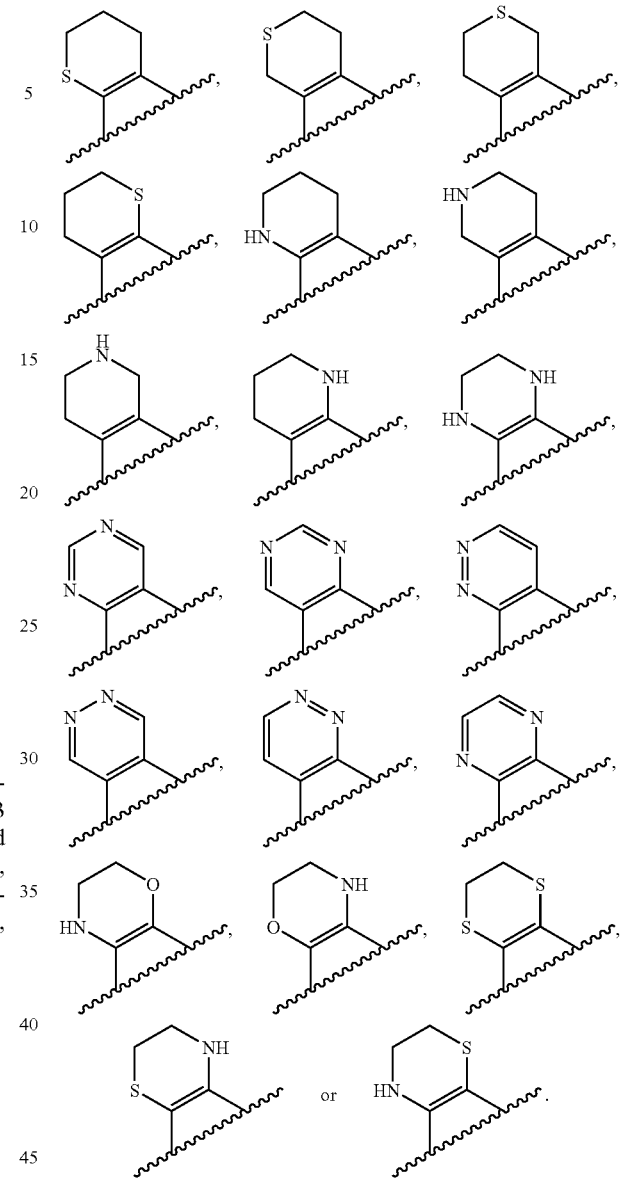

In another embodiment, R[1] is a single bond or an alkylene group having from 1 to 6 carbon atoms; R[10] is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR[9], —OR[9], —N(R[9])$_2$, —NHC(O)R[8], —NHSO$_2$R[11], —S(O)$_p$R[11] or —SO$_2$N(R[9])$_2$; R[3] is:

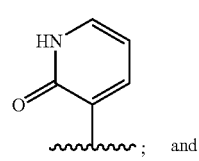 [SMILES: *c1ccc[nH]c1=O]

; and ring Z is:

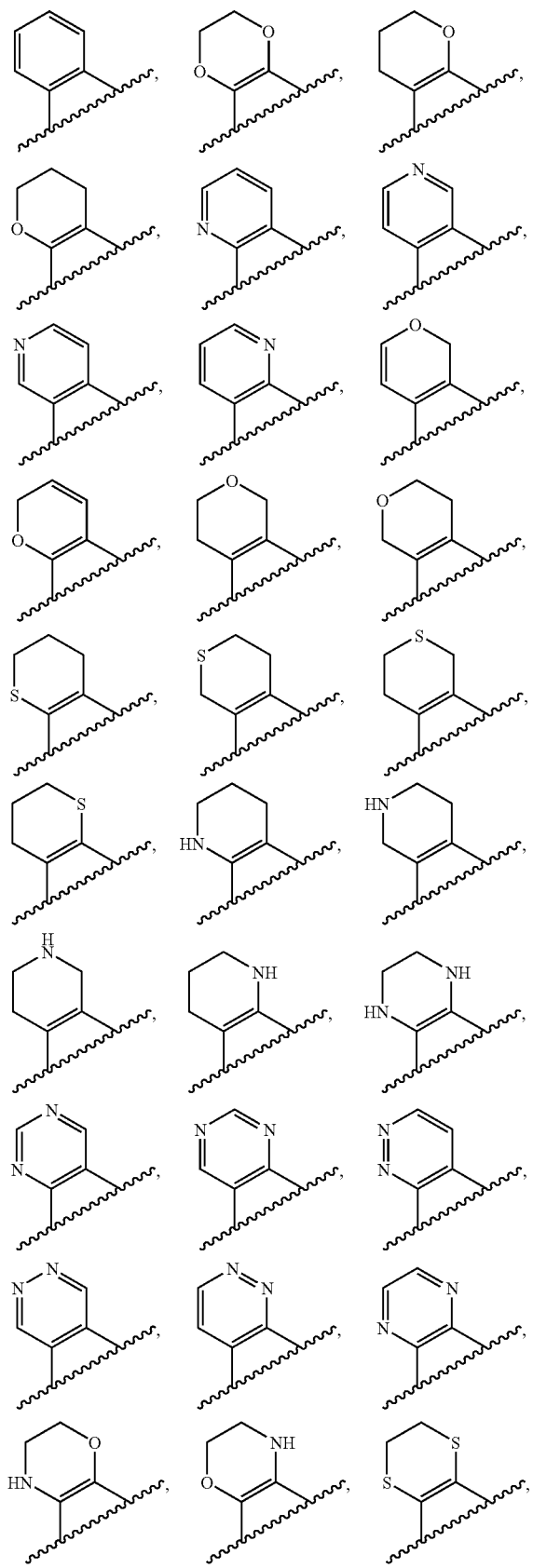

-continued

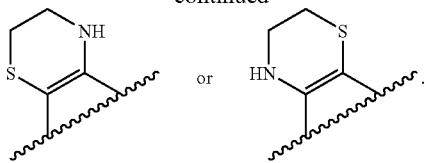

In one embodiment, $R^1$ is —CH$_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; $R^3$ is:

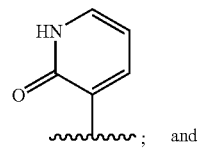 [SMILES: *c1ccc[nH]c1=O]

; and ring Z is:

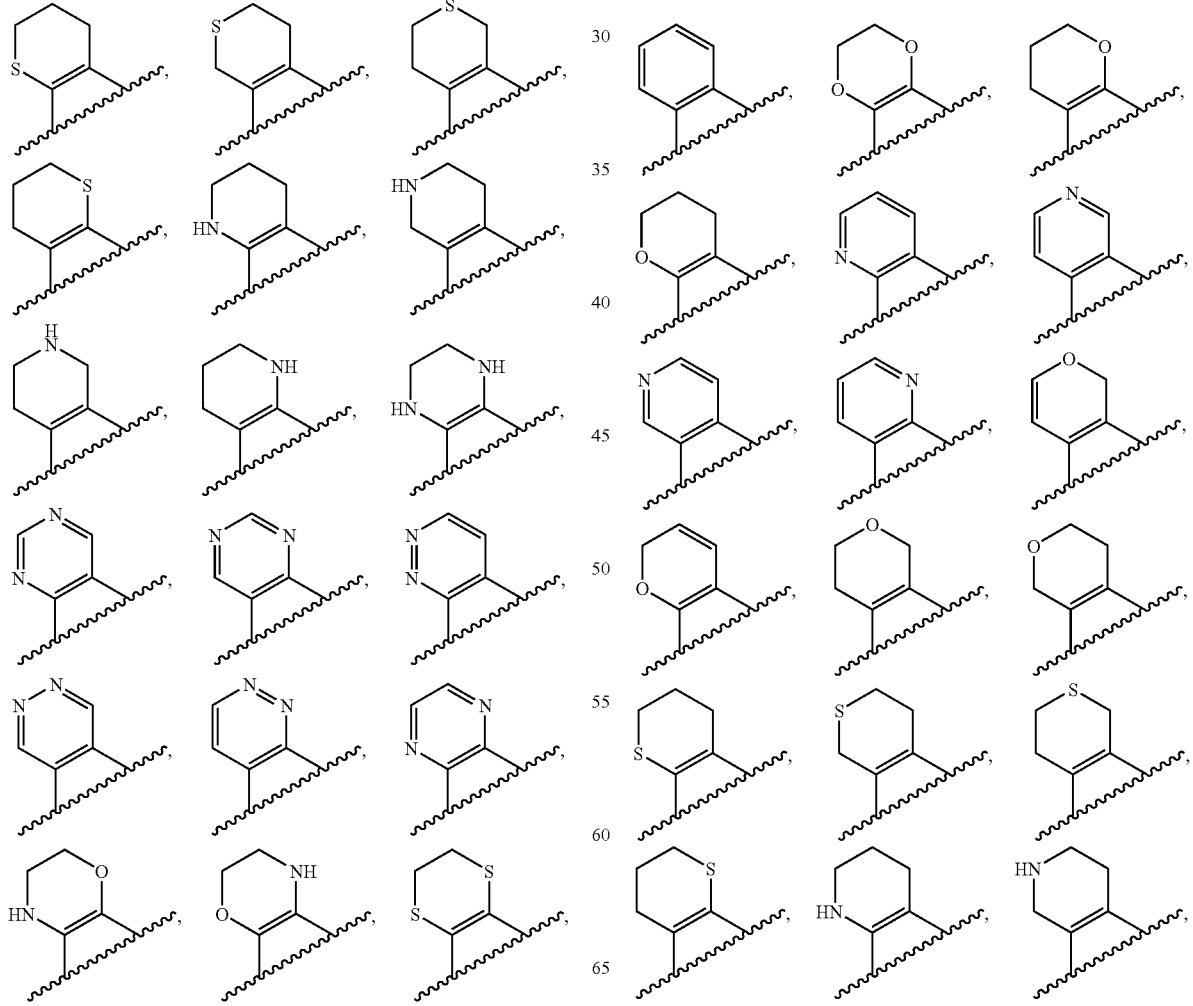

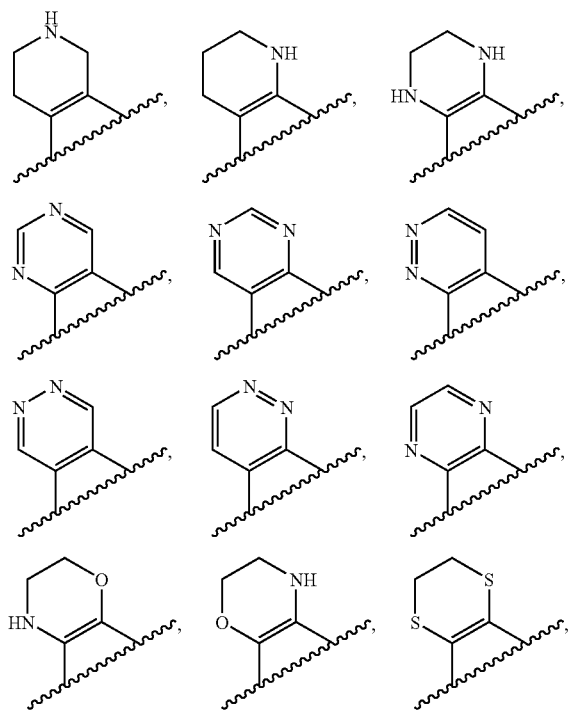
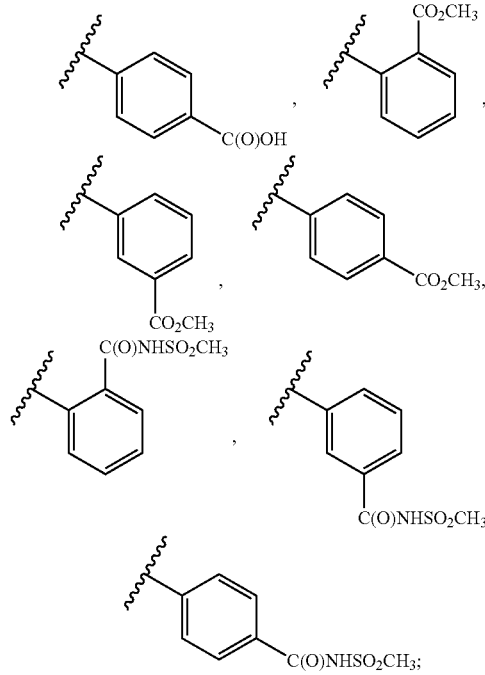
In another embodiment, R¹ is —CH₂—, and R¹⁰ is
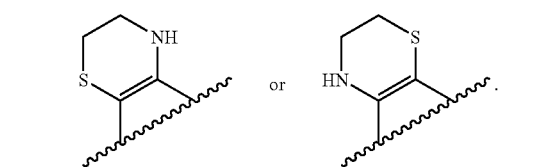
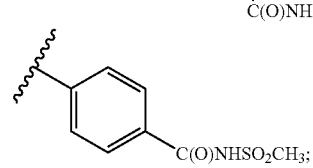
R³ is:
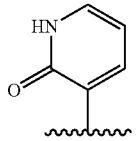 or 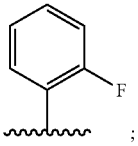 ; and
ring Z is:
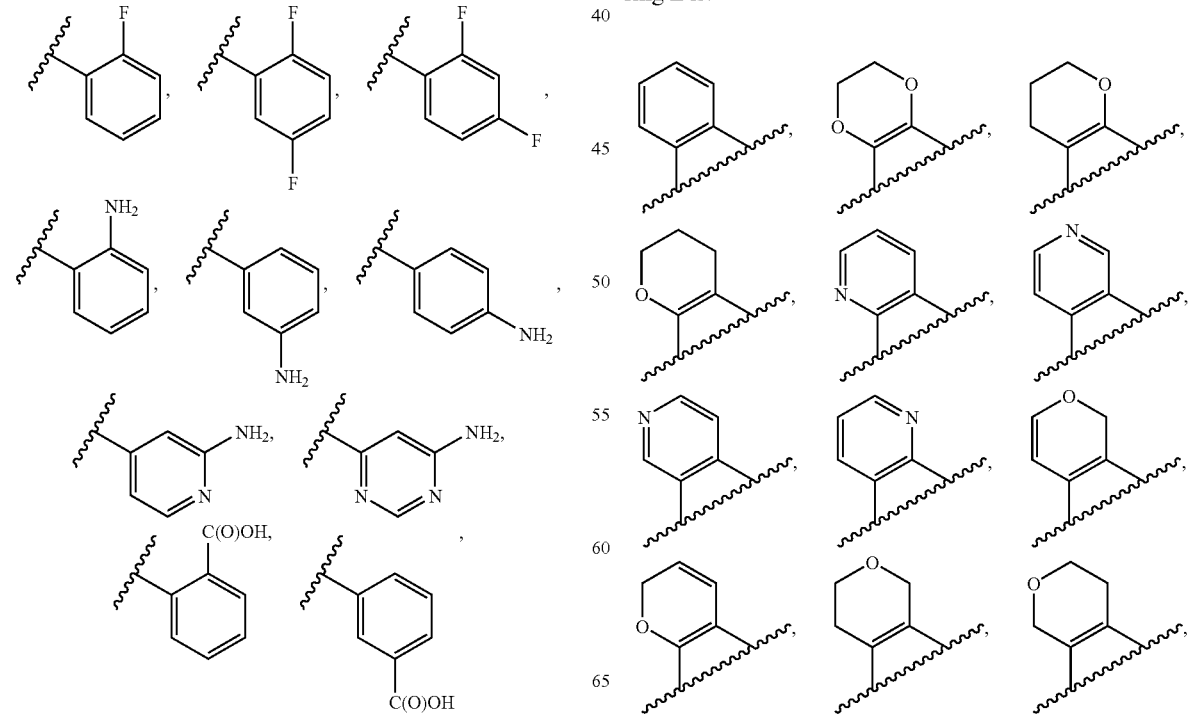

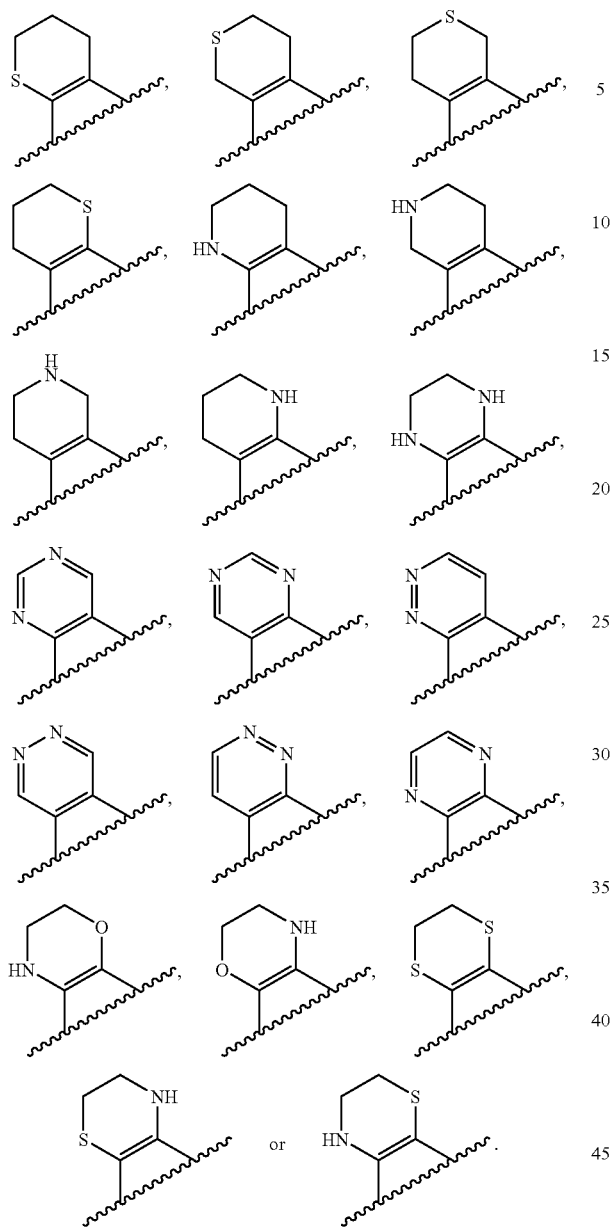

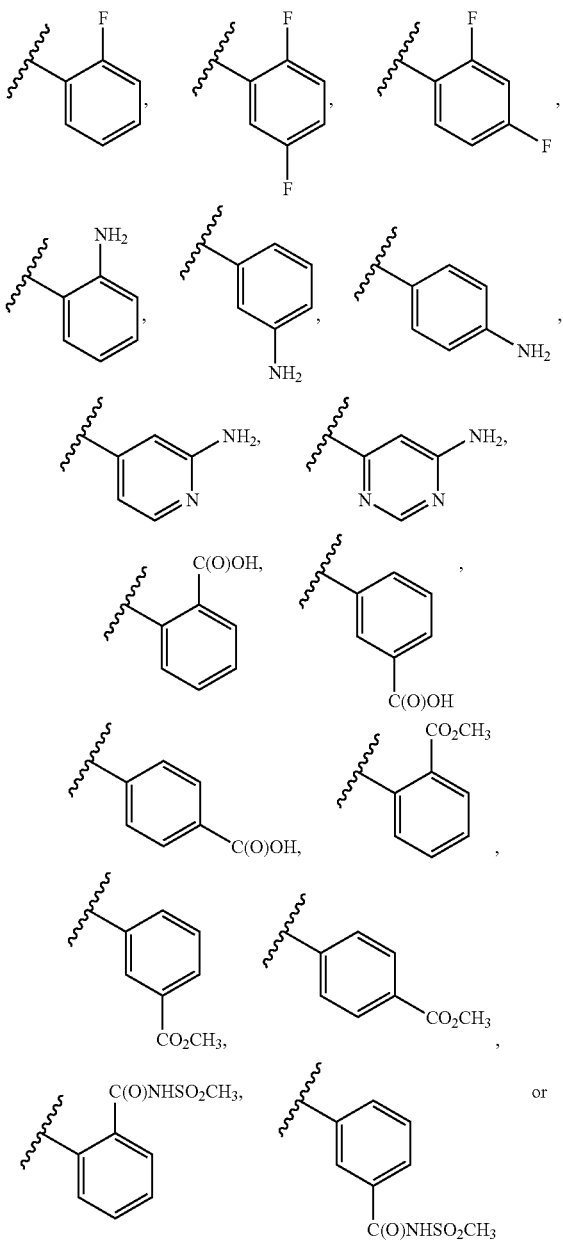

In one embodiment, $R^1$ is —$CH_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; and ring Z is:

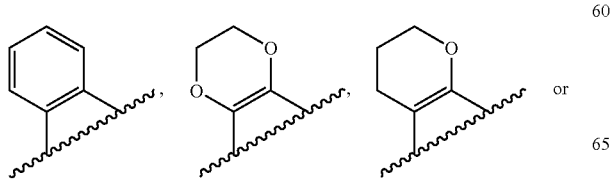

In another embodiment, $R^1$ is —$CH_2$—, and $R^{10}$ is and ring Z is:

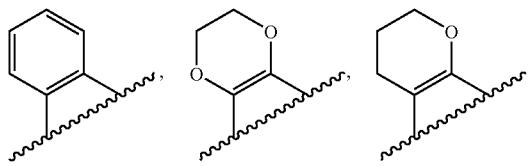

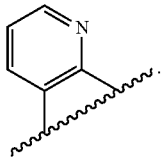

In still another embodiment, $R^1$ is —$CH_2$—, $R^{10}$ is

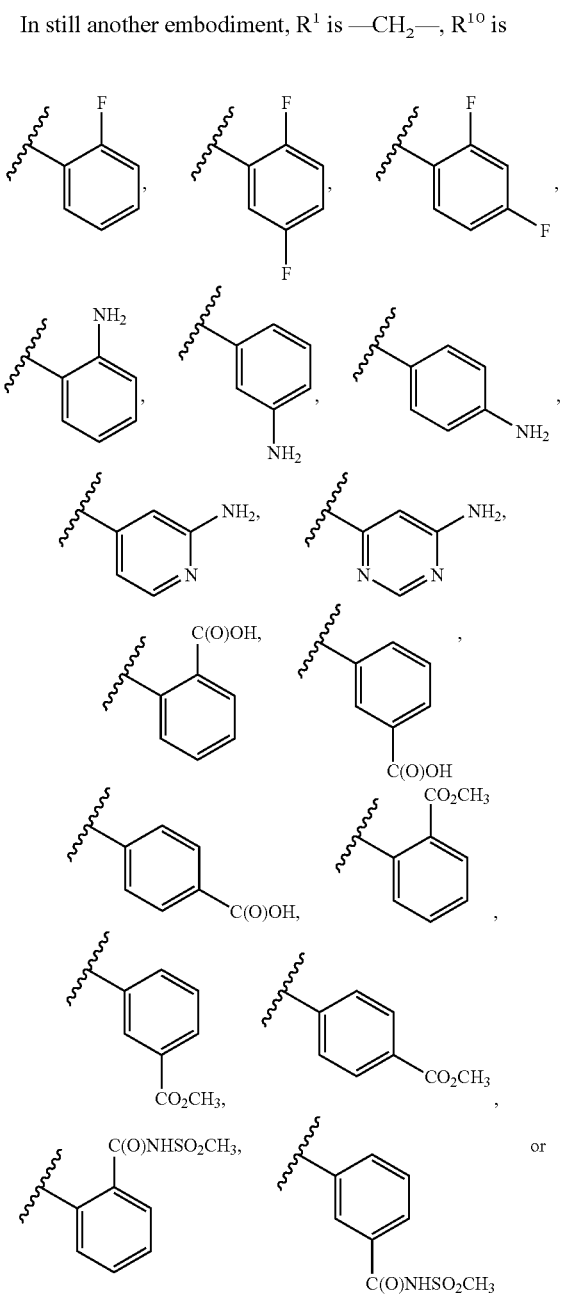

or

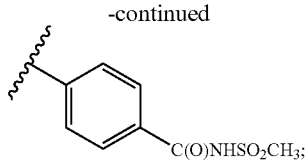

$R^2$ is —C(O)OH or —C(O)NHSO$_2R^{11}$; and
ring Z is:

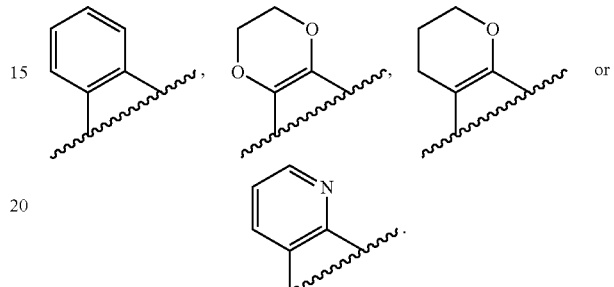

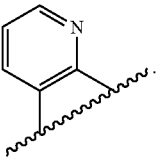

In yet another embodiment, $R^1$ is a single bond or an alkylene group having from 1 to 6 carbon atoms; $R^{10}$ is phenyl or 6-membered heteroaryl, which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2R^{11}$, —S(O)$_pR^{11}$ or —SO$_2$N(R$^9$)$_2$; $R^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and
ring Z is:

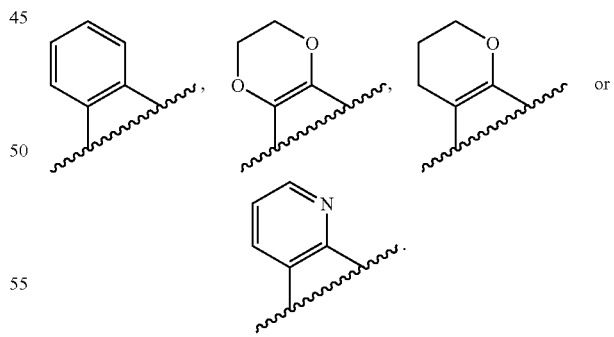

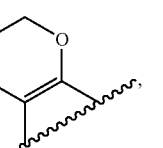

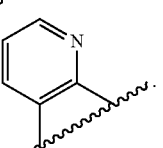

In another embodiment, $R^1$ is —$CH_2$—, and $R^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2R^{11}$, —S(O)$_pR^{11}$or —SO$_2$N(R$^9$)$_2$; $R^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

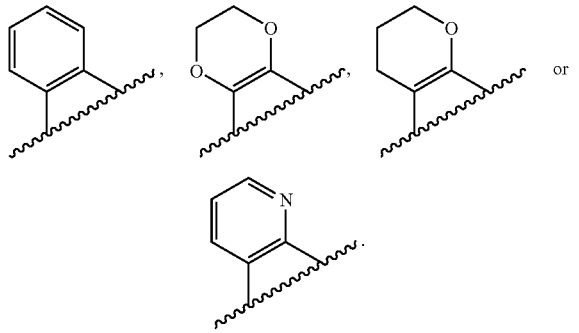

In a further embodiment, R$^1$ is —CH$_2$—, and R$^{10}$ is

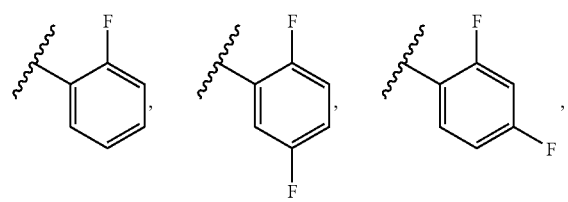

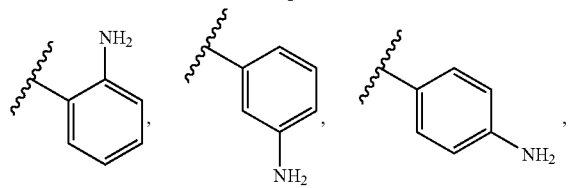

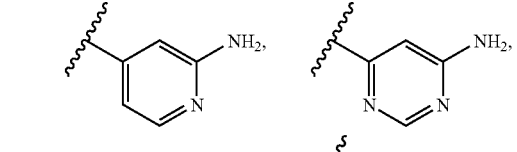

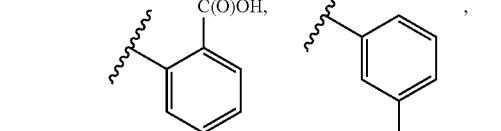

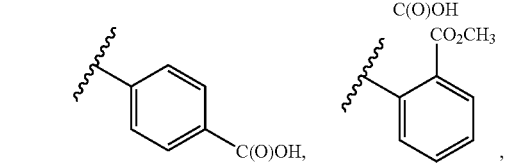

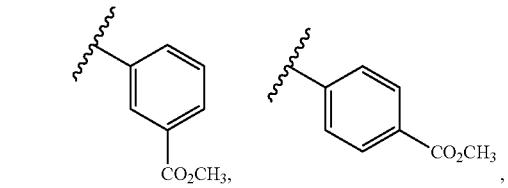

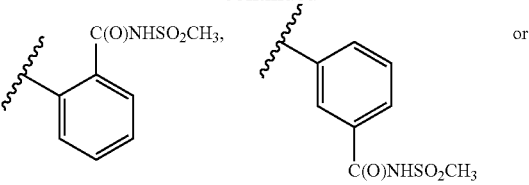

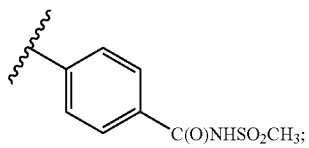

R$^3$ is aryl or heterocycloalkenyl, each of which is unsubstituted or optionally and independently substituted with up to 3 substituents, which are the same or different, and are selected from alkyl, CN, halo, haloalkyl, hydroxyalkyl, —C(O)alkyl, —C(O)NH$_2$, —OH, —NH$_2$, —C(O)NHalkyl, —O-haloalkyl, —NHalkyl, —NHC(O)NH$_2$, —NHC(O)NH-alkyl, —NHSO$_2$alkyl, —S(O)$_2$alkyl or —SO$_2$NHalkyl; and ring Z is:

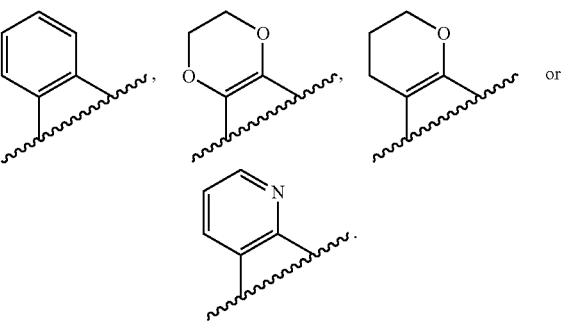

In another embodiment, R$^1$ is a single bond or an alkylene group having from 1 to 6 carbon atoms; R$^{10}$ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)$_2$, —OH, —O-benzyl, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; R$^3$ is:

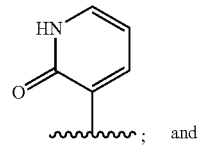

; and ring Z is:

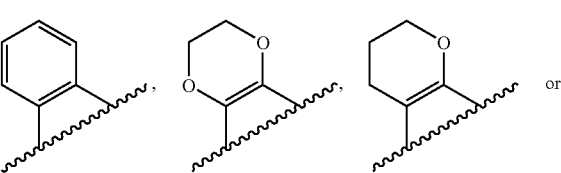

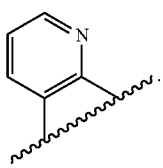

In one embodiment, R¹ is —CH₂—, and R¹⁰ is phenyl or 6-membered heteroaryl, each of which is unsubstituted or optionally and independently substituted with up to 3 substituents, which are the same or different, and are selected from —CN, alkyl, aryl, halo, haloalkyl, hydroxyalkyl, —C(O)alkyl, —C(O)Oalkyl, —C(O)N(alkyl)₂, —OH, —O-benzyl, -alkylene-OR⁹, —OR⁹, —N(R⁹)₂, —NHC(O)R⁸, —NHSO₂R¹¹, —S(O)$_p$R¹¹ or —SO₂N(R⁹)₂; R³ is:

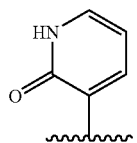; and ring Z is:

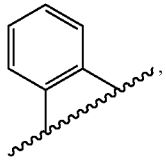, 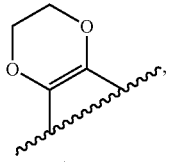, 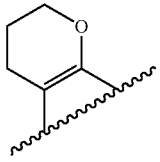 or

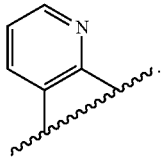.

In another embodiment, R¹ is —CH₂—, R¹⁰ is

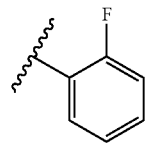, 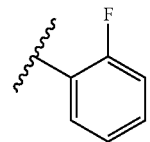, 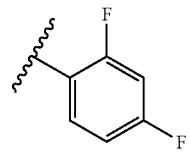,

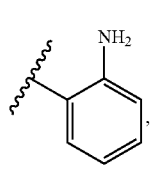, 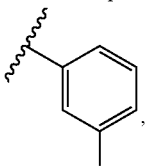, 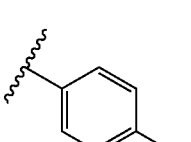,

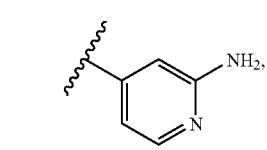, 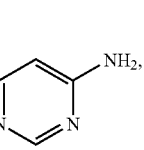,

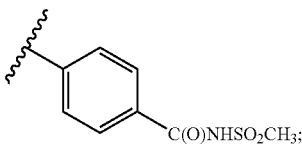

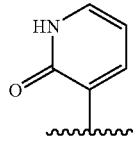 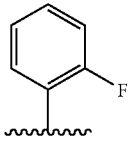

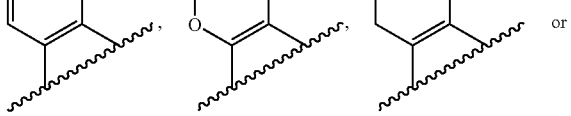

R³ is:

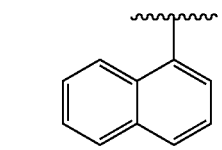 or 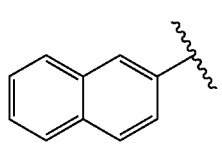; and ring Z is:

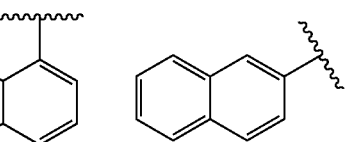

In another embodiment, R¹ is —CH₂—, R¹⁰ is

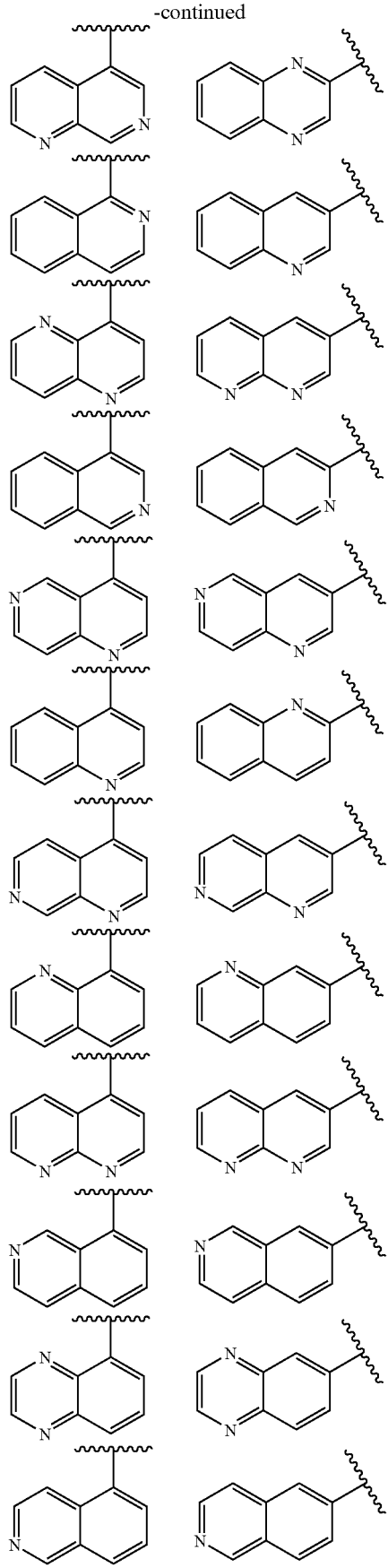
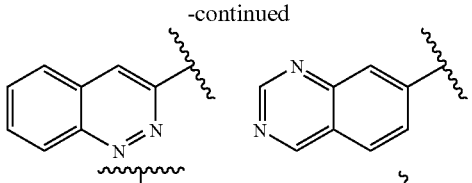
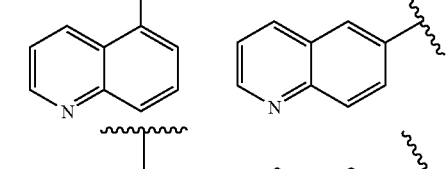
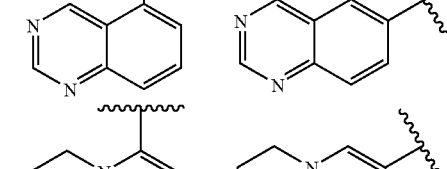
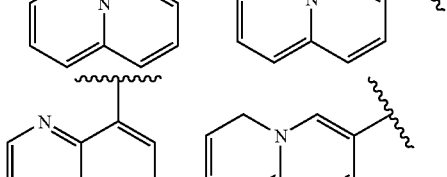
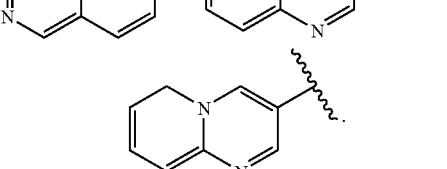
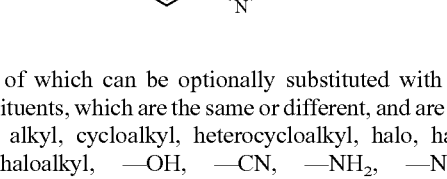
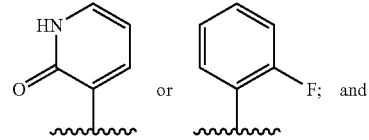 [SMILES: *c1ccc[nH]c1=O ; "or" ; *c1ccccc1F ; "and"] or
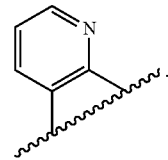
each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; R$^3$ is:
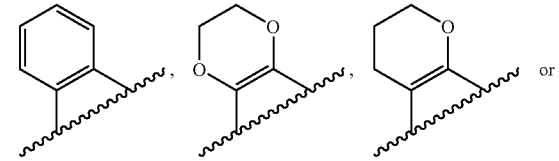
ring Z is:

In a further embodiment, $R^1$ is —CH$_2$—, $R^{10}$ is
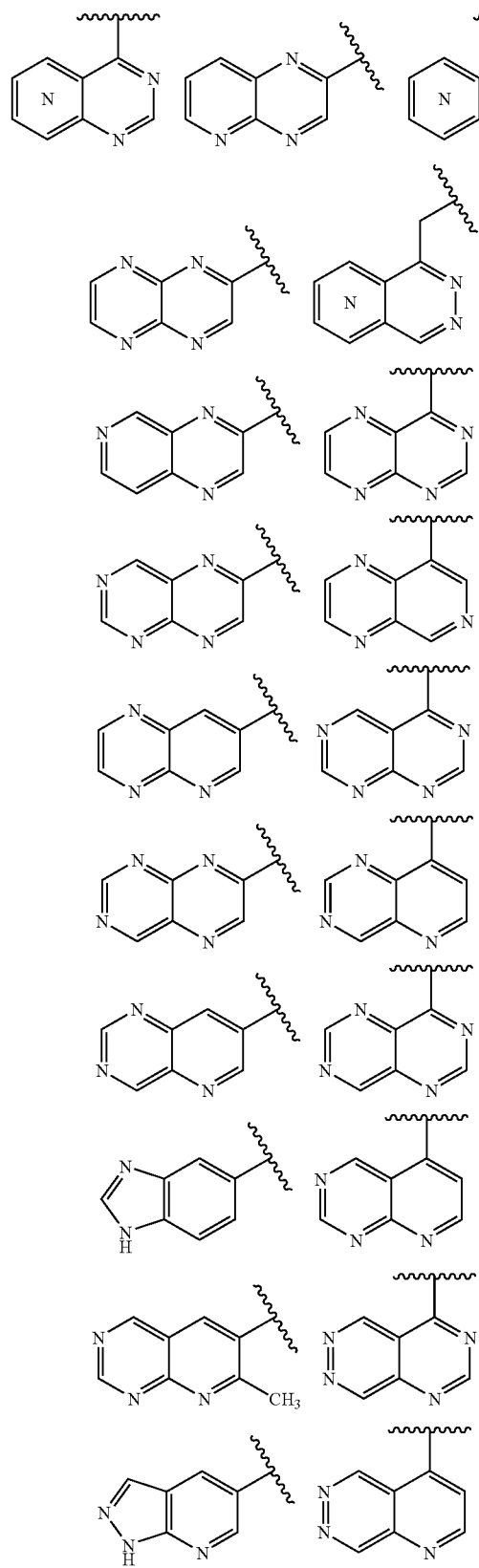
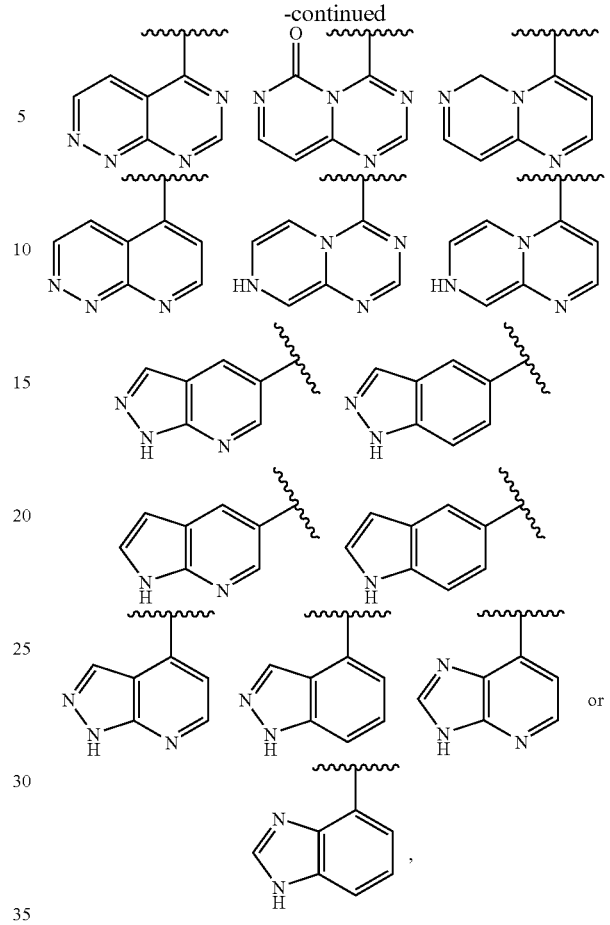
each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; $R^3$ is:
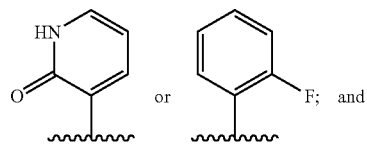 [SMILES: *c1ccc[nH]c1=O ; "or" ; *c1ccccc1F ; "and"]
; and
ring Z is:
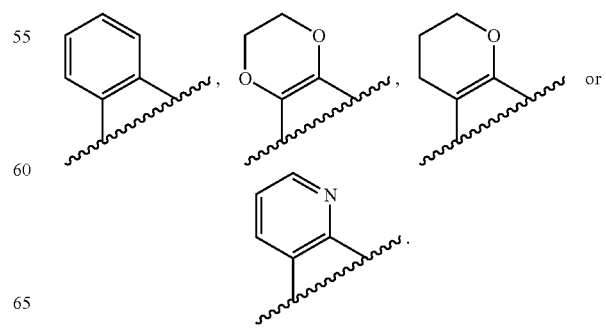

In one embodiment, the invention provides compounds of formula (I), wherein $R^1$ is a bond or —[C($R^{12}$)$_2$]$_r$—.

In another embodiment, the invention provides compounds of formula (I), wherein $R^1$ is a bond or —[C($R^{12}$)$_2$]$_r$—; and $R^{10}$ is phenyl, pyridyl or pyrimidinyl, each of which is unsubstituted or optionally and independently substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N($R^9$)$_2$, -alkylene-O$R^9$, —O$R^9$, —N($R^9$)$_2$, —NHC(O)$R^8$, —NHSO$_2$$R^{11}$, —S(O)$_p$$R^{11}$ or —SO$_2$N($R^9$)$_2$.

In another embodiment, the invention provides compounds of formula (I), wherein $R^2$ is —C(O)OH, —C(O)Oalkyl, —C(O)NH$_2$, —C(O)NH-alkyl, —C(O)NH-cycloalkyl, —C(O)NHSO$_2$$R^{11}$, heteroaryl,

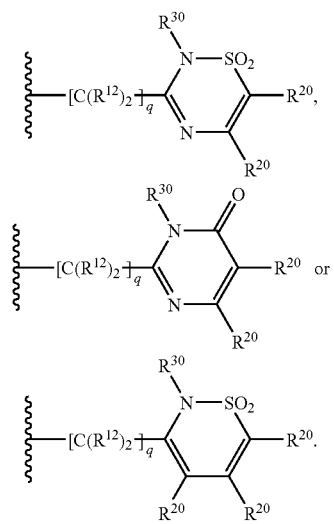

wherein a heteroaryl group can be optionally substituted with up to 3 substituents, which are the same or different, and are selected from alkyl, aryl, heteroaryl, halo, haloalkyl, hydroxyalkyl, hydroxy, —CN, —C(O)$R^8$, —C(O)O$R^9$, —C(O)N($R^9$)$_2$, —[C($R^{12}$)$_2$]$_q$—O$R^9$, —[C($R^{12}$)$_2$]$_q$—N($R^9$)$_2$, —NHC(O)$R^8$, —NHSO$_2$$R^{11}$, —S(O)$_p$$R^{11}$ or —SO$_2$N($R^9$)$_2$;

In still another embodiment, the invention provides compounds of formula (I), wherein
$R^2$ is —C(O)NHSO$_2$-alkyl, —C(O)NHSO$_2$-aryl, —C(O)NHSO$_2$-cycloalkyl or —C(O)NHSO$_2$-alkylene-cycloalkyl.

In yet another embodiment, the invention provides compounds of formula (I), wherein $R^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2$$R^{11}$, —S(O)$_2$$R^{11}$ or —SO$_2$NH$R^{11}$.

In a further embodiment, the invention provides compounds of formula (I), wherein $R^3$ is pyridyl, or phenyl which is unsubstituted or optionally and independently substituted with 1 to 3 substituents, which are the same or different, and are selected from alkyl, aryl, heteroaryl-, halo, haloalkyl, hydroxyalkyl, hydroxy, —CN, —C(O)$R^8$, —C(O)N($R^9$)$_2$, —[C($R^{12}$)$_2$]$_q$—O$R^9$, —[C($R^{12}$)$_2$]$_q$—N($R^9$)$_2$, or —NHC(O)$R^8$.

In one embodiment, the invention provides compounds of formula (I), wherein ring Z is 6-membered heterocycloalkyl, 6-membered heteroaryl, 6-membered heteroaryl or cyclopentyl.

In another embodiment, the invention provides compounds of formula (I), wherein ring Z is:

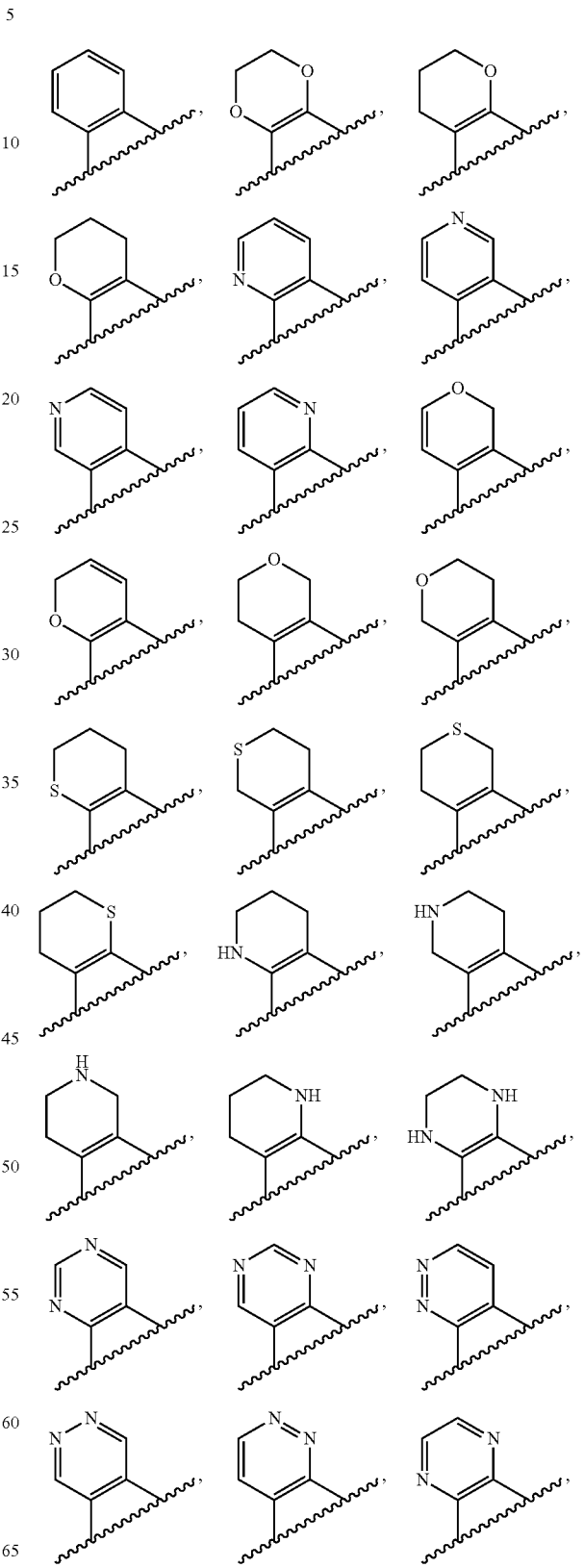

-continued

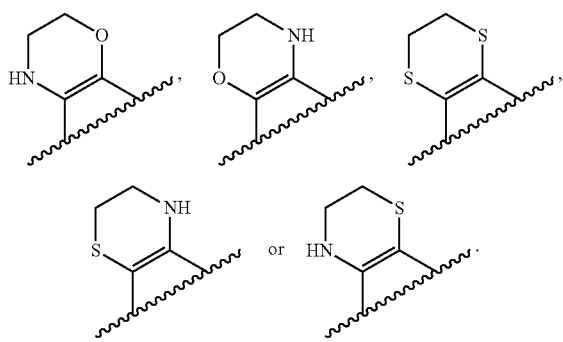

wherein the ring can be optionally substituted as set forth above for the compounds of formula (I).

In another embodiment, the invention provides compounds of formula (I), wherein $R^6$ and $R^7$ are each independently selected from H, alkyl, F, Cl, —$CF_3$, —OH, —O-alkyl, —$OCF_3$, —$NH_2$ or —$NHSO_2$-alkyl.

In another embodiment, $R^1$ is —$CH_2$—, $R^{10}$ is

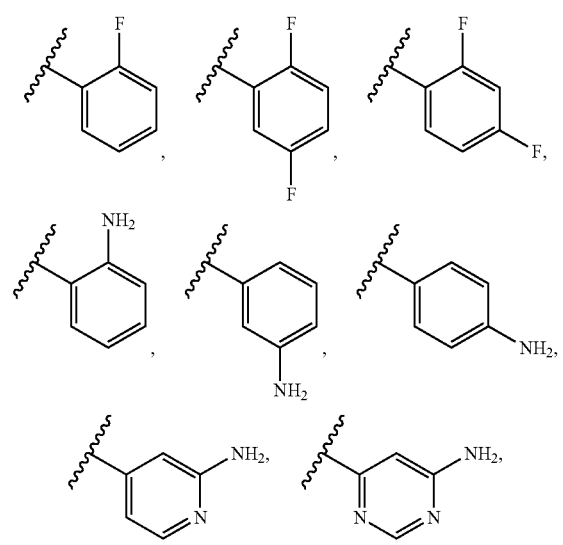

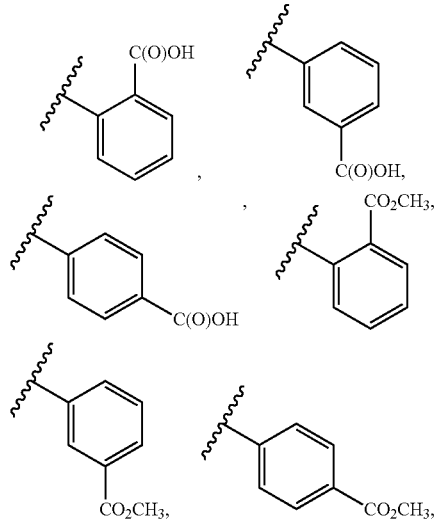

-continued

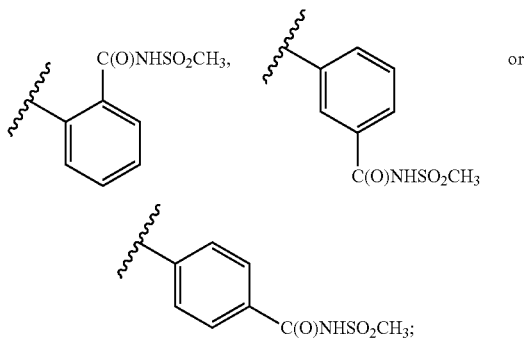

$R^2$ is —C(O)OH, —C(O)$NHSO_2$-alkyl or —C(O)$NHSO_2$-cycloalkyl; $R^3$ is:

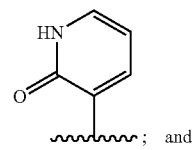

; and ring Z is:

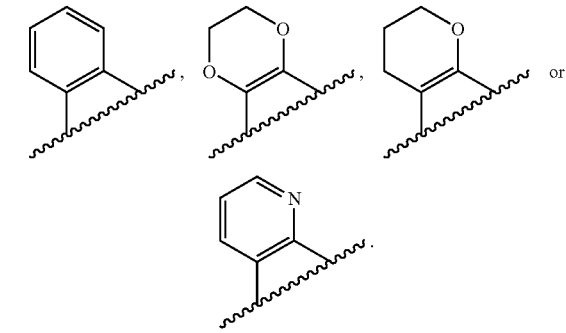

In another embodiment, $R^1$ is —$CH_2$—, $R^{10}$ is

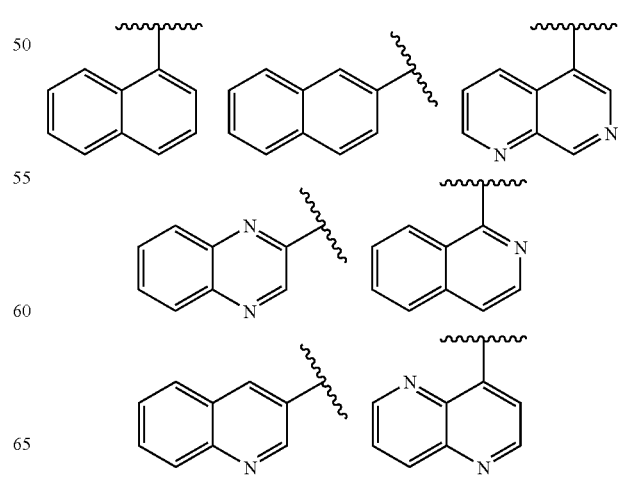

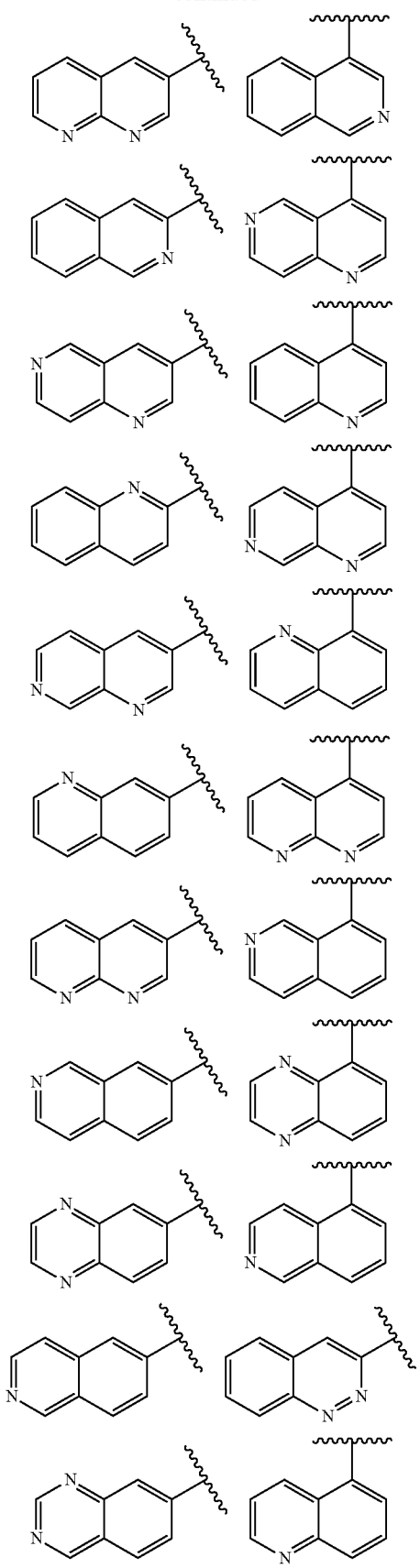
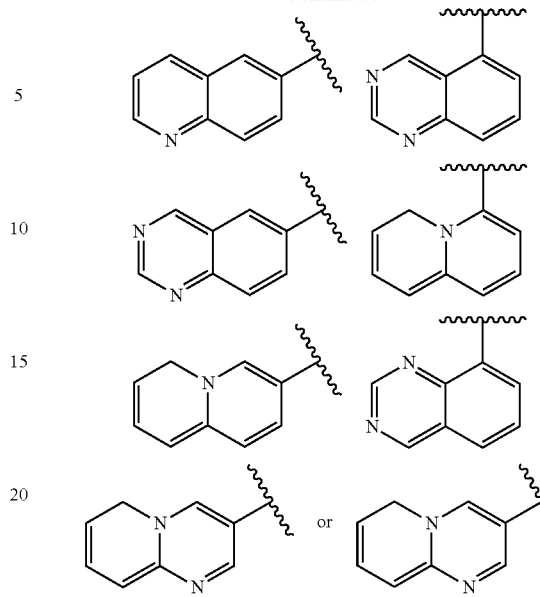
each of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl; $R^2$ is —C(O)OH, —C(O)NHSO$_2$-alkyl or —C(O)NHSO$_2$-cycloalkyl; $R^3$ is:
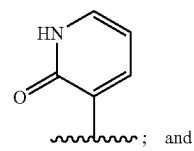 [SMILES: *c1ccc[nH]c1=O]; and
ring Z is:
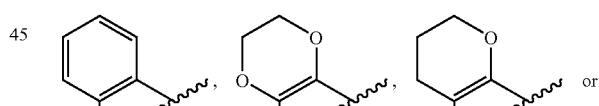
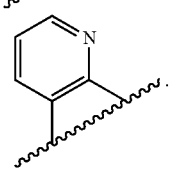.
In a further embodiment, $R^1$ is —$CH_2$—, $R^{10}$ is
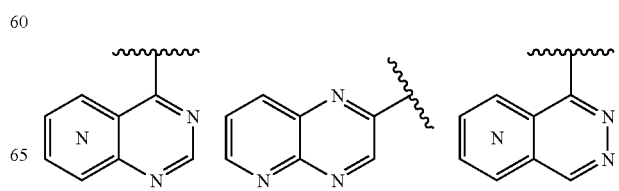

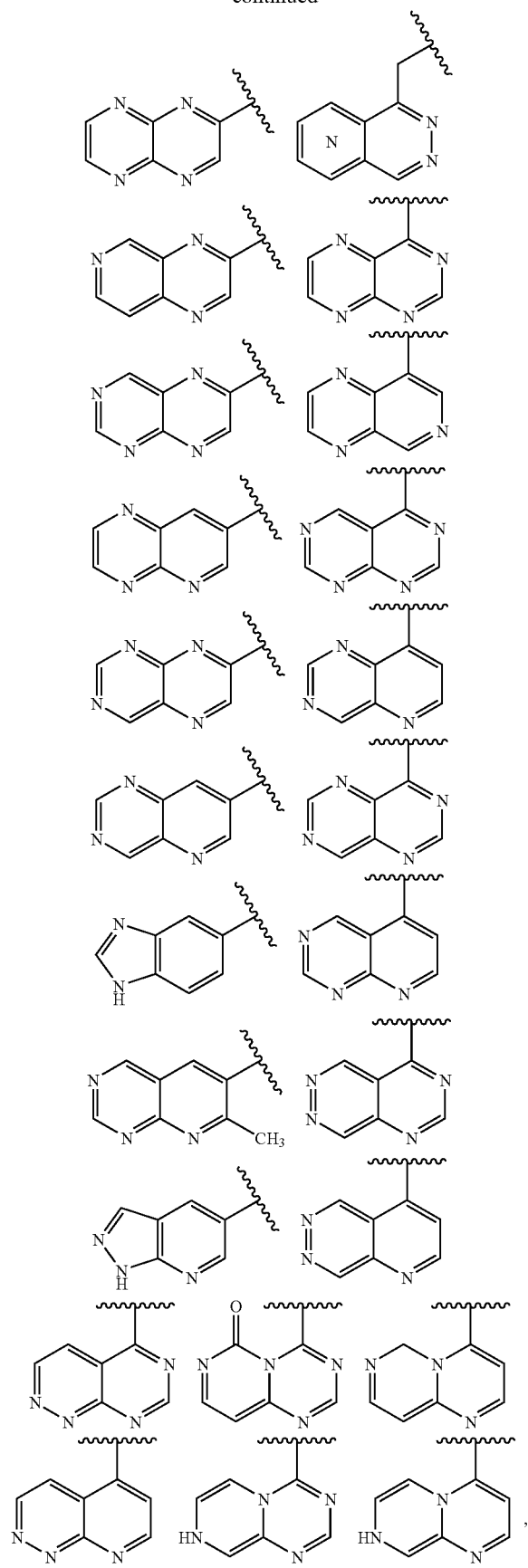
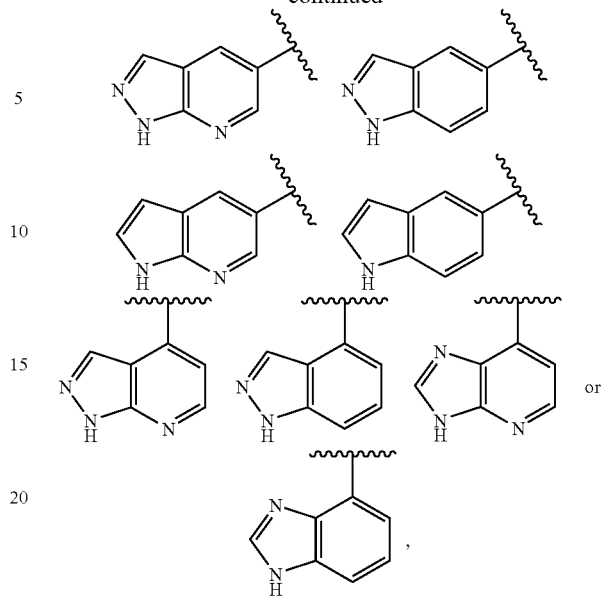

each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl; R$^2$ is —C(O)OH, —C(O)NHSO$_2$-alkyl or —C(O)NHSO$_2$-cycloalkyl; R$^3$ is:

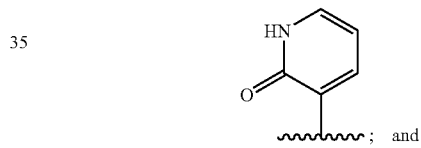; and ring Z is:

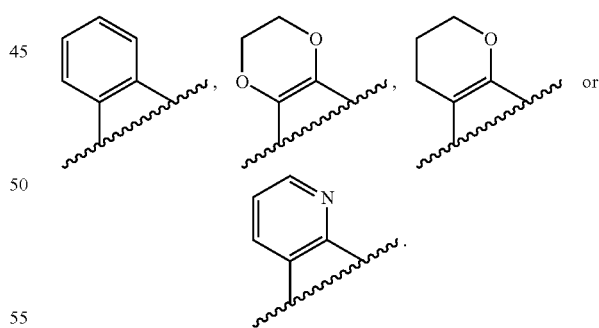

In still another embodiment, the invention provides compounds of formula (I), wherein ring Z is 6-membered heterocycloalkyl, 6-membered heteroaryl, 6-membered heteroaryl or cyclopentyl;

R$^2$ is —C(O)OH, heteroaryl, or —C(O)NHSO$_2$R$^{11}$;

R$^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R$^9$)$_2$, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

R⁶ and R⁷ are each independently selected from H, alkyl, F, Cl, —CF₃, —OH, —O-alkyl, —OCF₃, —NH₂ or —NHSO₂-alkyl; and R¹⁰ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R⁹)₂, -(alkylene)-OR⁹, —OR⁹, —N(R⁹)₂, —NHC(O)R⁸, —NHSO₂R¹¹, —S(O)ₚR¹¹ or —SO₂N(R⁹)₂

In yet another embodiment, the invention provides compounds of formula (I), wherein ring Z is 6-membered heterocycloalkyl, 6-membered heteroaryl, 6-membered heteroaryl or cyclopentyl;

R² is —C(O)OH, —C(O)NH₂, —C(O)NH-alkyl, —C(O)NHSO₂R¹¹,

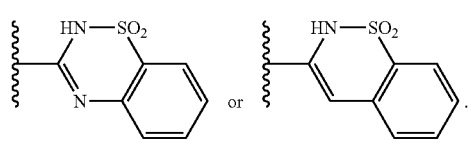

wherein the arylthiazin-yl- or arylthiadiazol-yl- group can be optionally substituted with up to 3 substituents, which are the same or different, and are selected from alkyl, heteroaryl, halo, haloalkyl, hydroxyalkyl, hydroxy, —CN, —C(O)N(R⁹)₂, —[C(R¹²)₂]_q—OR⁹, —[C(R¹²)₂]_q—N(R⁹)₂, —NHC(O)R⁸, —NHSO₂R¹¹, —S(O)ₚR¹¹ or —SO₂N(R⁹)₂;

R³ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

R⁶ and R⁷ are each independently selected from H, alkyl, F, Cl, —CF₃, —OH, —O-alkyl, —OCF₃, —NH₂ or —NHSO₂-alkyl; and R¹⁰ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R⁹)₂, -(alkylene)-OR⁹, —OR⁹, —N(R⁹)₂, —NHC(O)R⁸, —NHSO₂R¹¹, —S(O)ₚR¹¹ or —SO₂N(R⁹)₂.

In a further embodiment, the invention provides compounds of formula (I), wherein ring Z is 6-membered heterocycloalkyl, 6-membered heteroaryl, 6-membered heteroaryl or cyclopentyl;

R² is —C(O)OH, heteroaryl, or —C(O)NHSO₂R¹¹;

R³ is phenyl, pyridyl or

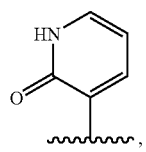

each of which can be optionally substituted with one to 3 substituents, which are the same or different, and are selected from alkyl, —CF₃, —CN, —C(O)alkyl, —C(O)NH₂, —C(O)NHalkyl, F, Cl, —OH, —OCF₃, —NH₂, —NHalkyl, —NHC(O)NH₂, —NHC(O)NH-alkyl, —NHSO₂alkyl, —S(O)₂-alkyl or —SO₂NHalkyl;

R⁶ and R⁷ are each independently selected from H, alkyl, F, Cl, —CF₃, —OH, —O-alkyl, —OCF₃, —NH₂ or —NHSO₂-alkyl; and R¹⁰ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R⁹)₂, -(alkylene)-OR⁹, —OR⁹, —N(R⁹)₂, —NHC(O)R⁸, —NHSO₂R¹¹, —S(O)ₚR¹¹ or —SO₂N(R⁹)₂.

In one embodiment, the invention provides compounds of formula (I), wherein ring Z is:

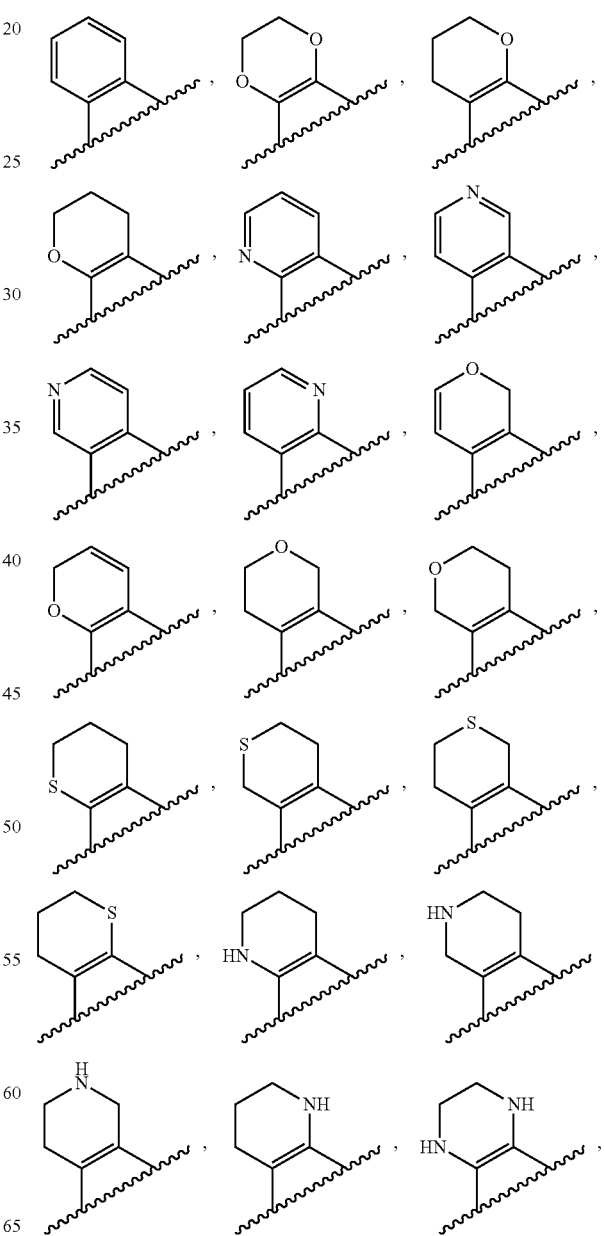

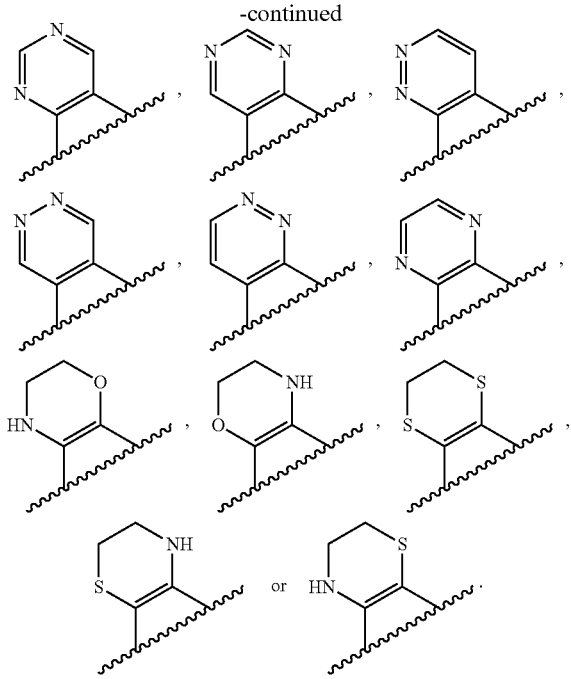
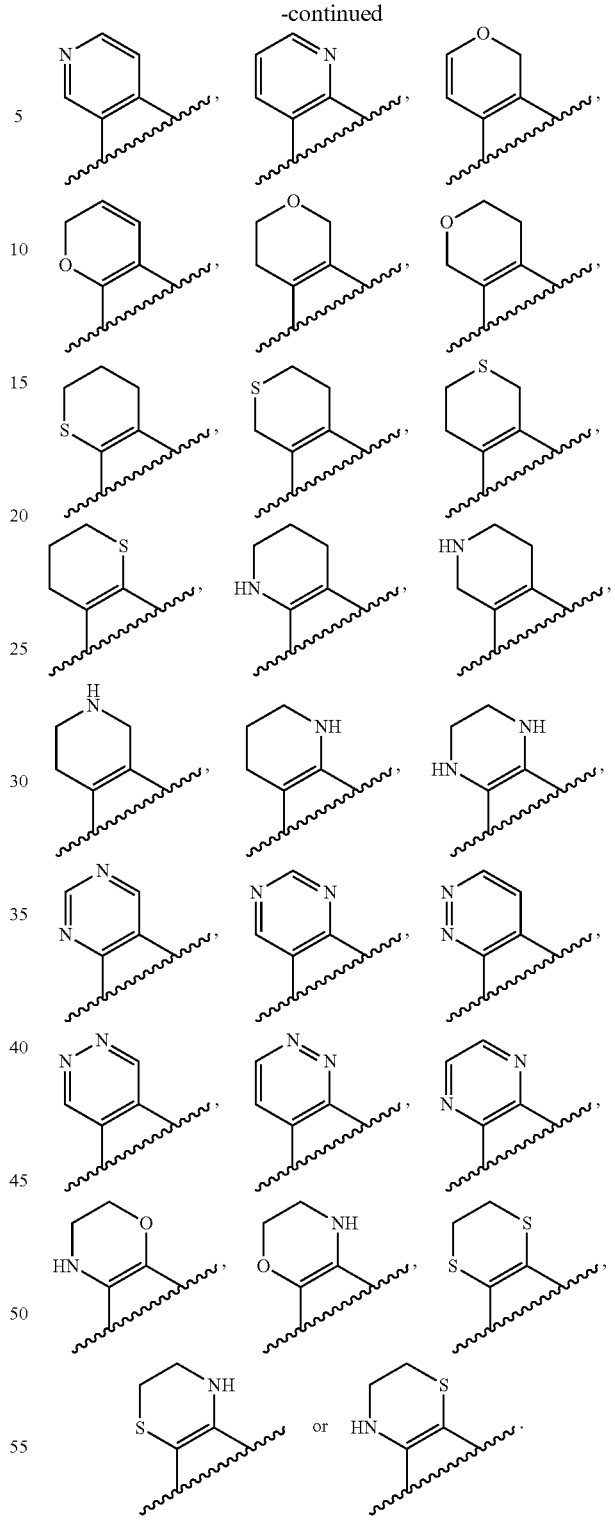

wherein the ring can be optionally substituted as set forth above for the compounds of formula (I);

R² is —C(O)OH, heteroaryl, or —C(O)NHSO₂R¹¹;

R³ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

R⁶ and R⁷ are each independently selected from H, alkyl, F, Cl, —CF₃, —OH, —O-alkyl, —OCF₃, —NH₂ or —NHSO₂-alkyl; and R¹⁰ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R⁹)₂, -(alkylene)-OR⁹, —OR⁹, —N(R⁹)₂, —NHC(O)R⁸, —NHSO₂R¹¹, —S(O)ₚR¹¹ or —SO₂N(R⁹)₂.

In another embodiment, the invention provides compounds of formula (I), wherein ring Z is:

wherein ring Z can be substituted with up to 3 optional ring carbon substituents, which are the same or different, and which are selected from H, alkyl, —OH, F, Cl, —O-alkyl, —CF₃, —OCF₃ and cycloalkyl;

R² is —C(O)OH, heteroaryl, or —C(O)NHSO₂R¹¹;

R³ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

R⁶ and R⁷ are each independently selected from H, alkyl, F, Cl, —CF₃, —OH, —O-alkyl, —OCF₃, —NH₂ or —NHSO₂-alkyl; and R¹⁰ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R⁹)₂, -(alkylene)-OR⁹, —OR⁹, —N(R⁹)₂, —NHC(O)R⁸, —NHSO₂R¹¹, —S(O)ₚR¹¹ or —SO₂N(R⁹)₂.

In another embodiment, the invention provides compounds of formula (I), wherein ring Z is:

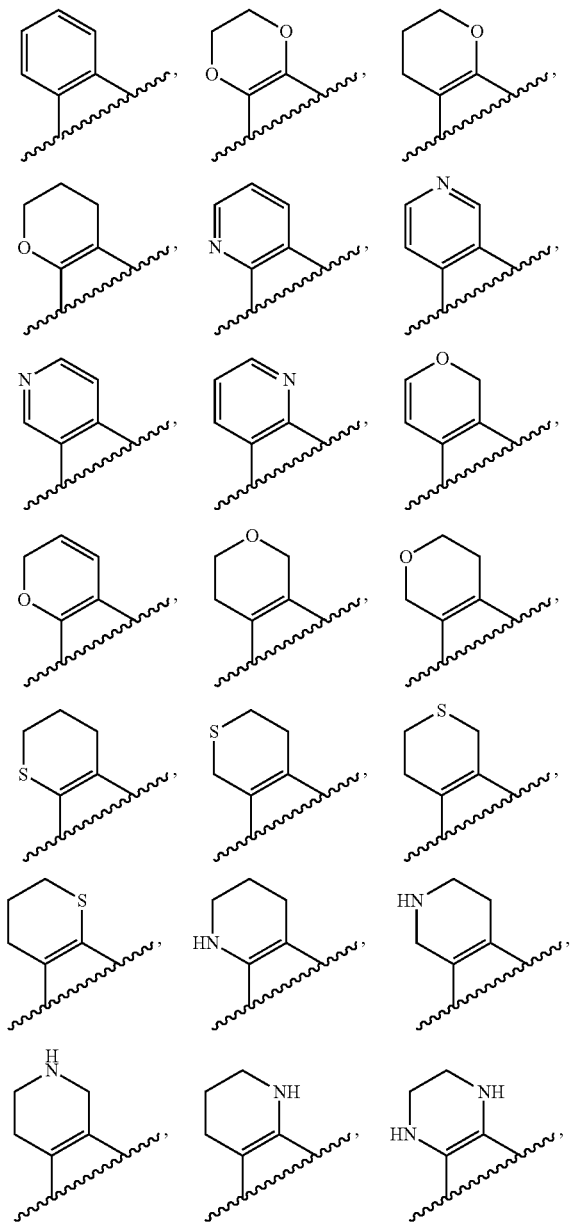

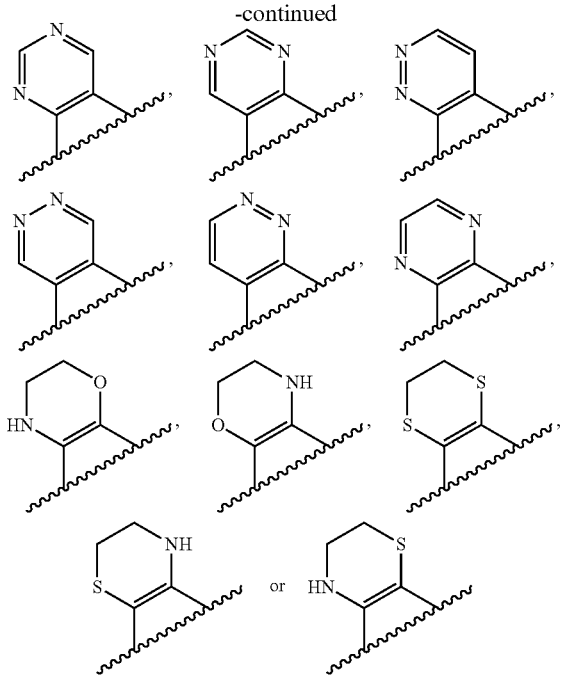

wherein the ring can be optionally substituted as set forth above for the compounds of formula (I);

R² is —C(O)OH, —C(O)NH₂, —C(O)NH-alkyl, —C(O)NHSO₂R¹¹,

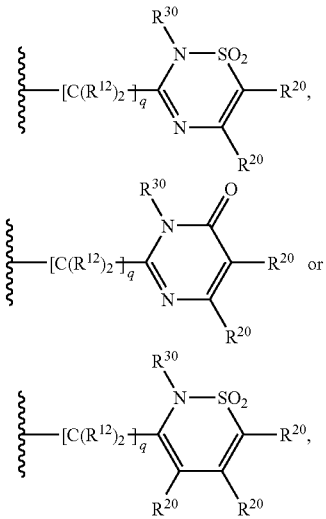

wherein the arylthiazin-yl- or arylthiadiazol-yl- group can be optionally substituted with up to 3 substituents, which are the same or different, and are selected from alkyl, heteroaryl, halo, haloalkyl, hydroxyalkyl, hydroxy, —CN, —C(O)N(R⁹)₂, —[C(R¹²)₂]_q—OR⁹, —[C(R¹²)₂]_q—N(R⁹)₂, —NHC(O)R⁸, —NHSO₂R¹¹, —S(O)ₚR¹¹ or —SO₂N(R⁹)₂;

R³ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

$R^6$ and $R^7$ are each independently selected from H, alkyl, F, Cl, —$CF_3$, —OH, —O-alkyl, —$OCF_3$, —$NH_2$ or —$NHSO_2$-alkyl; and $R^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N($R^9$)$_2$, -(alkylene)-$OR^9$, —$OR^9$, —N($R^9$)$_2$, —NHC(O)$R^8$, —$NHSO_2R^{11}$, —S(O)$_pR^{11}$ or —$SO_2N(R^9)_2$.

In still another embodiment, the invention provides compounds of formula (I), wherein ring Z is:

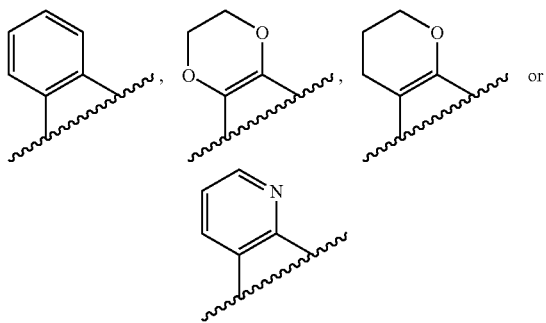

wherein ring Z can be optionally substituted as set forth above for the compounds of formula (I);

$R^2$ is —C(O)OH, —C(O)$NH_2$, —C(O)NH-alkyl, —C(O)$NHSO_2R^{11}$,

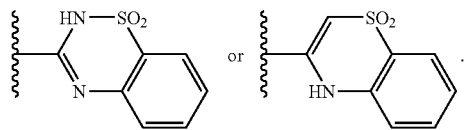

wherein the heteroaryl, arylthiazin-yl- or arylthiadiazol-yl-group can be optionally substituted with up to 3 substituents, which are the same or different, and are selected from alkyl, heteroaryl, halo, haloalkyl, hydroxyalkyl, hydroxy, —CN, —C(O)N($R^9$)$_2$, —[C($R^{12}$)$_2$]$_q$—$OR^9$, —[C($R^{12}$)$_2$]$_q$—N($R^9$)$_2$, —NHC(O)$R^8$, —$NHSO_2R^{11}$, —S(O)$_pR^{11}$ or —$SO_2N(R^9)_2$;

$R^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N($R^9$)$_2$, —N($R^9$)$_2$, —O-haloalkyl, —NHC(O)$NH_2$, —NHC(O)NH-alkyl, —$NHSO_2R^{11}$, —S(O)$_2R^{11}$ or —$SO_2NHR^{11}$;

$R^6$ and $R^7$ are each independently selected from H, alkyl, F, Cl, —$CF_3$, —OH, —O-alkyl, —$OCF_3$, —$NH_2$ or —$NHSO_2$-alkyl; and $R^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N($R^9$)$_2$, -(alkylene)-$OR^9$, —$OR^9$, —N($R^9$)$_2$, —NHC(O)$R^8$, —$NHSO_2R^{11}$, —S(O)$_pR^{11}$ or —$SO_2N(R^9)_2$.

In another embodiment, $R^1$ is —$CH_2$ and $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In another embodiment, $R^1$ is —$CH_2$ and $R^{10}$ is quinoline or quinolinone, either of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In still another embodiment, $R^1$ is —$CH_2$ and $R^{10}$ is pteridine or pteridinone, either of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In another embodiment, $R^1$ is —$CH_2$; $R^2$ is —C(O)OH, —C(O)$NHSO_2$-alkyl or —C(O)$NHSO_2$-cycloalkyl; and $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In another embodiment, $R^1$ is —$CH_2$; $R^2$ is —C(O)OH, —C(O)$NHSO_2$-alkyl or —C(O)$NHSO_2$-cycloalkyl; and $R^{10}$ is quinoline or quinolinone, either of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In still another embodiment, $R^1$ is —$CH_2$; $R^2$ is —C(O)OH, —C(O)$NHSO_2$-alkyl or —C(O)$NHSO_2$-cycloalkyl; and $R^{10}$ is pteridine or pteridinone, either of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In another embodiment, $R^1$ is —$CH_2$; $R^2$ is —C(O)OH, —C(O)$NHSO_2$-alkyl or —C(O)$NHSO_2$-cycloalkyl; $R^3$ is: and $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, halo, haloalkyl, —O-haloalkyl, —OH, —CN, —$NH_2$, —NH-alkyl, —N(alkyl)$_2$ or —$NHSO_2$-alkyl.

In another embodiment, $R^1$ is —$CH_2$; $R^2$ is —C(O)OH, —C(O)$NHSO_2$-alkyl or —C(O)$NHSO_2$-cycloalkyl; $R^3$ is:

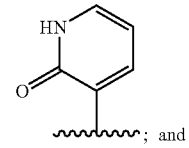 [SMILES: *c1ccc[nH]c1=O ; ";"]

; and $R^{10}$ is quinoline or quinolinone, either of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

In still another embodiment, R$^1$ is —CH$_2$; R$^2$ is —C(O)OH, —C(O)NHSO$_2$-alkyl or —C(O)NHSO$_2$-cycloalkyl; R$^3$ is:

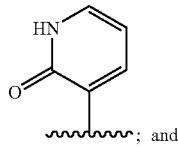 [SMILES: *c1ccc[nH]c1=O ; ";"]; and

R$^{10}$ is pteridine or pteridinone, either of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl. Z is 6-membered heterocycloalkyl, 6-membered heteroaryl, 6-membered heteroaryl or cyclopentyl;

In one embodiment, R$^{11}$ is —[C(R$^{12}$)$_2$]$_r$—; R$^2$ is —C(O)OH, —C(O)NH$_2$, —C(O)NH-alkyl, —C(O)NHSO$_2$R$^{11}$,

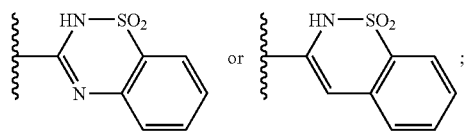

R$^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R$^9$)$_2$, —N(R$^9$)$_2$, —O-haloalkyl, —NHC(O)NH$_2$, —NHC(O)NH-alkyl, —NHSO$_2$R$^{11}$, —S(O)$_2$R$^{11}$ or —SO$_2$NHR$^{11}$;

R$^6$ and R$^7$ are each independently selected from H, alkyl, F, Cl, —CF$_3$, —OH, —O-alkyl, —OCF$_3$, —NH$_2$ or —NHSO$_2$-alkyl; and R$^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R$^9$)$_2$, -(alkylene)-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, R$^1$ is —[C(R$^{12}$)$_2$]$_r$—; R$^2$ is —C(O)OH or —C(O)NHSO$_2$R$^{11}$;

R$^3$ is:

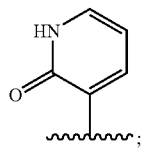;

R$^6$ and R$^7$ are each independently selected from H, alkyl, F, Cl, —CF$_3$, —OH, —O-alkyl, —OCF$_3$, —NH$_2$ or —NHSO$_2$-alkyl; and R$^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R$^9$)$_2$, -(alkylene)-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, R$^1$ is —[C(R$^{12}$)$_2$]$_r$—; R$^2$ is —C(O)OH or —C(O)NHSO$_2$R$^{11}$;

R$^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, —CN, —C(O)alkyl, —C(O)N(R$^9$)$_2$, —N(R$^9$)$_2$, —O-haloalkyl, —NHC(O)NH$_2$, —NHC(O)NH-alkyl, —NHSO$_2$R$^{11}$, —S(O)$_2$R$^{11}$ or —SO$_2$NHR$^{11}$;

R$^6$ and R$^7$ are each independently selected from H, alkyl, F, Cl, —CF$_3$, —OH, —O-alkyl, —OCF$_3$, —NH$_2$ or —NHSO$_2$-alkyl; and R$^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R$^9$)$_2$, -(alkylene)-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, R$^1$ is —[C(R$^{12}$)$_2$]$_r$—; R$^2$ is —C(O)OH or —C(O)NHSO$_2$R$^{11}$;

R$^3$ is:

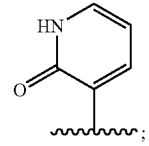 [SMILES: *c1ccc[nH]c1=O ; ";"];

R$^6$ and R$^7$ are each independently selected from H, alkyl, F, Cl, —CF$_3$, —OH, —O-alkyl, —OCF$_3$, —NH$_2$ or —NHSO$_2$-alkyl; and R$^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R$^9$)$_2$, -(alkylene)-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$; and ring Z is:

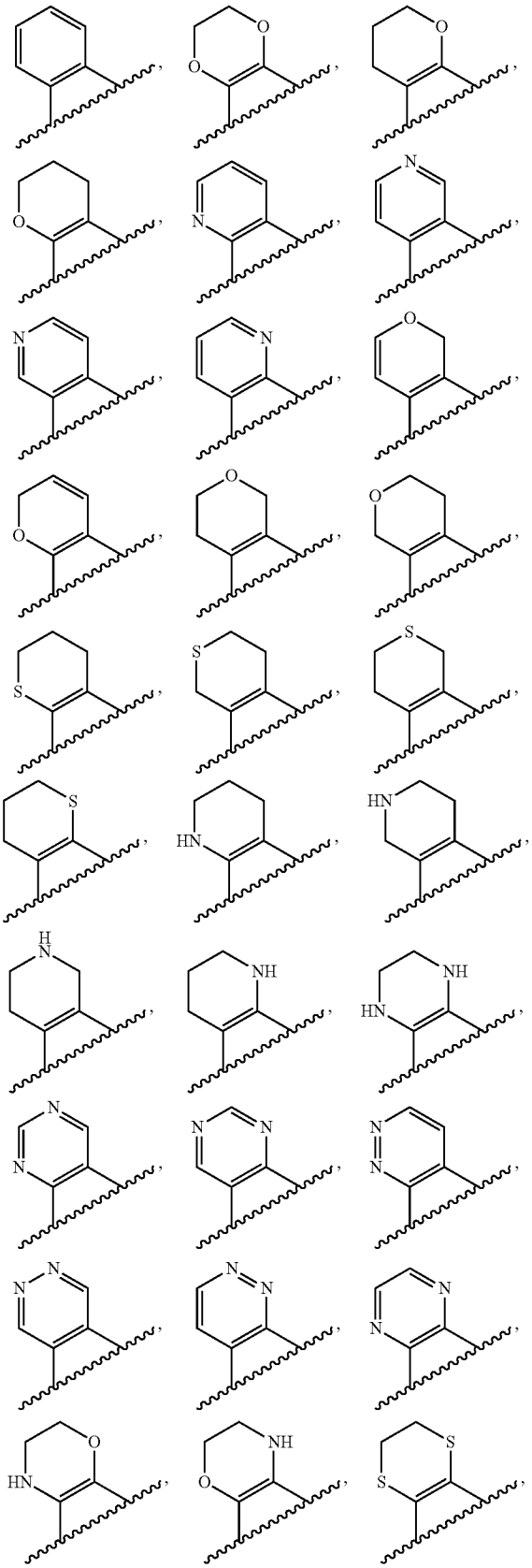

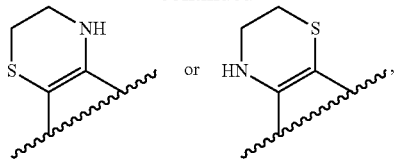

wherein the ring can be optionally substituted as set forth above in claim 1.

In another embodiment, $R^1$ is $-[C(R^{12})_2]_r-$; $R^2$ is $-C(O)OH$ or $-C(O)NHSO_2R^{11}$;

$R^3$ is aryl, heteroaryl or heterocycloalkenyl, each of which is unsubstituted or optionally and independently substituted with up to 3 substituents, which are the same or different, and are selected from alkyl, aryl, heteroaryl, halo, haloalkyl, hydroxyalkyl, hydroxy, $-CN$, $-C(O)$alkyl, $-C(O)N(R^9)_2$, $-N(R^9)_2$, $-O$-haloalkyl, $-NHC(O)NH_2$, $-NHC(O)NH$-alkyl, $-NHSO_2R^{11}$, $-S(O)_2R^{11}$ or $-SO_2NHR^{11}$;

$R^6$ and $R^7$ are each independently selected from H, alkyl, F, Cl, $-CF_3$, $-OH$, $-O$-alkyl, $-OCF_3$, $-NH_2$ or $-NHSO_2$-alkyl; and $R^{10}$ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, $-CN$, $-C(O)$alkyl, $-C(O)O$alkyl, $-C(O)N(R^9)_2$, -(alkylene)-$OR^9$, $-OR^9$, $-N(R^9)_2$, $-NHC(O)R^8$, $-NHSO_2R^{11}$, $-S(O)_pR^{11}$ or $-SO_2N(R^9)_2$; and ring Z is:

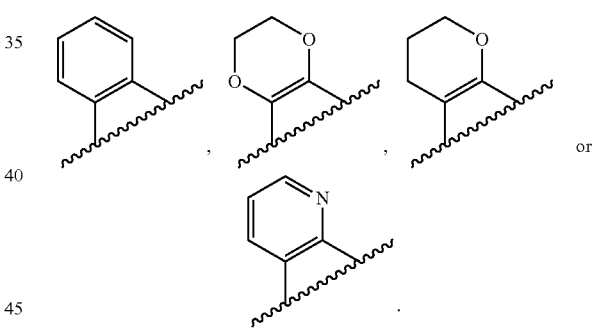

In one embodiment, $R^1$ is $-CH_2-$, $R^2$ is $-C(O)OH$ or $-C(O)NHSO_2R^{11}$; $R^3$ is:

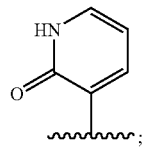 [SMILES: *c1ccc[nH]c1=O ; ";"]

$R^{10}$ is bicyclic heteroaryl; and ring Z is:

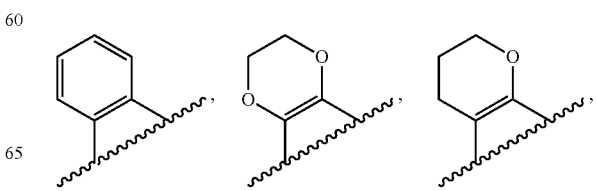

-continued

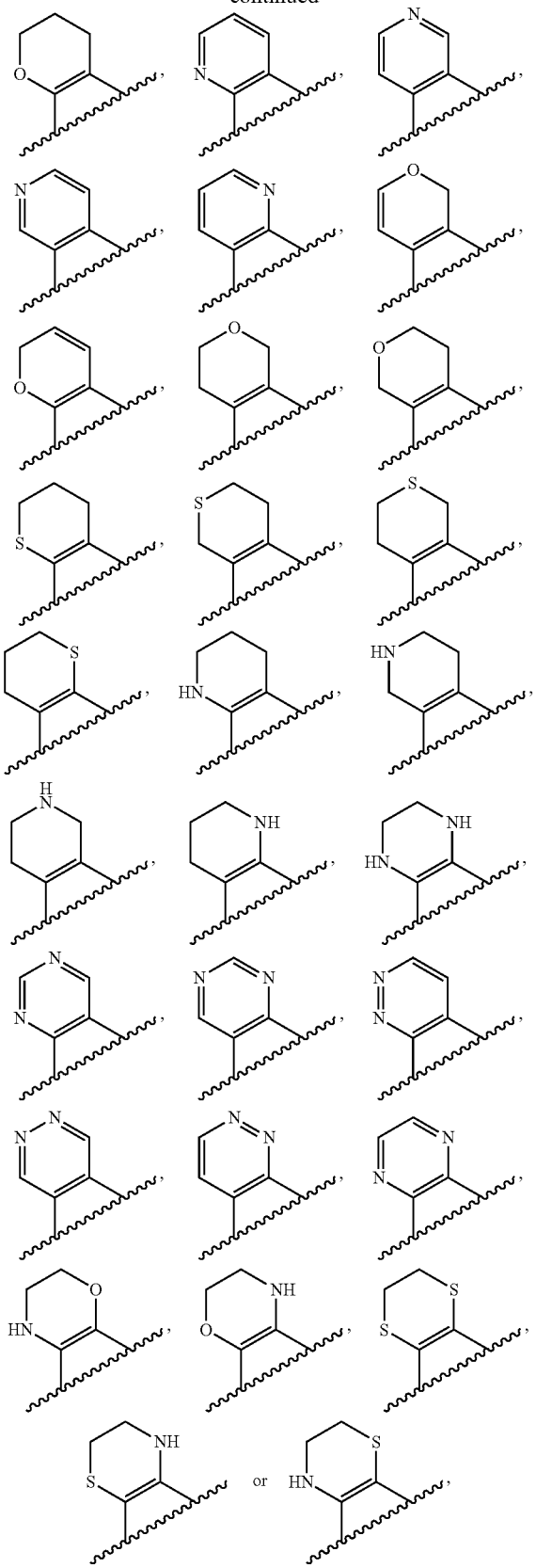

wherein the ring can be optionally substituted as set forth above in claim 1.

In another embodiment, $R^1$ is —CH$_2$—, $R^2$ is —C(O)OH or —C(O)NHSO$_2$R$^{11}$; $R^3$ is:

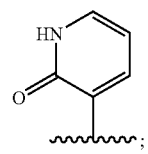

$R^{10}$ is bicyclic heteroaryl; and
ring Z is:

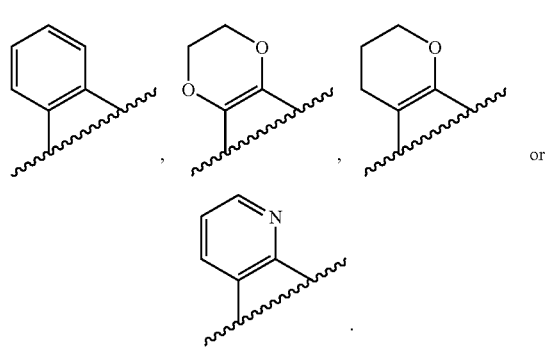

In one embodiment, for the Compounds of Formula (I), $R^1$, $R^2$, $R^3$, $R^6$, $R^7$, $R^{10}$ and Z are selected independently from each other.

In another embodiment, a Compound of Formula (I) is in purified form.

Illustrative examples of the Compounds of Formula (I) include, but are not limited to, the following compounds:

| Compound No. | Structure |
|---|---|
| 1 | 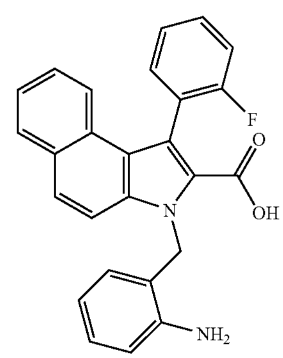 [SMILES: Nc1ccccc1Cn1c(C(=O)O)c(-c2ccccc2F)c2c3ccccc3ccc21] |

-continued
| Compound No. | Structure |
|---|---|
| 2 | 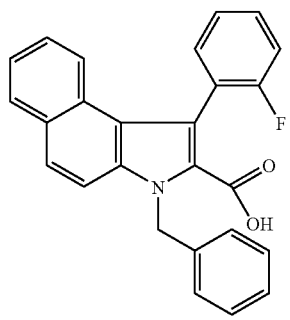 [SMILES: O=C(O)c1c(-c2ccccc2F)c2c3ccccc3ccc2n1Cc1ccccc1] |
| 3 | 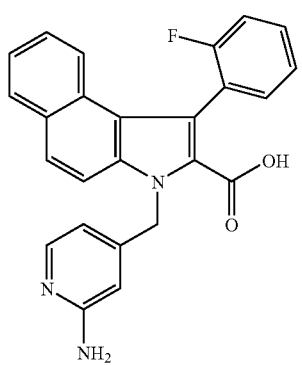 [SMILES: Nc1cc(Cn2c(C(=O)O)c(-c3ccccc3F)c3c4ccccc4ccc32)ccn1] |
| 4 | 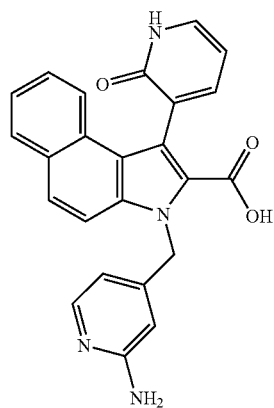 [SMILES: Nc1cc(Cn2c(C(=O)O)c(-c3ccc[nH]c3=O)c3c4ccccc4ccc32)ccn1] |
| 5 | 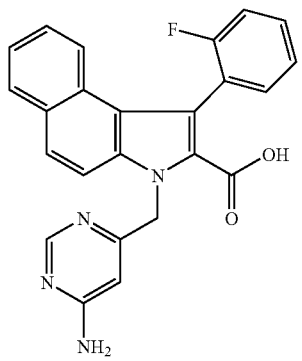 [SMILES: Nc1cc(Cn2c(C(=O)O)c(-c3ccccc3F)c3c4ccccc4ccc32)ncn1] |
-continued
| Compound No. | Structure |
|---|---|
| 6 | 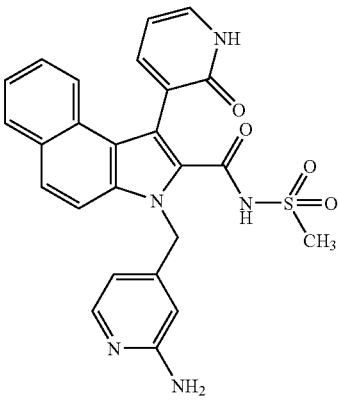 [SMILES: CS(=O)(=O)NC(=O)c1c(-c2ccc[nH]c2=O)c2c3ccccc3ccc2n1Cc1ccnc(N)c1] |
| 7 | 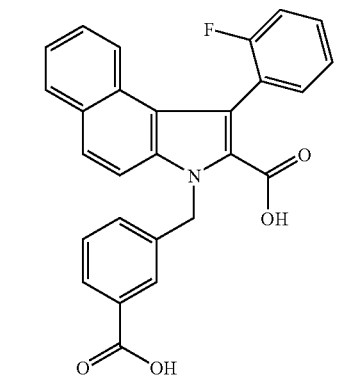 [SMILES: O=C(O)c1cccc(Cn2c(C(=O)O)c(-c3ccccc3F)c3c4ccccc4ccc32)c1] |
| 8 | 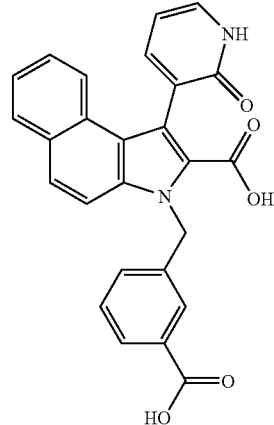 [SMILES: O=C(O)c1cccc(Cn2c(C(=O)O)c(-c3ccc[nH]c3=O)c3c4ccccc4ccc32)c1] |

-continued
| Compound No. | Structure |
|---|---|
| 9 | 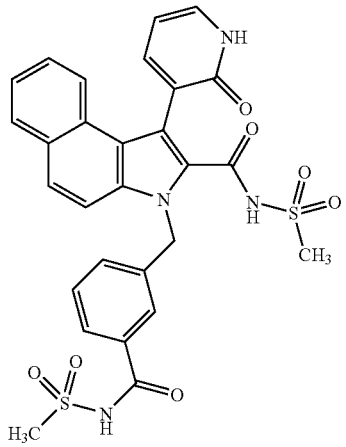 [SMILES: CS(=O)(=O)NC(=O)c1cccc(Cn2c(C(=O)NS(C)(=O)=O)c(-c3ccc[nH]c3=O)c3c4ccccc4ccc32)c1] |
| 10 | 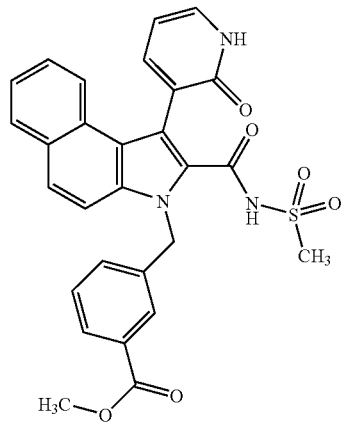 [SMILES: COC(=O)c1cccc(Cn2c(C(=O)NS(C)(=O)=O)c(-c3ccc[nH]c3=O)c3c4ccccc4ccc32)c1] |
| 11 | 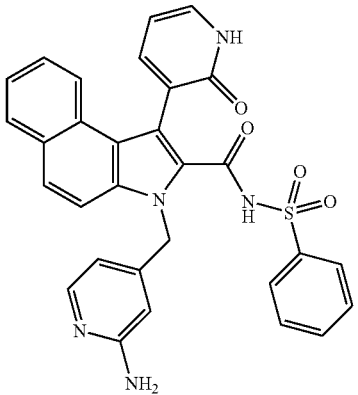 [SMILES: Nc1cc(Cn2c(C(=O)NS(=O)(=O)c3ccccc3)c(-c3ccc[nH]c3=O)c3c4ccccc4ccc32)ccn1] |
-continued
| Compound No. | Structure |
|---|---|
| 12 | 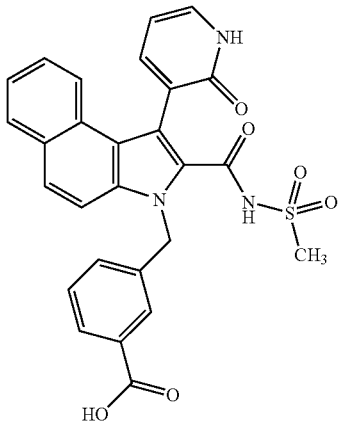 [SMILES: CS(=O)(=O)NC(=O)c1c(-c2ccc[nH]c2=O)c2c3ccccc3ccc2n1Cc1cccc(C(=O)O)c1] |
| 13 | 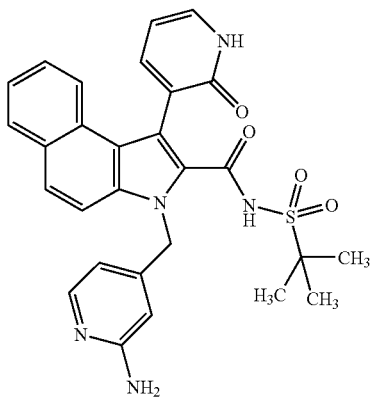 [SMILES: CC(C)(C)S(=O)(=O)NC(=O)c1c(-c2ccc[nH]c2=O)c2c3ccccc3ccc2n1Cc1ccnc(N)c1] |
| 14 | 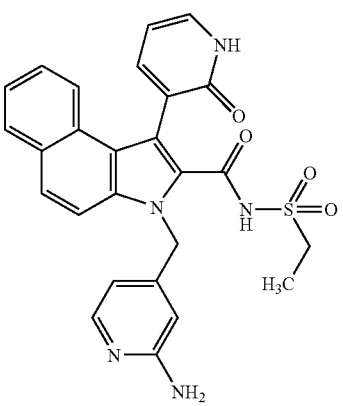 [SMILES: CCS(=O)(=O)NC(=O)c1c(-c2ccc[nH]c2=O)c2c3ccccc3ccc2n1Cc1ccnc(N)c1] |

| Compound No. | Structure |
|---|---|
| 15 | 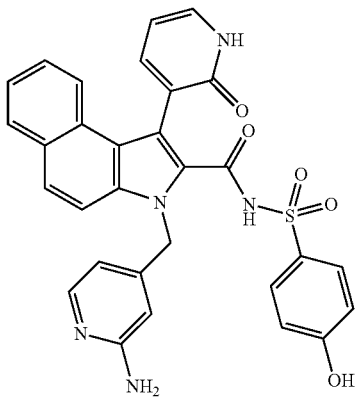 [SMILES: Nc1cc(Cn2c(C(=O)NS(=O)(=O)c3ccc(O)cc3)c(-c3ccc[nH]c3=O)c3c4ccccc4ccc32)ccn1] |
| 16 | 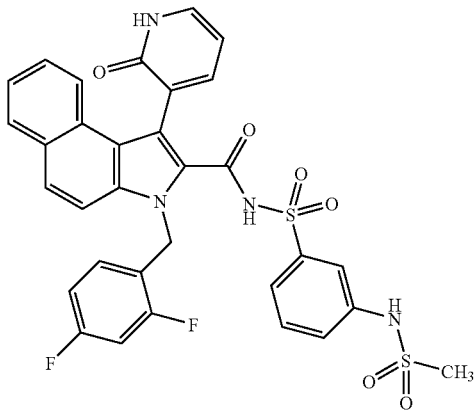 [SMILES: CS(=O)(=O)Nc1cccc(S(=O)(=O)NC(=O)c2c(-c3ccc[nH]c3=O)c3c4ccccc4ccc3n2Cc2ccc(F)cc2F)c1] |
| 17 | 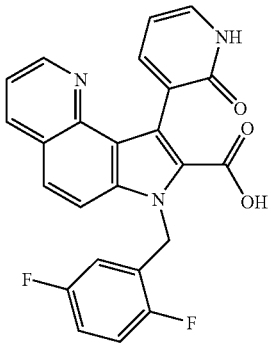 [SMILES: O=C(O)c1c(-c2ccc[nH]c2=O)c2c3ncccc3ccc2n1Cc1cc(F)ccc1F] |
| 18 | 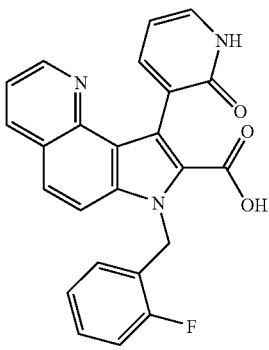 [SMILES: O=C(O)c1c(-c2ccc[nH]c2=O)c2c3ncccc3ccc2n1Cc1ccccc1F] |
| Compound No. | Structure |
|---|---|
| 19 | 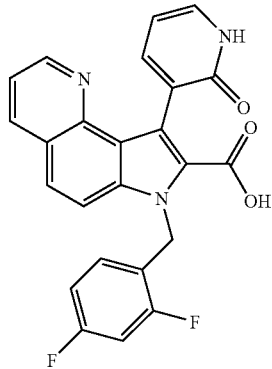 [SMILES: O=C(O)c1c(-c2ccc[nH]c2=O)c2c3ncccc3ccc2n1Cc1ccc(F)cc1F] |
| 20 | 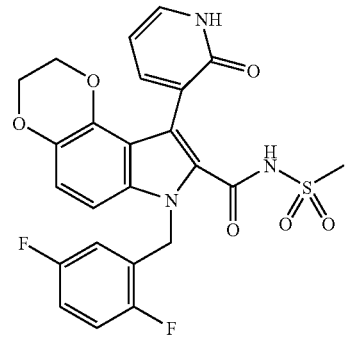 [SMILES: CS(=O)(=O)NC(=O)c1c(-c2ccc[nH]c2=O)c2c3c(ccc2n1Cc1cc(F)ccc1F)OCCO3] |
| 21 | 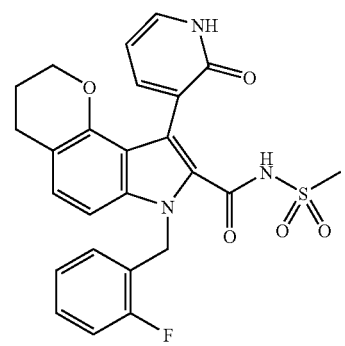 [SMILES: CS(=O)(=O)NC(=O)c1c(-c2ccc[nH]c2=O)c2c3c(ccc2n1Cc1ccccc1F)CCCO3] |
| 22 | 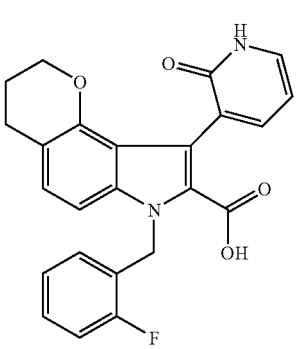 [SMILES: O=C(O)c1c(-c2ccc[nH]c2=O)c2c3c(ccc2n1Cc1ccccc1F)CCCO3] |

-continued
| Compound No. | Structure |
|---|---|
| 23 | 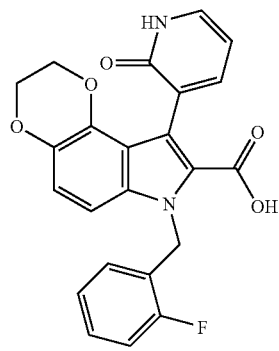 [SMILES: O=C(O)c1c(-c2ccc[nH]c2=O)c2c3c(ccc2n1Cc1ccccc1F)OCCO3] |
| 24 | 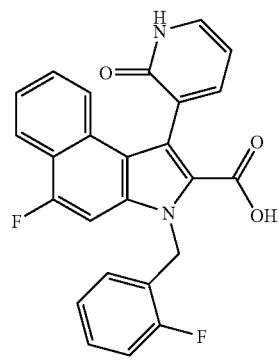 [SMILES: O=C(O)c1c(-c2ccc[nH]c2=O)c2c3ccccc3c(F)cc2n1Cc1ccccc1F] |
| 25 | 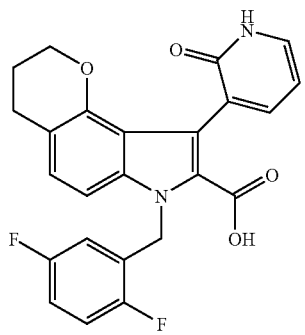 [SMILES: O=C(O)c1c(-c2ccc[nH]c2=O)c2c3c(ccc2n1Cc1cc(F)ccc1F)CCCO3] |
| 26 | 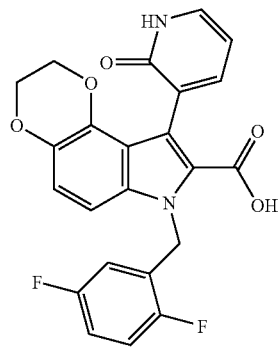 [SMILES: O=C(O)c1c(-c2ccc[nH]c2=O)c2c3c(ccc2n1Cc1cc(F)ccc1F)OCCO3] |
-continued
| Compound No. | Structure |
|---|---|
| 27 | 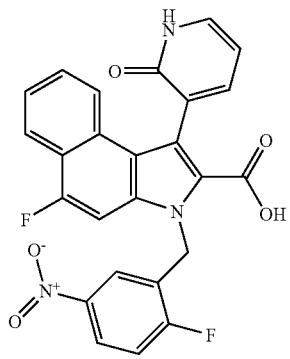 [SMILES: O=C(O)c1c(-c2ccc[nH]c2=O)c2c3ccccc3c(F)cc2n1Cc1cc([N+](=O)[O-])ccc1F] |
| 28 | 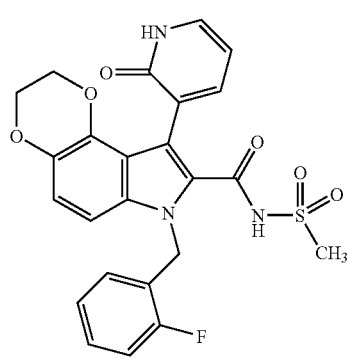 [SMILES: CS(=O)(=O)NC(=O)c1c(-c2ccc[nH]c2=O)c2c3c(ccc2n1Cc1ccccc1F)OCCO3] |
| 29 | 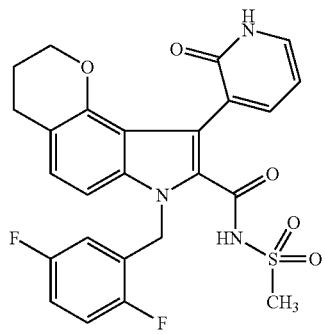 [SMILES: CS(=O)(=O)NC(=O)c1c(-c2ccc[nH]c2=O)c2c3c(ccc2n1Cc1cc(F)ccc1F)CCCO3] |
| 30 | 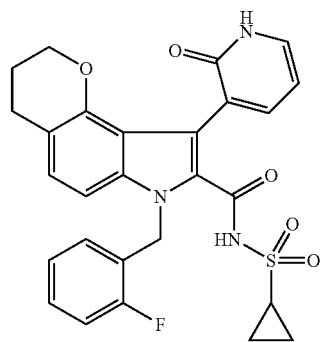 [SMILES: O=C(NS(=O)(=O)C1CC1)c1c(-c2ccc[nH]c2=O)c2c3c(ccc2n1Cc1ccccc1F)CCCO3] |

| Compound No. | Structure |
|---|---|
| 31 | 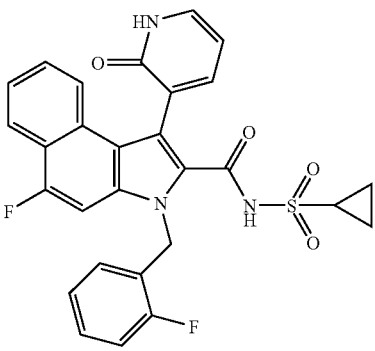 [SMILES: O=C(NS(=O)(=O)C1CC1)c1c(-c2ccc[nH]c2=O)c2c3ccccc3c(F)cc2n1Cc1ccccc1F] |
| 32 | 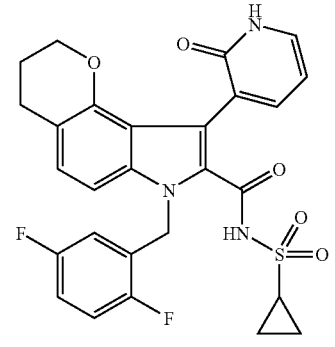 [SMILES: O=C(NS(=O)(=O)C1CC1)c1c(-c2ccc[nH]c2=O)c2c3c(ccc2n1Cc1cc(F)ccc1F)CCCO3] |
| 33 | 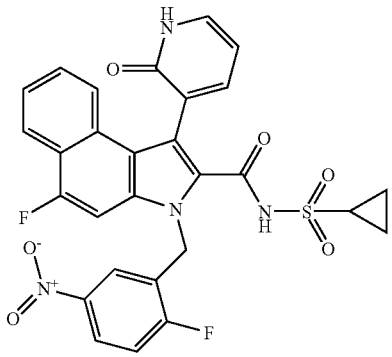 [SMILES: O=C(NS(=O)(=O)C1CC1)c1c(-c2ccc[nH]c2=O)c2c3ccccc3c(F)cc2n1Cc1cc([N+](=O)[O-])ccc1F] |
| 34 | 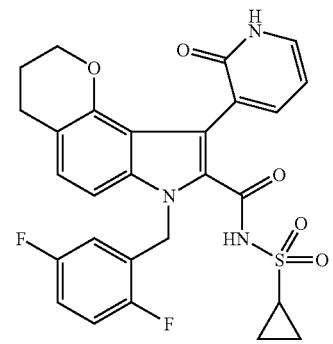 [SMILES: O=C(NS(=O)(=O)C1CC1)c1c(-c2ccc[nH]c2=O)c2c3c(ccc2n1Cc1cc(F)ccc1F)CCCO3] |
| Compound No. | Structure |
|---|---|
| 35 | 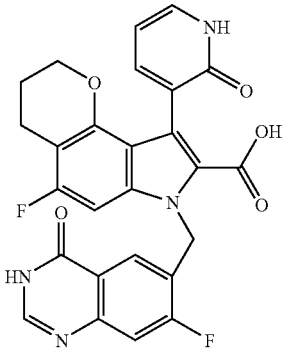 [SMILES: O=C(O)c1c(-c2ccc[nH]c2=O)c2c3c(c(F)cc2n1Cc1cc2c(=O)[nH]cnc2cc1F)CCCO3] |
| 36 | 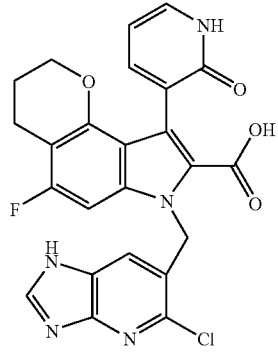 [SMILES: O=C(O)c1c(-c2ccc[nH]c2=O)c2c3c(c(F)cc2n1Cc1cc2[nH]cnc2nc1Cl)CCCO3] |
| 37 | 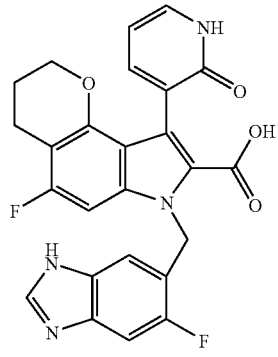 [SMILES: O=C(O)c1c(-c2ccc[nH]c2=O)c2c3c(c(F)cc2n1Cc1cc2[nH]cnc2cc1F)CCCO3] |
| 38 | 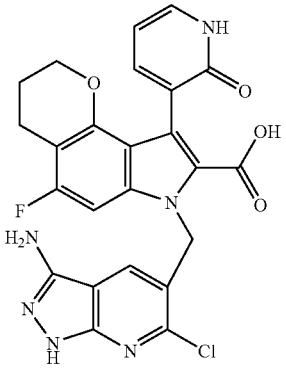 [SMILES: Nc1n[nH]c2cc(F)c(Cn3c(C(=O)O)c(-c4ccc[nH]c4=O)c4c5c(c(F)cc43)CCCO5)cc12] |

-continued

| Compound No. | Structure |
|---|---|
| 39 | 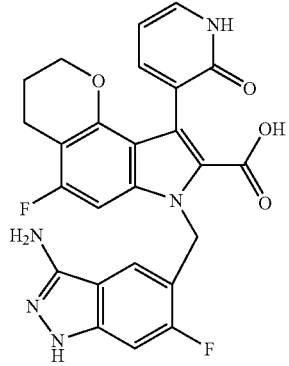 [SMILES: Nc1n[nH]c2cc(F)c(Cn3c(C(=O)O)c(-c4ccc[nH]c4=O)c4c5c(c(F)cc43)CCCO5)cc12] |
| 40 | 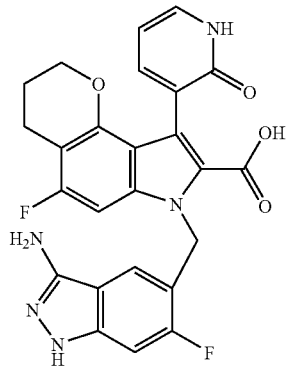 | and pharmaceutically acceptable salts, solvates, prodrugs and esters thereof.

Methods For Making the Compounds of Formula (I)

Methods useful for making the Compounds of Formula (I) are set forth in the Examples below and generalized in Schemes 1-9.

Scheme 1 shows one method for preparing compounds of formula A4, which are useful intermediates for making of the Compounds of Formula (I).

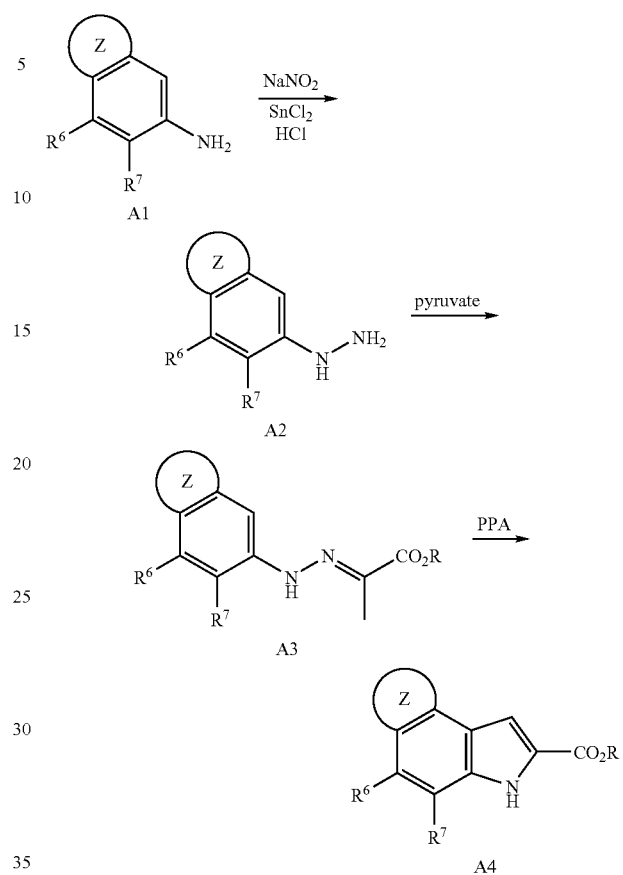

wherein $R^6$, $R^7$ and Z are defined above for the Compounds of Formula (I), and R is any carbonyl substituent that is encompassed by $R^2$, as defined above for the compounds of formula (I).

A 3,4-ring fused aniline compound of formula A1 can be converted to an indole compound of formula A4 using various indole syntheses that are well-known to those skilled in the art of organic synthesis, including but not limited to, a Fischer indole synthesis through intermediates of type A2 and A3, the method set forth in Nazare et al., *Angew. Chem.*, 116:4626-4629 (2004).

Scheme 2 shows methods useful for making compounds B4 and B6, which are useful intermediates for making of the Compounds of Formula (I).

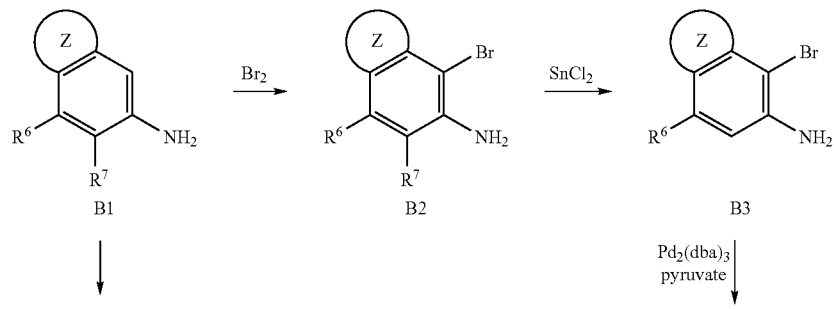

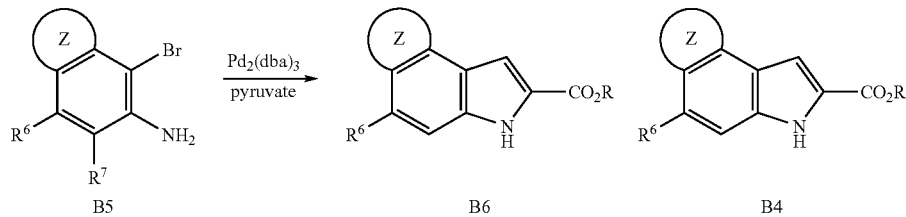

wherein $R^6$, $R^7$ and Z are defined above for the Compounds of Formula (I), and R is any carbonyl substituent that is encompassed by $R^2$, as defined above for the compounds of formula (I).

A bicyclic benzene derivative of formula B1, wherein $R^7$ is H, can be di-brominated to give compound B2. Selective de-bromination provides the corresponding monobromo analog B3, which under palladium catalyzed cyclization conditions provides the desired intermediate B4, wherein $R^7$ is H. Alternatively a compound of formula B1, wherein $R^7$ is other than H, can be monobrominated to give compound B5. Compound B5 can then undergo under palladium catalyzed cyclization conditions provides the desired intermediate B6, wherein $R^7$ is other than H.

Scheme 3 shows an alternative method to make compounds of formula C5, which are analogous to compounds B4 and B6 and are also useful intermediates for making of the Compounds of Formula (I).

Scheme 3

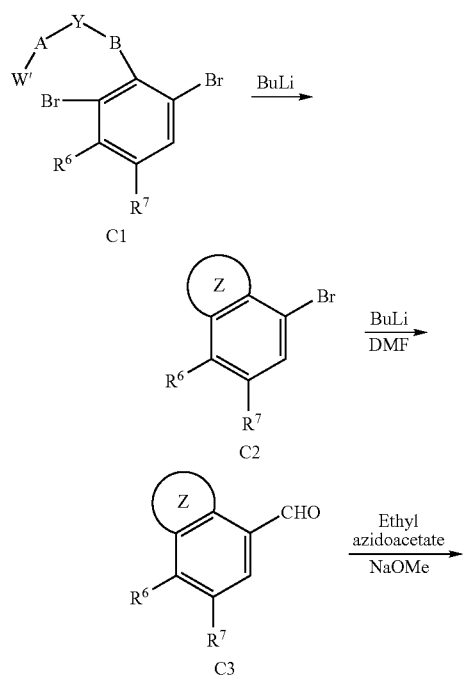

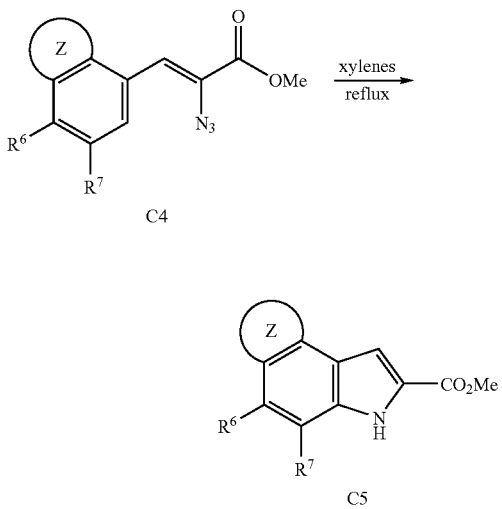

wherein $R^6$, $R^7$ and Z are defined above for the Compounds of Formula (I), and W', Y, A and B are defined below.

A 2,6-dibromophenol compound of formula C1, having a group —B—Y-A-W', wherein B, Y and A are atoms of ring Z and W' is a group capable of undergoing a ring formation reaction with the aryl bromide group in the presence of n-butyllithium, can be ring closed using ring formation reactions that are well-known to one skilled in the art of organic synthesis to provide compounds of formula C2. The bicyclic bromide C2 can in turn be converted to an aromatic aldehyde of formula C3. The aromatic aldehyde C3 can undergo a condensation reaction in the presence of an alkyl azido acetate to provide the azido compounds of formula C4 which can be converted to tricyclic indoles of formula C5 using methods well-known to those skilled in the art of synthetic organic chemistry.

Scheme 4 shows methods useful for making compounds of formula F, which are useful intermediates for making of the Compounds of Formula (I).

Scheme 4

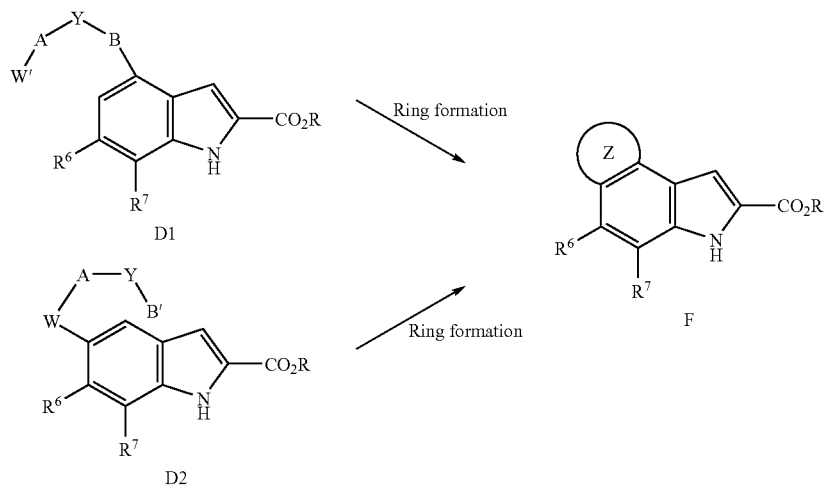

wherein $R^6$, $R^7$ and Z are defined above for the Compounds of Formula (I); R is any carbonyl substituent that is encompassed by $R^2$, as defined above for the compounds of formula (I); and W, W', Y, A, B and B' are defined below.

A compound of formula D1, having a group —B—Y-A-W', wherein B, Y and A are atoms of ring Z and W' is a group capable of undergoing a ring formation reaction with the benzene ring to which —B—Y-A-W' is attached, can undergo numerous ring formation reactions that are well-known to one skilled in the art of organic synthesis to form the tricyclic compounds of formula F. Similarly, a compound of formula D2, having a group —W-A-Y—B', wherein W, A and Y are atoms of ring Z and B' is a group capable of undergoing a ring formation reaction with the benzene ring to which —W-A-Y—B' is attached, can undergo numerous ring formation reactions that are well-known to one skilled in the art of organic synthesis to form the tricyclic compounds of formula F. Examples of ring formation methods include, but are not limited to, those disclosed in as *Comprehensive Heterocyclic Synthesis* (Pergamon Press); John et al., *J. Org. Chem.*, 47:2196 (1982); Maria et al., *Synthesis*, 1814 (2000); Martin et al., *J. Med. Chem.*, 44:1561 (2001); Morsy et al., *Pak. J. Sci. Ind. Res*, 43:208 (2000); Koguro et al., *Synthesis*, 911 (1998); Cowden et al., *Tet. Lett.*, 8661 (2000); Norton et al., *Synthesis*, 1406 (1994); Carl et al., *Tet. Lett.*, 2935 (1996); Gunter et al., *J. Org. Chem.*, 46:2824 (1981).

Scheme 5 illustrates methods by which intermediate compounds of formula F can be further derivatized to provide the Compounds of Formula (I), wherein $R^2$ is —C(O)OH.

Scheme 5

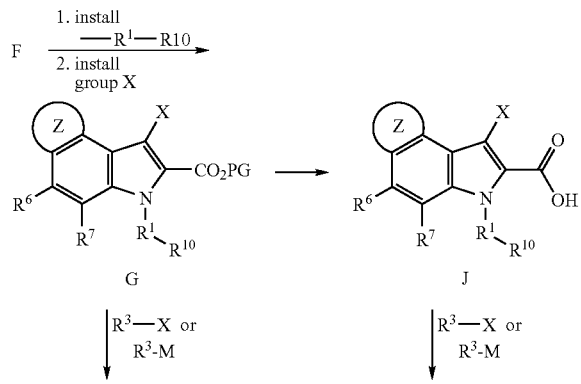

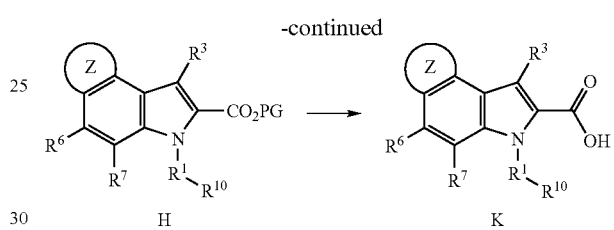

wherein $R^1$, $R^3$, $R^6$, $R^7$, $R^{10}$ and Z are defined above for the Compounds of Formula (I); PG is a carboxy protecting group; and X is halo, —O-triflate, —B(OH)$_2$, —Sn(alkyl)$_3$, —MgBr, —MgCl, —ZnBr, —ZnCl, or any metal which can participate in an organometallic cross-coupling reaction.

An intermediate compound of formula F can be converted to a 3-substituted indole of formula G using methods well-known to one skilled in the art of organic synthesis. A compound of formula G, wherein X is halo or —O-triflate can then be coupled with an appropriate compound of formula $R^3$-M (wherein M is —B(OH)$_2$, —Sn(alkyl)$_3$, —MgBr, —MgCl, —ZnBr, —ZnCl, or any metal which can participate in an organometallic cross-coupling reaction) using an organometallic cross-coupling method. Alternatively, a compound of formula G, wherein X is —B(OH)$_2$, —Sn(alkyl)$_3$, —MgBr, —MgCl, —ZnBr, —ZnCl, or any metal which can participate in an organometallic cross-coupling reaction, can then be coupled with an appropriate compound of formula $R^3$-M (wherein M is halo or —O-triflate) using an organometallic cross-coupling method. Suitable cross-coupling methods include, but not limited to, a Stille coupling (see Choshi et al., *J. Org. Chem.*, 62:2535-2543 (1997), and Scott et al., *J. Am. Chem. Soc.*, 106:4630 (1984)), a Suzuki coupling (see Miyaura et al., *Chem. Rev.*, 95:2457 (1995)), a Negishi coupling (see Zhou et al., *J. Am. Chem. Soc.*, 127:12537-12530 (2003)), and a Kumada coupling (see Kumada, *Pure Appl. Chem.*, 52:669 (1980) and Fu et al., *Angew. Chem.* 114:4363 (2002)) to provide a compound of formula H. The carboxy protecting group, PG, can then be removed from the compound of formula H and the resulting carboxylic acid can be derivatized using the methods described below in Schemes 6-8 in order to make the appropriate $R^2$ groups and make the compounds of formula K, which correspond to the compounds formula (I), wherein $R^2$ is —C(O)OH. Alternatively, a compound of formula F can first be deprotected and the $R^2$ group attached using the above methods to provide a compound of formula J. A compound of formula J can then be cross-coupled with a compound of R³—X or R³-M as described above to provide make the compounds of formula K.

Scheme 6 shows a method useful for making the Compounds of Formula (I), wherein R² is —C(O)N(R⁹)SO₂R¹¹.

Scheme 6

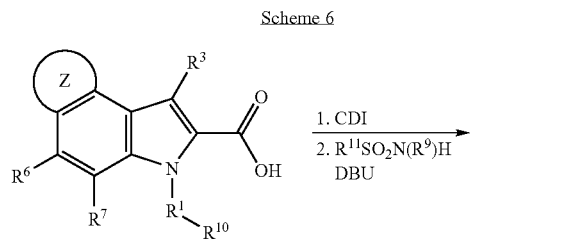

wherein R¹, R³, R⁶, R⁷, R⁹, R¹⁰, R¹¹ and Z are as defined for the Compounds of Formula (I).

A 2-carboxy indole compound of formula K can be coupled with a compound of formula R¹¹SO₂NH₂ in the presence of carbonyldiimidazole (CDI) and 1,8-diazabicyclo[5.4.0]undec-7-ene (DBU) to provide the compounds of formula L, which correspond to the Compounds of Formula (I) wherein R² is —C(O)NHSO₂R¹¹.

Scheme 7 shows a method useful for making the Compounds of Formula (I), wherein R² is —C(O)N(R⁹)₂.

Scheme 7

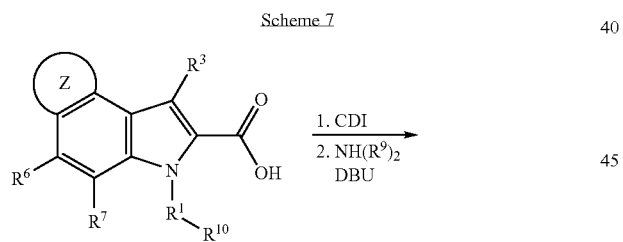

wherein R¹, R³, R⁶, R⁷, R⁹, R¹⁰ and Z are as defined for the Compounds of Formula (I).

A 2-carboxy indole compound of formula K can be coupled with an amine of formula NH(R⁹)₂ in the presence of carbonyldiimidazole (CDI) and 1,8-diazabicyclo[5.4.0]undec-7-ene (DBU) to provide the compounds of formula M, which correspond to the Compounds of Formula (I) wherein R² is —C(O)N(R⁹)₂.

Scheme 8 shows a method useful for making the Compounds of Formula (I), wherein R² is:

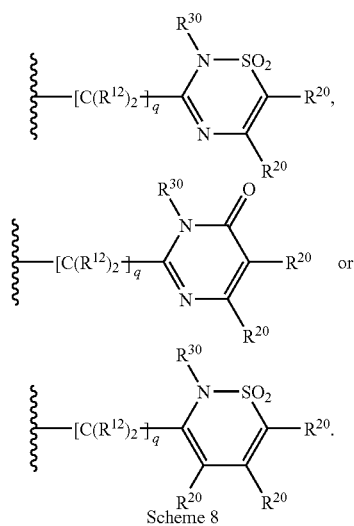

Scheme 8

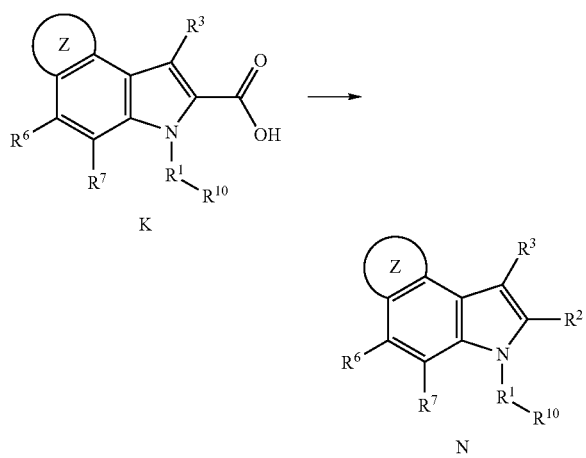

wherein R¹, R³, R⁶, R⁷, R¹⁰ and Z are as defined for the Compounds of Formula (I) and R² is:

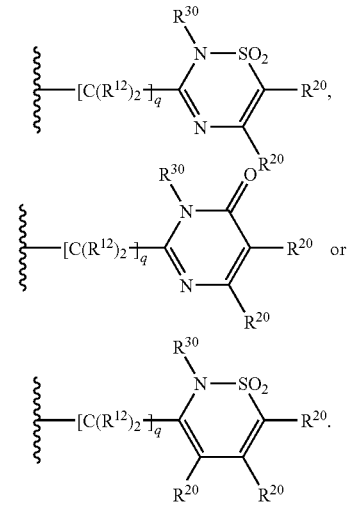

A 2-carboxy indole compound of formula K can be converted to the compounds of formula N, which correspond to the Compounds of Formula (I) wherein $R^2$ is:

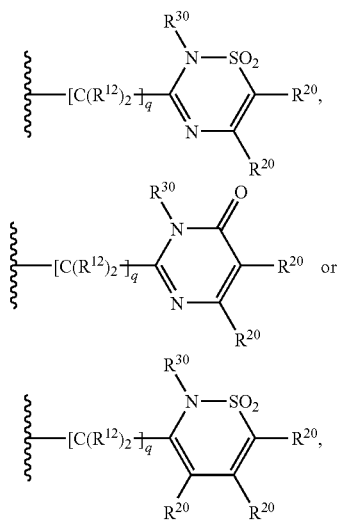

using the methods set forth in U.S. Patent Application No. US2005/0075331.

Scheme 9 shows a method useful for making the Compounds of Formula (I), wherein $R^3$ is 1H-pyridin-2-one-3-yl.

Scheme 9

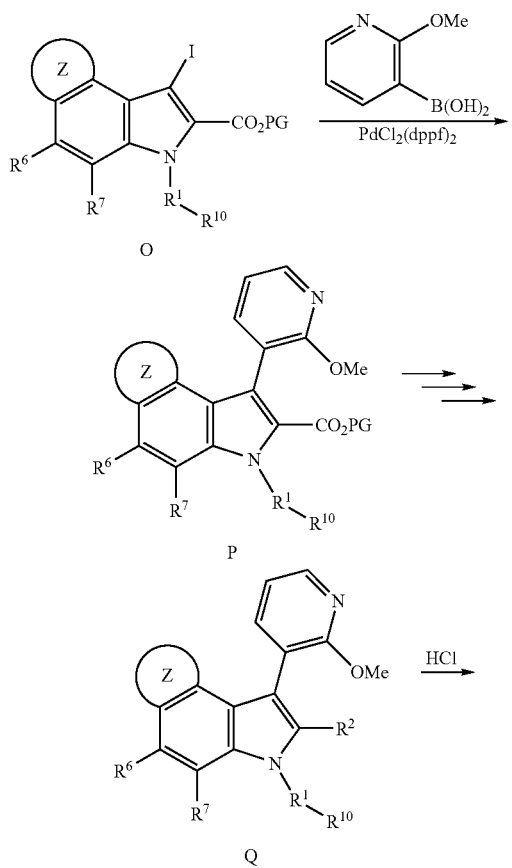

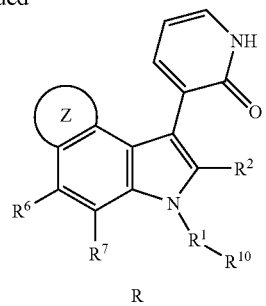

wherein $R^1$, $R^2$, $R^6$, $R^7$, $R^{10}$ and Z are as defined for the Compounds of Formula (I), and PG is a carboxy protecting group.

A 3-iodoindole compound of formula 0 can be coupled with a 2-alkoxypyridine-3-boronic acid using a Suzuki coupling reaction to provide the $R^3$-substituted indole compounds of formula P. A compound of formula P can be further elaborated using methods set forth above to provide the compounds of formula Q. The 2-alkoxypyridyl moiety of a compound of formula Q can then be reacted with hydrochloric acid to provide a compound of formula R, which corresponds to the Compounds of Formula (I), wherein $R^3$ is 1H-pyridin-2-one-3-yl.

The starting material and reagents depicted in Schemes 1-9 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of Compounds of Formula (I) may require the need for the protection of certain functional groups (i.e., derivatization for the purpose of chemical compatibility with a particular reaction condition). Suitable protecting groups for the various functional groups of the Compounds of Formula (I) and methods for their installation and removal can be found in Greene et al., *Protective Groups in Organic Synthesis*, Wiley-Interscience, New York, (1999).

One skilled in the art will also recognize that one route will be optimal depending on the choice of appendage substituents. Additionally, one skilled in the art will recognize that in some cases the order of steps may differ from that presented herein to avoid functional group incompatibilities and amend the synthetic route accordingly.

One skilled in the art will recognize that the synthesis of certain compounds of Formula 1 require the construction of an amide bond. Methods useful for making such amide bonds, include but are not limited to, the use of a reactive carboxy derivative (e.g. acid halide, or ester at elevated temperatures) or the use of an acid with a coupling reagent (e.g. DECI, DCC) with an amine.

The starting materials used and the intermediates prepared using the methods set forth in Schemes 1-9 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from Me₄Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH₃CN, 5 min—95% CH₃CN, 5-7 min—95% CH₃CN, 7 min—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound 2

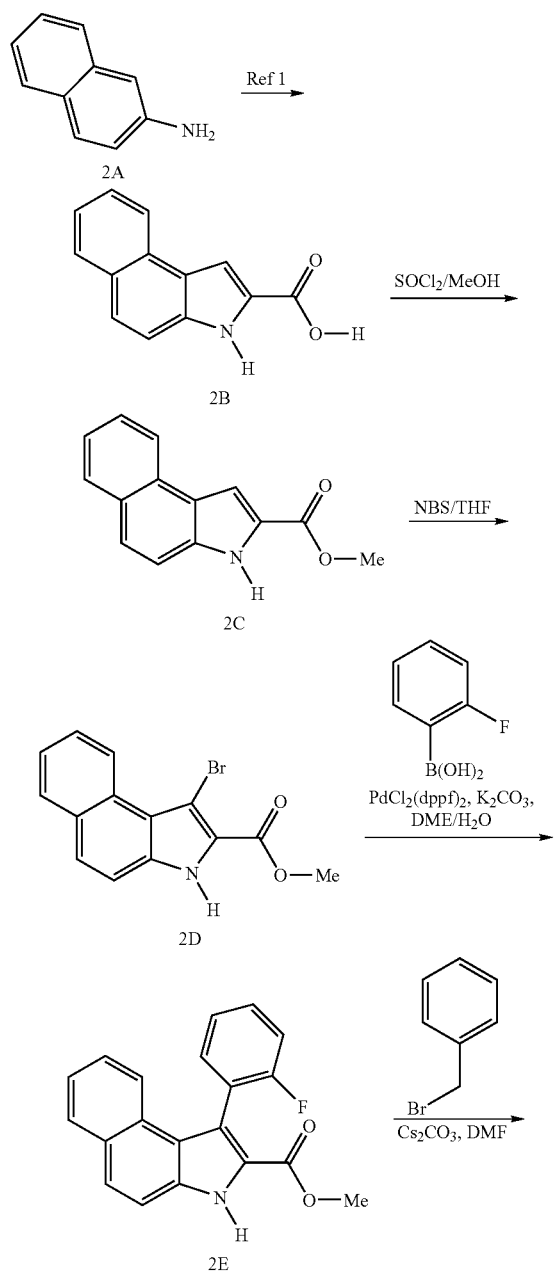

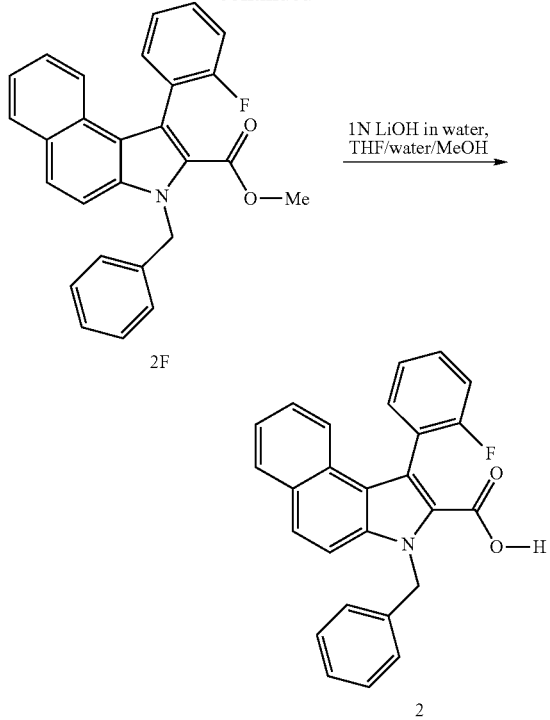

Step A—Synthesis of Compound 2B

Benzoindole carboxylic acid (2B), can be made from aminonaphthalene (2A, commercially available from Aldrich, St. Louis, Mo.), using the methods set forth in Goldsmith et al., *J. Org. Chem.*; 18:507-514 (1953).

Step B—Synthesis of Compound 2C

Compound 2B (1.0 g, 4.74 mmol) was dissolved into methanol (10 mL) and to the resulting solution was added thionylchloride (0.3 mL, 4.08 mmol) dropwise. The reaction mixture was stirred at reflux for 24 hours, then cooled to room temperature, anc concentrated in vacuo. Dichloromethane (100 mL) and water (20 mL) were added, and the organic layer was washed with brine (20 mL), dried over magnesium sulfate, filtered and concentrated in vacuo to provide compound 2C (0.70 g, 58%). ¹H NMR (500 MHz, CDCl₃): δ 9.25 (s, 1H), 8.25-8.22 (m, 1H), 7.91 & 7.89 (dd, J=0.6 Hz, 7.9 Hz, 1H), 7.76 & 7.75 (dd, J=0.95 Hz, 2.2 Hz, 1H), 7.71 (d, J=8.8 Hz, 1H), 7.62-7.58 (m, 1H), 7.52 & 7.50 (dd, J=0.95 Hz, 8.8 Hz, 1H), 7.49-7.45 (m, 1H), 3.98 (s, 3H).

Step C—Synthesis of Compound 2D

Compound 2C (0.2 g, 0.9 mmol) was dissolved in THF (25 mL) at room temperature and to the resulting solution was added N-bromosuccinimide (0.192 g, 1.08 mmol). The resulting suspension was stirred at room temperature for 14 hours, then quenched with aqueous saturate sodium thiosulfate solution (10 mL). The reaction was concentrated in vacuo, and the resulting residue was diluted with ethyl acetate (50 mL). The aqueous layer was extracted with ethyl acetate (50 mL) and the combined organic layers were washed with aqueous 1N sodium bicarbonate solution (10 mL) and brine (10 mL), then dried over magnesium sulfate, filtered and concentrated in vacuo to provide compound 2D (0.26 g, 95%), which was used without further purification. M.S. found: 304.03 (M+H)⁺.

Step D—Synthesis of Compound 2E

Compound 2D (200 mg, 0.66 mmol) was dissolved into 1,2-dimethoxyethane (15 mL) and to the resulting solution was added PdCl₂(dppf)₂ (10 mol %), and the reaction was heated to 90° C. and allowed to stir at this temperature for 30 minutes. 2-Fluorophenylboronic acid (1.98 mmol) and potassium carbonate (1.98 mmol) were then added to the reaction, followed by water (0.3 mL). The resulting reaction mixture was stirred at 90° C. for 2 hours, and then was cooled to room temperature and diluted with ethyl acetate (100 mL). The resulting solution was filtered through a celite pad and concentrated in vacuo to provide a crude residue which was purified using flash chromatography to provide compound 2E (0.13 g, 65%).

M.S. found: 320.2 (M+H)$^+$; $^1$H NMR (500 MHz, CDCl$_3$): δ 9.49 (s, 1H), 7.88-7.86 (m, 1H), 7.73 (d, J=8.8 Hz, 1H), 7.61 (d, J=8.5 Hz, 1H), 7.55 (d, J=9.1 Hz, 1H), 7.52-7.47 (m, 2H), 7.40-7.37 (m, 1H), 7.31-7.25 (m, 3H), 3.77 (s, 3H).

Step E—Synthesis of Compound 2F

Compound 2E (0.16 mmol) was dissolved into N,N-dimethylformamide (3 mL) at room temperature and to the resulting solution was added benzyl bromide (0.16 mmol) and cesium carbonate (0.24 mmol) and the resulting suspension was stirred at room temperature for 24 hours. Ethyl acetate (50 mL) and water (20 mL) were then added to the reaction mixture, and the layers were separated. The organic layer was washed with aqueous saturated sodium bicarbonate solution (10 mL), water (10 mL) and brine (10 mL) separately, then dried over magnesium sulfate, filtered and concentrated in vacuo. The crude product obtained was purified using flash chromatography to provide compound 2F (94%). M.S. found: 410.2 (M+H)$^+$.

Step F—Synthesis of Compound 2

Compound 2F (0.03 g, 0.073 mmol) was dissolved into tetrahydrofuran (5 mL), water (0.5 mL) at room temperature and to the resulting solution was added lithium hydroxide (0.14 mmol). The reaction was heated to 70° C. and allowed to stir at this temperature for 18 hours. The reaction was then cooled to room temperature, and was concentrated in vacuo to provide compound 2 as its lithium salt (100%), which was used without further purification. M.S. found: 396.2 (M+H)$^+$.

$^1$H NMR (500 MHz, CD$_3$OD): δ 7.87 (d, J=7.6 Hz, 1H), 7.73 (d, J=9.1 Hz, 1H), 7.62 (d, J=9.1 Hz, 1H), 7.55-7.45 (m, 3H), 7.37-7.31 (m, 2H), 7.31-7.27 (m, 3H), 7.25-7.19 (m, 2H), 7.14 (s, 1H), 7.11 (s, 1H), 6.07 (m, 2H).

Example 2

Preparation of Compound 6

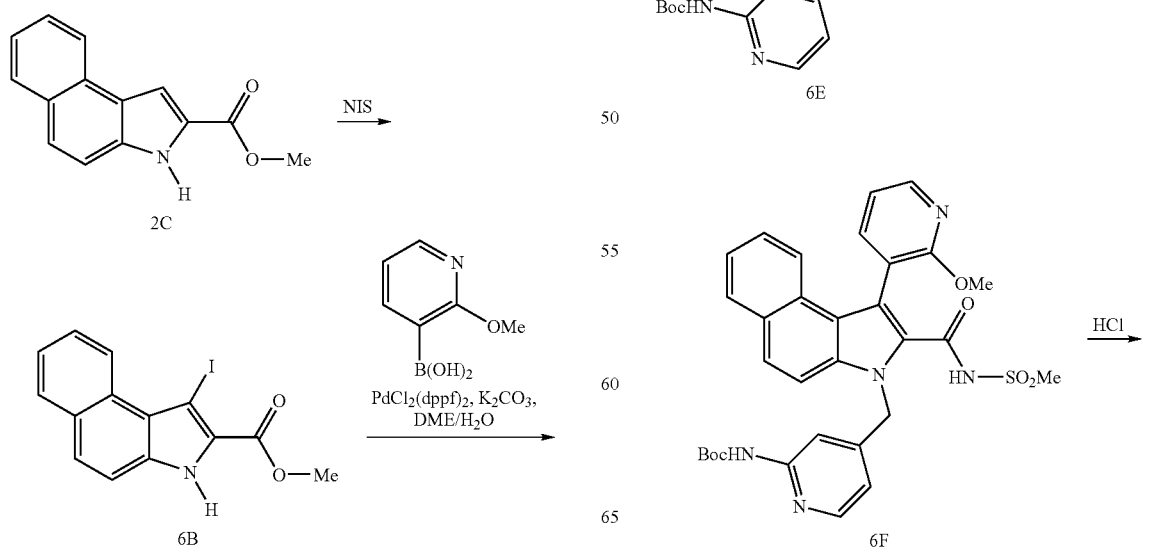

-continued

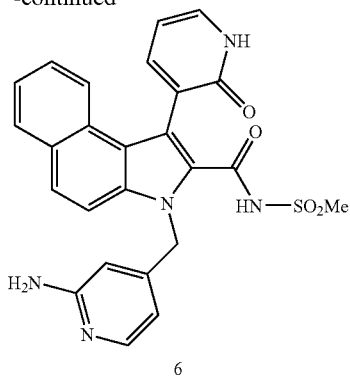

6

Step A—Synthesis of Compound 6B

Compound 2C (1.0 g, 4.4 mmol, made as described above in Example 1), was dissolved in chloroform (25 mL) at room temperature and to the resulting solution was added N-iodosuccinimide (1.0 g, 4.4 mmol) and the resulting suspension was stirred at room temperature for 24 hours. The reaction was quenched by addition of aqueous saturate sodium thiosulfate solution (10 mL) and the solvent was removed in vacuo. Ethyl acetate (50 mL) was added to dissolve the crude product, and the layers were separated. The aqueous layer was extracted with ethyl acetate (50 mL) and the combined organic layers were washed with aqueous 1N sodium bicarbonate solution (10 mL) and brine (10 mL) separately. The organic solution was then dried over magnesium sulfate, filtered and concentrated in vacuo to provide compound 6B (1.0 g, 64%). M.S. found: 351.96 (M+H)$^+$.

Step B—Synthesis of Compound 6C

To a solution of Compound 6B (200 mg, 0.57 mmol) in 1,2-dimethoxyethane (10 mL) was added PdCl$_2$(dppf)$_2$ (10 mol %) and the mixture was heated at 90° C. and allowed to stir at this temperature for 30 minutes. 2-methoxy-3-pyridine boronic acid (1.71 mmol) and potassium carbonate (1.71 mmol) were then added to the reaction, followed by water (0.5 mL). The resulting reaction mixture was stirred at 90° C. for 2 hours, then cooled to room temperature and diluted with ethyl acetate (100 mL). The resulting solution was filtered through a pad of celite and concentrated in vacuo to provide a crude product which was purified using flash chromatography to provide compound 6C (70 mg, 37%). $^1$H NMR (500 MHz, CDCl$_3$): δ 10.03 (s, 1H), 8.38 & 8.37 (dd, J=1.89 Hz+5.04 Hz, 1H), 7.86 (d, J=7.57 Hz, 1H), 7.72-7.68 (m, 2H), 7.60 (d, J=8.20 Hz, 1H), 7.48 (d, J=9.14 Hz, 1H), 7.41-7.38 (m, 1H), 7.34-7.31 (m, 1H), 7.07 (q, J=5.04 Hz+1.89 Hz, 1H), 3.89 (s, 3H), 3.76 (s, 3H). M.S. found: 333.14 (M+H)$^+$.

Step C—Synthesis of Compound 6D

Compound 6C (0.21 mmol) was dissolved into N,N-dimethyl formamide (2 mL) at room temperature and to the resulting solution was added (4-bromomethyl-pyridin-2-yl)-carbamic acid tert-butyl ester (0.25 mmol) and cesium carbonate (0.32 mmol) and the reaction was stirred at room temperature for 24 hours. Ethyl acetate (50 mL) and water (20 mL) were added to the reaction mixture, and the layers were separated. The organic layer was further washed with aqueous saturated sodium bicarbonate solution (10 mL), water (10 mL) and brine (10 mL), then dried over magnesium sulfate, filtered and concentrated in vacuo to afford the crude product. Further purification by flash chromatography provided compound 6D (80%). $^1$H NMR (500 MHz, CDCl$_3$): δ 9.33 (s, 1H), 8.35 & 8.34 (dd, J=1.9 Hz, 5.04 Hz, 1H), 8.17 (d, J=5.4 Hz, 1H), 8.06 (s, 1H), 7.85 (d, J=8.2 Hz, 1H), 7.72-7.68 (m, 2H), 7.57 (d, J=7.9 Hz, 1H), 7.40 (d, J=9.1 Hz, 1H), 7.39-7.37 (m, 1H), 7.33-7.29 (m, 1H), 7.07 (q, J=5.0 Hz, 2.2 Hz, 1H), 6.34 (d, J=5.0 Hz, 1H), 6.04 (d, J=17.3 Hz, 1H), 5.90 (d, J=17.3 Hz, 1H), 3.87 (s, 3H), 3.57 (s, 3H), 1.52 (s, 9H). M.S. found: 539.17 (M+H)$^+$.

Step D—Synthesis of Compound 6E

Compound 6D (0.09 g, 0.16 mmol) was dissolved into tetrahydrofuran (3 mL), and water (0.5 mL) at room temperature and to the resulting solution was added lithium hydroxide (0.34 mmol). The reaction was heated to 50° C. and allowed to stir at this temperature for 18 hours. The mixture was concentrated in vacuo to provide compound 6E, as its lithium salt (100%), which was used without further purification. M.S. found: 525.19 (M+H)$^+$.

Step E—Synthesis of Compound 6F

Compound 6E (50 mg, 0.095 mmol) was dissolved into tetrahydrofuran (5 mL) at room temperature and to the resulting solution was added carbonyl diimidazole (17 mg, 0.1 mmol) and the resulting suspension was stirred at reflux for 1 hour. The reaction mixture was cooled to room temperature and methanesulfonamide (29 mg, 0.1 mmol) and 1,8-diazabicyclo(5.4.0)undec-7-ene (0.1 mmol) were added and the reaction was allowed to stir at room temperature overnight. The reaction mixture was concentrated in vacuo, and the resulting residue was diluted with ethyl acetate (100 mL) and 1N HCl (10 mL). The mixture was then washed with water (10 mL) and brine (10 mL), the layers were separated, and the aqueous layer was extracted with ethyl acetate (2×20 mL). The combined organic layers were dried over magnesium sulfate, filtered and concentrated in vacuo to provide a crude product which was purified using flash chromatography to provide compound 6F (35%). $^1$H NMR (500 MHz, CDCl$_3$): δ 8.92 (s, 1H), 8.49 & 8.48 (dd, J=1.89 Hz+5.04 Hz, 1H), 8.22 (s, 1H), 8.14 (s, 1H), 7.86 (d, J=7.88 Hz, 1H), 7.79-7.77 (m, 2H), 7.73 (d, J=9.14 Hz, 1H), 7.45 (d, J=9.1 Hz, 1H), 7.42-7.38 (m, 1H), 7.33 (d, J=7.6 Hz, 1H), 7.31-7.28 (m, 1H), 7.18 (q, J=4.7 Hz+2.2 Hz, 1H), 6.60 (d, J=4.10 Hz, 1H), 5.87 (s, 2H), 4.02 (s, 3H), 3.13 (s, 3H), 1.50 (s, 9H). M.S. found: 602.3 (M+H)$^+$.

Step F—Synthesis of Compound 6

Compound 6F (20 mg, 0.033 mmol) was dissolved in methanol (3 mL) in a pressure tube, to the resulting solution was added HCl (4N in 1,4-dioxane, 1 mL), and the reaction mixture was heated at 90° C. in the sealed tube and allowed to stand at this temperature for 20 hours. The reaction mixture was cooled to room temperature then concentrated in vacuo to provide a crude product which was purified using flash chromatography to provide compound 6 (10 mg, 62%). $^1$H NMR (500 MHz, CD$_3$OD): δ 7.95-7.91 (t, J=9.5 Hz, 2H), 7.85-7.75 (m, 4H), 7.61 (d, J=9.1 Hz, 1H), 7.44-7.36 (m, 2H), 6.79 (q, J=6.6 Hz, 6.3 Hz, 2H), 6.33 (s, 1H), 5.87 (q, J=18.6 Hz, 7.25 Hz, 2H), 3.23 (s, 3H). M.S. found: 488.3 (M+H)$^+$.

Example 3

Preparation of Compound 16

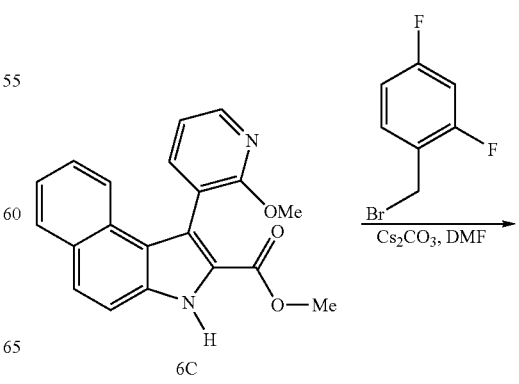

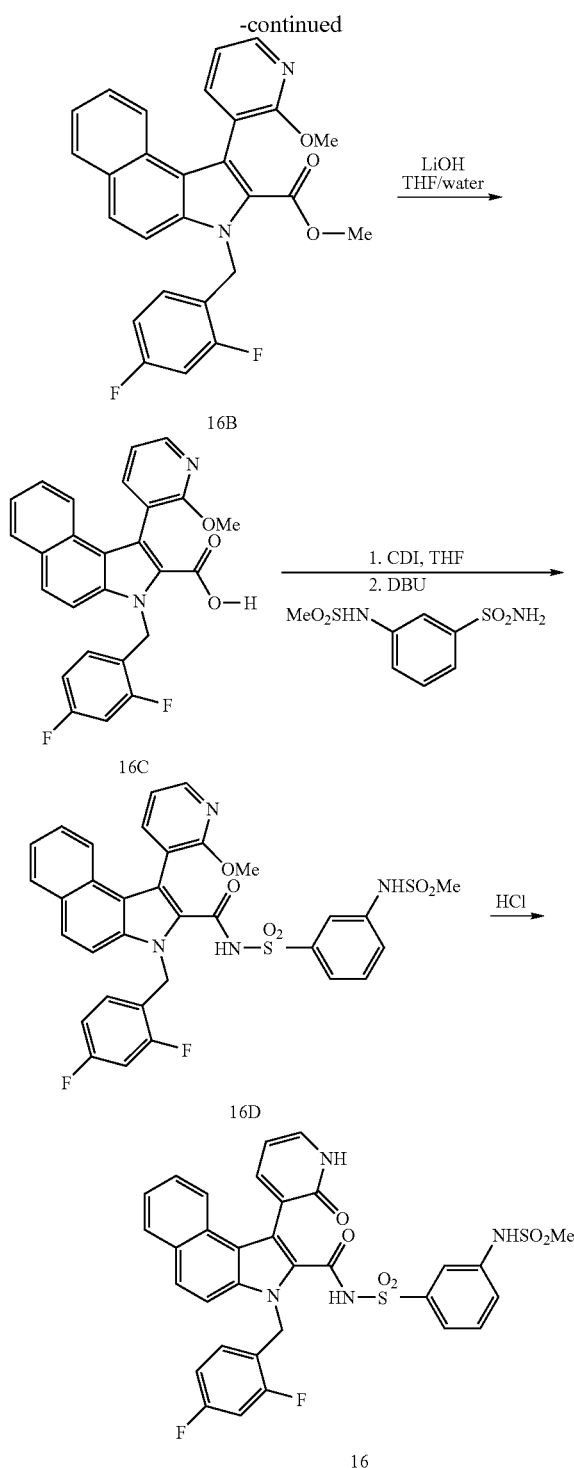

brine (10 mL). The separated organic layer was dried over magnesium sulfate, filtered and concentrated in vacuo to provide a crude product which was purified using flash-chromatography to provide compound 16B (120 mg).

Step B—Synthesis of Compound 16C

Compound 16B, was dissolved into tetrahydrofuran (3 mL) and water (0.5 mL) at room temperature and to the resulting solution was added lithium hydroxide (0.9 mmol). The reaction was heated to 70° C. and allowed to stir at this temperature for 24 hours. The reaction mixture was then concentrated in vacuo and the resulting residue was dissolved into ethyl acetate (100 mL), then 1N HCl (20 mL) was added. The layers were separated, and the aqueous layer was extracted with ethyl acetate (2×20 mL). The combined organic layers were dried over magnesium sulfate, filtered and concentrated in vacuo to provide compound 16C (110 mg, 82%), which was used without further purification. M.S. found: 445.01 $(M+H)^+$.

Step C—Synthesis of Compound 16D

Compound 16C (110 mg, 0.25 mmol) was taken up in tetrahydrofuran (10 mL), and to the resulting solution was added carbonyl diimidazole (49 mg, 0.3 mmol). The resulting suspension was heated to reflux and allowed to stir at this temperature for 1 hour, then cooled to room temperature. To the reaction mixture was added 3-methanesulfonylaminobenzenesulfonamide (62 mg, 0.25 mmol), followed by 1,8-diazabicyclo(5.4.0)undec-7-ene (0.3 mmol) and the reaction was allowed to stir overnight, then concentrated in vacuo. The resulting residue was diluted with ethyl acetate (100 mL) and water (10 mL), then the layers were separated, and the organic layer was washed with brine (10 mL). The aqueous layer was re-extracted with ethyl acetate (2×20 mL) and the combined organics were dried over magnesium sulfate, filtered and concentrated in vacuo to provide a crude residue which was purified using flash chromatography to provide compound 16D (15 mg).

Step D—Synthesis of Compound 16

Compound 16D was dissolved into 4N HCl in dioxane (3 mL) in a pressure tube and the resulting reaction mixture was heated to 90° C. and allowed to remain at this temperature for 2 hours. The reaction mixture was cooled to room temperature, then concentrated in vacuo to provide a crude product which was purified using flash chromatography to provide compound 16 (5 mg, 3%). $^1$H NMR (500 MHz, $CD_3OD$): δ 7.86 (d, J=6.9 Hz, 2H), 7.78 (d, J=6.3 Hz, 1H), 7.75-7.69 (m, 3H), 7.64 (d, J=9.1 Hz, 1H), 7.55-7.52 (m, 1H), 7.47 (d, J=6.3 Hz, 2H), 7.38-7.30 (m, 2H), 6.88-6.84 (m, 1H), 6.72-6.64 (m, 3H), 5.77 (d, J=16.4 Hz, 1H), 5.64 (d, J=17.0 Hz, 1H), 3.00 (s, 3H); M.S. found: 663.4 $(M+H)^+$.

Example 4

Preparation of Compound 19

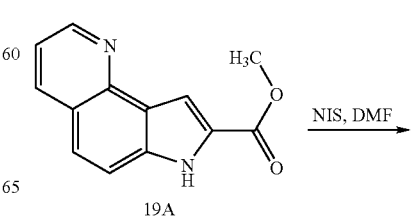

Step A—Synthesis of Compound 16B

Compound 6C (100 mg, 0.3 mmol, prepared as described above in Example 2) was dissolved into N,N-dimethyl formamide (3 mL) and to the resulting solution was added 2,4-difluorobenzyl bromide (0.3 mmol) and cesium carbonate (0.3 mmol). The resulting suspension was stirred at room temperature for 24 hours, then ethyl acetate (50 mL) and water (20 mL) were added, and the layers separated. The organic layer was further washed with aqueous saturate sodium bicarbonate solution (10 mL), water (10 mL) and -continued

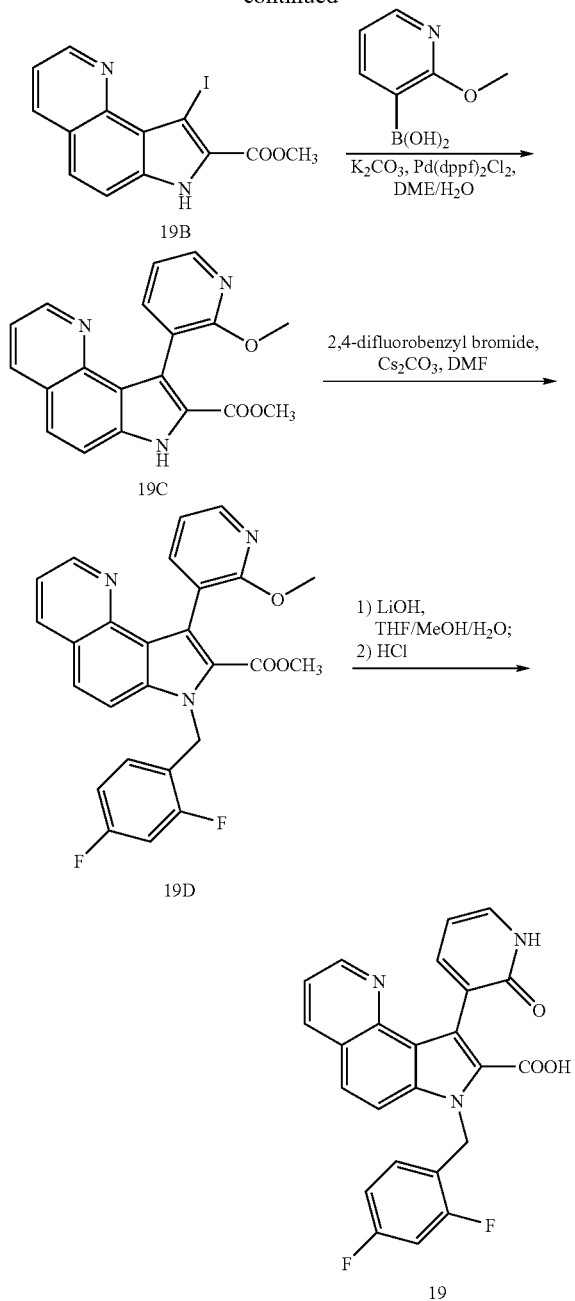

Step A—Preparation of Compound 19B

To a solution of indole 19A (1.00 g, 4.42 mmol) in DMF (40 mL) was added N-iodosuccinimide (1.19 g, 5.30 mmol) and the reaction was stirred at room temperature for 12 hours. The reaction mixture was then concentrated in vacuo, and the resulting residue was diluted with water. The aqueous layer was extracted with EtOAc (300 mL) and the combined organics were dried (MgSO$_4$), filtered, and concentrated in vacuo to provide a crude product which was purified using flash chromatography to provide compound 19B. $^1$H NMR (400 MHz, d$_6$-DMSO): δ 12.89 (s, 1H), 8.97-8.95 (m, 1H), 8.37 (d, J=7.3 Hz, 1H), 7.78 (d, J=8.7 Hz, 1H), 7.71 (d, J=8.7 Hz, 1H), 7.53 (q, J=4.6 Hz, 3.7 Hz, 1H), 3.92 (s, 3H).

Step B—Preparation of Compound 19C

Compound 19B (1.4 g, 3.98 mmol) in DMF (40 mL) were added 2-methoxy-3-pyridine boronic acid (1.83 g, 11.93 mmol) and PdCl$_2$(dppf)$_2$ (10 mol %, 324 mg) under nitrogen. The resulting mixture was stirred at room temperature for 15 minutes, then a solution of potassium carbonate (3.3 g, 23.88 mmol) in 40 mL of water was added. The reaction mixture was stirred at 90° C. for an addition hour, then diluted with EtOAc (300 mL). The mixture was concentrated in vacuo and the resulting residue was purified using flash chromatography (EtOAc/Hexanes, 0 to 70% EtOAc) to provide compound 19C. M.S. found for C$_{19}$H$_{15}$N$_3$O$_3$: 334 (M+H)$^+$.

Step C—Preparation of Compound 19D

To a solution of compound 19C (300 mg, 0.90 mmol) in DMF (10 mL) was added cesium carbonate (585 mg, 1.80 mmol) and 2,4-difluorobenzyl bromide (372 mg, 1.80 mmol). The reaction mixture was stirred at room temperature for 12 hours, and then diluted with EtOAc (250 mL) and washed with brine (2×100 mL). The organic layer was dried (MgSO$_4$), filtered, and concentrated in vacuo to provide a crude product which was purified using flash chromatography (EtOAc/Hexanes, followed by acetone/CH$_2$Cl$_2$) to provide compound 19D as a colorless solid. M.S. found for C$_{26}$H$_{19}$F$_2$N$_3$O$_3$: 460.3 (M+H)$^+$.

Step D—Preparation of Compound 19

To a solution of compound 19D in THF/water/methanol (1:1:1; 4 mL each) was added lithium hydroxide (10 mg). The reaction was stirred at reflux for 4 hours, diluted with aqueous HCl (1N, 5 mL) and concentrated in vacuo to provide a crude residue. A solution of the crude residue (70 mg, 0.14 mmol) in HCl 4 M in dioxane, 5 mL) and methanol (1 mL) was heated to 80° C. and allowed to stir at this temperature for 3 hours. The mixture was cooled to room temperature and concentrated in vacuo. The resulting residue was dissolved in 1 mL of methanol and triturated with ether to provide compound 19 as a crystalline material which was extensively washed with THF to remove residual LiCl. $^1$H NMR (300 MHz, d$_6$-DMSO) δ 8.82 & 8.80 (d, J=5.1 Hz, 1H), 8.71 & 8.69 (d, J=8.1 Hz, 1H), 8.08 & 8.05 J=9.5 Hz, 1H), 7.98 & 7.96 (d, J=9.5 Hz, 1H), 7.67 (s, 1H), 7.65-7.62 (m, 1H), 7.57 & 7.55 (d, J=6.6 Hz, 1H), 7.34-7.28 (m, 1H), 7.18-7.12 (m, 1H), 6.43 (t, J=6.6 Hz, 2H), 6.06 (s, 2H), 5.5-4.8 (bs, 1H). M.S. found for C$_{24}$H$_{15}$F$_2$N$_3$O$_3$: 432.08 (M+H)$^+$.

Example 5

Preparation of Compound 20

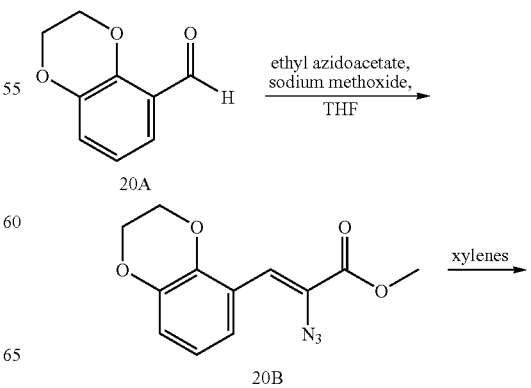

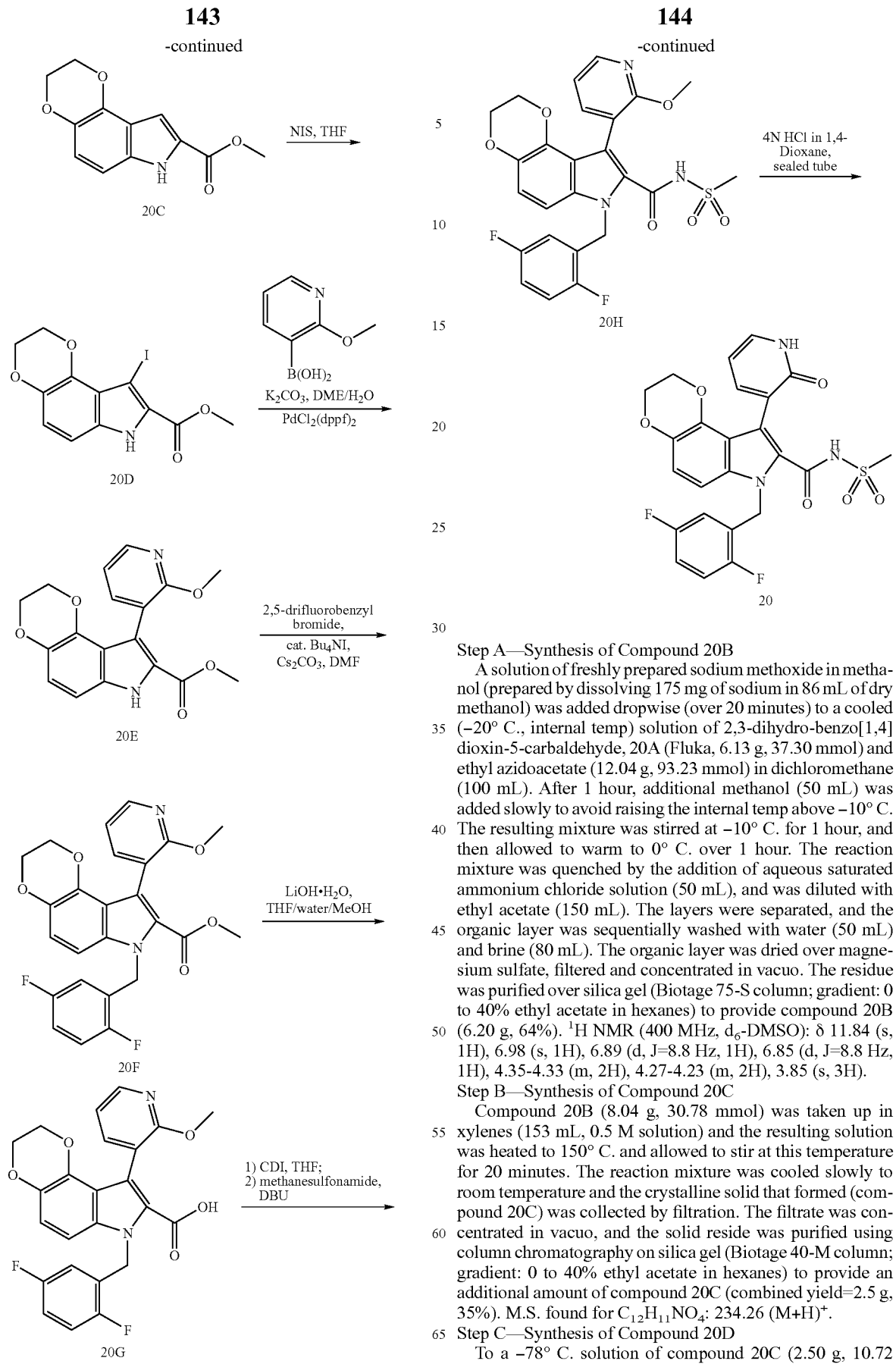

Step A—Synthesis of Compound 20B

A solution of freshly prepared sodium methoxide in methanol (prepared by dissolving 175 mg of sodium in 86 mL of dry methanol) was added dropwise (over 20 minutes) to a cooled (−20° C., internal temp) solution of 2,3-dihydro-benzo[1,4]dioxin-5-carbaldehyde, 20A (Fluka, 6.13 g, 37.30 mmol) and ethyl azidoacetate (12.04 g, 93.23 mmol) in dichloromethane (100 mL). After 1 hour, additional methanol (50 mL) was added slowly to avoid raising the internal temp above −10° C. The resulting mixture was stirred at −10° C. for 1 hour, and then allowed to warm to 0° C. over 1 hour. The reaction mixture was quenched by the addition of aqueous saturated ammonium chloride solution (50 mL), and was diluted with ethyl acetate (150 mL). The layers were separated, and the organic layer was sequentially washed with water (50 mL) and brine (80 mL). The organic layer was dried over magnesium sulfate, filtered and concentrated in vacuo. The residue was purified over silica gel (Biotage 75-S column; gradient: 0 to 40% ethyl acetate in hexanes) to provide compound 20B (6.20 g, 64%). $^1$H NMR (400 MHz, $d_6$-DMSO): δ 11.84 (s, 1H), 6.98 (s, 1H), 6.89 (d, J=8.8 Hz, 1H), 6.85 (d, J=8.8 Hz, 1H), 4.35-4.33 (m, 2H), 4.27-4.23 (m, 2H), 3.85 (s, 3H).

Step B—Synthesis of Compound 20C

Compound 20B (8.04 g, 30.78 mmol) was taken up in xylenes (153 mL, 0.5 M solution) and the resulting solution was heated to 150° C. and allowed to stir at this temperature for 20 minutes. The reaction mixture was cooled slowly to room temperature and the crystalline solid that formed (compound 20C) was collected by filtration. The filtrate was concentrated in vacuo, and the solid reside was purified using column chromatography on silica gel (Biotage 40-M column; gradient: 0 to 40% ethyl acetate in hexanes) to provide an additional amount of compound 20C (combined yield=2.5 g, 35%). M.S. found for $C_{12}H_{11}NO_4$: 234.26 (M+H)$^+$.

Step C—Synthesis of Compound 20D

To a −78° C. solution of compound 20C (2.50 g, 10.72 mmol) in 107 mL THF, was added N-iodosuccinimide (2.65 g, 11.79 mmol). The reaction was stirred at −78° C. until TLC (20% ethyl acetate in hexanes) analysis indicated the disappearance of compound 20C. The reaction mixture was quenched with saturated aqueous sodium bicarbonate solution (10 mL), and was then diluted with ethyl acetate (50 mL). The layers were separated, and the organic layer was washed with aqueous saturated sodium bicarbonate (50 mL), water (40 mL) and brine (50 mL) separately. The organic layer was dried over magnesium sulfate, filtered and concentrated in vacuo to provide a crude product which was purified using column chromatography on silica gel (Biotage 25-S column; gradient: 0 to 40% ethyl acetate in hexanes) to provide compound 20D (2.60 g, 68%). $^1$H NMR (400 MHz, d$_6$-DMSO): δ 12.13 (s, 1H), 6.93 (d, J=8.1 Hz, 1H), 6.88 (d, J=8.8 Hz, 1H), 4.35-4.33 (m, 2H), 4.24-4.23 (m, 2H), 3.86 (s, 3H).

Step D—Synthesis of Compound 20E

To a solution of compound 20D (2.54 g, 7.07 mmol) in 1,2-dimethoxyethane (70 mL) at room temperature was added Pd(dppf)$_2$Cl$_2$ (10 mol %, 577 mg) and the mixture was de-gassed (vacuum/argon flush) for 15 minutes at room temperature. A solution of aqueous 1 M potassium carbonate (5.86 g, 42.42 mmol) was added and the resulting reaction mixture was stirred at 90° C. for 1 hour. The reaction was cooled to room temperature, then diluted with ethyl acetate (80 mL). The layers were separated, and the organic layer was washed with aqueous saturated sodium bicarbonate (10 mL) and brine (10 mL). The organic layer was dried over magnesium sulfate, filtered and concentrated in vacuo to provide a crude residue which was purified using column chromatography on silica gel (Biotage 25-S column; gradient: 5 to 50% ethyl acetate in hexanes) to provide compound 20E (725 mg, 30%). M.S. found for C$_{18}$H$_{16}$N$_2$O$_5$: 341.20 (M+H)$^+$.

Step E—Synthesis of Compound 20F

To a 0° C. solution of 20E (350 mg, 1.03 mmol) in DMF (11 mL) was added 2,5-drifluorobenzyl bromide (234 mg, 1.13 mmol) and cesium carbonate (1.00 g, 3.08 mmol), with stirring. The ice-bath was removed, and a catalytic amount of tetrabutylammonium iodide (approx. 20 mg) was added. The reaction was stirred at room temperature for 2 hours, then diluted with ethyl acetate (200 mL). The resulting solution was washed with water (3×45 mL) and brine (80 mL) sequentially. The organic layer was dried over magnesium sulfate, filtered and concentrated in vacuo to provide a crude residue which was purified using column chromatography on silica gel (Biotage 25-S column; gradient: 0 to 25% ethyl acetate in hexanes) to provide compound 20F (380 mg, 80%).

Step F—Synthesis of Compound 20G

To a solution of compound 20F (350 mg, 0.78 mmol) in 12 mL of a mixture of tetrahydrofuran/water/methanol (4:1:1) was added lithium hydroxide monohydrate (163 mg, 3.92 mmol). The reaction was heated at 60° C. and allowed to stir at this temperature for 7 hours, then diluted with aqueous HCl solution (1N, 50 mL). The layers were separated, and the aqueous layer was extracted with dichloromethane (3×40 mL). The combined organic layers were dried (magnesium sulfite), filtered and concentrated in vacuo to provide compound 20G (335 mg, 95%) as a white solid, which was used without further purification. M.S. found for C$_{24}$H$_{18}$F$_2$N$_2$O$_5$: 453.11 (M+H)$^+$.

Step G—Synthesis of Compound 20H

To a solution of compound 20G (140 mg, 0.31 mmol) in tetrahydrofuran (3.1 mL) was added carbonyl diimidazole (56.8 mg, 0.35 mmol). The resulting mixture was stirred at reflux for 2 hours, then cooled to room temperature. Methanesulfonamide (38.3 mg, 0.40 mmol) and 1,8-diazabicyclo(5.4.0)undec-7-ene (0.057 mL, 0.40 mmol) were added and the resulting reaction mixture was stirred at 70° C. for an 18 hours. The reaction mixture was diluted with ethyl acetate (100 mL), and the resulting solution was washed with aqueous 1N HCl (20 mL) and brine (30 mL). The organic layer was dried over magnesium sulfate, filtered and concentrated in vacuo to provide a crude residue which was purified using column chromatography on silica gel (Biotage 25-S column; gradient: 0 to 20% acetone in methylene chloride) to provide compound 20H (110 mg, 67%). $^1$H NMR (400 MHz, d$_6$-DMSO): δ 11.61 (s, 1H), 8.13 & 8.11 (dd, J=1.5 Hz, 5.1 Hz, 1H), 7.74 (d, J=6.6 Hz, 1H), 7.31-7.26 (m, 1H), 7.19-7.13 (m, 1H), 7.09 (d, J=8.8 Hz, 1H), 7.05 (t, J=5.5 Hz, 1H), 6.92 (d, J=9.5 Hz, 1H), 6.61-6.56 (m, 1H), 5.63 (d, J=7.3 Hz, 2H), 4.18-4.13 (m, 4H), 3.74 (s, 3H), 3.05 (s, 3H).

Step H—Synthesis of Compound 20

Compound 20H (100 mg, 0.189 mmol) was dissolved into HCl (4N in 1,4-dioxane, 4.0 mL) in a pressure tube. Methanol (3.0 mL) was added, and the reaction mixture was heated to 90° C. and allowed to remain at this temperature in the sealed tube for 3 hours. The reaction mixture was cooled to room temperature then concentrated in vacuo to provide a crude product which was purified using reverse phase HPLC to provide compound 20 (67 mg, 69%). $^1$H NMR (500 MHz, d$_6$-DMSO): δ 12.67 (s, 1H), 12.55 (s, 1H), 7.76 & 7.74 (dd, J=2.2 Hz, 6.9 Hz, 1H), 7.60 (s, 1H), 7.32-7.28 (m, 1H), 7.18-7.14 (m, 1H), 7.04 (d, J=9.1 Hz, 1H), 6.94 (d, J=8.8 Hz, 1H), 6.61-6.57 (m, 1H), 6.52 (t, J=6.6 Hz, 1H), 5.64 (s, 2H), 4.18-4.13 (m, 4H), 3.23 (s, 3H); $^{13}$C NMR (125 MHz, d$_6$-DMSO): δ 162.66, 160.91, 158.98, 157.07, 156.63, 154.70, 145.48, 136.95, 136.40, 135.16, 133.69, 128.51, 126.82, 123.03, 116.99, 115.89, 114.97, 113.75, 106.67, 103.16, 64.12, 63.52, 41.59, 41.04.

Example 6

Preparation of Compound 21

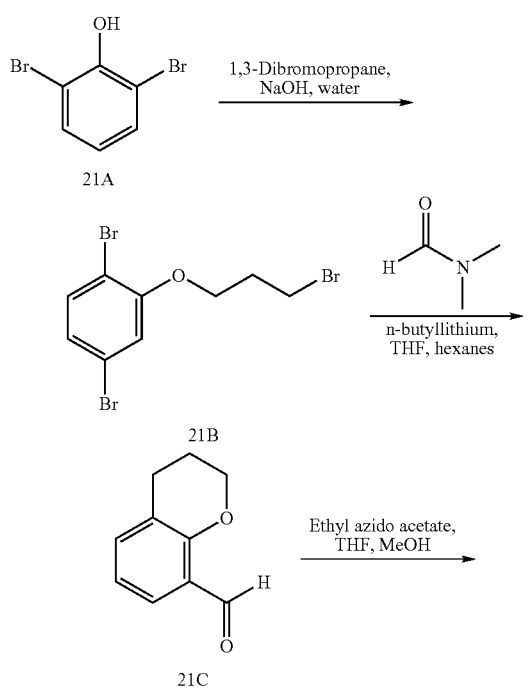

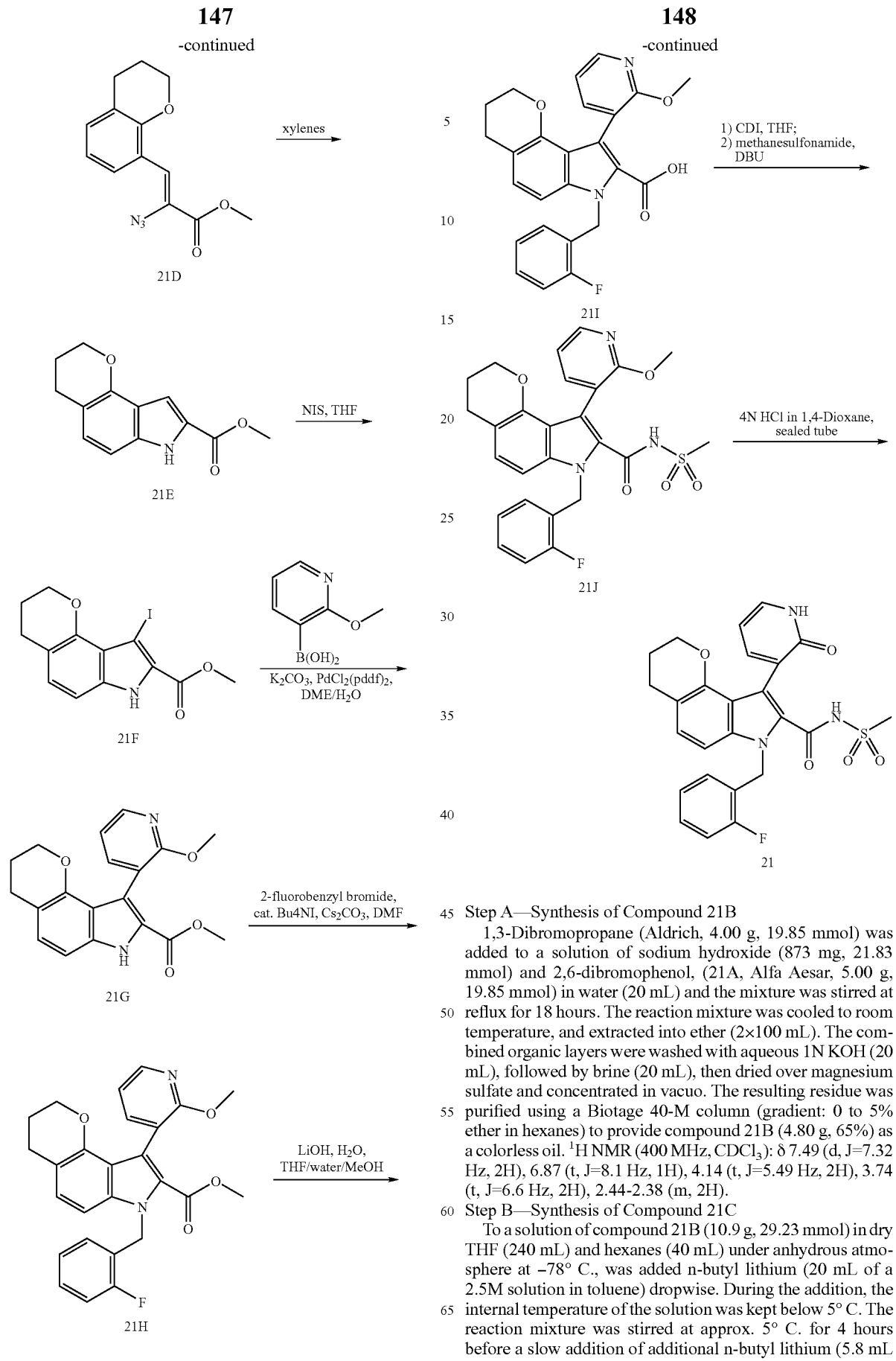

Step A—Synthesis of Compound 21B 1,3-Dibromopropane (Aldrich, 4.00 g, 19.85 mmol) was added to a solution of sodium hydroxide (873 mg, 21.83 mmol) and 2,6-dibromophenol, (21A, Alfa Aesar, 5.00 g, 19.85 mmol) in water (20 mL) and the mixture was stirred at reflux for 18 hours. The reaction mixture was cooled to room temperature, and extracted into ether (2×100 mL). The combined organic layers were washed with aqueous 1N KOH (20 mL), followed by brine (20 mL), then dried over magnesium sulfate and concentrated in vacuo. The resulting residue was purified using a Biotage 40-M column (gradient: 0 to 5% ether in hexanes) to provide compound 21B (4.80 g, 65%) as a colorless oil. $^1$H NMR (400 MHz, CDCl$_3$): δ 7.49 (d, J=7.32 Hz, 2H), 6.87 (t, J=8.1 Hz, 1H), 4.14 (t, J=5.49 Hz, 2H), 3.74 (t, J=6.6 Hz, 2H), 2.44-2.38 (m, 2H).

Step B—Synthesis of Compound 21C

To a solution of compound 21B (10.9 g, 29.23 mmol) in dry THF (240 mL) and hexanes (40 mL) under anhydrous atmosphere at −78° C., was added n-butyl lithium (20 mL of a 2.5M solution in toluene) dropwise. During the addition, the internal temperature of the solution was kept below 5° C. The reaction mixture was stirred at approx. 5° C. for 4 hours before a slow addition of additional n-butyl lithium (5.8 mL of a 2.5M solution in toluene diluted into 20 ml hexanes). The resulting mixture was stirred at 5° C. for 0.5 hours, followed by an addition of a solution of dimethyl formamide (3.38 mL, 43.84 mmol) in 10 mL of THF. The reaction mixture was stirred at 5° C. for 10 minutes, then was warmed to room temperature and stirred for an additional 0.5 hours, and quenched with aqueous 1 N HCl solution (100 mL). The layers were separated, and the aqueous layer was extracted with ether (3×200 mL). The combined organic layers were washed with brine (100 mL), dried over magnesium sulfate, filtered and concentrated in vacuo. The resulting residue was purified by column chromatography using a Biotage 75-M silica gel column (gradient: 0 to 20% ethyl acetate in hexanes) to provide compound 21C (4.20 g, 88%). $^1$H NMR (400 MHz, CDCl$_3$): δ 10.41 (s, 1H), 7.64 & 7.63 (dd, J=1.5 Hz, 8.1 Hz, 1H), 7.25 (d, J=5.13 Hz, 1H), 6.89 (t, J=7.3 Hz, 1H), 4.30 (t, J=5.1 Hz, 2H), 2.83 (t, J=6.2 Hz, 2H), 2.09-2.03 (m, 2H).

Step C—Synthesis of Compound 21D

To a solution of compound 21C (25.89 mmol) in 10 mL of methanol and 10 mL of THF at 0° C. was added a solution of ethyl azido acetate (10.0 g, 77.69 mmol) in 10 mL of methanol. The reaction was cooled to −20° C., and a solution of freshly prepared sodium methoxide in methanol (prepared by dissolving 1.78 g sodium in 80 mL of methanol) was added dropwise (the internal temperature was kept below 5° C.). The reaction mixture was stirred at approximately 5° C. for 0.5 hours, and then stirred at 0° C. for 5 hours. The reaction was quenched with aqueous saturated ammonium chloride solution (20 mL), then ethyl acetate (400 mL) and water (80 mL) were added, and the layers separated. The organic layer was washed with brine (80 mL), dried over magnesium sulfate, filtered and concentrated in vacuo. The crude product obtained was purified on a Biotage 75-M column (gradient: 0 to 25% ethyl acetate in hexanes) to provide compound 21D (2.68 g, 41%). $^1$H NMR (400 MHz, CDCl$_3$): δ 8.00 (d, J=8.1 Hz, 1H), 7.35 (s, 1H), 7.02 (d, J=8.1 Hz, 1H), 6.86 (t, J=7.7 Hz, 1H), 4.25 (t, J=5.1 Hz, 2H), 3.81 (s, 3H), 2.79 (t, J=6.2 Hz, 2H), 2.03-1.97 (m, 2H).

Step D—Synthesis of Compound 21E

Compound 21D (2.0 g, 7.71 mmol) was dissolved in 40 mL of xylenes. The mixture was stirred at 160° C. for 10 minutes, then cooled to room temperature and concentrated in vacuo to half of its original volume. The concentrated solution was then placed in an ice-water bath for 30 minutes and a white precipitate appeared. The solution was then concentrated in vacuo to provide a solid, which was collected and washed with hexanes (2×10 mL), then dried under vacuum to provide compound 21E (1.3 g, 73%). $^1$H NMR (500 MHz, d$_6$-DMSO): δ 11.81 (s, 1H), 6.99 (d, J=2.2 Hz, 1H), 6.91 (q, J=8.5 Hz, 3.2 Hz, 2H), 4.23 (t, J=4.7 Hz, 2H), 3.84 (s, 3H), 2.73 (t, J=6.2 Hz, 2H), 1.99-1.95 (m, 2H).

Step E—Synthesis of Compound 21F

To a solution of compound 21E (1.82 g, 7.87 mmol) in 50 mL of THF at −78° C. was slowly added a solution of N-iodosuccinimide (1.1 eq, 1.17 g) in 20 mL of THF. After the addition was complete (about 10 minutes), the reaction was stirred for 15 minutes at −78°, then was quenched by adding aqueous saturated sodium bicarbonate (1 mL). The mixture was warmed to room temperature, diluted with ethyl acetate (200 mL) and the organic layer was washed with aqueous saturated sodium bicarbonate (60 mL) and brine (50 mL) separately. The organic layer was then dried over magnesium sulfate, filtered and concentrated in vacuo to provide a crude product which was purified on a Biotage 40-M silica gel column (gradient: 0 to 30% THF in hexanes) to provide compound 21F (1.47 g, 53%). M.S. found for C$_{13}$H$_{12}$INO$_3$: 357.83 (M+H)$^+$.

Step F—Synthesis of Compound 21G

Compound 21F (1.45 g, 4.06 mmol) was dissolved in 40 mL of 1,2-dimethoxyethane at room temperature. The mixture was de-gassed (vacuum/argon flush), then PdCl$_2$(dppf)$_2$ (10 mol %, 331 mg) was added and the resulting mixture was stirred for 15 minutes at room temperature. A solution of potassium carbonate (24.3 mL of aqueous 1M solution) was then added, and the resulting brown reaction mixture was stirred at 85° C. for 1 hour. The reaction mixture was cooled to room temperature, diluted with ethyl acetate (200 mL) and the layers separated. The organic layer was washed with aqueous saturated sodium bicarbonate (50 mL) and brine (50 mL) separately. The organic layer was dried over magnesium sulfate, filtered and concentrated in vacuo to provide a crude residue which was purified using a Biotage 40-M column (gradient: 0 to 40% ethyl acetate in hexanes) to provide compound 21G (720 mg, 53%). $^1$H NMR (400 MHz, d$_6$-DMSO): δ 11.81 (s, 1H), 8.10 & 8.09 (dd, J=2.2 Hz, 5.1 Hz, 1H), 7.89 (s, 1H), 7.57 & 7.55 (dd, J=1.5 Hz, 7.3 Hz, 1H), 6.98-6.94 (m, 2H), 3.94-3.88 (M, 2H), 3.74 (s, 3H), 3.65 (s, 3H), 2.75-2.68 (m, 2H), 1.88-1.82 (m, 2H).

Step G—Synthesis of Compound 21H

To a solution of compound 21G (500 mg; 1.48 mmol) in 10 mL of DMF at 0° C. was added 2-fluorobenzyl bromide (335 mg, 1.77 mmol) and cesium carbonate (1.20 g, 3.69 mmol). The ice-water bath was then removed and a catalytic amount of tetrabutylammonium iodide (approx. 20 mg) was added. After stirring for 1 hour, the mixture was diluted with ethyl acetate (80 mL), then washed with water (2×10 mL) and brine (10 mL) sequentially. The organic layer was dried over magnesium sulfate, filtered and concentrated in vacuo to provide a crude residue which was purified on a 40-S Biotage column (gradient: 0 to 25% ethyl acetate in hexanes) to provide compound 21H (410 mg, 66%). $^1$H NMR (500 MHz, d$_6$-DMSO): δ 8.11 & 8.10 (dd, J=1.9 Hz & 5.0 Hz, 1H), 7.62+7.61 (dd, J=2.2 Hz, 7.3 Hz, 1H), 7.29 (q, J=6.9 Hz & 7.3 Hz, 1H), 7.21 (t, J=9.3 Hz, 1H), 7.07-6.97 (m, 4H), 6.63 (t, J=7.7 Hz, 1H), 5.85 (d, J=16.7 Hz, 1H), 5.75 (d, J=16.4 Hz, 1H), 3.97-3.90 (m, 2H), 3.75 (s, 3H), 3.47 (s, 3H), 2.72 (t, J=6.2 Hz, 2H), 1.88-1.84 (m, 2H).

Step H—Synthesis of Compound 21I

To a solution of compound 21H (400 mg; 0.90 mmol) in 8 mL of a THF/water/methanol mixture (2:1:1) was added lithium hydroxide monohydrate (188 mg, 4.48 mmol). The reaction was heated to 65° C. and allowed to stir at this temperature for 3 hours. The reaction mixture was then cooled to room temperature and the mixture diluted with aqueous 1N HCl (50 mL). The aqueous layer was extracted with dichloromethane (3×40 mL) and the combined organic layers were dried over magnesium sulfate, filtered and concentrated in vacuo to provide compound 21I (383 mg, 99%), which was used without further purification.

Step I—Synthesis of Compound 21J

To a solution of compound 21I (150 mg, 0.35 mmol) in 3 mL of THF at room temperature was added carbonyl dimidazole (67 mg, 0.42 mmol). The reaction was heated to 70° C. and allowed to stir at this temperature for 2 hours, then was cooled to room temperature. Methanesulfonamide (40 mg, 0.42 mmol) and DBU (79 mg, 0.52 mmol) were then added, and the resulting reaction was stirred at 45° C. for 18 hours. The mixture was diluted with ethyl acetate (60 mL), and was washed with aqueous 1N HCl (10 mL) and brine (10 mL) separately. The organic layer was dried over magnesium sulfate, filtered and concentrated in vacuo to provide a crude residue which was purified on a Biotage 25-S column (gradient: 0 to 20% THF in dichloromethane) to provide compound 21J (122 mg, 70%). M.S. found for $C_{26}H_{24}FN_3O_5S$: 510.13 $(M+H)^+$.

Step J—Synthesis of Compound 21

Compound 21J (110 mg, 0.22 mmol) was dissolved into 4 N HCl in 1,4-dioxane (3.0 mL) in a pressure tube. Methanol (1.0 mL) was added, and the reaction mixture was stirred at 90° C. in the sealed tube for 3 hours. The reaction mixture was cooled to room temperature, then concentrated in vacuo. The crude residue obtained was purified using reverse phase HPLC to provide compound 21 (81 mg, 78%). $^1$H NMR (500 MHz, $d_6$-DMSO): δ 12.67 (s, 1H), 12.57 (s, 1H), 7.68 & 7.67 (dd, J=1.9 Hz & 6.9 Hz, 1H), 7.60 (d, J=4.1 Hz, 1H), 7.31 (q, J=5.7 Hz & 7.3 Hz, 1H), 7.21 (t, J=9.3 Hz, 1H), 7.09-6.98 (m, 3H), 6.80 (t, J=7.7 Hz, 1H), 6.52 (t, J=6.6 Hz, 1H), 5.7 (s, 2H), 3.98 (t, J=4.7 Hz, 2H), 3.19 (s, 3H), 2.72 (t, J=6.2 Hz, 2H), 1.90-1.86 (m, 2H); $^{13}$C NMR (125 MHz, $d_6$-DMSO): δ 162.73, 161.04, 160.49, 158.54, 149.25, 145.63, 137.84, 135.07, 129.20, 128.51, 127.71, 124.76, 124.45, 123.40, 115.23, 115.11, 114.29, 112.23, 106.71, 102.77, 65.77, 41.50, 41.02, 23.91, 21.66; M.S. found for $C_{25}H_{22}FN_3O_5S$: 496.15 $(M+H)^+$.

Example 7

Preparation of Compound 27

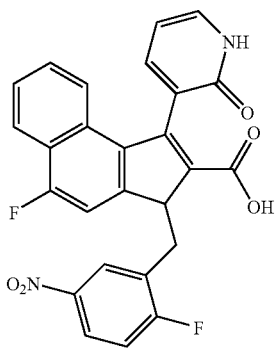

Step A—Synthesis of Compound 27B

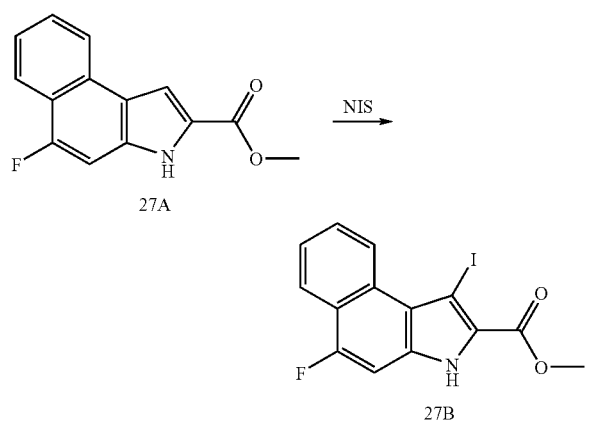

Compound 27A (commercially available, 1.0 g, 4.11 mmol) was dissolved in chloroform (75 mL) at room temperature and to the resulting solution was added N-iodosuccinimide (0.93 g, 4.11 mmol). The resulting suspension was allowed to stir at room temperature for 24 hours and the reaction mixture was then concentrated in vacuo. The residue obtained was diluted with ethyl acetate and the resulting solution was washed with water and brine, dried ($Na_2SO_4$), filtered, and concentrated in vacuo to provide compound 27B (1.5 g) which was used without further purification.

Step B—Synthesis of Compound 27C

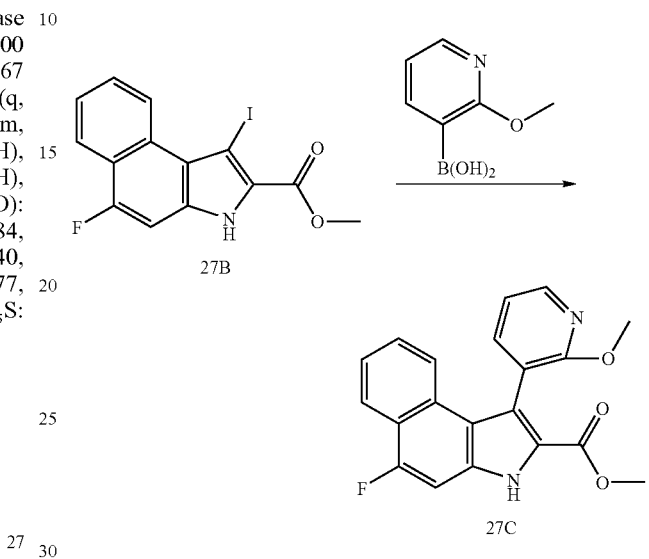

To a solution of compound 27B in 1,2-dimethoxyethane (75 mL) was added $PdCl_2(dppf)_2$ (10 mol %, 0.34 g, 0.411 mmol) and the mixture was heated to 95° C. and allowed to stir at this temperature for 30 minutes. 2-methoxy-3-pyridine boronic acid (12.33 mmol) and potassium carbonate (12.33 mmol), water (25 mL) were then added to the reaction in 3 portions in 10 minute intervals. The resulting reaction was stirred at 90° C. for 1 hour, then cooled to room temperature and diluted with ethyl acetate. The resulting solution was filtered through a pad of celite and concentrated in vacuo to provide a crude product which was diluted with EtOAc, washed with brine, dried ($Na_2SO_4$), filtered, and concentrated in vacuo. The residue obtained was purified using flash chromatography to provide compound 27C (0.6 g, 40%). M.S. found: 351.03 $(M+H)^+$.

Step C—Synthesis of Compound 27D

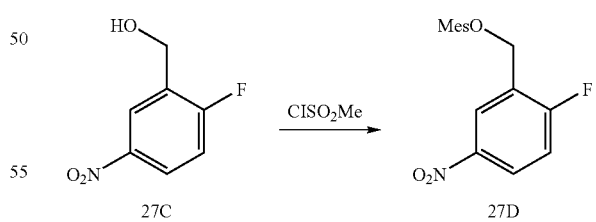

To a solution of compound 27C (0.044 g, 0.3 mmol) in THF (5 mL) and triethylamine (0.2 mL) was added dropwise a solution of methanesulfonyl chloride (0.01 mL) in THF (2 mL) and the reaction was allowed to stir at room temperature for 1 hour. The reaction mixture was then concentrated in vacuo and the residue obtained was diluted with EtOAc, washed with brine, dried ($Na_2SO_4$), filtered, and concentrated in vacuo to provide compound 27D which was used without further purification.

Step D—Synthesis of Compound 27F

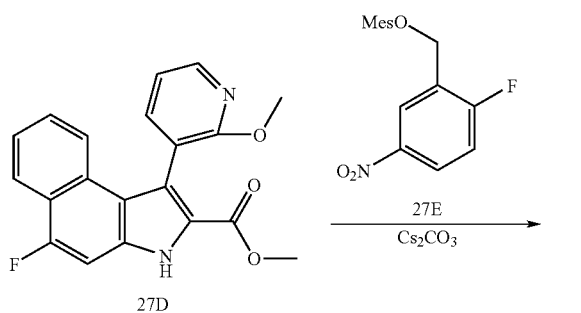

To a solution of compound 27E in DMF (5 mL) was added cesium carbonate (0.099 g, 0.3 mmol) and compound 27D (0.105 g, 0.3 mmol), and the resulting reaction was allowed to stir at room temperature for 24 hours. The reaction mixture was diluted with EtOAc and washed with water and brine. The combined organic layers were dried (Na$_2$SO$_4$), filtered, and concentrated in vacuo to provide compound 27F (0.140 g) which was used without further purification.

Step E—Synthesis of Compound 27G

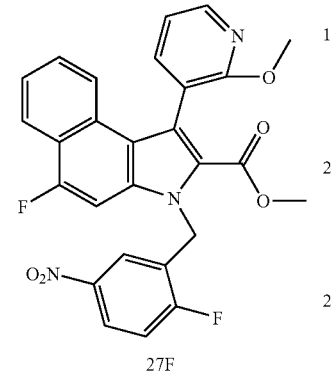
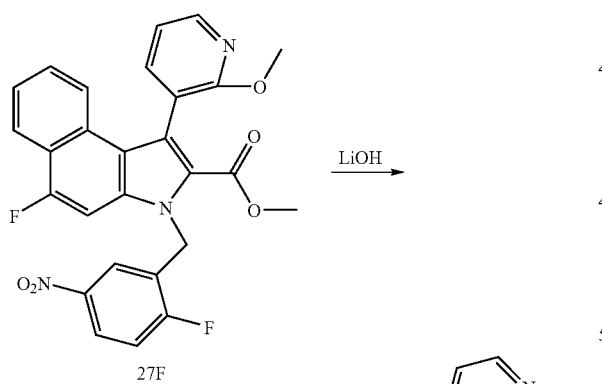

To a solution of compound 27F in a 1:1 mixture of water/THF (20 mL total) was added lithium hydroxide (0.043 g 1.8 mmol) and the resulting reaction was heated to 65° C. and allowed to stir at this temperature for about 15 hours. The reaction mixture was then cooled to room temperature, diluted with aqueous HCl and extracted into ethyl acetate. The combined organic layers were dried (Na$_2$SO$_4$), filtered, concentrated in vacuo to provide 0.136 g of the product 27G which was used without further purification.

Step F—Synthesis of Compound 27

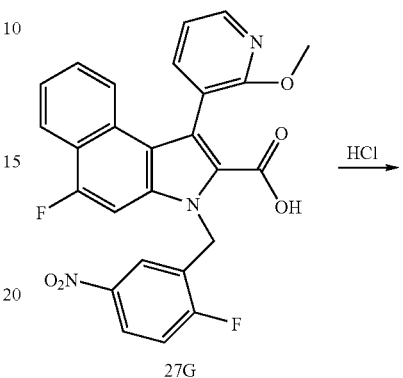
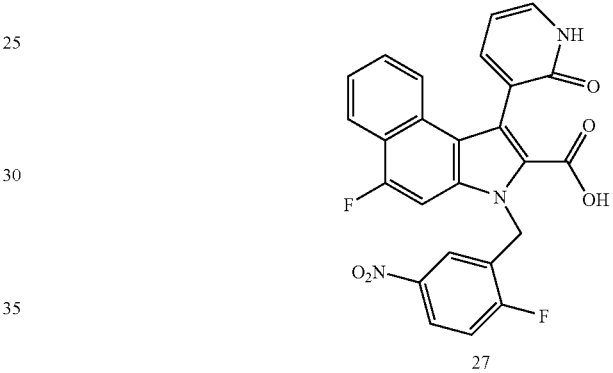

Compound 27G (0.01 g, 0.02 mmol) was dissolved in 1 ml dioxane (1 mL) and 4N HCl (1 mL) in a pressure tube and the resulting reaction mixture was heated to 90° C. and allowed to remain at this temperature for 1 hour. The reaction mixture was cooled to room temperature, then concentrated in vacuo to provide a residue which was purified using flash chromatography (CH$_2$Cl$_2$/MeOH) to provide compound 27H (3 mg, 30%). M.S. found: 476.3 (M+H)$^+$; $^1$H NMR (500 MHz, CD$_3$OD): δ 8.22 (m, 1H), 8.12 (m, 1H), 7.92 (m, 1H), 7.72 (m, 2H), 7.59 (m, 1H), 7.52-7.39 (m, 4H), 6.60 (m, 1H), 6.20 (m, 1H), 6.00 (m, 1H).

Example 8

Preparation of Compound 33

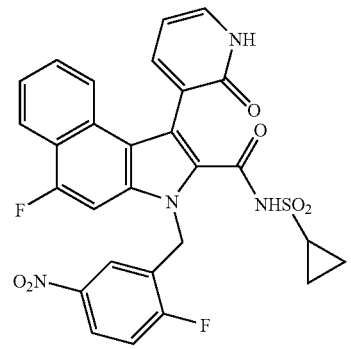

Step G—Synthesis of Compound 33A

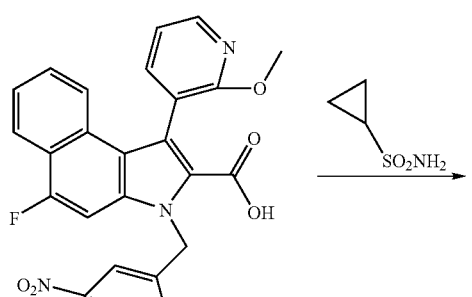

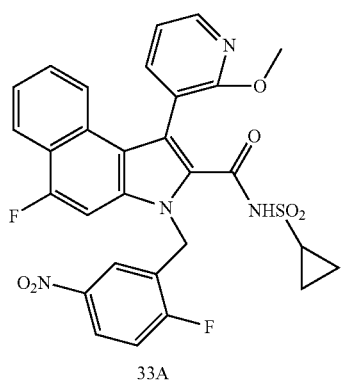

Compound 27G (120 mg, 0.25 mmol) was diluted with tetrahydrofuran (5 mL) and to the resulting solution was added carbonyldiimidazole (49 mg, 0.3 mmol) and the resulting reaction was heated to reflux and allowed to stir at this temperature for 1 hour. The reaction mixture was cooled to room temperature and cyclopropanesulfonamide (36 mg, 0.3 mmol) and 1,8-diazabicyclo(5.4.0)undec-7-ene (0.3 mmol) were added and the resulting reaction was allowed to stir at room temperature for about 15 hours. The reaction mixture was then concentrated in vacuo, and the resulting residue was diluted with ethyl acetate (100 mL) and 1N HCl (10 mL). The mixture was then washed with water (10 mL) and brine (10 mL), the layers were separated, and the aqueous layer was extracted with ethyl acetate (2×20 mL). The combined organic layers were dried over sodium sulfate, filtered and concentrated in vacuo to provide a crude product which was purified using flash chromatography to provide compound 33A (70 mg, 47%) which was used without further purification.

Step G—Synthesis of Compound 33

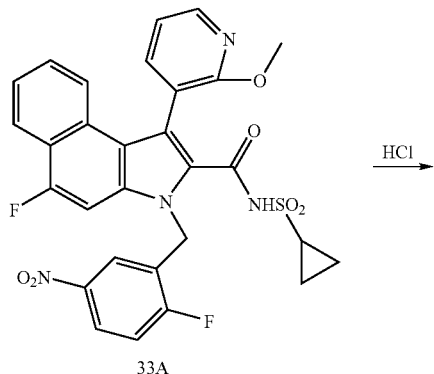

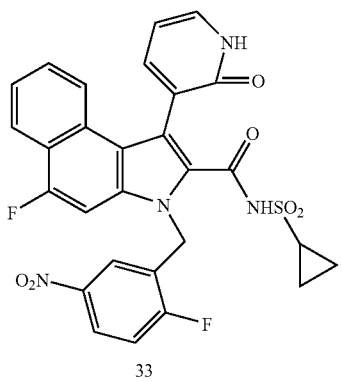

Compound 33A (70 mg, 0.12 mmol) was dissolved in a mixture of dioxane (3 mL) and 4N HCl (2 mL) in a pressure tube and the resulting reaction was heated to 90° C. and allowed to remain at this temperature for 1 hour. The reaction mixture was then cooled to room temperature and concentrated in vacuo to provide a crude residue which was purified using flash chromatography to provide compound 33 (14 mg, 21%). M.S. found: 579.3 (M+H)$^+$; $^1$H NMR (500 MHz, DMSO): δ 8.25 (m, 1H), 8.12 (d, J=7.6 Hz, 1H), 7.98 (m, 1H), 7.80-7.75 (m, 3H), 7.59 (s, 1H), 7.60-7.50 (m, 3H), 6.79 (s, 1H), 6.58 (s, 1H), 6.00 (d, J=17.0, 1H), 5.92 (d, J=17.0, 1H), 2.84 (m, 1H), 0.96-0.89 (m, 4H).

Example 9

Preparation of Intermediate Compound AA7

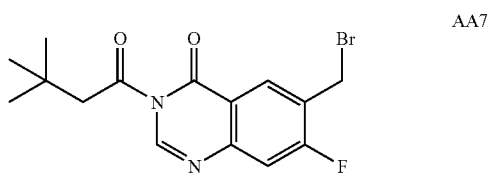 [SMILES: CC(C)(C)CC(=O)n1cnc2cc(F)c(CBr)cc2c1=O]

Step A—Synthesis of Compound AA2

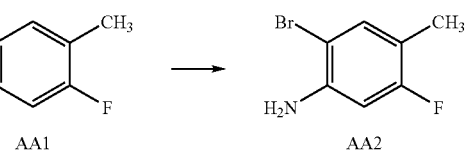

A mixture of compound AA1 (6.00 g, 47.9 mmol) and anhydrous potassium carbonate (6.70 g, 48.5 mmol) in anhydrous dichloromethane (130 mL) was cooled to −15° C. in a salt-ice bath and then added dropwise to a solution of bromine (7.70 g, 48.2 mmol) in anhydrous dichloromethane (80 mL). After addition was complete, the reaction was allowed to stir at −15° C. for 1 hour. Ice water (100 mL) was added to the reaction mixture and the aqueous layer was extracted with dichloromethane (2×100 mL). The combined organic layers were dried over MgSO$_4$ and concentrated in vacuo to provide compound AA2 (11.0 g, quant.), which was used without further purification.

Step B—Synthesis of Compound AA3

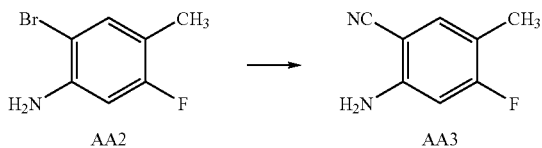

Compound AA2 was dissolved in DMF (150 mL) and to this solution was added copper (I) cyanide (11.0 g, 123 mmol). The mixture was heated to 160° C. and allowed to stir at this temperature for 20 h. After being cooled to room temperature, with water (200 mL), iron (III) chloride (42.0 g, 155 mmol) and concentrated hydrochloric acid (20 mL) were added to the reaction mixture and the resulting reaction was stirred for 45 minutes. The reaction mixture was then basified to pH>10 using commercial ammonium hydroxide solution. The basic solution was then extracted with ethyl acetate (4×400 mL). The combined organic extracts were washed with water, dried over magnesium sulfate, filtered and concentrated in vacuo. The residue obtained was purified using flash chromatography to provide compound AA3 (5.82 g, 81%). $^1$H NMR (400 MHz, $d_6$-DMSO): δ 7.34 (d, J=8.4 Hz, 1H), 6.52 (d, J=12.4 Hz, 1H), 6.10 (s, 2H), 2.08 (s, 3H).

Step C—Synthesis of Compound AA4

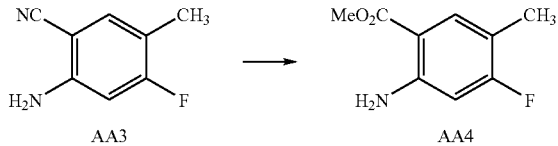

To the solution of AA3 (2.0 g, 13.3 mmol) in anhydrous methanol (15 mL) at room temperature was added concentrated sulfuric acid (4.0 mL). The reaction mixture was heated to 70° C. and stirred for four days. After cooled to room temperature, it was poured into with ice water. The mixture was then diluted with ethyl acetate (200 mL) and was made basic (pH>10) with commercial ammonium hydroxide solution. The layers were separated. The aqueous layer was extracted with ethyl acetate (2×100 mL). The combined organic solution was dried over $MgSO_4$ and concentrated in vacuo to provide the crude product which, was purified using flash chromatography to provide compound AA4 (1.0 g, 41%) and some recovered AA3. $^1$H NMR (400 MHz, $d_6$-DMSO): δ 7.61 (d, J=8.8 Hz, 1H), 6.69 (s, 2H), 6.51 (d, J=12.0 Hz, 1H), 3.77 (s, 3H), 2.06 (s, 3H).

Step D—Synthesis of Compound AA5

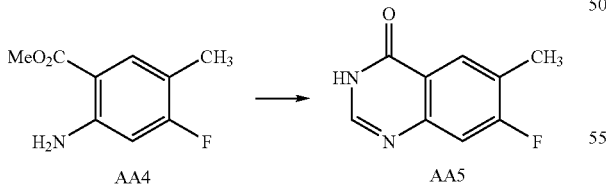

The solution of compound AA4 (500 mg, 2.73 mmol) in formamide (6.0 mL) was heated to 150° C. in an oil bath and stirred for 18 h. After cooled to room temperature, ethyl acetate (100 mL) and water (100 mL) were added and the layers were separated. The organic solution was washed with water (2×60 mL), dried over $MgSO_4$ and concentrated in vacuo to provide the crude product AA5 (0.50 g, quant.) which, was used without further purification. MS found for $C_9H_7FN_2O$: 179.0 (M+H)$^+$.

Step E—Synthesis of Compound AA6

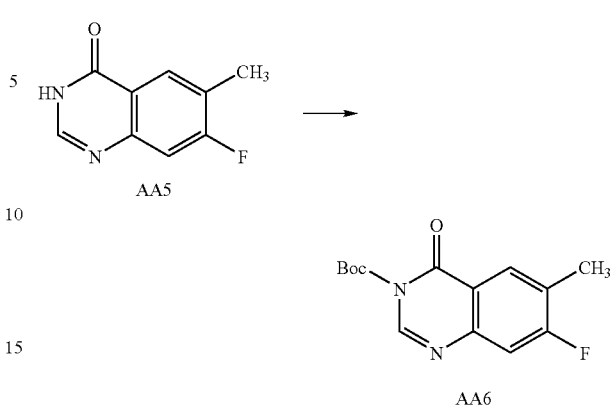

To the solution of AA5 (from Step 4) in anhydrous THF (20 mL) at room temperature was added di-tert-butyl dicarbonate (1.84 g, 8.43 mmol), 4-dimethylaminopyridine (350 mg, 2.86 mmol) and Methyl amine (0.40 mL, 2.87 mmol). The reaction mixture was stirred for 18 h. Ethyl acetate (100 mL) and water (100 mL) were added and the layers were separated. The aqueous layer was extracted with ethyl acetate (2×50 mL). The combined organic solution was dried over $MgSO_4$ and concentrated in vacuo to provide the crude product which, was purified using flash chromatography to provide compound AA6 (285 mg, 36%). MS found for $C_{14}H_{15}FN_2O_3$: 179.0 (M+H-100)$^+$.

Step F—Synthesis of Compound AA7

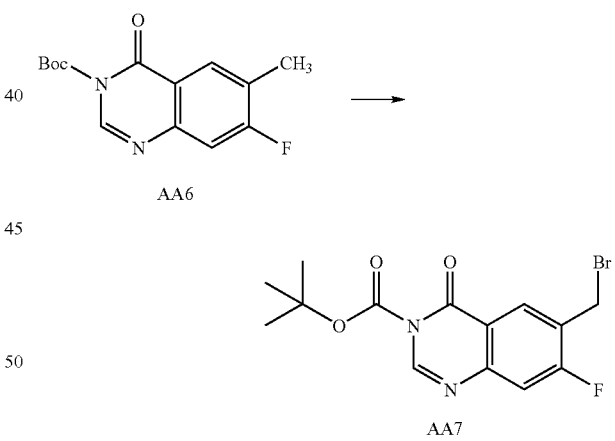

The mixture of AA6 (282 mg, 1.01 mmol), NBS (253 mg, 1.42 mmol) and AIBN (58 mg, 0.353 mmol) in anhydrous carbon tetrachloride (60 mL) was heated to 90° C. in an oil bath and stirred for 4 h. After cooled to room temperature and concentrated in vacuo, the residue was dissolved in ethyl acetate (100 mL) and water (100 mL). The layers were separated. The organic solution was washed with water (100 mL), dried over $MgSO_4$ and concentrated in vacuo to provide the crude product AA7 (453 mg, quant.) which, was used without further purification.

Example 10

Preparation of Intermediate Compound BB3

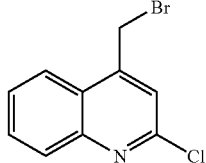

Step A—Synthesis of Compound BB1

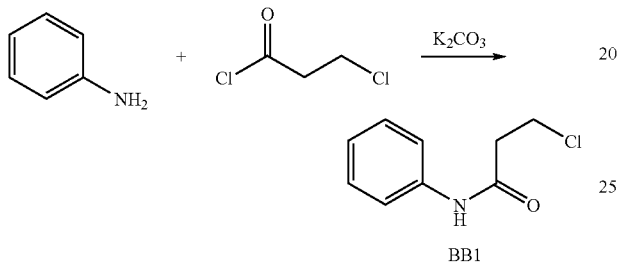

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at RT for 3 hours. The reaction mixture was filtered and the collected solid was washed sequentially with water (300 mL), aq. HCl (1M, 2×300 mL), and water (300 mL), then dried to provide compound BB1, which was used without purification (114.5 g, 87%).

Step B—Synthesis of Compound BB2

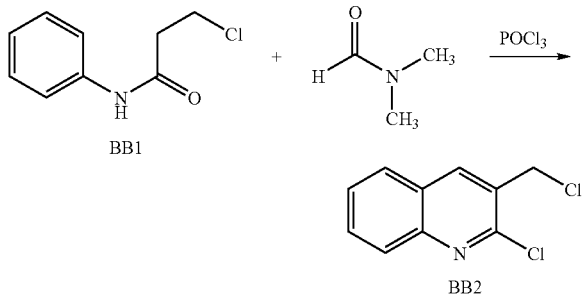

N,N-Dimethylformamide (53.7 mL, 694 mmol) was charged into a three necked flask and cooled to 0° C. and treated with phosphoryl chloride (177.7 mL, 1906 mmol) dropwise. The reaction was stirred at that temperature for 10 min and treated with 3-Chloro-N-phenylpropanamide BB1 (50.00 g, 272.3 mmol) and stirred at rt. for 30 min. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried ($MgSO_4$) filtered concentrated in vacuo and the residue obtained was recrystallized from boiling hexanes to provide compound BB2 (20 g).

Step C—Synthesis of Compound BB3

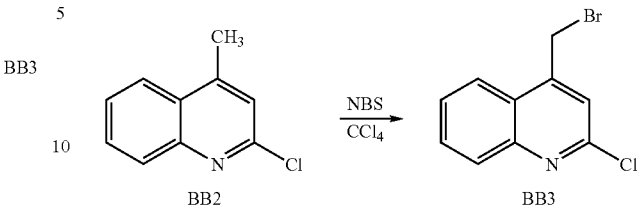

A mixture of compound BB2 (Fluka-Aldrich, 1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound BB3, and was used without further purification.

Example 11

Preparation of Intermediate Compound CC5

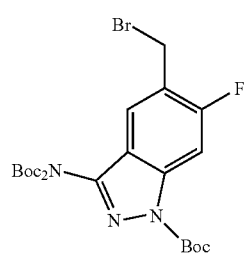

Step A—Synthesis of Compound CC1

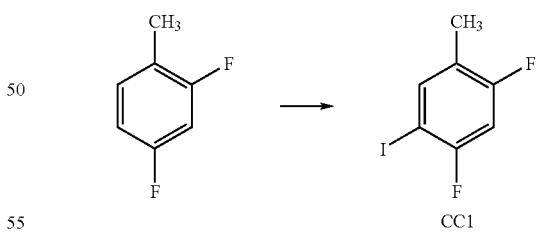

A solution of 2,4-difluorotoluene (4.72 g, 36.8 mmol) in trifluoroacetic acid (12.29 mL, 159.5 mmol) was cooled to 0° C., then N-Iodosuccinimide (9.59 g, 42.6 mmol) was added and the resulting reaction was allowed to stir at RT for about 15 hours. The reaction mixture was then concentrated in vacuo and the residue obtained was dissolved in hexanes (100 mL), washed with aqueous sodium thiosulfate (100 mL), brine (100 mL), then dried ($MgSO_4$), filtered and concentrated in vacuo. The resulting residue was purified using bulb-to-bulb distillation to provide compound CC1 (7.2 g, 77%) as a colorless oil.

Step B—Synthesis of Compound CC2

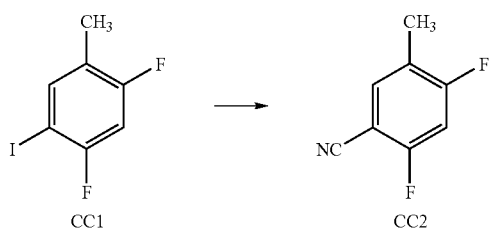

A solution of compound CC1 (7.11 g, 28.0 mmol), zinc cyanide (1.97 g, 16.8 mmol) and tetrakis(triphenylphosphine)palladium(0) (3.23 g, 2.80 mmol) in DMF (30 mL) was heated to 90° C. and allowed to stir at this temperature for 1.5 h. The reaction mixture was concentrated in vacuo and the residue obtained was taken up in water (400 mL) and extracted with ether (400 mL). The organic extract was washed with aqueous ammonium hydroxide solution (IN). The organic layer was dried (MgSO$_4$) filtered, concentrated in vacuo to provide a residue that was purified using flash column chromatography (SiO$_2$, EtOAc/Hexanes) to provide a mixture that contained product and triphenylphosphine. This mixture was further purified using sublimation at 1 mm/Hg at 45° C. to provide compound CC2 (1.8 g; Yield=42%).

Step C—Synthesis of Compound CC3

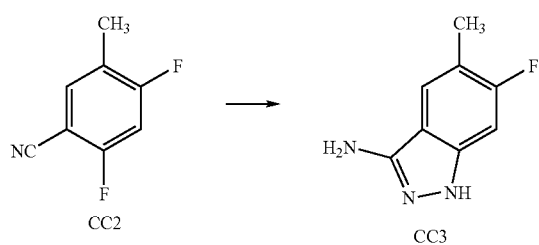

A solution of compound CC2 (1.400 g, 9.154 mmol) and hydrazine (0.700 mL, 22.3 mmol) in isopropyl alcohol (50.00 mL, 653.1 mmol), was heated to reflux and allowed to stir at this temperature for 24 hours. The reaction mixture was cooled to room temperature, concentrated in vacuo and the residue obtained was purified using flash column chromatography (SiO$_2$, Acetone/Hexanes 0→50%) to provide compound CC3 (330 mg, 22%).

Step D—Synthesis of Compound CC4

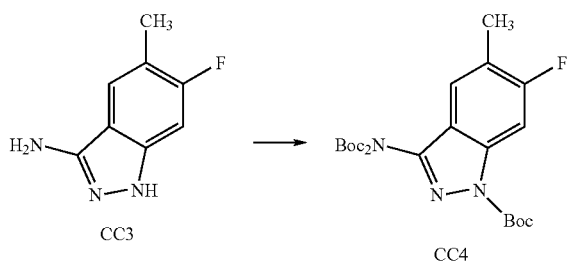

A solution of compound CC3 (330.00 mg, 1.998 mmol), di-tert-butyldicarbonate (2.6163 g, 11.98 mmol) and 4-dimethylaminopyridine (48.817 mg, 0.39959 mmol) in acetonitrile (15.00 mL, 287.2 mmol) was heated to reflux and allowed to stir at this temperature for 2 hours. The reaction mixture was cooled to room temperature, concentrated in vacuo, and the resulting residue was purified using flash column chromatography (SiO$_2$, EtOAc/Hexanes 0-20%) to provide compound CC4 (640.00 mg, 68%) as a colorless oil.

Step E—Synthesis of Compound CC5

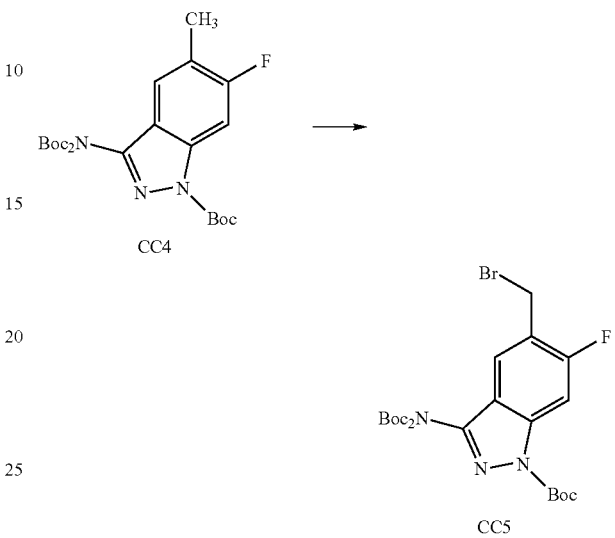

A solution of compound CC4 (630.00 mg, 1.3533 mmol), N-bromosuccinimide (337.22 mg, 1.8947 mmol) and benzoyl peroxide (65.563 mg, 0.27067 mmol) in carbon tetrachloride (20.00 mL) was heated to reflux and allowed to stir at this temperature for 3 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried (MgSO$_4$), filtered, and concentrated in vacuo. The residue obtained was purified using flash column chromatography (SiO$_2$, EtOAc/Hexanes) to provide compound CC5 as a colorless oil.

Example 12

Preparation of Intermediate Compounds DD5 and DD6

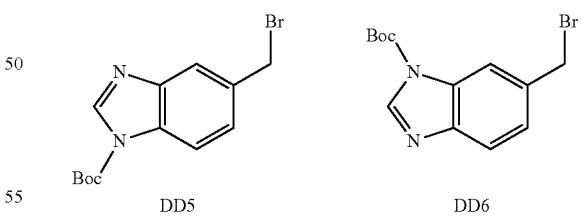

Step A—Synthesis of Compound DD2

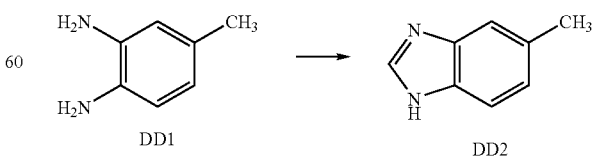

A solution of compound DD1 (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound DD2 (3.65 g), which was used without further purification. M.S. found for $C_8H_8N_2$: 133.2 $(M+H)^+$.

Step B—Synthesis of Compounds DD3 and DD4

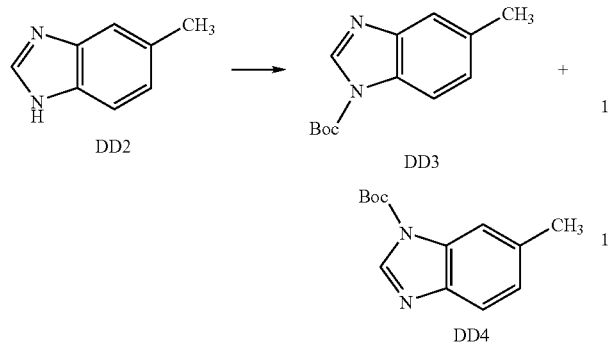

To a solution of compound DD2 (24.5 mmol) in $CH_3CN$ (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds DD3 and DD4 (5.38 g, 94.3% yield over steps A and B).

Step C—Synthesis of Compounds DD5 and DD6

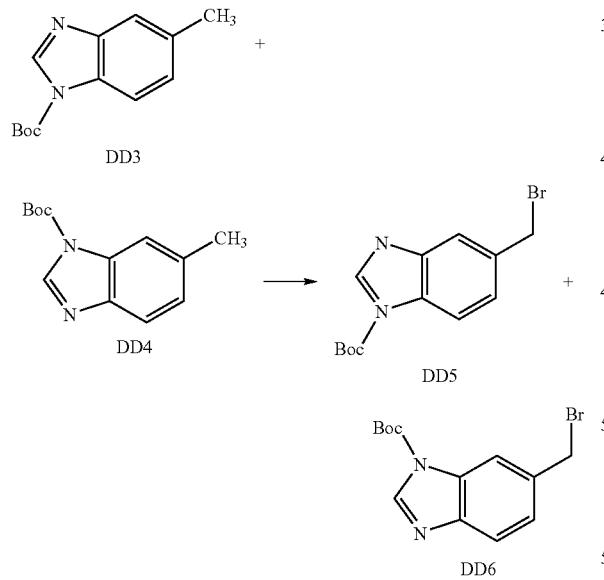

To a solution of compounds DD3 and DD4 (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds DD5 and DD6 (2.58 g) which was used without further purification. M.S. found for $C_{13}H_{15}BrN_2O_2$: 334.7 $(M+Na)^+$.

Example 13

Preparation of Intermediate Compound BB2

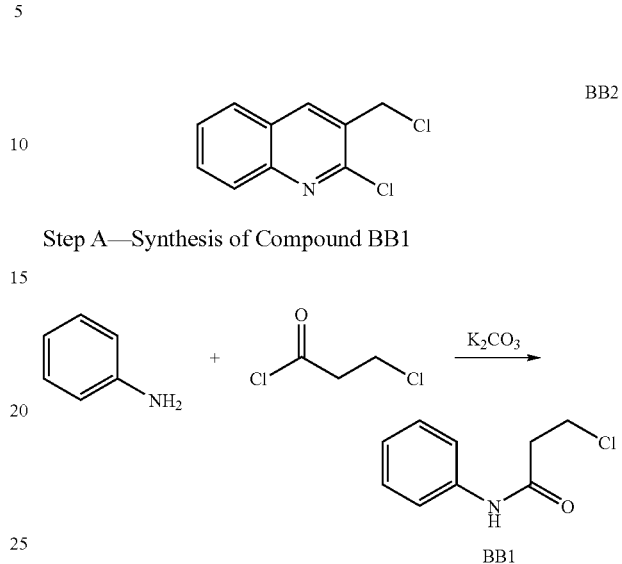

Step A—Synthesis of Compound BB1

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at RT for 3 hours. The reaction mixture was filtered and the collected solid was washed sequentially with water (300 mL), aq. HCl (1M, 2×300 mL), and water (300 mL), then dried to provide compound BB1, which was used without purification (114.5 g, 87%).

Step B—Synthesis of Compound BB2

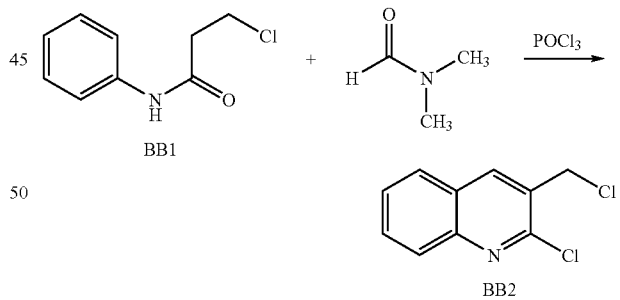

N,N-Dimethylformamide (53.7 mL, 694 mmol) was charged into a three necked flask and cooled to 0° C. and treated with phosphoryl chloride (177.7 mL, 1906 mmol) dropwise. The reaction was stirred at that temperature for 10 min and treated with 3-Chloro-N-phenylpropanamide BB1 (50.00 g, 272.3 mmol) and stirred at rt. for 30 min. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried ($MgSO_4$) filtered concentrated in vacuo and the residue obtained was recrystallized from boiling hexanes to provide compound BB2 (20 g).

Example 14

Preparation of Intermediate Compound EE2

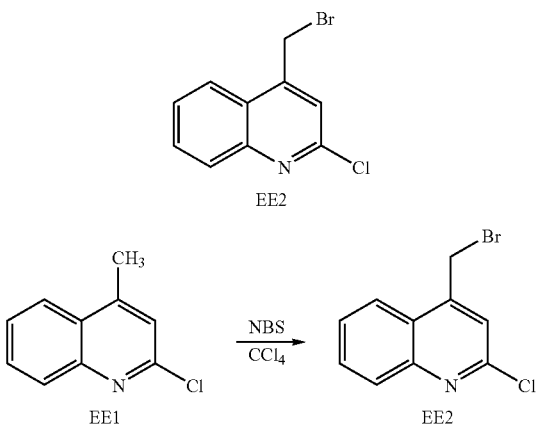

A mixture of compound EE1 (Fluka-Aldrich, 1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound EE2, and was used without further purification.

LCMS data for selected Compounds of Formula (I) is provided below in Table 1, wherein the compound numbers correspond to the compound numbering set forth in the above specification.

TABLE 1

| LCMS Data For Selected Compounds of Formula (I) | | | |
|---|---|---|---|
| Compound | M + H | Compound | M + H |
| 1 | 411.5 | 6 | 488.5 |
| 2 | 396.4 | 7 | 440.4 |
| 3 | 412.4 | 8 | 439.4 |
| 4 | 411.4 | 9 | 593.7 |
| 5 | 413.4 | 10 | 530.6 |
| 11 | 550.6 | 12 | 516.5 |
| 13 | 530.6 | 14 | 502.6 |
| 15 | 566.6 | 16 | 663.7 |
| 17 | 432.4 | 18 | 414.4 |
| 19 | 432.4 | 20 | 516.5 |
| 21 | 496.2 | 22 | 418.43 |
| 23 | 420.40 | 24 | 430.41 |
| 25 | 436.42 | 26 | 438.39 |
| 27 | 475.41 | 28 | 497.51 |
| 29 | 513.52 | 30 | 521.57 |
| 31 | 533.56 | 32 | 539.56 |
| 33 | 578.56 | | |

Example 15

Additional NMR Data for Selected Compounds of the Invention

NMR data for the compounds of the invention numbered 3, 7, 9, 10, 11, 14, 22, 23-26, 28, 29, 31 and 31 are provided below.

Compound 3
$^1$H NMR (500 MHz, CD$_3$OD): δ 7.88 (d, J=8.2 Hz, 1H), 7.74 (m, 2H), 7.60-7.45 (m, 4H), 7.37-7.18 (m, 4H), 6.57 (d, J=6.0 Hz, 1H), 6.26 (s, 1H), 6.02 (m, 2H), 4.77 (s, 2H).

Compound 7
$^1$H NMR (500 MHz, CD$_3$OD): δ 8.05 (s, 1H), 7.81 (m, 2H), 7.62-7.56 (m, 4H), 7.44 (m, 1H), 7.30-7.12 (m, 6H), 6.12 (d, J=16.1 Hz, 1H), 5.98 (d, J=16.1 Hz, 1H).

Compound 9
$^1$H NMR (500 MHz, CD$_3$OD): δ 7.89 (m, 2H), 7.80-7.60 (m, 6H), 7.38-7.28 (m, 4H), 7.68 (t, J=6.6 Hz 1H), 6.35 (d, J=16.3 Hz, 1H), 5.78 (d, J=16.3 Hz, 1H), 2.98 (s, 3H), 2.89 (s, 3H)

Compound 10
$^1$H NMR (500 MHz, CD$_3$OD): δ 7.95 (s, 1H), 7.85 (m, 4H), 7.75 (s, 1H), 7.65 (s, 2H), 7.45-7.30 (m, 4H), 6.65 (s, 1H), 6.02 (s, 1H), 5.92 (d, J=16.4 Hz, 1H), 3.87 (s, 3H).

Compound 11
$^1$H NMR (500 MHz, CD$_3$OD): δ 7.86 (m, 2H), 7.68 (m, 5H), 7.45 (m, 2H), 7.35 (m, 5H), 6.45 (t, J=6.3 Hz, 1H), 6.40 (s, 1H), 6.02 (s, 1H), 5.93 (s, 1H), 5.91 (s, 1H).

Compound 14
$^1$H NMR (500 MHz, CD$_3$OD): δ 7.92 (d, J=8.8 Hz, 1H), 7.86 (dd, J=1.9 Hz, J=6.9 Hz, 1H), 7.80 (m, 3H), 7.63 (d, J=6.6 Hz, 1H), 7.59 (d, J=9.1 Hz, 1H), 7.4 (m, 2H), 6.72 (t, J=Hz, 1H), 6.69 (d, J=6.6 Hz, 1H), 6.23 (s, 1H), 5.85 (m, 2H), 3.32 (m, 2H), 1.17 (t, J=7.3 Hz, 3H).

Compound 22
$^1$H-NMR (400 MHz, in dmso-d6): δ 11.55 (1H, broad s), 7.38 (1H, dd, J=2.19, 7.32 Hz), 7.31 (1H, dd, J=2.19, 6.59 Hz), 7.26 (1H, m), 7.20 (1H, dd, J=8.05, 9.52 Hz), 7.04 (1H, dd, J=6.59, 7.32 Hz), 6.96 (1H, d, J=8.78 Hz), 6.94 (1H, d, J=8.78 Hz), 6.57 (1H, t, J=7.32 Hz), 6.23 (1H, t, J=6.59 Hz), 5.81 (2H, s), 3.99 (2H, t, J=4.39 Hz), 2.72 (2H, t, J=6.59 Hz), 1.88 (2H, dt, J=4.39, 10.25 Hz).

Compound 23
$^1$H-NMR (400 MHz, in dmso-d6): δ 11.56 (1H, broad s), 7.42 (1H, dd, J=2.19, 7.32 Hz), 7.31 (1H, dd, J=2.19, 6.59 Hz), 7.27 (1H, m), 7.20 (1H, dd, J=8.05, 9.52 Hz), 7.05 (1H, dd, J=6.59, 7.32 Hz), 6.98 (1H, d, J=8.78 Hz), 6.86 (1H, d, J=8.78 Hz), 6.59 (1H, t, J=8.05 Hz), 6.23 (1H, t, J=6.59 Hz), 5.80 (2H, s), 4.14 (4H, m).

Compound 24
$^1$H NMR (500 MHz, CD$_3$OD): δ 8.10 (d, J=8.3 Hz, 1H), 7.91 (d, J=7.6 Hz, 1H), 7.72 (m, 1H), 7.60 (s, 1H), 7.46 (m, 2H), 7.35 (d, J=11.3 Hz, 1H), 7.27 (m, 1H), 7.15 (m, 1H), 7.02 (t, J=7.3 Hz, 1H), 6.81 (m, 1H), 6.59 (m, 1H) 6.09 (m, 2H).

Compound 25
$^1$H-NMR (400 MHz, in dmso-d6): δ 11.54 (1H, broad s), 7.37 (1H, d, J=5.12 Hz), 7.28 (2H, m), 7.12 (1H, m), 6.97 (1H, d, J=8.78 Hz), 6.94 (1H, d, J=8.78 Hz), 6.29 (1H, m), 6.20 (1H, dd, J=5.85, 6.59 Hz), 5.77 (2H, s), 3.98 (2H, m), 2.71 (2H, dd, J=5.85, 6.59 Hz), 1.87 (2H, m)

Compound 26
$^1$H-NMR (400 MHz, in dmso-d6): δ 11.56 (1H, broad s), 7.43 (1H, d, J=7.32), 7.30 (2H, m), 7.14 (1H, m), 7.01 (1H, d, J=8.78 Hz), 6.88 (1H, d, J=8.78 Hz), 6.35 (1H, ddd, J=3.66, 5.12, 8.78 Hz), 6.23 (1H, t, J=6.59 Hz), 5.78 (2H, s), 4.15 (4H, dd, J=3.66, 13.91 Hz).

Compound 28

¹H-NMR (400 MHz, in dmso-d6): δ 7.71 (1H, d, J=7.32 Hz), 7.58 (1H, m), 7.28 (1H, t, J=6.59 Hz), 7.19 (1H, dd, J=8.05, 10.25 Hz), 7.07 (1H, m), 7.04 (1H, d, J=8.78 Hz), 6.89 (1H, d, J=8.78 Hz), 6.81 (1H, dd, J=7.32, 8.05 Hz), 6.50 (1H, t, J=6.59 Hz), 5.64 (2H, s), 4.15 (2H, d, J=3.66 Hz), 4.10 (2H, d, J=3.66 Hz), 3.18 (3H, s).

Compound 29

¹H-NMR (400 MHz, in dmso-d6): δ 7.70 (1H, dd, J=2.19, 7.32 Hz), 7.61 (1H, t, J=5.12 Hz), 7.30 (1H, ddd, J=4.39, 9.52, 9.52 Hz), 7.16 (1H, m), 7.03 (1H, d, J=8.78 Hz), 7.01 (1H, d, J=8.78 Hz), 6.56 (1H, m), 6.52 (1H, dd, J=6.59, 7.32 Hz), 5.64 (2H, s), 3.99 (2H, dd, J=4.39, 5.12 Hz), 3.22 (3H, s), 2.74 (2H, dd, J=5.85, 6.59 Hz), 1.89 (2H, m).

Compound 31

¹H NMR (500 MHz, CDCl₃): δ 8.14 (d, J=8.2 Hz, 1H), 7.84 (dd, J=1.9 Hz, J=7.1 Hz, 1H), 7.79 (m, 1H), 7.61 (d, J=8.3 Hz, 1H), 7.46 (t, J=7.5 Hz, 1H), 7.37 (m, 1H), 7.30 (m, 1H), 7.23 (d, J=10.6 Hz, 1H), 7.14 (t, J=9.5 Hz, 1H), 7.08 (m, 1H), 7.01 (m, 1H), 6.71 (t, J=6.9 Hz, 1H), 6.03 (d, J=16.5 Hz, 1H), 5.70 (d, J=16.5 Hz, 1H), 2.92 (m, 1H), 1.32 (m, 1H), 1.12 (m, 1H), 1.00 (m, 1H), 0.88 (m, 1H).

Compound 32

¹H-NMR (400 MHz, in dmso-d6): δ 7.70 (1H, dd, J=2.19, 7.32 Hz), 7.63 (1H, broad s), 7.30 (1H, ddd, J=4.39, 9.52, 9.52 Hz), 7.17 (1H, ddd, J=3.66, 8.05 Hz), 7.05 (1H, d, J=8.78 Hz), 7.01 (1H, d, J=8.78 Hz), 6.56 (1H, m), 6.54 (1H, dd, J=6.59, 6.59 Hz), 5.66 (2H, s), 3.98 (2H, dd, J=4.39, 5.12 Hz), 2.90 (1H, m), 2.73 (2H, dd, J=5.85, 6.59), 1.88 (2H, m), 0.94 (4H, m).

Example 16

HCV NS5B Polymerase Inhibition Assay

An in vitro transcribed heteropolymeric RNA known as D-RNA or DCoH has been shown to be an efficient template for HCV NS5B polymerase (S.-E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., 12$^{th}$ International Symposium on HCV and Related Viruses, P-306 (2005). A soluble C-terminal 21-amino acid truncated NS5B enzyme form (NS5B☐CT21) was produced and purified from Escherichia coli as C-terminal polyhistidine-tagged fusion protein as described in Ferrari et al., J. Virol. 73:1649-1654 (1999). A typical assay contained 20 mM Hepes pH 7.3, 10 mM MgCl₂, 60 mM NaCl, 100 μg/ml BSA, 20 units/ml RNasin, 7.5 mM DTT, 0.1 μM ATP/GTP/UTP, 0.026 μM CTP, 0.25 mM GAU, 0.03 μM RNA template, 20 μCi/ml [³³P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the Compounds of Formula (I) on the polymerase activity was evaluated by adding various concentrations of a Compound of Formula (I), typically in 10 serial 2-fold dilutions, to the assay mixture. The starting concentrations of the indole derivatives ranged from 200 μM to 1 μM. An IC$_{50}$ value for the inhibitor, defined as the compound concentration that provides 50% inhibition of polymerase activity, was determined by fitting the cpm data to the Hill equation Y=100/(1+10^((Log IC50−X)*HillSlope)), where X is the logarithm of compound concentration, and Y is the % inhibition. Ferrari et al., 12$^{th}$ International Symposium on HCV and Related Viruses, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected Compounds of Formula (I) is provided below in Table 2, wherein the compound numbers correspond to the compound numbering set forth in the above specification. The data is designated as follows: "A" for IC$_{50}$ values less than 25 nanomolar (nM), "B" for IC$_{50}$ values between 25 to and 100 nM and "C" for IC$_{50}$ values greater than 100 nM.

TABLE 2

NS5B Polymerase Inhibition Assay Data for Selected Compounds of Formula (I)

| Compound | IC$_{50}$ (nM) | Compound | IC$_{50}$ (nM) |
|---|---|---|---|
| 1 | C | 12 | A |
| 2 | C | 13 | B |
| 3 | C | 14 | B |
| 4 | C | 15 | B |
| 5 | C | 16 | A |
| 6 | B | 17 | B |
| 7 | C | 18 | C |
| 8 | C | 19 | C |
| 9 | B | 20 | A |
| 10 | A | 21 | A |
| 11 | B | 22 | A |
| 23 | A | 24 | B |
| 25 | A | 26 | A |
| 27 | B | 28 | A |
| 29 | A | 30 | A |
| 31 | A | 32 | A |
| 33 | A | | |

Example 17

Cell-Based HCV Replicon Assay

To measure cell-based anti-HCV activity of the a Compound of Formula (I), replicon cells were seeded at 5000 cells/well in 96-well collagen I-coated Nunc plates in the presence of the Compound of Formula (I). Various concentrations of a Compound of Formula (I), typically in 10 serial 2-fold dilutions, were added to the assay mixture, the starting concentration of the compound ranging from 250 μM to 1 μM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA; 5B.2R, TTGATGGGCAGCTTGGTTTC; the probe sequence was FAM-labeled CACGCCATGCGCTGCGG. GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ACT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve $\Delta CT=1$ over the projected baseline; $EC_{90}$ the concentration necessary to achieve $\Delta CT=3.2$ over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for selected Compounds of Formula (I) is provided below in Table 3, wherein the compound numbers correspond to the compound numbering set forth in the above specification. The data is designated as follows: "A" for $EC_{50}$ values less than 1.0 micromolar (μM), "B" for $EC_{50}$ values between 1.0 and 10.0 μM and "C" for $EC_{50}$ values greater than 10.0 μM.

TABLE 3

HCV Replicon Assay Data for Selected Compounds of Formula (I)

| Compound No. | $EC_{50}$ (μM) | Compound No. | $E_{50}$ (μM) |
|---|---|---|---|
| 1 | C | 12 | C |
| 3 | B | 14 | B |
| 4 | B | 15 | B |
| 5 | C | 16 | A |
| 6 | C | 17 | B |
| 7 | C | 18 | B |
| 10 | B | 20 | A |
| 11 | B | 21 | A |
| 23 | B | 22 | A |
| 25 | A | 24 | B |
| 27 | A | 26 | A |
| 29 | A | 28 | A |
| 31 | A | 30 | A |
| 33 | A | 32 | A |

Uses of the Compounds of Formula (I)

The Compounds of Formula (I) are useful in human and veterinary medicine for treating or preventing a viral infection or a virus-related disorder in a patient. In accordance with the invention, the Compounds of Formula (I) can be administered to a patient in need of treatment or prevention of a viral infection or a virus-related disorder.

Accordingly, in one embodiment, the invention provides methods for treating a viral infection in a patient comprising administering to the patient an effective amount of at least one Compound of Formula (I) or a pharmaceutically acceptable salt, solvate, ester or prodrug thereof. In another embodiment, the invention provides methods for treating a virus-related disorder in a patient comprising administering to the patient an effective amount of at least one Compound of Formula (I) or a pharmaceutically acceptable salt, solvate, ester or prodrug thereof.

Treatment or Prevention of a Viral Infection

The Compounds of Formula (I) can be used to treat or prevent a viral infection. In one embodiment, the Compounds of Formula (I) can be inhibitors of viral replication. In a specific embodiment, the Compounds of Formula (I) can be inhibitors of HCV replication. Accordingly, the Compounds of Formula (I) are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The Compounds of Formula (I) can be used to treat or prevent a virus-related disorder. Accordingly, the Compounds of Formula (I) are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The Compounds of Formula (I) are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one Compound of Formula (I) or a pharmaceutically acceptable salt, solvate, ester or prodrug thereof.

Treatment or Prevention of a Disorder Related to HCV Infection

The Compounds of Formula (I) can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one Compound of Formula (I), or a pharmaceutically acceptable salt, solvate, ester or prodrug thereof.

Combination Therapy

In another embodiment, the present methods for treating or preventing a viral infection can further comprise the administration of one or more additional therapeutic agents which are not Compounds of Formula (I).

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Compound of Formula (I), or a pharmaceutically acceptable salt, solvate, ester or prodrug thereof, and (ii) at least one other antiviral agent that is other than a Compound of Formula (I), wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Compound of Formula (I) and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one Compound of Formula (I) is administered during at time when the additional antiviral agent(s) exert their prophylactic or therapeutic effect, or vice versa.

In another embodiment, the at least one Compound of Formula (I) and the additional antiviral agent(s) are administered in doses commonly employed when such agents are used as monotherapy for treating a viral infection.

In another embodiment, the at least one Compound of Formula (I) and the additional antiviral agent(s) are administered in doses lower than the doses commonly employed when such agents are used as monotherapy for treating a viral infection.

In still another embodiment, the at least one Compound of Formula (I) and the additional antiviral agent(s) act synergistically and are administered in doses lower than the doses commonly employed when such agents are used as monotherapy for treating a viral infection.

In one embodiment, the at least one Compound of Formula (I) and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one Compound of Formula (I) and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one Compound of Formula (I) and the additional antiviral agent(s) may inhibit the resistance of a viral infection to these agents.

Non-limiting examples of other therapeutic agents useful in the present compositions and methods include an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In another embodiment, the other antiviral agent is an antisense agent.

In another embodiment, the other antiviral agent is a therapeutic vaccine.

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and an immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule.

Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™, interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); and
International Publication Nos. WO 98/14181; WO 98/17679, WO 98/17679, WO 98/22496 and WO 99/07734.

Further examples of protease inhibitors useful in the present methods include, but are not limited to, Additional examples of other therapeutic agents useful in the present methods include, but are not limited to, Levovirin™ (ICN Pharmaceuticals, Costa Mesa, Calif.), VP 50406™ (Viropharma, Incorporated, Exton, Pa.), ISIS 14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., N.C.), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the Compound of Formula (I)(s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one Compound of Formula (I) and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU (12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A inteferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the Compounds of Formula (I) are useful in veterinary and human medicine. As described above, the Compounds of Formula (I) are useful for treating or preventing a viral infection or a virus-related disorder in a patient in need thereof.

When administered to a patient, the IDs can be administered as a component of a composition that comprises a pharmaceutically acceptable carrier or vehicle. The present invention provides pharmaceutical compositions comprising an effective amount of at least one Compound of Formula (I) and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Compounds of Formula (I) of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula (I) are administered orally.

In another embodiment, the one or more Compounds of Formula (I) are administered intravenously.

In another embodiment, the one or more Compounds of Formula (I) are administered topically.

In still another embodiment, the one or more Compounds of Formula (I) are administered sublingually.

In one embodiment, a pharmaceutical preparation comprising at least one Compound of Formula (I) is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the Compound of Formula (I)(s) by weight or volume. In various embodiments, the present compositions can contain, in one embodiment, from about 1% to about 70% or from about 5% to about 60% of the Compound of Formula (I)(s) by weight or volume.

The quantity of Compound of Formula (I) in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Compounds of Formula (I) will be regulated according to the judgment of the attending clinician considering such factors as age, condition and size of the patient as well as severity of the symptoms being treated. Generally, a total daily dosage of the Compounds of Formula (I) range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Compound of Formula (I) or a pharmaceutically acceptable salt, solvate, ester or prodrug thereof; (ii) one or more additional therapeutic agents that are not a Compound of Formula (I); and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one Compound of Formula (I), or a pharmaceutically acceptable salt, solvate, ester or prodrug of said compound and a pharmaceutically acceptable carrier, vehicle or diluent.

In another aspect the present invention provides a kit comprising an amount of at least one Compound of Formula (I), or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited herein, the entire disclosures of which are incorporated herein by reference.

What is claimed is:

1. A compound having the formula:

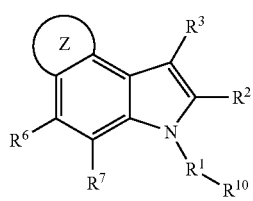

(I)

or a pharmaceutically acceptable salt or ester thereof, wherein ring Z of formula (I), is

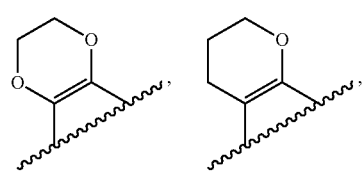

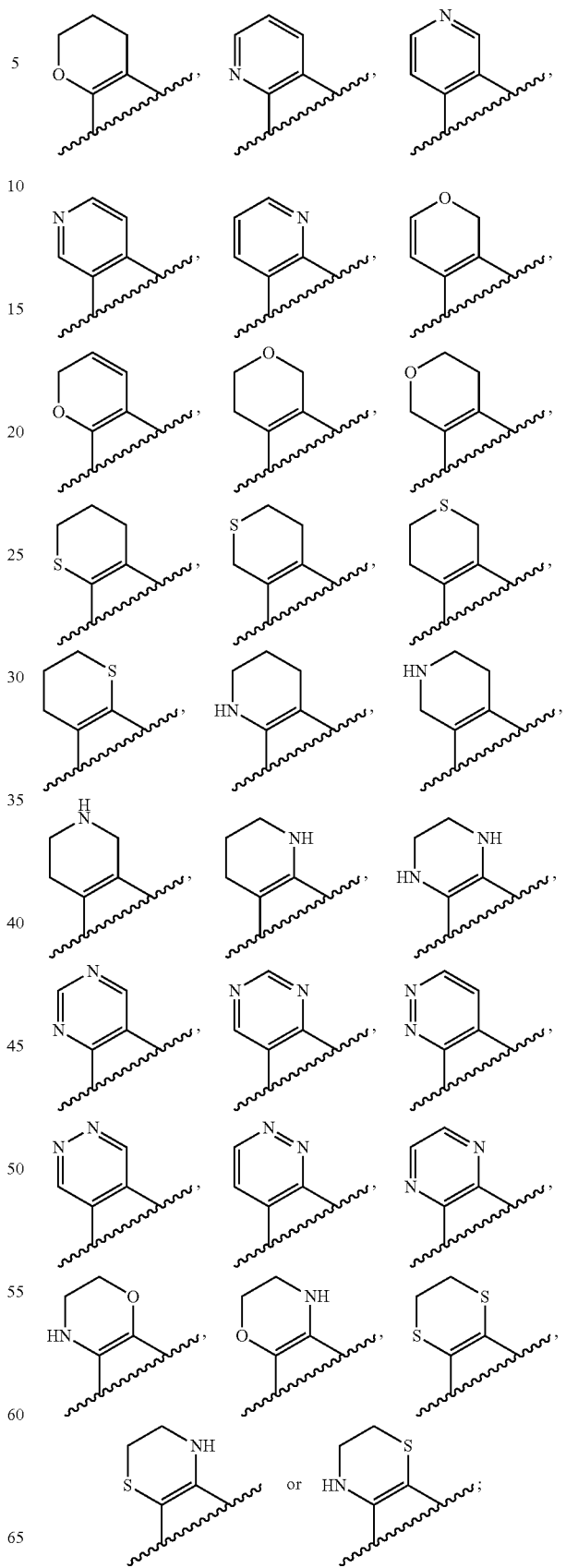

$R^1$ is —$CH_2$—

$R^2$ is —C(O)OH, —C(O)NHSO$_2$-alkyl, —C(O)NHSO$_2$-aryl, —C(O)NHSO$_2$-cycloalkyl, —C(O)NHSO$_2$-alkylene-cycloalkyl or C(O)NHSO$_2R^{11}$, wherein an aryl or cycloalkyl group can be optionally substituted with up to 4 substituents, which are each independently selected from alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2R^{11}$, —[C($R^{12}$)$_2$]$_q$—S(O)$_pR^{11}$, —[C($R^{12}$)$_2$]$_q$—SO$_2$N($R^9$)$_2$ and —SO$_2$N($R^9$)C(O)N($R^9$)$_2$;

$R^3$ is

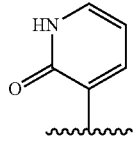

which can be optionally substituted with up to 3 substituents, which are the same or different, and are selected from alkyl, aryl, heteroaryl-, halo, haloalkyl, hydroxyalkyl, hydroxy, —CN, —C(O)$R^8$, —C(O)$OR^9$, —C(O)N($R^9$)$_2$, —[C($R^{12}$)$_2$]$_q$—$OR^9$, —[C($R^{12}$)$_2$]$_q$—N($R^9$)$_2$, and —NHC(O)$R^8$;

$R^6$ and $R^7$ are each, independently, H, alkyl, F, Cl, —CF$_3$ —OH, —O-alkyl, —OCF$_3$, —NH$_2$ and —NHSO$_2$-alkyl;

each occurrence of $R^8$ is independently H, alkyl, alkenyl, alkynyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocloalkyl, —[C($R^{12}$)$_2$]$_q$-heterocycloalkenyl, —[C($R^{12}$)$_2$]$_q$-heteroaryl, haloalkyl or hydroxyalkyl;

each occurrence of $R^9$ is independently H, alkyl, alkenyl, alkynyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocloalkyl, —[C($R^{12}$)$_2$]$_q$-heterocycloalkenyl, —[C($R^{12}$)$_2$]$_q$-heteroaryl, haloalkyl or hydroxyalkyl;

$R^{10}$ is heterocycloalkenyl, aryl, heteroaryl, wherein a heterocycloalkenyl, aryl or heteroaryl group can be optionally and independently substituted with up to 4 substituents, which are each independently selected from H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2R^{11}$, —[C($R^{12}$)$_2$]$_q$—S(O)$_pR^{11}$, —[C($R^{12}$)$_2$]$_q$—SO$_2$N($R^9$)$_2$ and —SO$_2$N($R^9$)C(O)N($R^9$)$_2$, cycloalkyl, heterocycloalkyl, hola, haloalkyl, —O-haloalkyl, —OH, —CN, —NH$_2$, —NH-alkyl, —N(alkyl)$_2$ or —NHSO$_2$-alkyl;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2$-alkyl, —[C($R^{12}$)$_2$]$_q$—NHSO$_2$-cycloalkyl, —[C($R^{12}$)$_2$]$_q$—NHSO$_2$aryl, —[C($R^{12}$)$_2$]$_q$—SO$_2$N($R^9$)$_2$ and —SO$_2$N($R^9$)C(O)N($R^9$)$_2$;

each occurrence of $R^{12}$ is independently H, halo, —N($R^9$)$_2$, —$OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C=O group;

each occurrence of p is independently 0, 1 or 2; and each occurrence of q is independently an integer ranging from 0 to 4.

2. The compound of claim 1, wherein $R^{10}$ is a bicyclic heteroaryl group.

3. The compound of claim 1, wherein $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

4. The compound of claim 1, wherein $R^2$ is —C(O)OH or —C(O)NHSO$_2R^{11}$.

5. The compound of claim 1 wherein Z is:

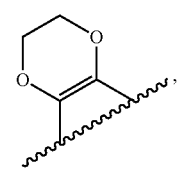

-continued
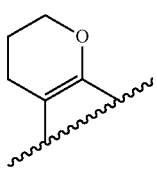 or 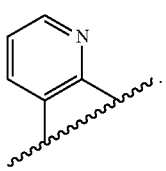.
6. A compound having the structure:
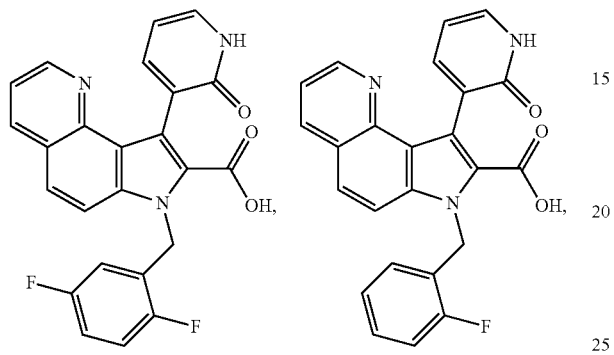
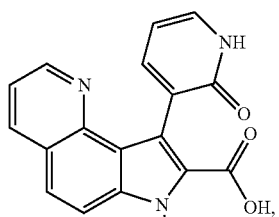
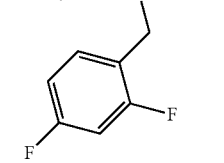
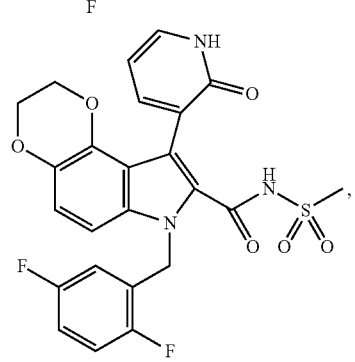
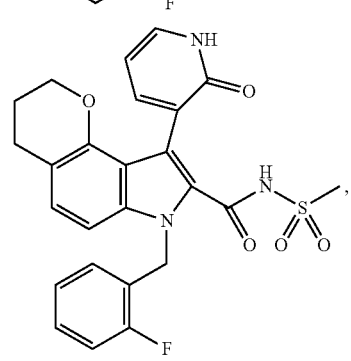
-continued
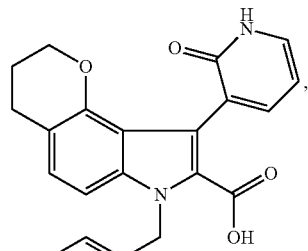
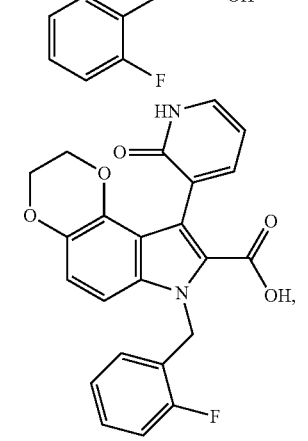
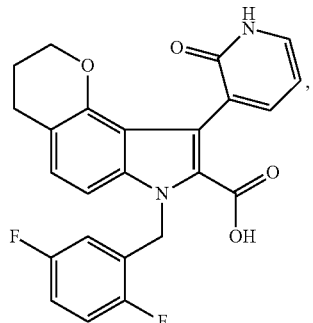
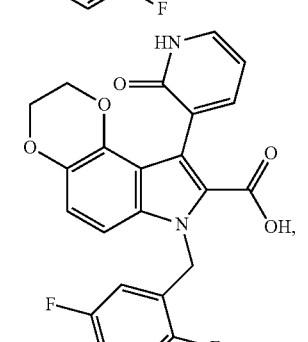
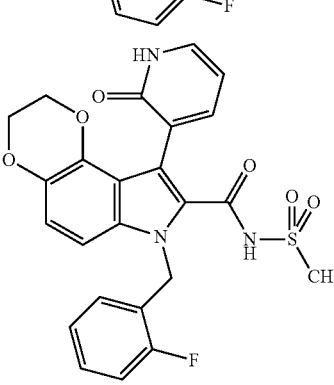

183
-continued
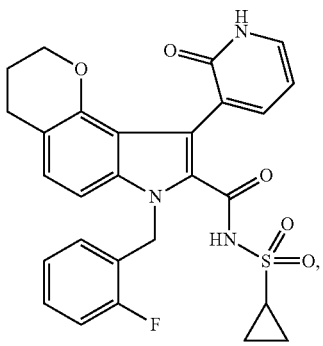
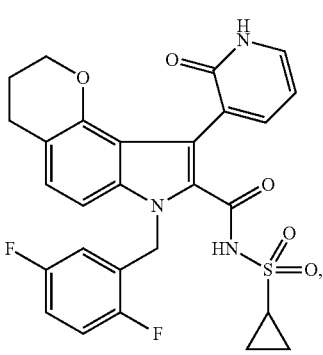
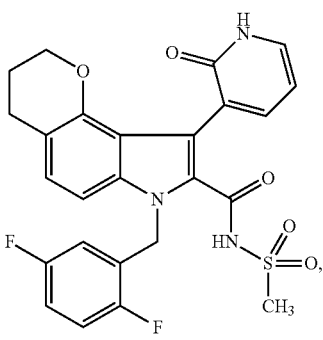
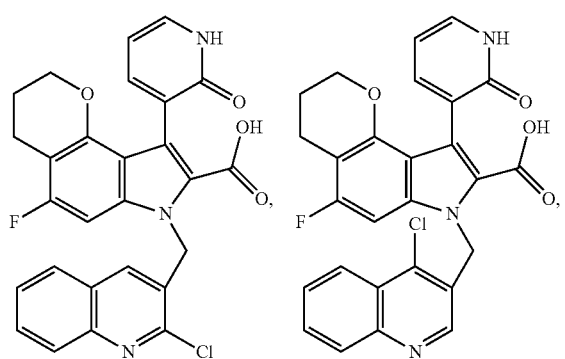
184
-continued
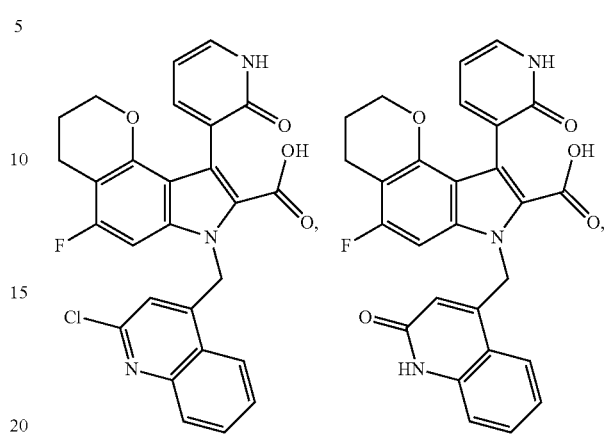
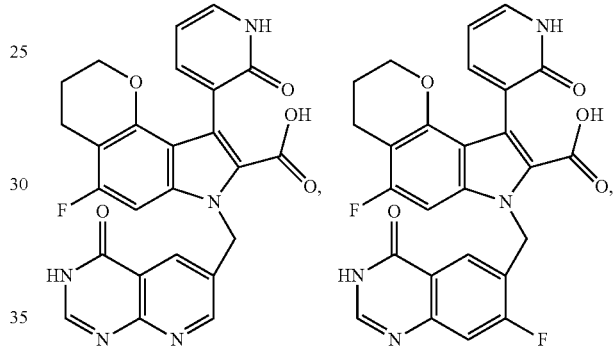
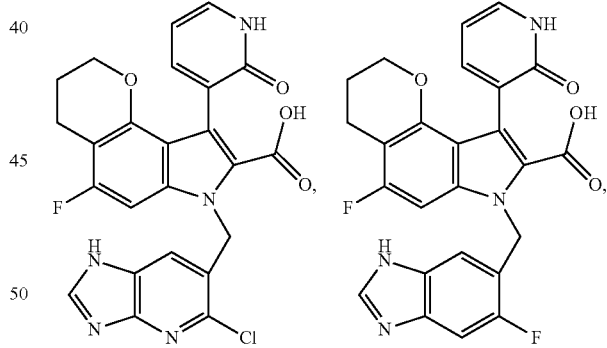
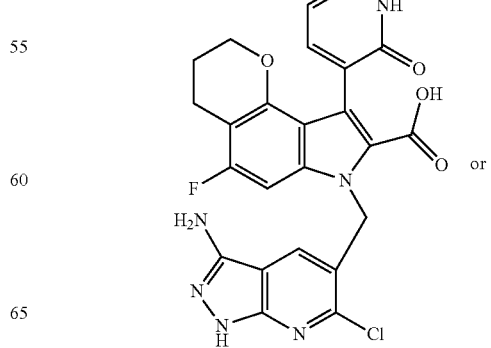

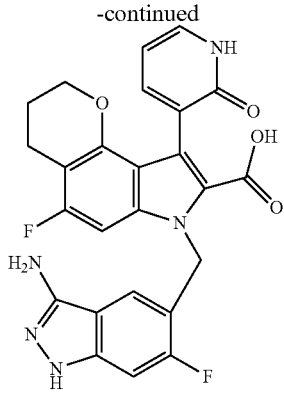

or a pharmaceutically acceptable salt or ester thereof.

7. A pharmaceutical composition comprising at least one compound of claim 1 or a pharmaceutically acceptable salt or ester thereof, and at least one pharmaceutically acceptable carrier.

8. The pharmaceutical composition of claim 7, further comprising at least one additional antiviral agent, wherein the additional agent selected from: an HCV polymerase inhibitor; an interferon; a RNA replication inhibitor; an antisense agent; a therapeutic vaccine; a protease inhibitor; and an antibody therapy (monoclonal or polyclonal).

9. A method for treating HCV infection in a patient, the method comprising administering to the patient an effective amount of at least one compound of claim 1 or a pharmaceutically acceptable salt or ester thereof.

10. The method of claim 9, further comprising administering to the patient at least one additional antiviral agent, wherein the additional agent is selected from: an HCV polymerase inhibitor; an interferon; a RNA replication inhibitor; an antisense agent; a therapeutic vaccine; a protease inhibitor; and an antibody therapy (monoclonal or polyclonal).

11. The compound of claim 3, wherein $R^{10}$ is phenyl or pyridyl.

12. The compound of claim 3, wherein $R^{10}$ is quinoline, quinolinone, pteridine, pteridinone, each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

13. The compound of claim 1, wherein $R^2$ is —C(O)OH, —C(O)NHSO$_2$—CH3 or —C(O)NHSO$_2$-cycloalkyl.

14. The compound of claim 1, wherein $R^3$ is

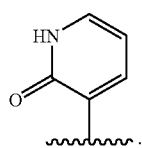

15. The compound of claim 4, wherein $R^3$ is

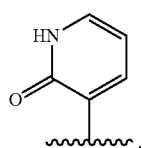

16. The compound of claim 4, wherein Z is

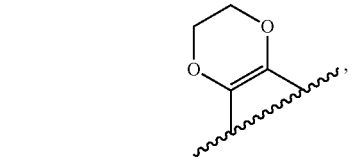

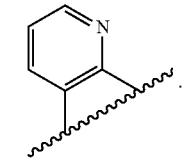

17. The compound of claim 1, wherein $R^{10}$ is

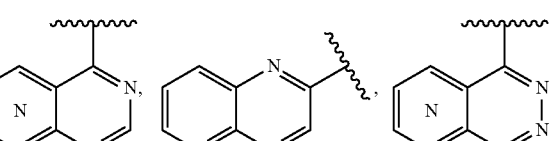

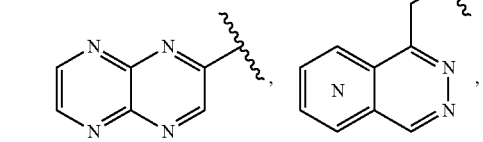

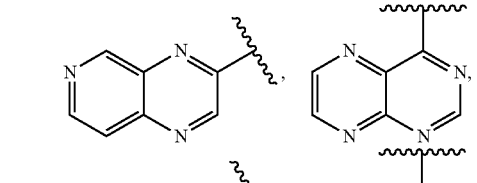

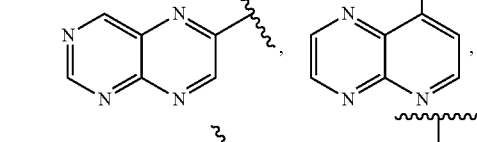

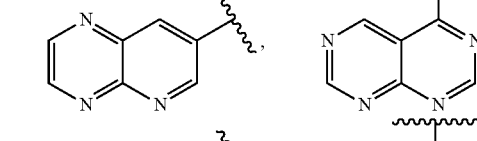

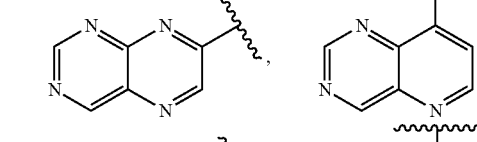

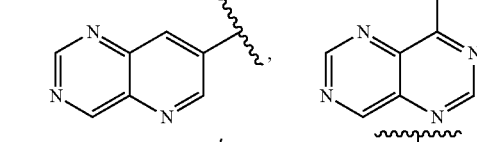

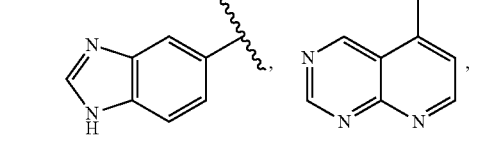

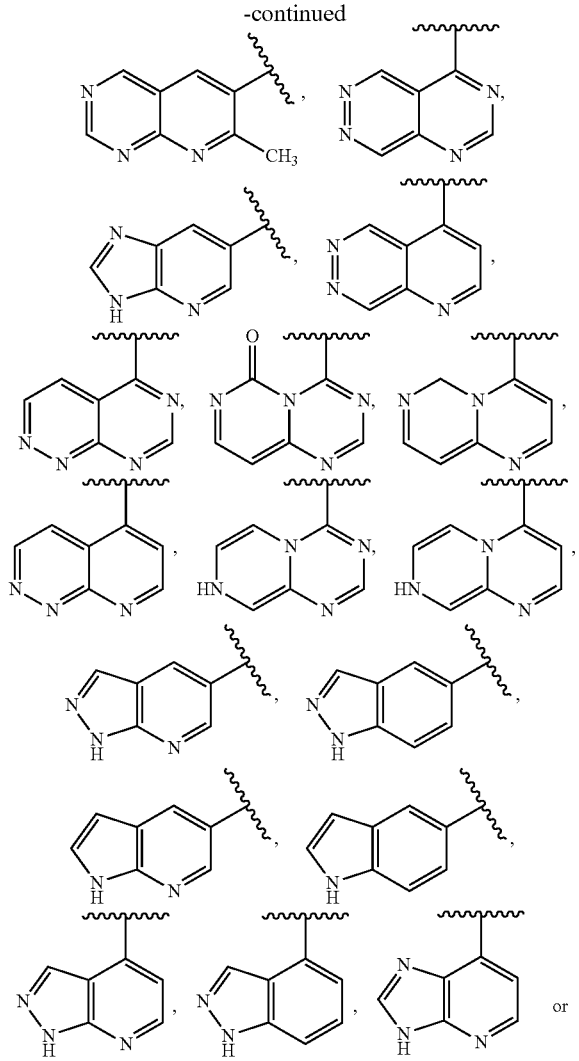

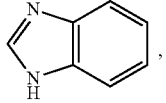

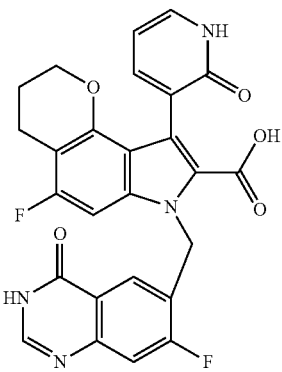 [SMILES: O=C(O)c1c(-c2ccc[nH]c2=O)c2c3c(c(F)cc2n1Cc1cc2c(=O)[nH]cnc2cc1F)CCCO3]

each of which can be optionally substituted with up to 3 substituents, which are the same or different, and are selected from alkyl, cycloalkyl, heterocycloalkyl, halo, haloalkyl, —O-haloalkyl, —OH, —CN, —NH$_2$, —NH-alkyl, —N(alkyl)$_2$ or —NHSO$_2$-alkyl.

18. The compound of claim 17, wherein and R$^2$ is —C(O)OH or —C(O)NHSO$_2$R$^{11}$.

19. The compound of claim 6 having the structure

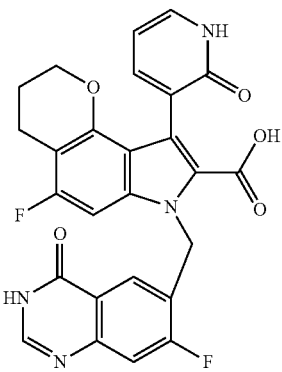 [SMILES: O=C(O)c1c(-c2ccc[nH]c2=O)c2c3c(c(F)cc2n1Cc1cc2c(=O)[nH]cnc2cc1F)CCCO3]

or a pharmaceutically acceptable salt or ester thereof.

* * * * *

UNITED STATES PATENT AND TRADEMARK OFFICE
CERTIFICATE OF CORRECTION

PATENT NO.        : 8,546,420 B2                                            Page 1 of 1
APPLICATION NO.   : 12/519728
DATED             : October 1, 2013
INVENTOR(S)       : Anilkumar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this

Fifteenth Day of September, 2015

Michelle K. Lee
*Director of the United States Patent and Trademark Office*